(12) United States Patent
Karmali et al.

(10) Patent No.: US 12,311,033 B2
(45) Date of Patent: May 27, 2025

(54) LIPID NANOPARTICLE FORMULATIONS AND COMPOSITIONS

(71) Applicant: CAPSTAN THERAPEUTICS, INC., San Diego, CA (US)

(72) Inventors: Priya Prakash Karmali, San Diego, CA (US); Steven Tanis, Carlsbad, CA (US); Yanjie Bao, San Diego, CA (US)

(73) Assignee: Capstan Therapeutics, Inc.

( * ) Notice: Subject to any disclaimer, the term of this patent is extended or adjusted under 35 U.S.C. 154(b) by 0 days.

(21) Appl. No.: 18/731,223

(22) Filed: May 31, 2024

(65) Prior Publication Data

US 2024/0398982 A1   Dec. 5, 2024

Related U.S. Application Data

(60) Provisional application No. 63/505,424, filed on May 31, 2023, provisional application No. 63/510,061, (Continued)

(51) Int. Cl.
*A61K 39/395* (2006.01)
*A61K 9/51* (2006.01)
(Continued)

(52) U.S. Cl.
CPC ........ *A61K 48/0033* (2013.01); *A61K 9/5123* (2013.01); *A61K 38/1774* (2013.01); *A61K 38/465* (2013.01); *A61K 47/60* (2017.08); *A61K 47/6849* (2017.08); *A61K 47/6889* (2017.08); *A61K 47/6929* (2017.08); *C12N 9/22* (2013.01);
(Continued)

(58) Field of Classification Search
None
See application file for complete search history.

(56) References Cited

U.S. PATENT DOCUMENTS 5,283,173 A   2/1994   Fields et al.
5,468,614 A   11/1995   Fields et al.
(Continued)

FOREIGN PATENT DOCUMENTS

CN   103396397 A   11/2013
CN   110716390 A   1/2020
(Continued)

OTHER PUBLICATIONS

Hou et al., Nat Rev Mater 6, 1078-1094 (2021) (Year: 2021).*
(Continued)

*Primary Examiner* — Karl J Puttlitz
(74) *Attorney, Agent, or Firm* — McDonnell Boehnen Hulbert & Berghoff LLP

(57) ABSTRACT

Disclosed are compositions of lipid nanoparticles (LNP) comprising an ionizable cationic lipid, a phospholipid, a sterol, and a PEG-lipid (non-functionalized and optionally functionalized). The functionalized PEG-lipid can be conjugated with a binding moiety to create a targeted LNP (tLNP). The disclosed tLNP preferentially deliver a nucleic acid molecule or other negatively charged payload to cells expressing a cell surface antigen recognized by the binding moiety of the tLNP, and are better tolerated, as compared to LNPs and tLNPs comprising ionizable cationic lipids found in marketed pharmaceuticals comprising LNPs.

30 Claims, 74 Drawing Sheets

Specification includes a Sequence Listing.

Related U.S. Application Data filed on Jun. 23, 2023, provisional application No. 63/520,303, filed on Aug. 17, 2023, provisional application No. 63/595,201, filed on Nov. 1, 2023.

(51) Int. Cl.

| | |
|---|---|
| *A61K 38/17* | (2006.01) |
| *A61K 38/46* | (2006.01) |
| *A61K 47/60* | (2017.01) |
| *A61K 47/68* | (2017.01) |
| *A61K 47/69* | (2017.01) |
| *A61K 48/00* | (2006.01) |
| *C12N 9/22* | (2006.01) |
| *C12N 15/11* | (2006.01) |
| *C12N 15/88* | (2006.01) |

(52) U.S. Cl.
CPC .............. *C12N 15/11* (2013.01); *C12N 15/88* (2013.01); *C12N 2310/20* (2017.05)

(56) References Cited

U.S. PATENT DOCUMENTS

| | | |
|---|---|---|
| 5,863,949 A | 1/1999 | Robinson et al. |
| 6,670,393 B2 | 12/2003 | Schwartz et al. |
| 7,223,887 B2 | 5/2007 | Gaucheron et al. |
| 7,446,190 B2 | 11/2008 | Sadelain et al. |
| 7,514,099 B2 | 4/2009 | Chen et al. |
| 7,893,302 B2 | 2/2011 | Chen et al. |
| 7,982,027 B2 | 7/2011 | MacLachlan et al. |
| 8,058,069 B2 | 11/2011 | Yaworski et al. |
| 8,252,723 B2 | 8/2012 | Jakobi et al. |
| 8,278,036 B2 | 10/2012 | Kariko et al. |
| 8,492,359 B2 | 7/2013 | Yaworski et al. |
| 8,691,966 B2 | 4/2014 | Kariko et al. |
| 8,748,089 B2 | 6/2014 | Kariko et al. |
| 8,748,667 B2 | 6/2014 | Budzik et al. |
| 8,802,863 B2 | 8/2014 | Budzik et al. |
| 8,822,668 B2 | 9/2014 | Yaworski et al. |
| 8,835,108 B2 | 9/2014 | Kariko et al. |
| 9,006,417 B2 | 4/2015 | Yaworski et al. |
| 9,061,063 B2 | 6/2015 | Maier et al. |
| 9,067,882 B2 | 6/2015 | Stanton et al. |
| 9,260,752 B1 | 2/2016 | May et al. |
| 9,364,435 B2 | 6/2016 | Yaworski et al. |
| 9,365,610 B2 | 6/2016 | Payne et al. |
| 9,402,816 B2 | 8/2016 | Colletti et al. |
| 9,404,127 B2 | 8/2016 | Yaworski et al. |
| 9,433,681 B2 | 9/2016 | Constien et al. |
| 9,458,087 B2 | 10/2016 | Bawiec, III et al. |
| 9,458,090 B2 | 10/2016 | Colletti et al. |
| 9,504,651 B2 | 11/2016 | MacLachlan et al. |
| 9,504,747 B2 | 11/2016 | Baryza |
| 9,518,272 B2 | 12/2016 | Yaworski et al. |
| 9,549,983 B2 | 1/2017 | Brown et al. |
| 9,567,296 B2 | 2/2017 | Payne et al. |
| 9,580,711 B2 | 2/2017 | Payne et al. |
| 9,593,077 B2 | 3/2017 | Payne et al. |
| 9,604,908 B2 | 3/2017 | Stanton et al. |
| 9,642,804 B2 | 5/2017 | Cameron et al. |
| 9,669,097 B2 | 6/2017 | Stanton et al. |
| 9,670,152 B2 | 6/2017 | Payne et al. |
| 9,717,690 B2 | 8/2017 | Guild et al. |
| 9,750,824 B2 | 9/2017 | Kariko et al. |
| 9,765,254 B2 | 9/2017 | Lucente-Schultz et al. |
| 9,850,202 B2 | 12/2017 | Payne et al. |
| 9,868,692 B2 | 1/2018 | Benenato |
| 9,877,919 B2 | 1/2018 | DeRosa et al. |
| 9,951,002 B2 | 4/2018 | Payne et al. |
| 10,059,655 B2 | 8/2018 | Brito et al. |
| 10,092,655 B2 | 10/2018 | Sasaki et al. |
| 10,125,092 B2 | 11/2018 | Beckwith et al. |
| 10,166,298 B2 | 1/2019 | Ansell et al. |
| 10,201,620 B2 | 2/2019 | Meis et al. |
| 10,207,010 B2 | 2/2019 | Besin et al. |
| 10,221,127 B2 | 3/2019 | Du et al. |
| 10,232,055 B2 | 3/2019 | Kariko et al. |
| 10,252,974 B2 | 4/2019 | Hoashi |
| 10,342,760 B2 | 7/2019 | Ramsay et al. |
| 10,383,929 B2 | 8/2019 | Morgan et al. |
| 10,383,952 B2 | 8/2019 | Payne et al. |
| 10,399,937 B2 | 9/2019 | Payne et al. |
| 10,426,737 B2 | 10/2019 | Brito et al. |
| 10,426,797 B2 | 10/2019 | Orentas et al. |
| 10,428,141 B2 | 10/2019 | Orentas et al. |
| 10,435,616 B2 | 10/2019 | Lucente-Schultz et al. |
| 10,526,284 B2 | 1/2020 | Payne et al. |
| 10,543,263 B2 | 1/2020 | Orentas et al. |
| 10,556,861 B2 | 2/2020 | Payne et al. |
| 10,722,599 B2 | 7/2020 | Barenholz et al. |
| 10,781,169 B2 | 9/2020 | Payne et al. |
| 10,844,128 B2 | 11/2020 | Orentas et al. |
| 10,898,574 B2 | 1/2021 | De Fougerolles et al. |
| 10,906,867 B2 | 2/2021 | Brito et al. |
| 10,920,246 B2 | 2/2021 | Peer et al. |
| 10,934,337 B2 | 3/2021 | Zhang et al. |
| 10,934,363 B2 | 3/2021 | Fan et al. |
| 10,961,188 B2 | 3/2021 | Payne et al. |
| 10,980,895 B2 | 4/2021 | Payne et al. |
| 11,026,975 B2 | 6/2021 | Zhou et al. |
| 11,066,355 B2 | 7/2021 | Benenato et al. |
| 11,135,312 B2 | 10/2021 | Von Der Mülbe et al. |
| 11,141,378 B2 | 10/2021 | Yaworski et al. |
| 11,229,609 B2 | 1/2022 | Cheng et al. |
| 11,241,493 B2 | 2/2022 | Rauch et al. |
| 11,246,933 B1 | 2/2022 | Maier et al. |
| 11,291,682 B2 | 4/2022 | Geall et al. |
| 11,324,770 B2 | 5/2022 | Geall et al. |
| 11,326,182 B2 | 5/2022 | Paul et al. |
| 11,382,979 B2 | 7/2022 | Maier et al. |
| RE49,233 E | 10/2022 | Payne et al. |
| 11,510,977 B2 | 11/2022 | Mng |
| 11,524,932 B2 | 12/2022 | Du |
| 11,525,006 B2 | 12/2022 | Wang et al. |
| 11,542,225 B2 | 1/2023 | Du |
| 11,591,544 B2 | 2/2023 | Drummond et al. |
| 11,596,645 B2 | 3/2023 | Geall et al. |
| 11,603,396 B2 | 3/2023 | Wesselhoeft et al. |
| 11,638,693 B2 | 5/2023 | Geall |
| 11,638,694 B2 | 5/2023 | Geall |
| 11,666,534 B2 | 6/2023 | Geall |
| 11,679,120 B2 | 6/2023 | Horhota et al. |
| 11,690,861 B2 | 7/2023 | Geall et al. |
| 11,690,862 B1 | 7/2023 | Geall et al. |
| 11,690,864 B2 | 7/2023 | Geall et al. |
| 11,707,482 B2 | 7/2023 | Geall et al. |
| 11,717,529 B2 | 8/2023 | Geall et al. |
| 11,739,300 B2 | 8/2023 | Kariko et al. |
| 11,766,401 B2 | 9/2023 | Geall |
| 11,771,652 B2 | 10/2023 | Casimiro et al. |
| 11,771,653 B2 | 10/2023 | Casimiro et al. |
| 11,786,467 B2 | 10/2023 | Geall |
| 11,801,314 B2 | 10/2023 | Kariko et al. |
| 11,802,144 B2 | 10/2023 | Wesselhoeft et al. |
| 11,851,389 B2 | 12/2023 | Peer et al. |
| 11,883,534 B2 | 1/2024 | Geall |
| 11,964,051 B2 | 4/2024 | DeRosa et al. |
| 11,993,570 B2 | 5/2024 | Matsumoto et al. |
| 12,065,396 B2 | 8/2024 | Du |
| 12,065,664 B2 | 8/2024 | Peer et al. |
| 2006/0134189 A1 | 6/2006 | Maclachlan et al. |
| 2006/0135773 A1 | 6/2006 | Semple et al. |
| 2009/0286852 A1 | 11/2009 | Kariko et al. |
| 2010/0093776 A1 | 4/2010 | Beckwith |
| 2012/0058144 A1 | 3/2012 | Manoharan et al. |
| 2012/0264810 A1 | 10/2012 | Lin et al. |
| 2013/0005573 A1 | 1/2013 | Roe et al. |
| 2013/0017223 A1 | 1/2013 | Hope et al. |
| 2013/0037977 A1 | 2/2013 | Burke et al. |
| 2013/0108685 A1 | 5/2013 | Kuboyama et al. |
| 2013/0115274 A1 | 5/2013 | Knopov et al. |
| 2013/0129811 A1 | 5/2013 | Kuboyama et al. |
| 2013/0280305 A1 | 10/2013 | Kuboyama et al. |

(56) References Cited

U.S. PATENT DOCUMENTS

| | | |
|---|---|---|
| 2013/0330401 A1 | 12/2013 | Payne et al. |
| 2014/0039032 A1 | 2/2014 | Kuboyama et al. |
| 2014/0045913 A1 | 2/2014 | Kuboyama et al. |
| 2014/0308304 A1 | 10/2014 | Manoharan et al. |
| 2015/0141678 A1 | 5/2015 | Payne et al. |
| 2016/0095924 A1 | 4/2016 | Hope et al. |
| 2016/0317676 A1 | 11/2016 | Hope et al. |
| 2016/0367638 A1 | 12/2016 | Byers et al. |
| 2017/0051068 A1 | 2/2017 | Pillarisetti et al. |
| 2017/0101370 A1 | 4/2017 | Payne et al. |
| 2017/0101639 A1 | 4/2017 | Yabuuchi et al. |
| 2017/0105960 A1 | 4/2017 | Elmer et al. |
| 2017/0190661 A1 | 7/2017 | Payne et al. |
| 2017/0349914 A1 | 12/2017 | Cox et al. |
| 2018/0057500 A1 | 3/2018 | Billedeau et al. |
| 2018/0119003 A1 | 5/2018 | Eluru et al. |
| 2018/0221402 A1 | 8/2018 | Prieve et al. |
| 2018/0369407 A1 | 12/2018 | Goldberg et al. |
| 2020/0093936 A1 | 3/2020 | Muzykantov et al. |
| 2020/0225215 A1 | 7/2020 | Ciufolini et al. |
| 2020/0246381 A1 | 8/2020 | Zhou et al. |
| 2020/0261503 A1 | 8/2020 | Chang et al. |
| 2020/0283372 A1 | 9/2020 | Du |
| 2020/0297634 A1 | 9/2020 | Karmali et al. |
| 2020/0308111 A1 | 10/2020 | Suzuki et al. |
| 2020/0339699 A1 | 10/2020 | Li et al. |
| 2020/0345641 A1 | 11/2020 | De Koker et al. |
| 2021/0002217 A1 | 1/2021 | Payne et al. |
| 2021/0023011 A1 | 1/2021 | Teo et al. |
| 2021/0052646 A1 | 2/2021 | Kuwae et al. |
| 2021/0069336 A1 | 3/2021 | Dong et al. |
| 2021/0087295 A1 | 3/2021 | Albelda et al. |
| 2021/0108228 A1 | 4/2021 | Peer et al. |
| 2021/0169804 A1 | 6/2021 | Patwardhan et al. |
| 2021/0230112 A1 | 7/2021 | Hamilton et al. |
| 2021/0252163 A1 | 8/2021 | Payne et al. |
| 2021/0254185 A1 | 8/2021 | Taniguchi et al. |
| 2021/0275689 A1 | 9/2021 | Karve et al. |
| 2021/0301274 A1 | 9/2021 | Bryson |
| 2021/0323914 A1 | 10/2021 | Payne et al. |
| 2021/0363245 A1 | 11/2021 | Kochenderfer et al. |
| 2022/0001025 A1 | 1/2022 | Barz et al. |
| 2022/0002424 A1 | 1/2022 | Trager et al. |
| 2022/0011934 A1 | 1/2022 | Tatapudi et al. |
| 2022/0047723 A1 | 2/2022 | Cheng et al. |
| 2022/0098142 A1 | 3/2022 | Matsumoto et al. |
| 2022/0119341 A1 | 4/2022 | Scully et al. |
| 2022/0142923 A1 | 5/2022 | Casimiro et al. |
| 2022/0160633 A1 | 5/2022 | Androsavich et al. |
| 2022/0168231 A1 | 6/2022 | Xu et al. |
| 2022/0204690 A1 | 6/2022 | Nose |
| 2022/0218614 A1 | 7/2022 | Ali et al. |
| 2022/0218746 A1 | 7/2022 | Zhang et al. |
| 2022/0226480 A1 | 7/2022 | Chen et al. |
| 2022/0227743 A1 | 7/2022 | Choi et al. |
| 2022/0249693 A1 | 8/2022 | Sago et al. |
| 2022/0249694 A1 | 8/2022 | Shehata et al. |
| 2022/0265857 A1 | 8/2022 | Besin et al. |
| 2022/0304929 A1 | 9/2022 | Zaifman et al. |
| 2022/0323480 A1 | 10/2022 | Goodman et al. |
| 2022/0325245 A1 | 10/2022 | Rezvani et al. |
| 2022/0347100 A1 | 11/2022 | Casimiro et al. |
| 2022/0370357 A1 | 11/2022 | Stanton et al. |
| 2022/0378917 A1 | 12/2022 | Thomas et al. |
| 2022/0389422 A1 | 12/2022 | Rajappan et al. |
| 2022/0396548 A1 | 12/2022 | Jain et al. |
| 2022/0402862 A1 | 12/2022 | Scully et al. |
| 2023/0067722 A1 | 3/2023 | De Koker et al. |
| 2023/0136350 A1 | 5/2023 | Brudno et al. |
| 2023/0159459 A1 | 5/2023 | Stanton et al. |
| 2023/0181764 A1 | 6/2023 | Stanton et al. |
| 2023/0201127 A1 | 6/2023 | Peer et al. |
| 2023/0202966 A1 | 6/2023 | Jayaraman et al. |
| 2023/0202977 A1 | 6/2023 | Jayaraman et al. |
| 2023/0203538 A1 | 6/2023 | Parhiz et al. |
| 2023/0226096 A1 | 7/2023 | Goodman et al. |
| 2023/0227826 A1 | 7/2023 | Tachikawa et al. |
| 2023/0233706 A1 | 7/2023 | Parhiz et al. |
| 2023/0257338 A1 | 8/2023 | Matsumoto et al. |
| 2023/0295081 A1 | 9/2023 | Rajappan et al. |
| 2023/0295257 A1 | 9/2023 | Becraft et al. |
| 2023/0312713 A1 | 10/2023 | Parhiz et al. |
| 2023/0320993 A1 | 10/2023 | Gallagher et al. |
| 2023/0320995 A1* | 10/2023 | Karmali ............... A61K 9/5123 |
| 2023/0323345 A1 | 10/2023 | Tachikawa et al. |
| 2023/0331656 A1 | 10/2023 | Hamilton et al. |
| 2023/0331657 A1 | 10/2023 | Patwardhan et al. |
| 2023/0348359 A1 | 11/2023 | Shehata et al. |
| 2023/0355524 A1 | 11/2023 | Boeglin et al. |
| 2023/0357133 A1 | 11/2023 | Hamilton et al. |
| 2024/0002331 A1 | 1/2024 | Ali et al. |
| 2024/0042015 A1 | 2/2024 | Wesselhoeft et al. |
| 2024/0067598 A1 | 2/2024 | Scully et al. |
| 2024/0115511 A1 | 4/2024 | Hamilton et al. |
| 2024/0130969 A1 | 4/2024 | Jayaraman et al. |
| 2024/0166593 A1 | 5/2024 | Ramishetti et al. |
| 2024/0182412 A1 | 6/2024 | Jayaraman et al. |
| 2024/0216523 A1 | 7/2024 | Parhiz et al. |
| 2024/0239908 A1 | 7/2024 | Ayres et al. |
| 2024/0390271 A1 | 11/2024 | Mirko et al. |
| 2024/0391870 A1 | 11/2024 | Kumar et al. |

FOREIGN PATENT DOCUMENTS

| | | |
|---|---|---|
| CN | 113185421 A | 7/2021 |
| CN | 114763383 A | 7/2022 |
| DE | 102006020530 A1 | 11/2007 |
| EP | 0071433 A1 | 2/1983 |
| EP | 3303598 A1 | 4/2018 |
| EP | 3865122 A1 | 8/2021 |
| JP | H10120866 A | 5/1998 |
| JP | H10147719 A | 6/1998 |
| JP | 2001161177 A | 6/2001 |
| JP | 2001199018 A | 7/2001 |
| JP | 2003096376 A | 4/2003 |
| JP | 2003212957 A | 7/2003 |
| JP | 2006254877 A | 9/2006 |
| JP | 2008231344 A | 10/2008 |
| WO | 2003044136 A1 | 5/2003 |
| WO | 2005007196 A2 | 1/2005 |
| WO | 2006053430 A1 | 5/2006 |
| WO | 2006084116 A2 | 8/2006 |
| WO | 2007086883 A2 | 8/2007 |
| WO | 2009129385 A1 | 10/2009 |
| WO | 2009129387 A2 | 10/2009 |
| WO | 2010048536 A2 | 4/2010 |
| WO | 2010104949 A2 | 9/2010 |
| WO | 2012163805 A1 | 12/2012 |
| WO | 2015187528 A1 | 12/2015 |
| WO | 2016/081029 A1 | 5/2016 |
| WO | 2017004143 A1 | 1/2017 |
| WO | 2017048770 A1 | 3/2017 |
| WO | 2017075038 A1 | 5/2017 |
| WO | 2017075531 A1 | 5/2017 |
| WO | 2017181110 A1 | 10/2017 |
| WO | 2018028647 A1 | 2/2018 |
| WO | 2018096011 A1 | 5/2018 |
| WO | 2018118102 A1 | 6/2018 |
| WO | 2018119163 A1 | 6/2018 |
| WO | 2018213337 A1 | 11/2018 |
| WO | 2018226762 A1 | 12/2018 |
| WO | 2019006072 A1 | 1/2019 |
| WO | 2019036008 A1 | 2/2019 |
| WO | 2019040516 A1 | 2/2019 |
| WO | 2019191780 A1 | 10/2019 |
| WO | 2019213308 A1 | 11/2019 |
| WO | 2019240287 A1 | 12/2019 |
| WO | 2019246203 A1 | 12/2019 |
| WO | 2020081938 A1 | 4/2020 |
| WO | 2020257716 A1 | 12/2020 |
| WO | 2021046265 A1 | 3/2021 |
| WO | 2021155274 A1 | 8/2021 |
| WO | 2021183563 A1 | 9/2021 |
| WO | 2021189059 A2 | 9/2021 |

(56) References Cited

FOREIGN PATENT DOCUMENTS

| | | |
|---|---|---|
| WO | 2021191265 A1 | 9/2021 |
| WO | 2021231854 A1 | 11/2021 |
| WO | 2021/250263 A1 | 12/2021 |
| WO | 2022032087 A1 | 2/2022 |
| WO | 2022067446 A1 | 4/2022 |
| WO | 2022081694 A1 | 4/2022 |
| WO | 2022081699 A1 | 4/2022 |
| WO | 2022081702 A1 | 4/2022 |
| WO | 2022101470 A1 | 5/2022 |
| WO | 2022101486 A1 | 5/2022 |
| WO | 2022112855 A1 | 6/2022 |
| WO | 2022120388 A2 | 6/2022 |
| WO | 2022/155598 A2 | 7/2022 |
| WO | 2022/166213 A1 | 8/2022 |
| WO | 2022/204288 A1 | 9/2022 |
| WO | 2022/221688 A1 | 10/2022 |
| WO | 2022/221697 A1 | 10/2022 |
| WO | 2022/225918 A1 | 10/2022 |
| WO | 2022226008 A2 | 10/2022 |
| WO | 2022232514 A1 | 11/2022 |
| WO | 2022232540 A1 | 11/2022 |
| WO | 2022235935 A2 | 11/2022 |
| WO | 2022235972 A1 | 11/2022 |
| WO | 2022/246555 A1 | 12/2022 |
| WO | 2022/246568 A1 | 12/2022 |
| WO | 2022/246571 A1 | 12/2022 |
| WO | 2022/261490 A2 | 12/2022 |
| WO | 2022251959 A1 | 12/2022 |
| WO | 2022266032 A1 | 12/2022 |
| WO | 2023278754 A1 | 1/2023 |
| WO | 2023287861 A2 | 1/2023 |
| WO | 2023/023055 A1 | 2/2023 |
| WO | 2023015223 A2 | 2/2023 |
| WO | 2023/045366 A1 | 3/2023 |
| WO | 2023/056033 A1 | 4/2023 |
| WO | 2023/091490 A1 | 5/2023 |
| WO | 2023/091787 A1 | 5/2023 |
| WO | 202308651 A1 | 5/2023 |
| WO | 2023081526 A1 | 5/2023 |
| WO | 2023086514 A1 | 5/2023 |
| WO | 2023114937 A2 | 6/2023 |
| WO | 2023114943 A2 | 6/2023 |
| WO | 2023114944 A1 | 6/2023 |
| WO | 2023135305 A1 | 7/2023 |
| WO | 2023141576 A1 | 7/2023 |
| WO | 2023/172774 A1 | 9/2023 |
| WO | 2023/178167 A1 | 9/2023 |
| WO | 2023/183616 A1 | 9/2023 |
| WO | 2023/196931 A1 | 10/2023 |
| WO | 2023196445 A1 | 10/2023 |
| WO | 2023/225621 A2 | 11/2023 |
| WO | 2023248125 A1 | 12/2023 |
| WO | 2024/026029 A2 | 2/2024 |
| WO | 2024/044728 A1 | 2/2024 |
| WO | 2024040194 A1 | 2/2024 |
| WO | 2024040195 A1 | 2/2024 |
| WO | 2024077232 A2 | 4/2024 |
| WO | 2024085190 A1 | 4/2024 |
| WO | 2024086614 A2 | 4/2024 |
| WO | 2024094125 A1 | 5/2024 |
| WO | 2024097307 A1 | 5/2024 |
| WO | 2024100656 A1 | 5/2024 |
| WO | 2024102768 A2 | 5/2024 |
| WO | 2024102769 A2 | 5/2024 |
| WO | 2024102770 A1 | 5/2024 |
| WO | 2024102772 A2 | 5/2024 |
| WO | 2024/133853 A1 | 6/2024 |
| WO | 2024118634 A2 | 6/2024 |
| WO | 2024119039 A2 | 6/2024 |
| WO | 2024119103 A1 | 6/2024 |
| WO | 2024163905 A1 | 8/2024 |
| WO | 2024165039 A1 | 8/2024 |
| WO | 2024193649 A1 | 9/2024 |
| WO | 2024243031 A1 | 11/2024 |

OTHER PUBLICATIONS

Billingsley et al., Nano Lett. Jan. 12, 2022;22(1):533-542 (Year: 2022).*
Zhou et al., MedComm. 2022; 3:e155 (Year: 2022).*
International Search Report and Written Opinion of International Patent Application No. PCT/US2023/017647, mailed Aug. 23, 2023, 9 pages.
Akinc et al. "Targeted Delivery of RNAi Therapeutics With Endogenous and Exogenous Ligand-Based Mechanisms" Molecular Therapy, 2010, vol. 18, No. 7, pp. 1357-1364.
Jayaraman et al. "Maximizing the Potency of siRNA Lipid Nanoparticles for Hepatic Gene Silencing In Vivo." Angew. Chem. Int. Ed. 2012, vol. 51, pp. 8529-8533.
Billingsley et al. "Ionizable Lipid Nanoparticle-Mediated mRNA Delivery for Human CAR T Cell Engineering." Nano Lett. 2020, vol. 20, No. 3, pp. 1578-1589.
Buschmann et al. "Nanomaterial Delivery Systems for mRNA Vaccines." Vaccines, 2021, vol. 9, No. 65, pp. 1-30.
Carrasco et al. "Ionization and structural properties of mRNA lipid nanoparticles influence expression in intramuscular and intravascular administration." Communications Biology, 2021, vol. 4.956, pp. 1-15.
Evers et al. "State-of-the-Art Design and Rapid-Mixing Production Techniques of Lipid Nanoparticles for Nucleic Acid Delivery." Small Methods, 2018, vol. 2, No. 1700375, 20 pages.
Finn et al. "A Single Administration of CRISPR/Cas9 Lipid Nanoparticles Achieves Robut and Persistent In Vivo Genome Editing." Cell Reports, 2018, vol. 22, pp. 2227-2235.
Gaviria et al. "A network analysis of COVID-19 mRNA vaccine patents." Nature Biotechnology, 2021, vol. 39, pp. 546-549.
Hassett et al. "Optimization of Lipid Nanoparticles for Intramuscular Administration of mRNA Vaccines." Molecular Therapy: Nucleic Acid, 2019, vol. 15, pp. 1-11.
Hou et al. "Lipid nanoparticles for mRNA delivery." Nature Reviews Materials, 2021, vol. 6, pp. 1078-1094.
Maier et al. "Biodegradable Lipids Enabling Rapidly Eliminated Lipid Nanoparticles for Systemic Delivery of RNAi Therapeutics." Molecular Therapy, 2013, vol. 12, No. 8, pp. 1570-1578.
Rajappan et al. "Property-Driven Design and Development of Lipids for Efficient Delivery of siRNA." J. Med. Chem. 2020, vol. 63, pp. 12992-13012.
Rajappan et al. "Development of Safe and Scalable Process for the Production of a High-Purity Thiocarbamate-Based Ionizable Lipid as an Excipient in mRNA-Encapsulating Lipid Nanoparticles." Org. Process Res. Dev., 2021, vol. 25, pp. 1383-1390.
Ramishetti et al. "Systemic Gene Silencing in Primary T Lymphocytes Using Targeted Lipid Nanoparticles." ACS Nano, 2015, vol. 9, No. 7, pp. 6706-6716.
Sabnis et al. "A Novel Amino Lipid Series for mRNA Delivery: Improved Endosomal Escape and Sustained Pharmacology and Safety in Non-human Primates." Molecular Therapy, 2018, vol. 26, No. 6, pp. 1509-1519.
Semple et al. "Rational design of cationic lipids for siRNA delivery." Nature Biotechnology, 2010, vol. 28, No. 2, pp. 172-176.
Sheperd et al. "Microfluidic formulation of nanoparticles for biomedical applications." Biomaterials, 2021, vol. 274, No. 120826, 16 pages.
Wilkinson et al. "Systematic analysis of the varied designs of 819 therapeutic antibodies and Fc fusion proteins assigned international nonproprietary names" MAbs, 2022, vol. 14., No. 2123299, 16 pages.
Parhiz et al. "PECAM-1 directed re-targeting of exogenous mRNA providing two orders of magnitude enhancement of vascular delivery and expression in lungs independent of apolipoprotein E-mediated uptake" Journal of Controlled Release, 2018, vol. 291, p. 06-115.
Kolb et al. "Click Chemistry: Diverse Chemical Function from a Few Good Reactions" Angewandte Chemie International Edition, 2001, vol. 40, No. 11, p. 2004-2021.
Tombacz et al., "Highly efficient CD4+ T cell targeting and genetic recombination using engineered CD4+ cell-homing mRNA-LNPs" Molecular Therapy, 2021, vol. 29, No. 11, p. 3293-3304.

(56) References Cited

OTHER PUBLICATIONS

U.S. Appl. No. 63/595,753, Matsuda et al.
U.S. Appl. No. 63/610,917, Nguyen et al.
U.S. Appl. No. 63/611,092, Matsuda et al.
U.S. Appl. No. 63/632,940, Karmali et al.
U.S. Appl. No. 63/708,461, Nguyen et al.
U.S. Appl. No. 63/708,529, Matsuda et al.
Anzalone et al. "Genome editing with CRISPR-Cas nucleases, base editors, transposases and prime editors". Nat Biotechnol. 38(7):824-844, (2020).
Binder et al., "CD2 Immunobiology" Front Immunol 9:11:1090 (2020).
Carpenter et al., "B-cell maturation antigen is a promising target for adoptive T-cell therapy of multiple myeloma" Clin Cancer Res 19(8): 2048-2060 (2013).
Evans, "The Rise of Azide-Alkyne 1,3-Dipolar 'Click' Cycloaddition and its Application to Polymer Science and Surface Modification" Australian Journal of Chemistry 60(6): 384-395 (2007).
Friedman et al., "Effective Targeting of Multiple B-Cell Maturation Antigen-Expressing Hematological Malignances by Anti-B-Cell Maturation Antigen Chimeric Antigen Receptor T Cells." Hum. Gene Ther. 29(5): 585-601 (2018).
Fujii et al., "AJICAP Second Generation: Improved Chemical Site-Specific Conjugation Technology for Antibody-Drug Conjugate Production" Bioconjugate Chemistry 34 (4): 728-738 (2023).
Gilleron et al., "Image-based analysis of lipid nanoparticle-mediated siRNA delivery, intracellular trafficking and endosomal escape". Nat Biotechnol 31(7):638-46, (2013).
Lam et al., "Anti-BCMA chimeric antigen receptors with fully human heavy-chain-only antigen recognition domains" Nat. Commun. 11(1): 283 (2020).
Li et al., "Ligand-induced conformational change within the CD2 ectodomain accompanies receptor clustering: implication for molecular lattice formation" J Mol Biol 263:209-26 (1996).
Liang et al., "Safety and efficacy of a novel anti-CD20 chimeric antigen receptor (CAR)-T cell therapy in relapsed/ refractory (r/r) B-cell non-Hodgkin lymphoma (B-NHL) patients after failing CD19 Car-T therapy." J. Clin. Oncol. 39(15) suppl:2508 (2021).
Matsuda et al., "Chemical Site-Specific Conjugation Platform to Improve the Pharmacokinetics and Therapeutic Index of Antibody-Drug Conjugates" Mol Pharm 18:4058-4066 (2021).
Moliner-Morro et al., "Picomolar SARS-CoV-2 Neutralization Using Multi-Arm PEG Nanobody Constructs" Biomolecules 10(12): 1661 (2020).
Munson et al. "A high-throughput Galectin-9 imaging assay for quantifying nanoparticle uptake, endosomal escape and functional RNA delivery". Commun Biol. 4(1):211, (2021).
Nicholson et al., "Construction and characterisation of a functional CD19 specific single chain Fv fragment for immunotherapy of B lineage leukaemia and lymphoma" Mol Immunol 34(16-17): 1157-65 (1997).
Rajappan et al., "Property-Driven Design and Development of Lipids for Efficient Delivery of siRNA" J. Med Chem 63:12992-13012 (2020).
Rodriguez et al., "Minimal "Self" peptides that inhibit phagocytic clearance and enhance delivery of nanoparticles" Science 339(6122):971-5 (2013).
Sakuma et al. "From nuclease-based gene knock-in to prime editing - promising technologies of precision gene engineering". Gene and Genome Editing 3-4: 100017, (2022).
Scatchard et al. "The attractions of proteins for small molecules and ions". Ann. N. Y. Acad. Sci. 51:660, (1949).
Shadman et al., "CD20 Targeted CAR-T for High-Risk B-Cell Non-Hodgkin Lymphomas" Blood 134(Suppl. 1):3235 (2019).
Tsai et al., "Inhibition of "self" engulfment through deactivation of myosin-II at the phagocytic synapse between human cells" J. Cell Biol. 180(5):989-1003 (2008).
Wu et al., "Multimerization of a chimeric anti-CD20 single-chain Fv-Fc fusion protein is mediated through variable domain exchange" Protein Engineering 14(12): 1025-1033 (2001).
Zhao et al., "A phase 1, open-label study of LCAR-B38M, a chimeric antigen receptor T cell therapy directed against B cell maturation antigen, in patients with relapsed or refractory multiple myeloma" J Hematol Oncol 11(1): 141 (2018).
Zhou et al. "Current landscape of gene-editing technology in biomedicine: Applications, advantages, challenges, and perspectives". MedComm 3(3):e155, (2020).
U.S. Appl. No. 63/595,753, filed Nov. 2, 2023, mRNAs for In Vivo Transfection, Application Dispatched from Preexam, Not Yet Docketed Nov. 13, 2023.
U.S. Appl. No. 63/610,917, filed Dec. 15, 2023, Humanized Anti-CD8 Antibodies and Uses Thereof, Application Dispatched from Preexam, Not Yet Docketed Dec. 27, 2023.
U.S. Appl. No. 63/611,092, filed Dec. 15, 2023, mRNAs for In Vivo Transfection, Application Dispatched from Preexam, Not Yet Docketed Jan. 19, 2024.
U.S. Appl. No. 63/632,940, filed Apr. 11, 2024, Ionizable Cationic Lipids and Lipid Nanoparticles, Application Dispatched from Preexam, Not Yet Docketed Apr. 18, 2024.
U.S. Appl. No. 63/708,461, filed Oct. 17, 2024, Humanized Anti-CD8 Antibodies and Uses Thereof, Application Undergoing Preexam Processing, Oct. 17, 2024.
U.S. Appl. No. 63/708,529, filed Oct. 17, 2024, mRNAs for In Vivo Transfection, Application Undergoing Preexam Processing, Oct. 17, 2024.
Bergmann et al., "Treatment of a patient with severe systemic sclerosis (SSc) using CD19-targeted Car T cells". Ann Rheum Dis. 82(8): 1117-1120, (2023).
Christakopolulos et al., "Gene Therapy and Gene Editing for β-Thalassemia". Hematol Oncol Clin North Am. 37(2): 433-447, (2023).
Haghikia et al., "Anti-CD19 CAR T cells for refractory myasthenia gravis". Lancet Neurol. 22(12): 1104-1105, (2023).
Kakade et al., "Carbohydrate anchored lipid nanoparticles". Int J Pharm 25:618:121681, (2022).
Kasiewicz et al., "GalNAc-Lipid nanoparticles enable non-LDLR dependent hepatic delivery of a CRISPR base editing therapy". Nat Commun. 14(1): 2776, (2023).
Lee et al., "DNA aptamer-conjugated lipid nanoparticle for targeted PTEN mRNA delivery to prostate cancer cells". Int J Pharm. 5:662:124519, (2024).
Liang et al., "Aptamer-functionalized lipid nanoparticles targeting osteoblasts as a novel RNA interference-based bone anabolic strategy". Nat Med. 21(3): 288-294, (2015).
Mackensen et al., "Anti-CD19 CAR T cell therapy for refractory systemic lupus erythematosus". Nat Med. 28(10): 2124-2132, (2022).
Muller et al., "CD19 CAR T-Cell Therapy in Autoimmune Disease—A Case Series with Follow-up". N Engl J Med. 390(8): 687-700, (2024).
Muller et al., "CD19-targeted CAR T cells in refractory antisynthetase syndrome". Lancet 401(10379): P815-818, (2023).
Park et al., "CD19-targeted CAR T-cell therapeutics for hematologic malignancies: interpreting clinical outcomes to date". Blood 127(26): 3312-3320, (2016).
Pecher et al., "CD19-Targeting CAR T Cells for Myositis and Interstitial Lung Disease Associated With Antisynthetase Syndrome". JAMA 329(24): 2154-2162, (2023).
Ray et al., "Enhanced target cell specificity and uptake of lipid nanoparticles using RNA aptamers and peptides". Beilstein J Org Chem. 17: 891-907, (2021).
Rurik et al., "CAR T cells produced in vivo to treat cardiac injury". Science 376(6576): 91-96, (2022).
Sargent, "Aptamer-lipid nanoparticle conjugates for RNAi in bone". Nat Rev Endocrinol. 11(4): 194, (2015).
Taubman et al., "Rescue therapy of antisynthetase syndrome with CD19-targeted CAR-T cells after failure of several B-cell depleting antibodies". Rheumatology (Oxford) 63(1): e12-e14, (2024).
Tenchov et al., "PEGylated Lipid Nanoparticle Formulations: Immunological Safety and Efficiency Perspective". Bioconjug Chem. 34(6): 941-960, (2023).
Wikipedia. "Phospholipid"; last edited Jul. 15, 2024; last accessed Sep. 30, 2024, [https://en.wikipedia.org/wiki/Phospholipid].

(56) References Cited

OTHER PUBLICATIONS

Wikipedia. "Sterol"; last edited Jul. 31, 2024; last accessed Sep. 30, 2024, [https://en.wikipedia.org/wiki/Sterol].
U.S. Appl. No. 18/610,897, Karmali et al.
Allen et al. "Adventures in Targeting", J. Liposome Research, 12(1-2);5012 (2002).
Chen et al., "Targeted delivery of anti-CD19 liposomal doxorubicin in B-cell lymphoma: a comparison of whole monoclonal antibody, Fab' fragments and single chain Fv", J Control Release, 126(1):50-8 (2008).
Kim et al., "Targeted gene therapy of LS174 T human colon carcinoma by anti-TAG-72 immunoliposomes" Cancer Gene Ther 15(5): 331-40 (2008).
Kirpotin et al., "Sterically stabilized anti-HER2 immunoliposomes: design and targeting to human breast cancer cells in vitro" Biochemistry 36(1): 66-75 (1997).
Zheng et al., "In vivo targeting of adoptively transferred T-cells with antibody- and cytokine-conjugated liposome" J Control Release, 172(2): 426-35 (2013).
Chen et al. (2016). "Influence of particle size on the in vivo potency of lipid nanoparticle formulations of siRNA." J. Control. Release 235, 236-244.
Chen et al. (2022). "Lipid nanoparticle-mediated lymph node-targeting delivery of mRNA cancer vaccine elicits robust CD8+T cell response." Proc. Natl. Acad. Sci. U.S.A. 119(34), e2207841119, p. 1-10.
Christensen et al. (2014). "Biodistribution and Metabolism Studies of Lipid Nanoparticle-Formulated Internally [3H]-Labeled siRNA in Mice." Drug Metab. Dispos. 42, 431-440.
Conway et al. (2019). "Non-viral Delivery of Zinc Finger Nuclease mRNA Enables Highly Efficient In Vivo Genome Editing of Multiple Therapeutic Gene Targets." Mol. Ther. 27(4), 866-877.
CSPC Pharmaceutical Group Limited, press release. Jun. 25, 2024. p. 1-2.
Eygeris et al. (2020). "Deconvoluting Lipid Nanoparticle Structure for Messenger RNA Delivery." Nano Lett. 20(6), 4543-4549.
Fenton et al. (2018). "Customizable Lipid Nanoparticle Materials for the Delivery of siRNAs and mRNAs." Angew. Chem. Int. Ed. 57(41), 13582-13586.
Hassett et al. (2021). "Impact of lipid nanoparticle size on mRNA vaccine immunogenicity." J. Control. Release 335, 237-246.
Huayamares et al. (2023). "High-throughput screens identify a lipid nanopaticle that preferentially delivers mRNA to human tumors in vivo." J. Control. Release 357, 394-403.
Johnson et al. (2022). "Lipid Nanoparticle (LNP) Chemistry Can Endow Unique In Vivo RNA Delivery Fates within the Liver That Alter Therapeutic Outcomes in a Cancer Model." Mol. Pharm. 19(11), 3973-3986.
Kang et al. (2023). "Lipid Nanoparticle-Mediated Delivery of miRNA Mimics to Myeloid Cells." In Inflammation and Cancer: Methods and Protocols,. Methods in Molecular Biology, vol. 2691, ed. Brendan J. Jenkins. p. 337-350.
Kauffman et al. (2015). "Optimization of Lipid Nanoparticle Formulations for mRNA Delivery in Vivo with Fractional Factorial and Definitive Screening Designs." Nano Lett. 15, 7300-7306.
Kraft et al. (2014). "Emerging Research and Clinical Development Trends of Liposome and Lipid Nanoparticle Drug Delivery Systems." J. Pharm. Sci. 103(1), 29-52.
Lam et al. (2023). "Unsaturated, Trialkyl Ionizable Lipids are Versatile Lipid-Nanoparticle Components for Therapeutic and Vaccine Applications." Adv. Mater. 2209624, p. 1-12.
Lin et al. (2013). "Influence of cationic lipid composition on uptake and intracellular processing of lipid nanoparticle formulations of siRNA." Nanomedicine 9, 233-246.
Ma et al. (2023). "A Unified Strategy to Improve Lipid Nanoparticle Mediated mRNA Delivery Using Adenosine Triphosphate." J. Am. Chem. Soc. 145(36), 19800-19811.
Mahaila et al. (2011). "Lipid nanoparticle purification by Spin Centrifugation-Dialysis (SCD): A facile and high-throughput approach for small scale preparation of siRNA-lipid complexes." Int. J. Pharm. 420, 118-121.
Nogueira et al. (2020). "Polysarcosine-Functionalized Lipid Nanoparticles for Therapeutic mRNA Delivery." ACS Appl. Nano Mater. 3, 10634-10645.
Oberli et al. (2017). "Lipid Nanoparticle Assisted mRNA Delivery for Potent Cancer Immunotherapy." Nano Lett. 17, 1326-1335.
O'Brien Laramy et al. (2023). "Process Robustness in Lipid Nanoparticle Production: A Comparison of Microfluidic and Turbulent Jet Mixing." Mol. Pharm. 20(8), 4285-4296.
Packer et al. (2021). "A novel mechanism for the loss of mRNA activity in lipid nanoparticle delivery systems." Nat. Commun. 12, 6777, p. 1-11.
Patel et al. (2017). "Boosting intracellular delivery of lipid nanoparticle-encapsulated messenger RNA." Nano Lett. 17(9), 5711-5718.
Patel et al. (2020). "Naturally-occurring cholesterol analogues in lipid nanoparticles induce polymorphic shape and enhance intracellular delivery of mRNA." Nat. Commun. 11, 983, p. 1-13.
Qiu et al. (2021). "Lipid nanoparticle-mediated codelivery of Cas9 mRNA and single-guide RNA achieves liver-specific in vivo genome editing of Angptl3." Proc. Natl. Acad. Sci. U.S.A. 118(10), e2020401118, p. 1-10.
Sago et al. (2022). "Augmented lipid-nanoparticle-mediated in vivo genome editing in the lungs and spleen by disrupting Cas9 activity in the liver." Nat. Biomed. Eng. 6(2), 157-167.
Sato et al. (2017). "Highly specific delivery of siRNA to hepatocytes circumvents endothelial cell-mediated lipid nanoparticle-associated toxicity leading to the safe and efficacious decrease in the hepatitis B virus." J. Control. Release 266, 216-225.
Sedic et al. (2018). "Safety Evaluation of Lipid Nanoparticle-Formulated Modified mRNA in the Sprague-Dawley Rat and Cynomolgus Monkey." Vet. Pathol. 55(2), 341-354.
Semple et al. (2022). "Lipid Nanoparticle Delivery Systems to Enable mRNA-Based Therapeutics." Pharmaceutics 14, 398, p. 1-23.
Tilsed et al. (2024). "IL7 increases targeted lipid nanoparticle-mediated mRNA expression in T cells in vitro and in vivo by enhancing T cell protein translation." Proc. Natl. Acad. Sci. U.S.A. 121(13), e2319856121, p. 1-11.
Zheng et al. (2023). "Lipid nanoparticle topology regulates endosomal escape and delivery of RNA to the cytoplasm." Proc. Natl. Acad. Sci. U.S.A. 120(27), e2301067120, p. 1-10.
Zimmerman et al. (2001). "Electrolyte- and pH-stabilities of aqueous solid lipid nanoparticle (SLN™) dispersions in artificial gastrointestinal media." Eur. J. Pharm. Biopharm. 52, 203-210.
Finn et al. (2018). "A Single Administration of CRISPR/Cas9 Lipid Nanoparticles Achieves Robust and Persistent In Vivo Genome Editing." Cell Rep. 22(9): 2227-2235.
Cannon et al. (2021). "Safe and Effective In Vivo Targeting and Gene Editing in Hematopoietic Stem Cells: Strategies for Accelerating Development." Hum. Gene Ther. 32(1-2), 31-42.
Dever et al. (2016). "CRISPR/Cas9 β-globin gene targeting in human haematopoietic stem cells." Nature 539(7629), 384-389.
Endsley et al. (2012). "Enhanced Anti-HIV Efficacy of Indinavir After Inclusion in CD4-Targeted Lipid Nanoparticles." J. Acquir. Immune Defic. Syndr. 61(4), 417-424.
Malone et al. (1989). "Cationic liposome-mediated RNA transfection." Proc. Natl. Acad. Sci. U.S.A. 86(16), 6077-6081.
Veiga et al. (2018). "Cell specific delivery of modified mRNA expressing therapeutic proteins to leukocytes." Nat. Commun. 9, article 4493, pp. 1-9.
International Search Report and Written Opinion issued for PCT/US2024/031141 and mailed on Nov. 19, 2024.
International Search Report and Written Opinion issued for PCT/US2024/035902 and mailed on Nov. 5, 2024.
Zong et al., "Lipid Nanoparticle (LNP) Enables mRNA Deliver for Cancer Therapy" Adv Mater 35(51): e2303261 (2023).

* cited by examiner

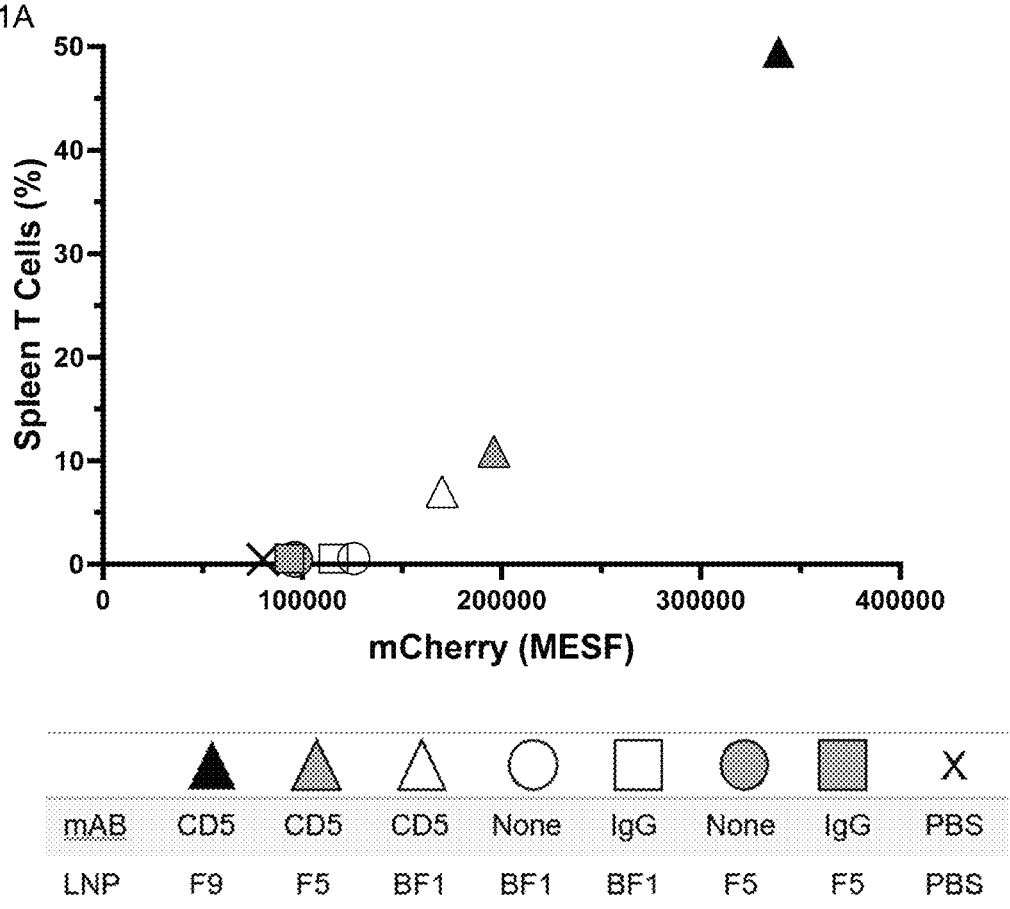

Cytokine release from monkeys administered BF1 CD5-targeted tLNPs

Cytokine release from monkeys administered F5 CD5-targeted tLNPs

SEQUENCE LISTING

```
Sequence total quantity: 4
SEQ ID NO: 1            moltype = AA  length = 5
FEATURE                 Location/Qualifiers
source                  1..5
                        mol_type = protein
                        organism = synthetic construct
SEQUENCE: 1
LPXTG                                                                    5

SEQ ID NO: 2            moltype = RNA  length = 17
FEATURE                 Location/Qualifiers
source                  1..17
                        mol_type = other RNA
                        organism = synthetic construct
modified_base           1
                        mod_base = OTHER
                        note = 2'-O-Methyl
modified_base           2
                        mod_base = OTHER
                        note = 2'-O-Methyl
modified_base           3
                        mod_base = OTHER
                        note = 2'-O-Methyl
modified_base           17
                        mod_base = OTHER
                        note = 2'-O-Methyl
modified_base           1..3
                        mod_base = OTHER
                        note = 3' phosphorothioate bond
modified_base           16..17
                        mod_base = OTHER
                        note = 3' phosphorothioate bond
SEQUENCE: 2
gtctctcagc tggtaca                                                      17

SEQ ID NO: 3            moltype = AA  length = 20
FEATURE                 Location/Qualifiers
source                  1..20
                        mol_type = protein
                        organism = synthetic construct
SEQUENCE: 3
NYTCEVTELS REGKTVIELK                                                   20

SEQ ID NO: 4            moltype = AA  length = 20
FEATURE                 Location/Qualifiers
source                  1..20
                        mol_type = protein
                        organism = synthetic construct
MOD_RES                 1
                        note = Polyethylene glycol (PEG4) linker at the N terminal
SEQUENCE: 4
NYTCEVTELS REGKTVIELK                                                   20
```

LIPID NANOPARTICLE FORMULATIONS AND COMPOSITIONS

CROSS-REFERENCE TO RELATED APPLICATIONS

This application claims priority to U.S. provisional application No. 63/595,201, filed Nov. 1, 2023; U.S. provisional application No. 63/520,303, filed Aug. 17, 2023; U.S. provisional application No. 63/510,061, filed Jun. 23, 2023; and U.S. provisional application No. 63/505,424, filed May 31, 2023; the disclosures of which are expressly incorporated by reference herein.

REFERENCE TO AN ELECTRONIC SEQUENCE LISTING

The instant application contains a Sequence Listing that has been submitted electronically and is hereby incorporated by reference in its entirety. The Sequence Listing was created on May 31, 2024, is named "24-0226-WO_SequenceListing.xml", and is 8,266 bytes in size.

BACKGROUND

Lipid compositions have been used in the laboratory for the delivery of nucleic acids into cells. Early compositions based on the cationic lipid 1,2-dioleoyl-3-trimethylammonium propane (DOTAP) and the ionizable, fusogenic lipid dioleoylphosphatidyl ethanolamine (DOPE) had a large particle size and were problematic when used in vivo, exhibiting too rapid clearance, tropism for the lung, and toxicity. Lipid nanoparticles (LNPs) comprising ionizable cationic lipids have been developed to address these issues to the extent that RNA based products, such as the SiRNA ONPATTRO® and two mRNA-based SARS-COV-2 vaccines, have received regulatory approval and entered the market.

There is limited ability to control which tissues or cells take up the LNP once administered. LNP administered intravenously are taken up primarily in the liver, lung, or spleen depending to a significant degree on net charge and particle size. It is possible to direct >90% of LNP to the liver by a combination of formulation and intravenous administration. Intramuscular administration can provide a clinically useful level of local delivery and expression. LNP can be redirected to other tissues or cell types by conjugating a binding moiety with specificity for the target tissue or cell type, for example, conjugating to the LNP a polypeptide containing an antigen binding domain from an antibody. Nonetheless, avoiding uptake by the liver remains a challenge. Moreover, with current systems, only a minor portion of the encapsulated nucleic acid is successfully delivered to the cells of interest and into the cytoplasm. Current compositions may release only 2-5% of the administered RNA into the cytoplasm (see, for example, Gilleron et al., *Nat. Biotechnol.* 31:638-646, 2013, and Munson et al., *Commun. Biol.* 4:211-224, 2021). Thus, there are remaining issues of off-target delivery, poor efficiency of release of nucleic acid into the cytoplasm, and toxicity associated with accumulation of the component lipids.

Therefore, this disclosure provides lipid nanoparticles and lipid nanoparticle formulations and compositions to satisfy an urgent need in the field.

BRIEF DESCRIPTION OF THE DRAWINGS

FIGS. 1A-B show improved LNP and tLNP function using lipids and compositions as disclosed herein. FIG. 1A depicts transfection rate (percentage of cells expressing the mRNA) versus expression level (as Molecules of Equivalent Soluble Fluorochrome (MESF)) for splenic T cells from mice administered various LNP or tLNP. FIG. 1B depicts transfection rate (percentage of cells expressing the mRNA) versus expression level (as mean fluorescence intensity (MFI)) for hepatocytes from mice administered various LNP or tLNP.

FIG. 2A shows a plot of transfection rate versus expression level in mouse splenic T cells in in vitro culture. FIGS. 2C-E show results of in vivo transfection with the tLNP plotting of transfection rate versus expression level in splenic T cells (2C), CD45$^-$ liver cells (hepatocytes; 2D), and CD45$^+$/CD11$^+$ liver cells (Kupffer cells; 2E) while FIG. 2B presents the same transfection rate data as FIG. 2C but versus binder ratio as a bar chart. FIG. 2F shows a plot of transfection rate versus expression level in cynomolgus macaque (non-human primate) blood T cells in in vitro culture.

FIGS. 10A-E depict mCherry transfection rate or expression level (as MFI) in bar graphs for CD4+, CD8+ and total T cells in blood and spleen from NSG mice engrafted with human peripheral blood lymphocytes following administration of tLNP targeted to either CD5+ or CD8+ cells. Results for transfection rate in blood and splenic T cells are displayed in FIGS. 10A and 10C, respectively. Results for expression level in blood and splenic T cells are displayed in FIGS. 10B and 10D, respectively. FIG. 10E depicts CAR transfection rate in bar graphs for CD4⁺, CD8⁺ and total T cells in blood 24 hours after the mice received a third dose. FIG. 10F portrays tumor burden and/or clearance in groups of mice treated with CD5-targeted tLNP carrying either mCherry or anti-CD19 CAR mRNA or CD8-targeted tLNP carrying anti-CD19 CAR mRNA. The X's represent mice that died due to graft versus host disease and/or tumor burden as apparent from the figure. The speckling over whole animal seen is some images is an artifact.

FIGS. 11A-C depict the levels of three acute phase proteins in rats administered the indicated doses of the BF1 LNP at 6 and 24 hours after administration, specifically 1-acid glycoprotein (FIG. 11A), α2-macroglobulin (FIG. 11B), and haptoglobin (FIG. 11C). FIGS. 11D-E plot median liver enzyme levels at 24 hours versus dosage from a second study in rats comparing composition BF1 to F5 for aspartate aminotransferase (AST) (FIG. 11D) and alanine amino transferase (ALT) (FIG. 11E).

FIGS. 11F-J show a comparison of the responses to the BF1 and F5 tLNPs for the same series of markers. FIGS. 11K-L show ALT and AGP levels, respectively, in rats injected with the indicated dosages of either anti-human CD8-bearing F9 tLNP encapsulating an mRNA encoding an anti-CD19 CAR or a rat CD5-targeted tLNP encapsulating an mRNA encoding mCherry. The horizontal grey band in FIG. 11K represents the ALT range observed in 21 naïve rats in a previous study.

FIGS. 12A-D related to a first study and FIGS. 12E-J relate to a second study. FIG. 12A shows responses of the liver enzymes ALT and AST in individual cynomolgus macaques over time after administration of embodiments of CD5-targeted tLNPs of BF1 (upper panels) and F5 (lower panels), respectively. "Ref Norm Low" and "Ref Norm High" indicate the normal range for these liver enzymes. FIG. 12B shows cytokine secretion for the same animals for IL-6, MCP-1 IOL-2, IFNγ, TNFα, TGFα, IL-8, and gm-CSF. FIG. 12C is a plot of transfection efficiency of blood T cells (as % mCherry+ cells) at 4 and 24 hours for individual animals after infusion of the embodiment of the CD5-targeted tLNP of composition F5 which encapsulated an mCherry mRNA. FIG. 12D is a bar chart depicting T cell transfection efficiency in spleen, lymph node, and bone marrow tissue 24 hours after infusion of the embodiment of the CD5-targeted tLNP of F5 which encapsulated an mCherry mRNA. FIGS. 12E-F depict responses of the liver enzymes ALT and AST in individual cynomolgus macaques over time after a single administration of embodiments of the CD5- and CD8-targeted tLNP of composition F9, which encapsulated an anti-CD19 CAR mRNA (FIG. 12E) or multiple administrations of the CD5-targeted tLNP of F9, at a lower dosage (FIG. 12F). FIG. 12G is a plot of transfection efficiency of blood T cells (as % CAR+ cells) at 8 and 24 hours for individual animals after infusion of the embodiments of the CD5- and CD8-targeted tLNP of F9 which encapsulated an anti-CD19 CAR mRNA. FIG. 12H is a bar chart depicting T cell transfection efficiency in spleen, lymph node, bone marrow, and liver tissue 24 hours after infusion of the embodiments of the CD5- and CD8-targeted tLNP of F9 which encapsulated an anti-CD19 CAR mRNA. Asterisks indicate data from bone marrow and lymph node biopsy samples collected at 24 hours after infusion from the two animals that were observed out to 96 hours post infusion, whereas the other animals were euthanized 24 hours after infusion and necropsy samples of all four tissues assessed. FIG. 12I is a plot of transfection efficiency at time points after each of multiple infusions (doses) of the embodiment of the CD5-targeted tLNP of F9 which encapsulated the anti-CD19 CAR mRNA. FIG. 12J presents box-and-whiskers plots of CAR expression level in individual animals 24 hours after the single administration of the embodiments of the CD5- and CD8-targeted tLNP of F9 which encapsulated the anti-CD19 CAR mRNA. Captions above each panel indicate targeting and payload dosage. FIG. 12K shows a compilation of liver enzyme data from three studies following a single administration of various tLNP. FIG. 12L depicts liver enzyme levels over the course of 3 administrations of CD8-targeted tLNP.

FIG. 13A depicts a conceptual biodegradation scheme for CICL1 (above the line) and the starting compound and end products of biodegradation (below the line). The disclosed ionizable cationic lipids having structure CICL may undergo biodegradation according to such a conceptual scheme, without being bound to any particular theory. However, according to this scheme esterase cleavage or other hydrolysis of CICL1 would be predicted to produce tetra-alcohol B and 4 equivalents of nonanoic acid. Cyclization should then result in the production of 2 equivalents of butyrolactone C and 1 equivalent of diol D. Esterase hydrolysis of C would result in the production of 2 equivalents of diol-acid E. FIG. 13B depicts the amount of ionizable cationic lipid detected in plasma, liver, and spleen 24 hours after administration of CD5-targeted LNP containing either ALC-0315 or ClCL1 to cynomolgus macaques (n=2). FIGS. 13C-E depict time courses of the disappearance of the ionizable cationic lipids ClCL1 and ALC-0315 following administration of F9 and BF1 tLNP to mice in plasma, spleen, and liver, respectively, plotted as LC-MS-based detection of lipid concentration; mean±standard deviation (SD) shown. The tLNP were targeted to mouse CD8 and encapsulated an mRNA encoding an anti-human CD19 CAR. FIGS. 13F-H depict time courses of the disappearance of the encapsulated mRNA in plasma, spleen, and liver, respectively from the same mice as in 13C-E as detected by digital PCR and normalized to a spiked control (plasma) or GAPDH (spleen and liver).

FIGS. 20A-B depict mCherry transfection rate (FIG. 20A) and expression level (FIG. 20B) in human T cells 24 hours after transfection with one of four preparations of CD5-targeted tLNP of lipid composition F5 encapsulating mCherry mRNA. Untransfected cells were used as a negative control. Each of the four tLNP preparations used a different antibody conjugation chemistry. FIGS. 20C-D depict mCherry transfection rate (FIG. 20C) and expression level (FIG. 20D) in human T cells 24 hours after NSG mice engrafted with human PBMCs were administered one of four preparations of CD5-targeted tLNP of lipid composition F5 encapsulating mCherry mRNA. Untransfected cells (PBS) were used as a negative control. Each of the four tLNP preparations used a different antibody conjugation chemistry.

DETAILED DESCRIPTION

Figure 1B:
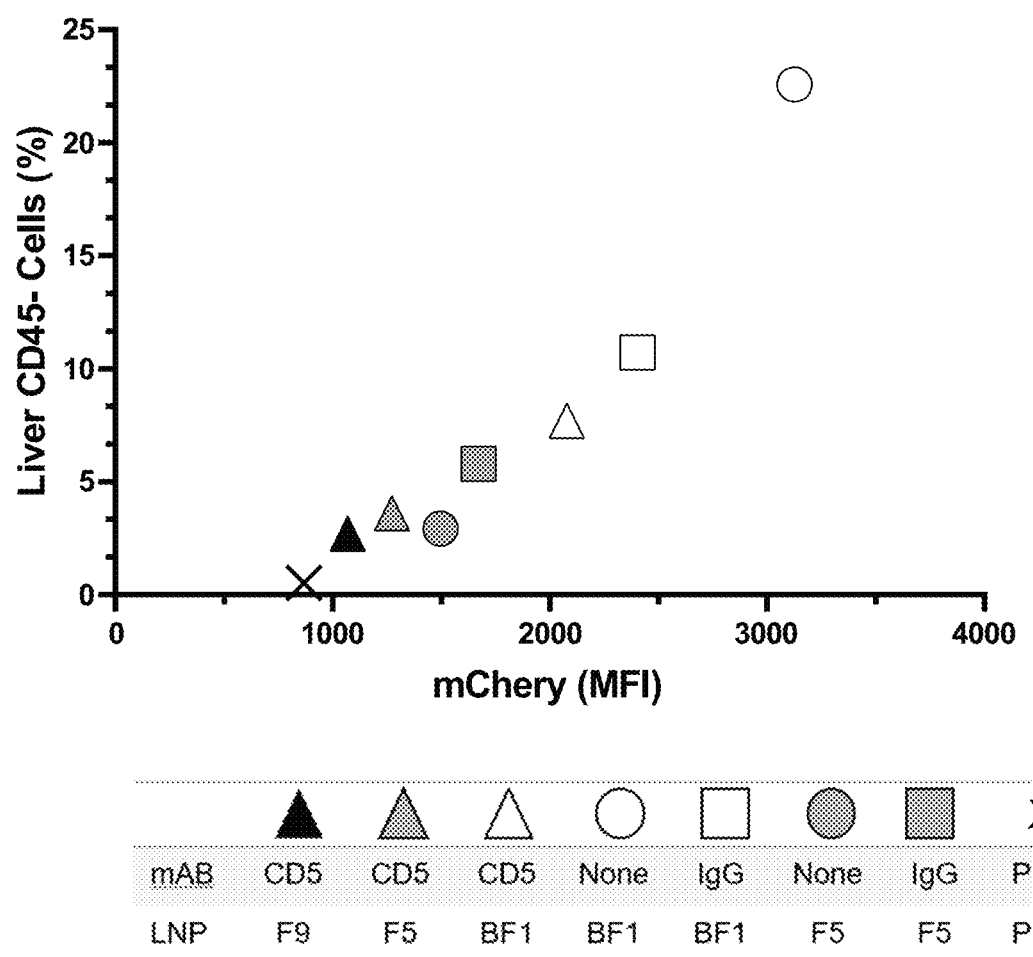

This disclosure provides lipid nanoparticles (LNP) and LNP compositions and pharmaceutical compositions (or formulations) for the delivery of a payload, for example one or more nucleic acid species, into targeted cell types or tissues. The LNP may comprise a functionalized polyethylene glycol (PEG)-lipid that can be, or is, conjugated to a binding moiety that binds to a surface marker on a targeted cell type, thus constituting a targeted LNP (tLNP). The binding moiety directs the tLNP to the targeted tissue or targeted cell type so that tLNP delivers to the targeted cell type with the encapsulated nucleic acid molecule or other negatively charged payload. Transfection can be carried out in vivo (also referred to as in situ), extracorporeally, or ex vivo. This disclosure further provides methods of reprogramming or conditioning a cell by transfecting or contacting the cell with a tLNP. Also provided are methods of making LNP containing functionalized PEG-lipid and methods of making tLNP.

While the present disclosure is capable of being embodied in various forms, the description below of several embodiments is made with the understanding that the present disclosure is to be considered as an exemplification of the invention and is not intended to limit the invention to the specific embodiments illustrated.

While the present disclosure is capable of being embodied in various forms, the description below of several embodiments is made with the understanding that the present disclosure is to be considered as an exemplification of the invention and is not intended to limit the invention to the specific embodiments illustrated.

Headings are provided for convenience only and are not to be construed to limit the invention in any manner. Embodiments illustrated under any heading may be combined with embodiments illustrated under any other heading.

To the extent any materials incorporated herein by reference conflict with the present disclosure, the present disclosure controls.

Prior to setting forth this disclosure in more detail, it may be helpful to provide abbreviations and definitions of certain terms to be used herein. Additional definitions are set forth throughout this disclosure.

Definitions

As used in the specification and claims, the singular form "a," "an," and "the" includes plural references unless the context clearly dictates otherwise. It should be understood that the terms "a" and "an" as used herein refer to "one or more" of the enumerated components.

The use of the alternative (e.g., "or") should be understood to mean either one, both, or any combination thereof of the alternatives.

The term "about" as used herein in the context of a number refers to a range centered on that number and spanning 10% less than that number and 10% more than that number. The term "about" used in the context of a range refers to an extended range spanning 10% less than that the lowest number listed in the range and 10% more than the greatest number listed in the range.

Throughout this disclosure, any concentration range, percentage range, ratio range, or integer range is to be understood to include the value of any integer within the recited range and, when appropriate, fractions thereof (such as one tenth and one hundredth of an integer), unless otherwise indicated. Also, any number range of this disclosure relating to any physical feature, such as polymer subunits, size, or thickness, are to be understood to include any integer within the recited range, unless otherwise indicated. Throughout this disclosure, numerical ranges are inclusive of their recited endpoints, unless specifically stated otherwise.

Unless the context requires otherwise, throughout the present specification and claims, the word "comprise" and variations thereof, such as, "comprises" and "comprising" are to be construed in an open, inclusive sense, that is, as "including, but not limited to." As used herein, the terms "include" and "comprise" are used synonymously.

The phrase "at least one of" when followed by a list of items or elements refers to an open-ended set of one or more of the elements in the list, which may, but does not necessarily, include more than one of the elements.

"Derivative," as used herein, refers to a chemically or biologically modified version of a compound that is structurally similar to a parent compound and (actually or theoretically) derivable from that parent compound. Generally, a "derivative" differs from an "analogue" in that a parent compound may be the starting material to generate a "derivative," whereas the parent compound may not necessarily be used as the starting material to generate an "analogue." A derivative may have different chemical or physical properties than the parent compound. For example, a derivative may be more hydrophilic or hydrophobic, or it may have altered reactivity as compared to the parent compound. Although a derivative can be obtained by physical (for example, biological or chemical) modification of the parent compound, a derivative can also be conceptually derived, for example, as when a protein sequence is designed based on one or more known sequences, an encoding nucleic acid is constructed, and the derived protein obtained by expression of the encoding nucleic acid.

As used herein "expansion" refers to proliferation of cells increasing their number. Activating agents can be used to stimulate proliferation (among other metabolic changes) but can also result in activation induced death upon initial exposure so that there is no immediate expansion. For T cells treated in vitro with activating agents such as IL-2 or CD3/CD28 activators, doubling time can be about 24 hours (which is fairly typical of mammalian cells in vitro generally); in vivo doubling time can be substantially shorter, depending on the presence and type of stimulation. Accordingly, during the limited time of extracorporeal manipulation, even when activating agents are used, such protocols will be effectively expansion-less.

As used herein an "exogenous protein" refers to a synthetic, recombinant, or other peptide or protein that is not produced by a wild-type cell of that type or is expressed at a lower level in a wild-type cell than in a cell containing the exogenous polypeptide. In some embodiments, an exogenous peptide is a peptide or protein encoded by a nucleic acid that was introduced into the cell, which nucleic acid is optionally not retained by the cell.

As used herein "extracorporeal" is used in reference to cells, such as peripheral blood or bone marrow cells, harvested or extracted from the body and the manipulation or modification of those cells prior to their intended return (reinfusion). Manipulation and modification of cells generally relates to cell separation and washing procedures and exposure to activation agents (e.g., biological response modifiers (BRMs)) and transfection agents (e.g., LNPs, tLNPs), over a time interval of several hours, for example, less than 6 hours, less than 5 hours, less than 4 hours, less than 3 hours, less than 2 hours, or less than 1 hour; and in space to a single institution. Extracorporeal is used in contradistinction to ex vivo which, as used herein, includes more extensive manipulation including extended periods of cell culture and expansion, and/or refrigerated or cryogenic storage or shipment, over several days or longer.

As used herein "transfection" or "transfecting" refers to the introduction of nucleic acids into cells by non-viral methods. Transfection can be mediated by calcium phosphate, cationic polymers, magnetic beads, electroporation, and lipid-based reagents. In preferred embodiments disclosed herein transfection is mediated by solid lipid nanoparticles (LNP) including targeted LNP (tLNP) (which can also be used to deliver non-nucleic acid payloads into cells). The term transfection is used in distinction to transduction—transfer of genetic material from cell to cell or virus to cell—and transformation—the uptake of extracellular genetic material by the natural processes of a cell. As used herein, phrases such as "delivering a nucleic acid into a cell" are synonymous with transfection.

"Reprogramming," as used herein with respect to immune cells, refers to changing the functionality of an immune cell with respect to antigenic specificity by causing expression of an exogenous T cell receptor (TCR), a chimeric antigen receptor (CAR), or an immune cell engager ("reprogramming agents"). Generally, T lymphocytes and natural killer (NK) cells could be reprogrammed with a TCR, a CAR, or an immune cell engager while only a CAR or an immune cell engager would be used in reprogramming monocytes. As used herein with respect to stem cells, for example hematopoietic stem cells (HSC) or mesenchymal stem cells (MSC), "reprogramming" refers to correction or amelioration of a genetic defect (for example, a hemoglobinopathy) so that the modified or corrected gene and gene product are the reprogramming agents. Reprogramming can be transient or durable depending on the nature of the engineering agent.

"Engineering agent," as used herein, refers to agents that confer the expression of a reprogramming agent by an immune cell, particularly a non-B lymphocyte or monocyte. Engineering agents can include nucleic acids, including mRNA, that encode the reprogramming agent. Engineering agents can also include nucleic acids that are or encode components of gene editing systems such as RNA-guided nucleases, guide RNA, and nucleic acid templates for knocking-in a reprogramming agent or knocking-out an endogenous antigen receptor. Gene editing systems comprise base-editors, prime-editors or gene-writers. RNA-guided nucleases include CRISPR nucleases such as Cas9, Cas12, Cas13, Cas3, CasMINI, Cas7-11, and CasX. For transient expression of a reprogramming agent, such as a CAR, an mRNA encoding the reprogramming agent can be used as the engineering agent. For durable expression of the reprogramming agent, such as an exogenous, modified, or corrected gene (and its gene product), the engineering agent can comprise mRNA-encoded RNA-directed nucleases, guide RNAs, nucleic acid templates and other components of gene/genome editing systems.

Examples of gene editing components that are encoded by a nucleic acid molecule include an mRNA encoding an RNA-guided nuclease, a gene or base editing protein, a prime editing protein, a Gene Writer protein (e.g., a modified or modularized non-long terminal repeat (LTR) retrotransposon), a retrotransposase, an RNA writer, a zinc finger nuclease (ZFN), a transcription activator-like effector nuclease (TALEN), a meganuclease, a transposase, a retrotransposon, a reverse transcriptase (e.g., M-MLV reverse transcriptase), a nickase or inactive nuclease (e.g., Cas9, nCas9, dCas9), a DNA recombinase, a CRISPR nuclease (e.g., Cas9, Cas12, Cas13, Cas3, CasMINI, Cas7-11, CasX), a DNA nickase, a Cas9 nickase (e.g., D10A or H840A), or any fusion or combination thereof. Other components include a guide RNA (gRNA), a single guide RNA (sgRNA), a prime editing guide RNA (pegRNA), a clustered regularly interspaced short palindromic repeat (CRISPR) RNA (crRNA), a trans-activating clustered regularly interspaced short palindromic repeat (CRISPR) RNA (tracrRNA), or a DNA molecule to be inserted or serve as a template for double-strand break (DSB) repair at a specific genomic locus. Genome-, gene-, and base-editing technology are reviewed in Anzalone et al., *Nature Biotechnology* 38:824-844, 2020, Sakuma, *Gene and Genome Editing* 3-4:100017, 2022, and Zhou et al., MedComm 3 (3): e155, 2022, each of which is incorporated by reference for all that they teach about the components and uses of this technology to the extent that it does not conflict with the present disclosure.

"Conditioning agent," as used herein, refers to a biological response modifier (BRM) that enhances the efficiency of engineering an immune cell, expands the number of immune cells available to be engineered or the number of engineered cells in a target tissue (for example, a tumor, fibrotic tissue, or tissue undergoing autoimmune attack), promotes activity of the engineered cell in a target tissue, or broadens the range of operative mechanisms contributing to a therapeutic immune reaction. A conditioning agent may be provided by delivering an encoding nucleic acid in a tLNP. Exemplary BRMs include cytokines, such as IL-7, IL-15, or IL-18.

"Immune cell," as used herein, can refer to any cell of the immune system. However, particular aspects can exclude polymorphonuclear leukocytes and/or B cells, or be limited to non-B lymphocytes such as T cell and/or NK cells, or to monocytes such as dendritic cells and/or macrophages in their various forms.

The LNPs of this disclosure are multicomponent compositions comprising a payload and multiple lipid components, including an ionizable cationic lipid, non-functionalized and/or functionalized PEG-lipids, a phospholipid, and a sterol. In certain aspects the payload comprises one or more species of nucleic acid molecule or other negatively charged molecules. That is, in some embodiments, the payload comprises only a single species of nucleic acid or other negatively charged molecule (or consists of such species or molecule) while in other embodiments, the payload comprises multiple species of nucleic acid or other negatively charged molecules, for example, 2, 3, or 4 such species or molecules. In some embodiments in which the payload comprises multiple nucleic acid species or other negatively charged molecules, more than one of the species up to and including all of the species are reactive, or encode a polypeptide that is reactive, with a same target. As used herein "LNP composition" refers to the lipid components present in an LNP, their molar ratios (e.g., mol %) relative to each other, and the ratio of payload to total lipid. The payload to total lipid ratio can be expressed on a weight to weight (w/w) basis or for nucleic acid molecules as an N/P ratio, wherein an "N/P ratio" means the ratio of positively chargeable lipid amine (N=nitrogen) groups to negatively-charged nucleic acid molecule phosphate (P) groups. The tLNPs of this disclosure are multicomponent compositions comprising an LNP and a binding moiety. As used herein "tLNP composition" refers to the same features as LNP composition with the addition of a binding moiety that serves as a targeting moiety and the binding moiety's density on the tLNP may be expressed as a ratio to the payload on a w/w basis. As used herein, "LNP formulation" or "tLNP formulation" refers to the complete respective composition plus buffers, carriers, solvents and/or other excipients, which may also be referred to as a pharmaceutical composition.

LNP Compositions

The LNP composition contributes to the formation of stable LNPs and tLNPs, efficient encapsulation of a payload, protection of a payload from degradation until it is delivered into a cell, and promotion of endosomal escape of a payload into the cytoplasm. These functions are primarily independent of the specificity of the binding moiety (or moieties) serving to direct or bias a tLNP to a particular cell type(s).

In certain aspects, this disclosure provides an LNP or tLNP, wherein the LNP or tLNP comprises about 35 mol % to about 65 mol % of an ionizable cationic lipid, about 0.5 mol % to about 3 mol % of a PEG-lipid (including non-functionalized PEG-lipid and optionally a functionalized PEG-lipid), about 7 mol % to about 13 mol % of a phospholipid, and about 30 mol % to about 50 mol % of a sterol. In some embodiments, an LNP or tLNP comprises a payload with a net negative charge for example, a peptide, a polypeptide, a protein, a small molecule, or a nucleic acid molecule, and combinations thereof. A payload is generally encompassed by or in the interior of an LNP or tLNP. As disclosed herein dosages always refer to the amount of payload being provided. In some embodiments, a payload comprises one or more species of nucleic acid molecule. In some instances, the N/P ratio is from about 3 to about 9, about 3 to about 7, about 3 to about 6, about 4 to about 6, about 5 to about 6, or about 6. In some instances, the N/P ratio is from 3 to 9, 3 to 7, 3 to 6, 4 to 6, 5 to 6, or 6. In some embodiments, an LNP or tLNP comprises about 40 mol % to about 62 mol % ionizable cationic lipid. In some embodiments, an LNP or tLNP comprises about 1 mol % to about 2 mol % total PEG-lipid. In certain embodiments, an LNP or tLNP comprises about 0.1 mol % to about 0.3 mol %, for example about 0.1 mol %, about 0.2 mol %, or about 0.3 mol % functionalized PEG-lipid. In some embodiments, a binding moiety is conjugated to functionalized PEG-lipid. In certain instances, a tLNP is an LNP that further comprises an antibody (for example, a whole IgG) as the binding moiety which is present at an antibody: mRNA ratio (w/w) of about 0.3 to about 1.0.

Overview of Improved LNPs

The LNPs (and tLNPs thereof) disclosed herein are greatly improved over prior art LNPs for delivery to a targeted cell type, such as T cells or hematopoietic stem cells (HSCs), and for detargeting undesired cells or tissues, such as hepatocytes and liver. As is evident in FIG. 1B, detargeting liver cells could be markedly improved by using a cationic lipid of this disclosure in the LNP composition (F5, grey circle) as compared to an ionizable lipid from the prior art (ALC-0315 used in Comirnaty®) (BF1, open circle). By further adding a binding moiety to an LNP of this disclosure a useful level of transfection of a desired cell type was also achieved in vivo in mice (e.g., FIGS. 1A and 1B) and non-human primate (e.g, Example 12, FIGS. 12A-J). For example, FIG. 1A shows that CD5 targeted tLNPs (triangles) were able to transfect splenic T cells but LNP without a binding moiety (circles) or with irrelevant antibody (squares) were not distinguishable from background. Moreover, tLNP containing an ionizable cationic lipid of this disclosure (e.g., F5, grey triangle; and F9, black triangle) increased targeting of splenic T cells much more than those LNPs containing the prior art lipid ALC-0315 (BF1, open triangle)) (It must be noted that the F9, CD5-targeted tLNP (black triangle) also differed from the others in that the mCherry mRNA contained $N^1$-methylpseudouridine instead of the 5-methoxyuridine used in the others). Overall, liver detargeting arose due to two effects, lipid composition of the LNP and the addition of a targeting moiety. Thus, LNPs and tLNPs disclosed herein represent an improvement for targeted delivery over commercial LNP or tLNP.

Ionizable Cationic Lipids

Ionizable cationic lipids are useful components for complexing with negatively charged payloads and for promoting delivery of the payload into the cytoplasm of a cell following endocytosis. Accordingly, each of the hereinbelow disclosed genera and species of ionizable cationic lipid can be used in defining the scope of embodiments of the herein disclosed LNP and tLNP compositions and pharmaceutical compositions, and methods of using them. In certain embodiments, ionizable cationic lipid(s) of an LNP having a measured pKa of 6 to 7 can remain essentially neutral in the blood stream and interstitial spaces but ionize after uptake into cells as the endosomes acidify. Upon acidification in the endosomal space, the lipid becomes protonated, and associates more strongly with the phosphate backbone of the nucleic acid, which destabilizes the structure of the LNP and promotes nucleic acid release from the LNP into the cell cytoplasm (also referred to as endosomal escape). Thus, the herein disclosed ionizable cationic lipids constitute means for destabilizing LNP structure (when ionized) or means for promoting nucleic acid release or endosomal escape.

In some embodiments, the ionizable cationic lipid has the structure CICL:

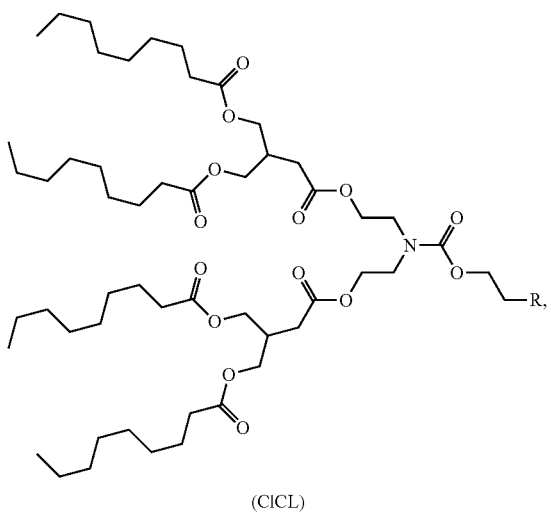

(CICL)

wherein R is

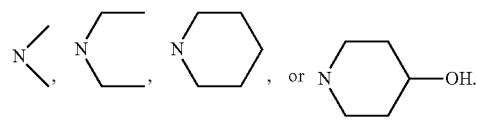

In certain embodiments, the ionizable cationic lipid of CICL is referred to as CICL1 when R is

that is

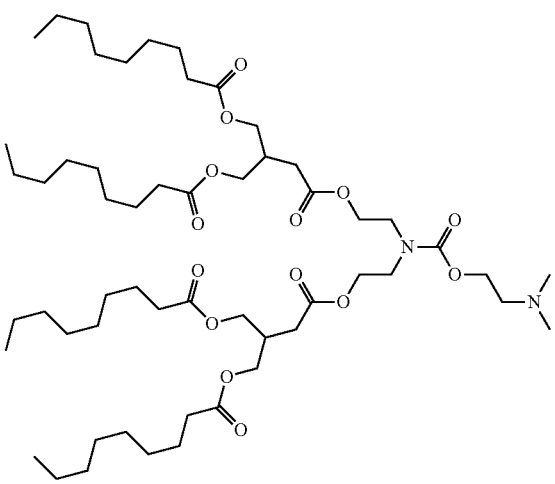 [SMILES: CCCCCCCCC(=O)OCC(COC(=O)CCCCCCCC)CC(=O)OCCN(CCOC(=O)CC(COC(=O)CCCCCCCC)COC(=O)CCCCCCCC)C(=O)OCCN(C)C]

In certain embodiments, the ionizable cationic lipid of CICL is referred to as CICL2 when R is

that is
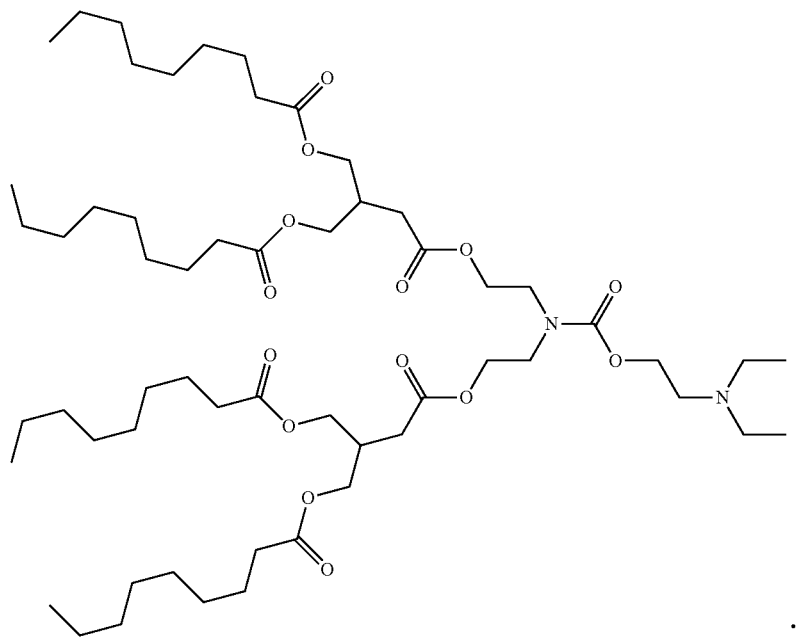 [SMILES: CCCCCCCCC(=O)OCC(COC(=O)CCCCCCCC)CC(=O)OCCN(CCOC(=O)CC(COC(=O)CCCCCCCC)COC(=O)CCCCCCCC)C(=O)OCCN(CC)CC]
In certain embodiments, the ionizable cationic lipid of CICL is referred to as CICL3 when R is
that is
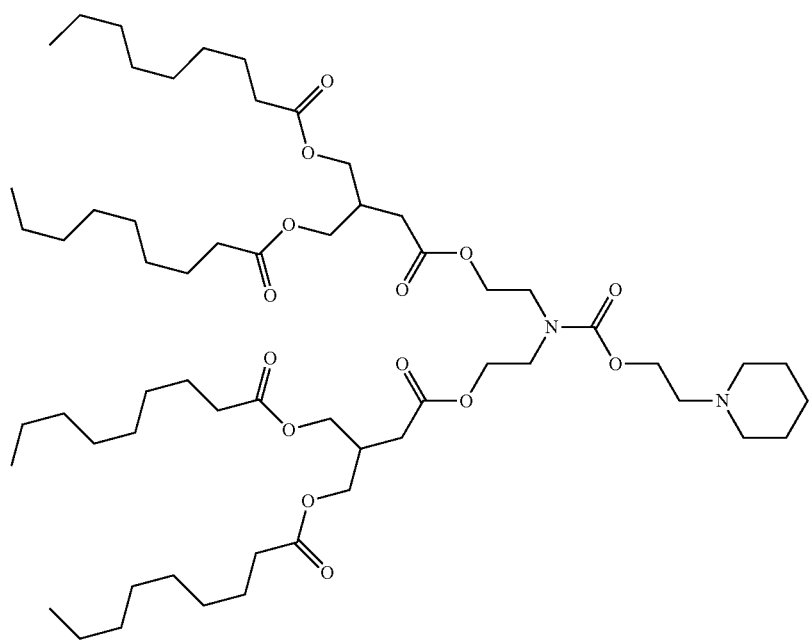 [SMILES: CCCCCCCCC(=O)OCC(COC(=O)CCCCCCCC)CC(=O)OCCN(CCOC(=O)CC(COC(=O)CCCCCCCC)COC(=O)CCCCCCCC)C(=O)OCCN1CCCCC1]

In certain embodiments, the ionizable cationic lipid of CICL is referred to as CICL4 when R is

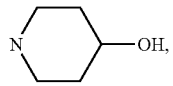

that is

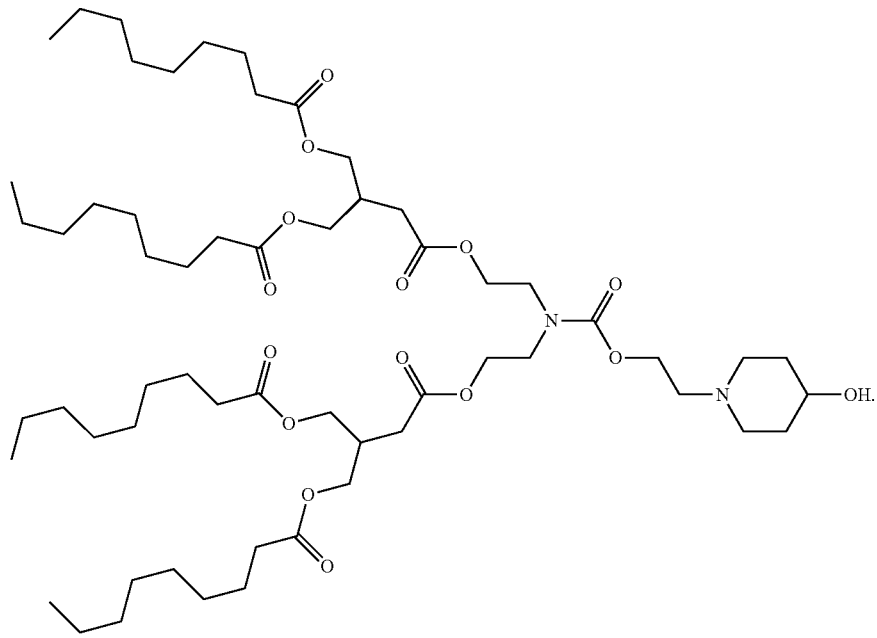 [SMILES: CCCCCCCCC(=O)OCC(COC(=O)CCCCCCCC)CC(=O)OCCN(CCOC(=O)CC(COC(=O)CCCCCCCC)COC(=O)CCCCCCCC)C(=O)OCCN1CCC(O)CC1]

In some embodiments, the ionizable cationic lipid has the structure CICL-IE:

(CICL-IE)

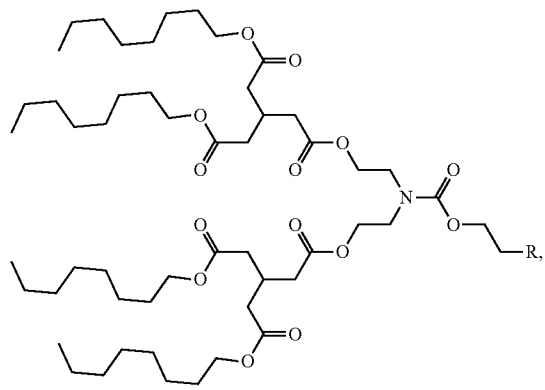

wherein R is

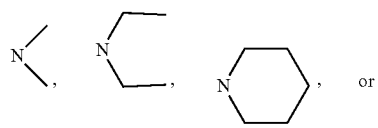, or

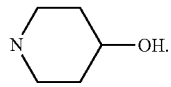

In certain embodiments, the ionizable cationic lipid of CICL-IE is referred to as CICL250 when R is

that is

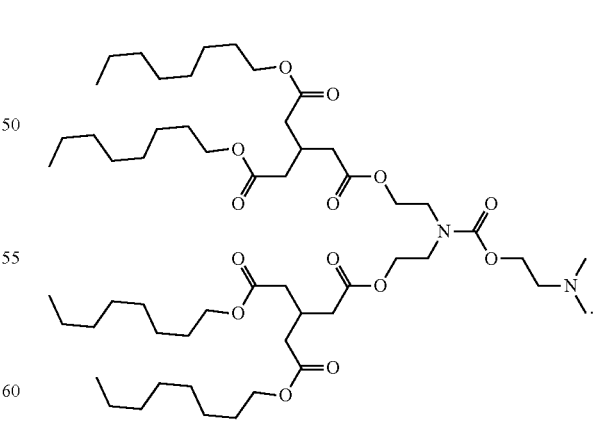

In certain embodiments, the ionizable cationic lipid of CICL-IE is referred to as CICL250.2 when R is

that is
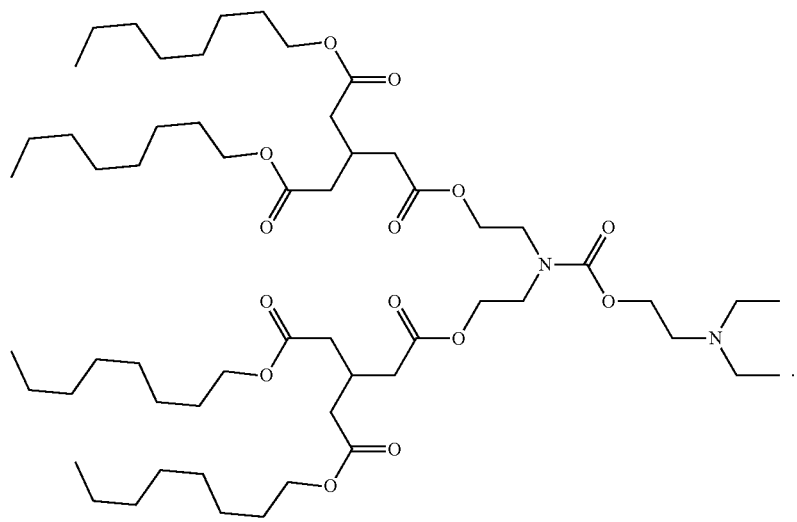 [SMILES: CCCCCCCCOC(=O)CC(CC(=O)OCCCCCCCC)CC(=O)OCCN(CCOC(=O)CC(CC(=O)OCCCCCCCC)CC(=O)OCCCCCCCC)C(=O)OCCN(CC)CC]
In certain embodiments, the ionizable cationic lipid of CICL-IE is referred to as CICL250.3 when R is
that is
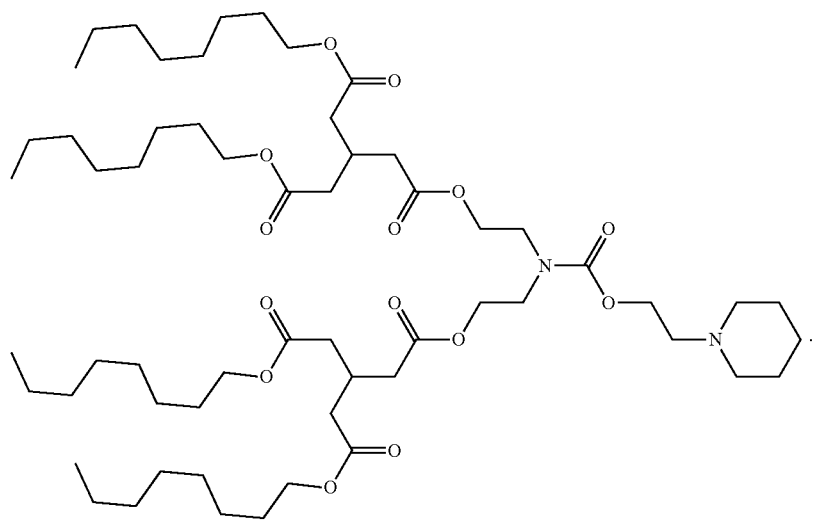 [SMILES: CCCCCCCCOC(=O)CC(CC(=O)OCCCCCCCC)CC(=O)OCCN(CCOC(=O)CC(CC(=O)OCCCCCCCC)CC(=O)OCCCCCCCC)C(=O)OCCN1CCCCC1]

In certain embodiments, the ionizable cationic lipid of CICL-IE is referred to as CICL250.4 when R is

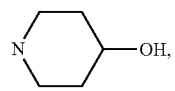

that is

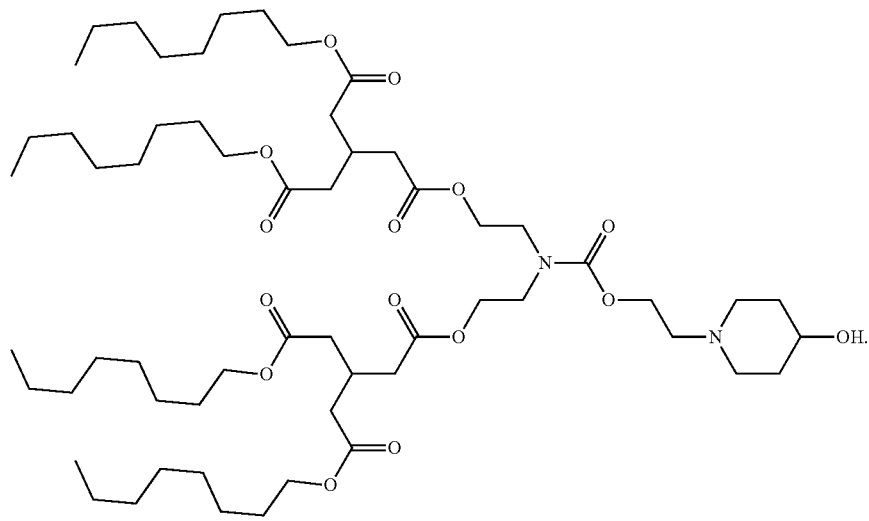 [SMILES: CCCCCCCCOC(=O)CC(CC(=O)OCCCCCCCC)CC(=O)OCCN(CCOC(=O)CC(CC(=O)OCCCCCCCC)CC(=O)OCCCCCCCC)C(=O)OCCN1CCC(O)CC1]

Synthesis of lipids having the structures of CICL or CICL-IE is described in US Patent Application Publication No. 2023/0320995 and U.S. Patent Application No. 63/632,940, respectively, each of which is incorporated by reference in its entirety for all that it teaches about the synthesis of such lipids.

Ionizable cationic lipids of this disclosure have a branched structure to give the lipid a conical rather than cylindrical shape and such structure helps promote endosomolytic activity. The greater the endosomolytic activity, the more efficient is release of the biologically active payload (e.g., one or more species of nucleic acid molecules).

Ionizable cationic lipids as described herein, can be useful as a component of lipid nanoparticles for delivering nucleic acids, including DNA, mRNA, or siRNA into cells. The ionizable cationic lipids may have a c-pKa (calculated pKa) in the range of from about 6, 7, or 8 to about 9, 10, or 11. For example, in various embodiments as described herein, the ionizable cationic lipids have a c-pKa ranging from about 6 to about 10, about 7 to about 10, about 8 to about 10, about 8 to about 9, 6 to 10, 7 to 10, 8 to 10, or 8 to 9. In certain embodiments, the ionizable cationic lipids have a c-pKa ranging from about 8.4 to about 8.7 or 8.4 to 8.7. The ionizable cationic lipids as described herein may have cLogD ranging from about 9 to about 18, for example, ranging from about 10 to about 18, or about 10 to about 16, to about 10 to about 14, or about 11 to about 18, or about 11 to about 15, or about 11 to about 14. The ionizable cationic lipids as described herein may have cLogD ranging from 9 to 18, for example, ranging from 10 to 18, or 10 to 16, to 10 to 14, or 11 to 18, or 11 to 15, or 11 to 14. In certain embodiments, the ionizable cationic lipids have a cLogD ranging from about 13.6 to about 14.4 or from 13.6 to 14.4.

In certain embodiments, the ionizable cationic lipids as described herein may have a c-pKa ranging from about 8 to about 11 or from 8 to 11 and a cLogD ranging from about 9 to about 18 or from 9 to 18. For example, in certain embodiments, the ionizable cationic lipids have a c-pKa ranging from about 8.4 to about 8.7 or from 8.4 to 8.7 and cLogD ranging from about 13.6 to about 14.4 or from 13.6 to 14.4. These ranges can lead to a measured pKa in the LNP ranging from about 6 to about 7 or from 6 to 7, which facilitates ionization in an endosome after delivery into a cell.

In some embodiments, somewhat greater basicity may be desirable and can be obtained from ionizable cationic lipids with c-pKa and cLogD in the ranges disclosed herein. In some embodiments, cLogD of ionizable cationic lipids of this disclosure is about 9, about 10, about 11, about 12, about 13, about 14, about 15, about 16, about 17, about 18, or in a range bound by any pair of these values. Lipid design also accounts for potential biodegradability pathways of target lipids, such as by way of esterases in plasma, liver, and other tissues. Another consideration in lipid design is the fate of fragments of ionizable lipids resulting from degradation, such as after esterase cleavage(s). Preferably, the resulting fragments are rapidly cleared from the body without the need for hepatic oxidative metabolism.

In some embodiments, an LNP or tLNP comprises about 35 mol % to about 65 mol %, about 40 mol % to about 62 mol %, or about 54 mol % to about 60 mol % ionizable cationic lipid. In some embodiments, the lipid composition is at least 40 mol % and/or does not exceed 62 mol % ionizable cationic lipid. In certain embodiments, an LNP of tLNP comprises about 54 mol %, about 58 mol %, or about 62 mol % ionizable cationic lipid. In further embodiments an LNP comprises 35 mol % to 65 mol %, 40 mol % to 62 mol %, or 54 mol % to 60 mol % ionizable cationic lipid. In still further embodiments, an LNP has at least 40 mol % or does not exceed 62 mol % ionizable cationic lipid. In certain embodiments, an LNP comprises 54 mol %, 58 mol %, or 62 mol % ionizable cationic lipid.

Sterols

The disclosed LNP and tLNP comprise a sterol. Sterol refers to a subgroup of steroids that contain at least one hydroxyl (OH) group. Examples of sterols include, without limitation, cholesterol, ergosterol, B-sitosterol, stigmasterol, stigmastanol, 20-hydroxycholesterol, 22-hydroxycholesterol, and the like. With respect to LNPs or tLNPs of this disclosure, in various embodiments, the sterol is cholesterol, 20-hydroxycholesterol, 20 (S)-hydroxycholesterol, 22-hydroxycholesterol, or a phytosterol, or combinations thereof. In further embodiments, the phytosterol comprises campesterol, sitosterol, or stigmasterol, or combinations thereof. In certain embodiments, the cholesterol is not animal-sourced but is obtained by synthesis using a plant sterol as a starting point. LNPs incorporating C-24 alkyl (such as methyl or ethyl) phytosterols have been reported to provide enhanced gene transfection. The length of the alkyl tail, the flexibility of the sterol ring, and polarity related to a retained C-3-OH group are important to obtaining high transfection efficiency. While B-sitosterol and stigmasterol performed well, vitamin D2, D3 and calcipotriol, (analogs lacking intact body of cholesterol) and betulin, lupeol ursolic acid and olenolic acid (comprising a 5th ring) should be avoided. Sterols serve to fill space between other lipids in the LNP or tLNP and influence LNP or tLNP shape. Sterols also control fluidity of lipid compositions, reducing temperature dependence. Thus, sterols such as cholesterol, ergosterol, 20-hydroxycholesterol, 22-hydroxycholesterol, campesterol, fucosterol, B-sitosterol, and stigmasterol constitute means for controlling LNP shape and fluidity or sterol means for increasing transfection efficiency. Some embodiments specifically include one or more of the above sterols while other embodiments specifically exclude one or more of the above sterols.

In some embodiments, an LNP or tLNP has about 27 mol % or about 30 mol % to about 50 mol % sterol, or about 30 mol % to about 38 mol % sterol. In certain embodiments, an LNP or tLNP has about 30.5 mol %, about 33.5 mol %, or about 37.5 mol % sterol. In certain instances, the sterol is cholesterol. In certain embodiments the sterol is a mixture of sterols, for example, cholesterol and B-sitosterol or cholesterol and 20-hydroxycholesterol. In some instances, the sterol is about 25 mol % 20-hydroxycholesterol and about 75 mol % cholesterol. In some instances, the sterol is about 25 mol % B-sitosterol and about 75 mol % cholesterol. In some instances, the sterol is about 50 mol % B-sitosterol and about 50 mol % cholesterol. In certain embodiments, an LNP or tLNP has 27 mol % or 30 mol % to 50 mol % sterol or 30 mol % to 38 mol % sterol. In further embodiments, an LNP or tLNP has 30.5 mol %, 33.5 mol %, or 37.5 mol % sterol. In certain instances, a sterol is cholesterol. In certain embodiments, a sterol is a mixture of sterols, for example, cholesterol and B-sitosterol or cholesterol and 20-hydroxycholesterol. In some instances, a sterol is 25 mol % 20-hydroxycholesterol and 75 mol % cholesterol. In further instances, a sterol is 25 mol % B-sitosterol and 75 mol % cholesterol. In still further instances, a sterol is 50 mol % B-sitosterol and 50 mol % cholesterol.

Phospholipids

The disclosed LNP and tLNP comprise a phospholipid. With respect to LNPs or tLNPs of this disclosure, in various embodiments, the phospholipid comprises dimyristoylphosphatidyl glycerol (DMPG), dimyristoylphosphatidyl choline (DMPC), dipalmitoyl phosphatidylcholine (DPPC), distearoylphosphatidylcholine (DSPC), distearoyl-glycerophosphate (18:0 PA, DSGP), dioleoylphosphatidyl ethanolamine (DOPE), dioleoyl-glycero-phosphate (18:1 PA, DOGP), or diarachidoylphosphotidylcholine (DAPC), or a combination thereof. Phospholipids can contribute to formation of a membrane, whether monolayer, bilayer, or multi-layer, surrounding the core of the LNP or tLNP. Additionally, phospholipids such as DSPC, DMPC, DPPC, DAPC impart stability and rigidity to membrane structure. Phospholipids, such as DOPE, impart fusogenicity. Further phospholipids, such as DMPG, which attains negative charge at physiologic pH, facilitates charge modulation. Thus, phospholipids constitute means for facilitating membrane formation, means for imparting membrane stability and rigidity, means for imparting fusogenicity, and means for charge modulation. Some embodiments specifically include one or more of the above phospholipids while other embodiments specifically exclude one or more of the above phospholipids.

In some embodiments, an LNP or tLNP has about 7 mol % to about 13 mol % phospholipid, about 7 mol % to about 10 mol % phospholipid, or about 10 mol % to about 13 mol % phospholipid. In certain embodiments, an LNP has about 7 mol %, about 10 mol %, or about 13 mol % phospholipid. In certain instances, the phospholipid is DSPC. In certain instances, the phospholipid is DAPC.

PEG-Lipids

In certain embodiments, the LNP is a tLNP comprising one or more functionalized PEG-lipids that has been conjugated to a binding moiety. In certain embodiments, the tLNP also comprises PEG-lipids not functionalized or conjugated with a binding moiety. In some embodiments the functionalization is a maleimide. In some embodiments the functionalization is a bromomaleimide or bromomaleimide amide, alkynylamide, or alkynylimide moiety at the terminal hydroxyl end of the PEG moiety. In some embodiments, the binding moiety comprises an antibody or antigen binding portion thereof. In some embodiments, the binding moiety is a polypeptide comprising a binding domain and an N- or C-terminal extension comprising an accessible thiol group. In some embodiments, the conjugation linkage comprises a reaction product of a thiol in the binding moiety with a functionalized PEG-lipid. In some embodiments the functionalization is a maleimide, azide, alkyne, dibenzocyclooctyne (DBCO), bromomaleimide or bromomaleimide amide, alkynylamide, or alkynylimide. In some embodiments, the binding moiety comprises an antibody or antigen binding portion thereof. In some embodiments, the binding moiety is a polypeptide comprising a binding domain and an N- or C-terminal extension comprising an accessible thiol group.

The disclosed LNP and tLNP comprise PEG-lipids, that is, a lipid conjugated to a polyethylene glycol. Generally, the lipid is a C14-C20 lipid. In certain embodiments, the PEG-lipid contains a C18 and/or C20 lipid. Common PEG-lipids fall into two classes diacyl glycerols and diacyl phospholipids. Examples of diacyl glycerol PEG-lipids include DMG-PEG (1,2-dimyristoyl-glycero-3-methoxypolyethylene glycol), DPG-PEG (1,2-dipalmitoyl-glycero-3-methoxypolyethylene glycol), DSG-PEG (1,2-distearoyl-glycero-3-methoxypolyethylene glycol), and DOG-PEG (1,2-dioleoyl-glycero-3-methoxypolyethylene glycol). Examples of diacyl phospholipids include DMPE-PEG (1,2-dimyristoyl-glycero-3-phosphoethanolamine-3-methoxypolyethylene glycol), DPPE-PEG (1,2-dipalmitoyl-glycero-3-phosphoethanolamine-3-methoxypolyethylene glycol), DSPE-PEG (1,2-distearoyl-glycero-3-phosphoethanolamine-3-methoxypolyethylene glycol), and DOPE-PEG (1,2-dioleoyl-glycero-3-phosphoethanolamine-3-methoxypolyethylene glycol). The glycerol in these lipids is chiral. Thus, in some embodiments, the PEG-lipid is racemic. Alternatively, optically pure antipodes of the glycerol portion can be employed, that is, the glycerol portion is homochiral. As used herein with respect to glycerol moieties, optically pure means ≥95% of a single enantiomer (D or L). In some embodiments, the enantiomeric excess is ≥98%. In some embodiments, the enantiomeric excess is ≥99%. Further PEG-lipids as well as the use of PEG-lipids and functionalized PEG-lipids and LNP incorporating them are disclosed in International Application Number PCT/US2023/017648 (Publication Number WO2023196445A1) which is incorporated for all that it teaches about PEG-lipids.

The above examples are presented as methoxypolyethylene glycols, but the terminus need not necessarily be methoxyl. With respect to any of the PEG-lipids that have not been functionalized, in alternative embodiments, the PEG moiety of the PEG lipids can terminate with a methoxyl, a benzyloxyl, a 4-methoxybenzyloxyl, or a hydroxyl group (that is, an alcohol). The terminal hydroxyl facilitates functionalization. The methoxyl, benzyloxyl, and 4-methoxybenzyloxyl groups are advantageously provided for PEG-lipid that will be used as a component of the LNP without functionalization. However, all four of these alternatives are useful as the (non-functionalized) PEG-lipid component of LNPs. The 4-methoxybenzyloxyl group, often used as a protecting group during synthesis of the PEG-lipid, is readily removed to generate the corresponding hydroxyl group. Thus the 4-methoxybenzyloxyl group offers a convenient path to the alcohol when it is not synthesized directly. The alcohol is useful for being functionalized, prior to incorporation of the PEG-lipid into a LNP, so that a binding moiety can be conjugated to it as a targeting moiety for the LNP (making it a tLNP). As used herein, the terminus of the PEG moiety, and similar constructions, refers to the end of the PEG moiety that is not attached to the lipid.

In some embodiments, an LNP or tLNP comprises about 0.5 mol % to about 3 mol % or 0.5 mol % to 3 mol % PEG-lipid comprising functionalized and non-functionalized PEG-lipid. In certain embodiments, an LNP or tLNP comprises DSG-PEG. In other embodiments, an LNP or tLNP comprises DMG-PEG or DPG-PEG. In certain embodiments, an LNP or tLNP comprises DSPE-PEG. In some embodiments, the functionalized and non-functionalized PEG-lipids are not the same PEG-lipid, for example, the non-functionalized PEG-lipid can be a diacylglycerol and the functionalized PEG-lipid a diacyl phospholipid. tLNP with such mixtures have reduced expression in the liver, possibly due to reduced uptake. In certain embodiments the functionalized PEG-lipid is DSPE-PEG and the non-functionalized PEG-lipid is DSG-PEG. In some embodiments, an LNP or tLNP comprises about 0.4 mol % to about 2.9 mol % or about 0.9 mol % to about 1.4 mol % non-functionalized PEG lipid. In certain embodiments, an LNP or tLNP comprises about 1.4 mol % or 1.4 mol % non-functionalized PEG lipid. In some embodiments, an LNP or tLNP comprises about 0.1 mol % to about 0.3 mol % or 0.1 mol % to 0.3 mol % functionalized lipid. In some instances, the functionalized lipid is DSPE-PEG. In certain instances, an LNP or tLNP comprises about 0.1 mol %, about 0.2 mol %, or about 0.3 mol % DSPE-PEG. In certain instances, an LNP or tLNP comprises 0.1 mol %, 0.2 mol %, or 0.3 mol % DSPE-PEG. In certain instances, the functionalized PEG-lipid is conjugated to a binding moiety. As used herein, the phrase "is conjugated to" and similar constructions are meant to convey a state of being, that is, a structure, and not a process, unless context dictates otherwise.

In certain aspects, the LNP comprises one or more PEG-lipids and/or functionalized PEG-lipids; when both a functionalized and unfunctionalized PEG-lipid, the PEG-lipid present they can be the same or different; and one or more ionizable cationic lipids; the LNP can further comprise a phospholipid, a sterol, a co-lipid, or any combination thereof. The term "functionalized PEG-lipid" refers to a PEG-lipid in which the PEG moiety has been derivatized with a chemically reactive group that can be used for conjugating a targeting moiety to the PEG-lipid. The functionalized PEG-lipid can be reacted with a binding moiety so that the binding moiety is conjugated to the PEG portion of the lipid. The conjugated binding moiety can thus serve as a targeting moiety for the LNP to constitute a tLNP. In some embodiments, the binding moiety is conjugated to the functionalized PEG-lipid after an LNP comprising the functionalized PEG-lipid is formed. In other embodiments, the binding moiety is conjugated to the PEG-lipid and then the conjugate is inserted into a previously formed LNP.

PEG can be made in a large range of sizes. In certain embodiments, the PEG of the disclosed LNP and tLNP is PEG-1000 to PEG-5000. It is to be understood that polyethylene preparations of these sizes are polydisperse and that the nominal size indicates an approximate average molecular weight of the distribution. Taking the molecular weight of an individual repeating unit of $(OCH_2CH_2)_n$ to be 44, a PEG molecule with n=22 would have a molecular weight of 986, with n=45 a molecular weight of 1998, and with n=113 a molecular weight of 4990. n≈22 to 113 is used to represent PEG-lipids incorporating PEG moieties in the range of PEG-1000 to PEG-5000 such as PEG-1000, PEG-1500, PEG-2000, PEG-2500, PEG-3000, PEG-3500, PEG-4000, PEG-4500, and PEG-5000, although some molecules from preparations at the average molecular weight boundaries will have n outside that range. For individual preparations n≈22 is used to represent PEG-lipids incorporating PEG moieties from PEG-1000, n≈45 is used to represent PEG-lipids incorporating PEG moieties from PEG-2000 n≈67 is used to represent PEG-lipids incorporating PEG moieties from PEG-3000, n≈90 is used to represent PEG-lipids incorporating PEG moieties from PEG-4000, n≈113 is used to represent PEG-lipids incorporating PEG moieties from PEG-5000. Some embodiments incorporate PEG moieties in a range bounded by any pair of the foregoing values of n or average molecular weight. Some embodiments incorporate PEG moieties of PEG-1000, PEG-2000, or PEG-5000. Certain embodiments comprise a DSG-PEG, for example, DSG-PEG-2000. Certain embodiments comprise a DSPE-PEG, for example, DSPE-PEG-2000. Certain embodiments comprise both DSG-PEG-2000 and/or DSPE-PEG2000.

A PEG-moiety provides a hydrophilic surface on the LNP, inhibiting aggregation or merging of LNP, thus contributing to their stability and reducing polydispersity. Additionally, a PEG moiety may impede binding by the LNP, including binding to plasma proteins. These plasma proteins include apoE which is understood to mediate uptake of LNP by the liver so that inhibition of binding can lead to an increase in the proportion of LNP reaching other tissues and cell types. These plasma proteins also include opsonins so that inhibition of binding reduces recognition by the reticuloendothelial system.

The PEG-moiety can also be functionalized to serve as an attachment point for a binding moiety which serves as a targeting moiety. Conjugating a cell- or tissue-specific binding moiety to the PEG-moiety enables a tLNP to avoid the liver and bind to its target tissue or cell type, greatly increasing the proportion of LNP that reaches the targeted tissue or cell type. PEG-lipid can thus serve as means for inhibiting LNP binding, and PEG-lipid conjugated to a binding moiety can serve as means for LNP-targeting. As used herein, the term "functionalized PEG-lipid" and similar constructions refer generally to both the unreacted and reacted entities. The lipid composition of a LNP may be described referencing the reactive species even after conjugation has taken place (forming a tLNP). For example, a lipid composition may be described as comprising DSPE-PEG-maleimide and may be said to further comprise a binding moiety without explicitly noting that upon reaction to form the conjugate the maleimide will have been converted to a succinimide (or hydrolyzed succinimide). Similarly, if the reactive group is bromomaleimide, after conjugation it will be maleimide. These differences of chemical nomenclature for the unreacted and reacted species are to be implicitly understood even when not explicitly stated. Certain embodiments comprise a DSG-PEG, for example, DSG-PEG-2000. Certain embodiments comprise a functionalized DSPE-PEG, for example, functionalized DSPE-PEG-2000. Certain embodiments comprise both DSG-PEG-2000 and functionalized DSPE-PEG-2000. In some instances, the functionalized PEG-lipid is functionalized with a maleimide moiety, for example, DSPE-PEG-2000-MAL.

In certain embodiments, the PEG-lipid and/or functionalized PEG-lipid comprises a scaffold selected from Formula S1, Formula S2, Formula S3, or Formula S4:

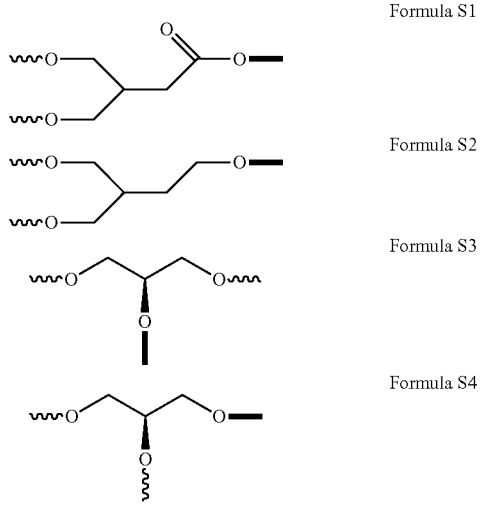

Formula S1

Formula S2

Formula S3

Formula S4 wherein ⌇⌇ represents the points of ester connection with a fatty acid, and ━ represents the point of ester (S1) or ether (S2, S3, and S4) formation with the PEG moiety. In some embodiments, the fatty acid esters are $C_{14}$-$C_{20}$ straight-chain alkyl fatty acids. In some embodiments, the PEG moiety is functionalized and the fatty acid esters are $C_{16}$-$C_{20}$ straight-chain alkyl fatty acids. For example, the straight-chain alkyl fatty acid is $C_{14}$, $C_{15}$, $C_{16}$, $C_{17}$, $C_{18}$, $C_{19}$, or $C_{20}$. In some embodiments, the fatty acid esters are $C_{14}$-$C_{20}$ symmetric branched-chain alkyl fatty acids. For example, the branched-chain alkyl fatty acid is $C_{14}$, $C_{15}$, $C_{16}$, $C_{17}$, $C_{18}$, $C_{19}$, or $C_{20}$. By symmetric it is meant that each alkyl branch has the same number of carbons. In some embodiments, the branch is at the 3, 4, 5, 6, or 7 position of the fatty acid ester. The synthesis and use of PEG-lipids built on scaffolds S1-S4 is disclosed in WO2023/196445A1 which is incorporated by reference for all that it teaches about PEG-lipids and their use.

In some embodiments, the PEG moiety is PEG-500 to PEG-5000 such as PEG-500, PEG-1000, PEG-1500, PEG-2000, PEG-2500, PEG-3000, PEG-3500, PEG-4000, PEG-4500, and PEG-5000. In some instances, the PEG moiety is PEG-2000. In some embodiments, the PEG unit has a MW of 2000 Da. In some instances, the MW2000 PEG-lipid comprises DMG-PEG2000 (1,2-dimyristoyl-glycero-3-methoxypolyethylene glycol-2000), DPG-PEG2000 (1,2-dipalmitoyl-glycero-3-methoxypolyethylene glycol-2000), DSG-PEG2000 (1,2-distearoyl-glycero-3-methoxypolyethylene glycol-2000), DOG-PEG2000 (1,2-dioleoyl-glycero-3-methoxypolyethylene glycol-2000), DMPE-PEG200 (1,2-dimyristoyl-glycero-3-phosphoethanolamine-3-methoxypolyethylene glycol-2000), DPPE-PEG2000 (1,2-dipalmitoyl-glycero-3-phosphoethanolamine-3-methoxypolyethylene glycol-2000), DSPE-PEG2000 (1,2-distearoyl-glycero-3-phosphoethanolamine-3-methoxypolyethylene glycol-2000), DOPE-PEG2000 (1,2-dioleoyl-glycero-3-phosphoethanolamine-3-methoxypolyethylene glycol-2000), or combinations thereof. In some embodiments, the glycerol moiety is racemic. Alternatively, optically pure antipodes of the glycerol portion can be employed, that is, the glycerol portion is homochiral.

Conjugation

Multiple suitable chemistries to conjugate the binding moiety to the PEG of the PEG-lipid, including maleimide (see Parhiz et al., Journal of Controlled Release 291:106-115, 2018) and click (see Kolb et al., Angewandte Chemie International Edition 40 (11): 2004-2021, 2001; and Evans, Australian Journal of Chemistry 60 (6): 384-395, 2007) chemistries. Reagents for such reactions include lipid-PEG-maleimide, lipid-PEG-cysteine, lipid-PEG-alkyne, lipid-PEG-dibenzocyclooctyne (DBCO), and lipid-PEG-azide. Further conjugations reactions make use of lipid-PEG-bromomaleimide, lipid-PEG-alkylnoic amide, PEG-alkynoic imide, and lipid-PEG-alkyne reactions, as disclosed in PCT/US23/17648 entitled PEG-Lipids and Lipid Nanoparticles, which is incorporated by reference for all that it teaches about conjugation chemistry and alternative PEG-lipids. On the binding moiety side of the reaction one can use an existing cysteine sulfhydryl, or derivatize the protein by adding a sulfur containing carboxylic acid, for example, to the epsilon amino of a lysine to react with maleimide, bromomaleimide, (collectively, "a maleimide"), alkylnoic amide, or alkynoic imide. Alternatively, one can add an alkyne to a sulfhydryl or an epsilon amino of a lysine to participate in a click chemistry reaction.

To modify an epsilon amino of a binding moiety lysine to react with a maleimide functionalized PEG-lipid the binding moiety (e.g., an antibody) can be reacted with N-succinimidyl S-acetylthioacetate (SATA). SATA is then deprotected, for example, using 0.5 M hydroxylamine followed by removal of the unreacted components by G-25 Sephadex Quick Spin Protein columns (Roche Applied Science, Indianapolis, IN). The reactive sulfhydryl group on the binding moiety is then conjugated to maleimide moieties on LNPs of the disclosure using thioether conjugation chemistry. Purification can be performed using Sepharose CL-4B gel filtration columns (Sigma-Aldrich). tLNPs (LNPs conjugated with a targeting antibody) can be stored frozen at −80° C. until needed. Others have conjugated antibody to free functionalized PEG-lipid and then incorporated the conjugated lipid into pre-formed LNP. However, we have found that the present procedure is more controllable and produces more consistent results.

There are also several approaches to site-specific conjugation. Particularly but not exclusively suitable for truncated forms of antibody, C-terminal extensions of native or artificial sequences containing a particularly accessible cysteine residue are commonly used. Partial reduction of cystine bonds in an antibody, for example, with tris(2-carboxy) phosphine (TCEP), can also generate thiol groups for conjugation which can be site-specific under defined conditions with an amenable antibody fragment. Alternatively, the C-terminal extension can contain a sortase A substrate sequence, LPXTG (SEQ ID NO: 1) which can then be functionalized in a reaction catalyzed by sortase A and conjugated to the PEG-lipid, including through click chemistry reactions (see, for example, Moliner-Morro et al., Biomolecules 10 (12): 1661, 2020 which is incorporated by reference herein for all that it teaches about antibody conjugations mediated by the sortase A reaction and/or click chemistry). The use of click chemistry for the conjugation of a targeting moiety, such as various forms of antibody, is disclosed, for example, in WO2024/102,770 which is incorporated by reference in its entirety for all that it teaches about the conjugation of targeting moieties to LNPs that is not inconsistent with this disclosure.

For whole antibody and other forms comprising an Fc region, site-specific conjugation to either (or both) of two specific lysine residues (Lys248 and Lys288) can be accomplished without any change to or extension of the native antibody sequence by use of one of the AJICAP® reagents (see, for example, Matsuda et al., Molecular Pharmaceutics 18:4058-4066, 2021, Fujii et al., Bioconjugate Chemistry 34 (4): 728-738, 2023 (https://doi.org/10.1021/acs.bioconjchem.3c00040), 2023, and WO2019/240,247 all of which are incorporated by reference herein for all that they teach about conjugation of antibodies with AJICAP reagents). The AJICAP reagents are modified affinity peptides that bind to specific loci on the Fc and react with an adjacent lysine residue. The peptide is then cleaved with base to leave behind a thiol-functionalized lysine residue which can then undergo conjugation through maleimide or haloamide reactions, for example). Functionalization with azide or dibenzocyclooctyne (DBCO) for conjugation by click chemistry is also possible.

Accordingly, in some embodiments the binding moiety is conjugated to the PEG moiety of the PEG-lipid through a thiol modified lysine residue. In some embodiments the conjugation is through a cysteine residue in a native or added antibody sequence. In other embodiments, the conjugation is through a sortase A substrate sequence. In still other embodiments, the conjugation is through a specific lysine residue (Lys248 or Lys288) in the Fc region.

Nucleic Acids

In certain embodiments, the disclosed LNP and tLNP comprise a payload comprising or consisting of one or more nucleic acid species. In some embodiments, the LNP or tLNP payload comprises only one nucleic acid species while in other embodiments the LNP or tLNP payload comprises multiple nucleic acid species, for example, 2, 3, or 4 nucleic acid species. For example, in embodiments in which the payload comprises a nucleic acid encoding a CAR or immune cell engager (ICE), the payload can comprise or consist of 1) a single nucleic acid species encoding a single species of CAR or ICE, 2) a single nucleic acid species encoding 2 or more species of CAR or ICE (or a mixture of CAR and ICE) such as a bicistronic or multicistronic mRNA in which each CAR and/or ICE has specificity for a same target antigen, 3) a single nucleic acid species encoding 2 or more species of CAR or ICE (or a mixture of CAR and ICE) such as a bicistronic or multicistronic mRNA in which at least one CAR and/or ICE has specificity for a different target antigen than the other(s), 4) two or more nucleic acid species encoding 2 or more species of CAR or ICE (or a mixture of CAR and ICE) in which each CAR and/or ICE has specificity for a same target antigen, 5) two or more nucleic acid species encoding 2 or more species of CAR or ICE (or a mixture of CAR and ICE) in which at least one CAR and/or ICE has specificity for a different target antigen than the other(s). When two or more CAR and/or ICE have specificity for a same target antigen, they can have specificity for different epitopes of the same target antigen. Further variations will be apparent to one of skill in the art (e.g., multiple bi- or multicistronic nucleic acids, nucleic acids encoding a TCR and the like). The nucleic acid can be RNA or DNA. The nucleic acid can be multicistronic, for example, bicistronic. In some embodiments, the mRNA encodes a reprogramming agent or comprises or encodes a conditioning agent. In some embodiments, the nucleic acid comprises small interfering RNA (siRNA), microRNA (miRNA), antisense oligonucleotide (ASO). In some embodiments, the nucleic acid comprises a self-replicating RNA or a circular RNA.

In some embodiments, the reprogramming agent comprises an immune receptor (for example, a chimeric antigen receptor or a T cell receptor) or an immune cell engager (for example, a bispecific T cell engager (BiTE), a bispecific killer cell engager (BIKE), a trispecific kill cell engager (TriKE), a dual affinity retargeting antibody (DART), a TRIDENT (linking two DART units or a DART unit and a Fab domain), a macrophage engager (e.g., BiME), an innate cell engager (ICE), and the like).

In some embodiments, the nucleic acid is an RNA, for example, mRNA, and the RNA comprises at least one modified nucleoside. In some embodiments, the modified nucleoside is pseudouridine, N1-methylpseudouridine, 5-methylcytosine, 5-methyluridine, N6-methyladenosine, 2'-O-methyluridine, or 2-thiouridine. In certain embodiments all of the uridines are substituted with a modified nucleoside. Further disclosure of modified nucleosides and their use can be found in U.S. Pat. No. 8,278,036 which is incorporated herein by reference for those teachings.

In some embodiments, the reprogramming agent encodes or is a gene/genome editing component. In some embodiments, the gene/genome editing component is a guide RNA for an RNA-directed nuclease or other nucleic acid editing enzyme, clustered regularly interspaced short palindromic repeat RNA (crisprRNA), a trans-activating clustered regularly interspaced short palindromic repeat RNA (tracrRNA). In some embodiments, the gene/genome editing component is a nucleic acid-encoded enzyme, such as RNA-guided nuclease, a gene or base editing protein, a zinc finger nuclease (ZFN), a transcription activator-like effector nuclease (TALEN), a meganuclease, a transposase, or a CRISPR nuclease (e.g., Cas9 or Cas 12, etc.). In some embodiments, the gene/genome editing component is DNA to be inserted or that serves as a template in gene or genome editing for example a template for repair of a double-strand break.

In some embodiments comprising multiple agents, the nucleic acid can be multicistronic. In other embodiments comprising multiple agents or components, each agent or component is encoded or contained is a separate nucleic acid species. In some embodiments involving multiple payload nucleic acid species, two or more nucleic acid species are packaged together in a single LNP species. In other embodiments, a subset of the payload nucleic acid species to be delivered, (e.g., a single nucleic acid species) is packaged in one LNP or tLNP species while another subset of the nucleic acid species is packaged in another LNP or tLNP species. The different (t) LNP species can differ by only the payload they contain. The different (t) LNP species may be combined in a single formulation or pharmaceutical composition for administration.

Binding Moieties

The tLNP of the various disclosed aspects comprise a binding moiety, such as an antibody or antigen binding domain thereof or a cell surface receptor ligand. As used herein, a "binding moiety" or "targeting moiety" refers to a protein, polypeptide, oligopeptide or peptide, carbohydrate, nucleic acid, or combinations thereof capable of specifically binding to a target or multiple targets. A binding domain includes any naturally occurring, synthetic, semi-synthetic, or recombinantly produced binding partner for a biological molecule or another target of interest. Exemplary binding moieties of this disclosure include an antibody, a Fab', F(ab')$_2$, Fab, Fv, rIgG, scFv, hcAb (heavy chain antibody), a single domain antibody, VHH, VNAR, sdAb, nanobody, receptor ectodomain or ligand-binding portions thereof, or ligand (e.g., cytokines, chemokines). An "Fab" (antigen binding fragment) is the part of an antibody that binds to antigens and includes the variable region and CH1 of the heavy chain linked to the light chain via an inter-chain disulfide bond. In other embodiments, a binding moiety comprises a ligand-binding domain of a receptor or a receptor ligand. In some embodiments, a binding moiety can have more than one specificity including, for example, bispecific or multispecific binders. A variety of assays are known for identifying binding moieties of this disclosure that specifically bind a particular target, including Western blot, ELISA, biolayer interferometry, and surface plasmon resonance. A binding moiety, such as a binding moiety comprising immunoglobulin light and heavy chain variable domains (e.g., scFv), can be incorporated into a variety of protein scaffolds or structures as described herein, such as an antibody or an antigen binding fragment thereof, a scFv-Fc fusion protein, or a fusion protein comprising two or more of such immunoglobulin binding domains.

The fundamental ability of the tLNP to deliver a payload into the cytoplasm of a cell is agnostic with respect to, and does not depend upon, a particular binding specificity. Of course, a binding moiety is a determinant of which cells a payload is delivered into. There are many known antibodies with specificity for one or another cell surface marker associated with particular cell type(s) that could be used as the target of the binding moiety on a disclosed tLNP and there are several sources that have compiled such information. An excellent source of information about antibodies for which an International Non-proprietary Name (INN) has been proposed or recommended is Wilkinson & Hale, *MAbs* 14 (1): 2123299, 2022, including its Supplementary Tables, which is incorporated by reference herein for all that it teaches about individual antibodies and the various antibody formats that can be constructed. U.S. Pat. No. 11,326,182 and especially its Table 9 Cancer, Inflammation and Immune System Antibodies, is a source of sequence and other information for a wide range of antibodies including many that do not have an INN and is incorporated herein by reference for all that it teaches about individual antibodies. Sequence information is not always readily available for antibodies mentioned in the art, even when commercially available. This is not necessarily an impediment to their use. Where the antibody or a cell line is commercially available or obtainable from its originator it can be used as the binding moiety of tLNP without any need for sequence information. Even where sequence information is needed, it is well within the capabilities of the skilled artisan to sequence the antibody protein (or have it done by a contract laboratory) so that the antibody's variable region can be incorporated into a scFv, a diabody, a minibody, or some other antibody format, or be humanized. In choosing among available antibodies in the art for the development of an agent to be used in humans, a human antibody is preferred to a humanized antibody is preferred to a non-human antibody, other factors being equal. Other factors can include stability and ease of production of the antibody, affinity of the antibody, and cross-reactivity for the cognate antigen in model species to be used in product development.

In some embodiments, a binding moiety may be an antibody or an antigen-binding portion thereof; an antigen; a ligand-binding domain of a receptor; or a receptor ligand. In some embodiments, a binding moiety can have more than one specificity including, for example, bispecific or multispecific binders.

In some embodiments, a binding moiety comprises an antibody or an antigen-binding portion thereof. As used herein, "antibody" refers to a protein comprising an immunoglobulin domain having hypervariable regions determining the specificity with which the antibody binds antigen, termed complementarity determining regions (CDRs). The term antibody can thus refer to intact or whole antibodies as well as antibody fragments and constructs comprising an antigen binding portion of a whole antibody. While the canonical natural antibody has a pair of heavy and light chains, camelids (from camels, alpacas, llamas, etc.) produce antibodies with both the canonical structure and antibodies comprising only heavy chains. The variable region of the camelid heavy chain-only antibody has a distinct structure with a lengthened CDR3 referred to as VHH or, when produced as a fragment, a nanobody. Antigen binding fragments and constructs of antibodies include F(ab)$_2$, F(ab), minibodies, Fv, single-chain Fv (scFv), diabodies, and VH. Such elements may be combined to produce bi- and multi-specific reagents, including various immune cell engagers, such as BiTEs (bi-specific T-cell engagers). The term "monoclonal antibody" arose out of hybridoma technology but is now used to refer to any singular molecular species of antibody regardless of how it was originated or produced. Antibodies can be obtained through immunization, selection from a naïve or immunized library (for example, by phage display), alteration of an isolated antibody-encoding sequence, or any combination thereof. Numerous antibodies that can be used as binding moieties are known in the art. An excellent source of information about antibodies for an International Non-proprietary Name (INN) has been proposed or recommended, including sequence information, is Wilkinson & Hale, 2022, *MAbs* 14 (1): 2123299, including its Supplementary Tables, which is incorporated by reference herein for all that it teaches about individual antibodies and the various antibody formats that can be constructed. U.S. Pat. No. 11,326,182 and especially its Table 9 entitled "Cancer, Inflammation and Immune System Antibodies," is a source of sequence and other information for a wide range of antibodies including many that do not have an INN and is incorporated herein by reference for all that it teaches about individual antibodies.

An antibody or other binding moiety (or a fusion protein thereof) "specifically binds" a target if it binds the target with an affinity or Ka (i.e., an equilibrium association constant of a particular binding interaction with units of 1/Molar or 1/M) equal to or greater than $10^5$ M$^{-1}$, while not significantly binding other components present in a test sample. Binding domains (or fusion proteins thereof) can be classified as "high affinity" binding domains (or fusion proteins thereof) and "low affinity" binding domains (or fusion proteins thereof). "High affinity" binding domains refer to those binding domains with a Ka of at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$, preferably at least $10^8$ M-1 or at least $10^9$ M$^{-1}$. "Low affinity" binding domains refer to those binding domains with a Ka of up to $10^8$ M$^{-1}$, up to $10^7$ M$^{-1}$, up to $10^6$ M$^{-1}$, up to $10^5$ M$^{-1}$. Alternatively, affinity may be defined as an equilibrium dissociation constant (Kd) of a particular binding interaction with units of M (e.g., $10^{-5}$ M to $10^{-13}$ M). Affinities of binding domain polypeptides and fusion proteins according to this disclosure can be readily determined using conventional techniques (see, e.g., Scatchard et al., 1949, Ann. N.Y. Acad. Sci. 51:660; and U.S. Pat. Nos. 5,283,173, 5,468,614, or the equivalent).

A diabody is a dimer of scFv fragment that consists of the $V_H$ and $V_L$ regions noncovalently connected by a small peptide linker or covalently linked to each other. A BiTE is a fusion protein having two scFvs of different antibodies, usually an antibody for a tumor-associated antigen and antibody for CD3, on a single peptide chain, thus forming a cytolytic synapse between T cells and target antigen-bearing cells. The term "antigen-binding portion" may refer to a portion of an antibody as described that possesses the ability to specifically recognize, associate, unite, or combine with a target molecule. An antigen-binding portion includes any naturally occurring, synthetic, semi-synthetic, or recombinantly produced binding partner for a specific antigen. Thus, antibodies and antigen-binding portions thereof constitute means for binding to the surface molecule on a cell. In various embodiments, the cell can be an immune cell, a leukocyte, a lymphocyte, a monocyte, a stem cell, an HSC or an MSC, according to the specificity of the antibody.

In some embodiments, the antibody or antigen-binding portion thereof may be derived from a mammalian species, for example, mice, rats, or human. Antibody variable regions can be those arising from one species, or they can be chimeric, containing segments of multiple species possibly further altered to optimize characteristics such as binding affinity or low immunogenicity. For human applications, it is desirable that the antibody has a human sequence. In the cases where the antibody or antigen-binding portion thereof is derived from a non-human species, the antibody or antigen-binding portion thereof may be humanized to reduce immunogenicity in a human subject. For example, if a human antibody of the desired specificity is not available, but such an antibody from a non-human species is, the non-human antibody can be humanized, e.g., through CDR grafting, in which the CDRs from the non-human antibody are placed into the respective positions in a framework of a compatible human antibody. Less preferred is an antibody in which only the constant region of the non-human antibody is replaced with human sequence. Such antibodies are commonly referred to as chimeric antibodies in distinction to humanized antibodies.

In some embodiments, the antibody or antigen-binding portion thereof is non-immunogenic. In some embodiments, the antibody may be modified in its Fc region to reduce or eliminate secondary functions, such as FcR engagement, antibody-dependent cellular cytotoxicity (ADCC), antibody-dependent cellular phagocytosis (ADCP), and/or complement-dependent cytotoxicity (CDC).

A binder density on the tLNP can be defined according to the ratio of antibody (binder) to mRNA (w/w) either based on the amount of antibody input in the conjugation reaction or as measured in the tLNP. For an intact antibody (e.g., whole IgG), in some embodiments, preferred ratios are about 0.3 to about 1.0, about 0.3 to about 0.7, about 0.3 to about 0.5, about 0.5 to about 1.0, and about 0.5 to about 0.7 for either the input or final measured binder ratio. In certain embodiments, a tLNP has an antibody ratio of 0.3 to 1.0, 0.3 to 0.7, 0.3 to 0.5, 0.5 to 1.0, and 0.5 to 0.7 for either the input or final measured binder ratio. In some embodiments, if the binder is different in size from an intact antibody (for example a scFv, diabody, or minibody, etc.) the w/w ratio is adjusted for the different size of the binder.

In certain embodiments, a LNP or tLNP comprises a binding moiety derived from an anti-CD40*‡ antibody, an anti-LRRC15†‡ antibody, an anti-CTSK antibody, an anti-ADAM12‡ antibody, an anti-ITGA11 antibody, an anti-FAP*†‡ antibody, an anti-NOX4 antibody, an anti-SGCD antibody, an anti-SYNDIG1 antibody, an anti-CDH11‡ antibody, an anti-PLPP4 antibody, an anti-SLC24A2 antibody, an anti-PDGFRB*‡ antibody, an anti-THY1‡ antibody, an anti-ANTXR1‡ antibody, an anti-GAS1 antibody, an anti-CALHM5 antibody, an anti-SDC1*‡ antibody, an anti-HER2*†‡ antibody, an anti-TROP2*†‡ antibody, an anti-MSLN*‡ antibody, an anti-Nectin4†‡ antibody, or an anti-MUC16*†‡ antibody. In further embodiments, a LNP (or tLNP) comprises a binding moiety specific for an immune cell antigen selected from CD1, CD2*†‡, CD3*†‡, CD4*†‡, CD5†‡, CD7†‡, CD8†, CD11b‡, CD14++, CD16, CD25++, CD26*‡, CD27*†‡, CD28*†‡, CD30*†‡, CD32*, CD38*‡, CD39‡, CD40*†‡, CD40L (CD154)*†‡, CD44*‡, CD45†‡, CD64*‡, CD62†‡, CD68, CD69‡, CD73†‡, CD80*‡, CD83‡, CD86*‡, CD95‡, CD103‡, CD119‡, CD126‡, CD137 (41BB)†‡, CD150‡, CD153‡, CD161‡, CD166‡, CD183 (CXCR3)‡, CD183 (CXCR5)‡, CD223 (LAG-3)*†‡, CD254‡, CD275‡, CD45RA, CTLA-4*†*†, DEC205, OX40‡, PD-1*†‡, GITR†, TIM-3*†‡, FasL*‡, IL18R1, ICOS (CD278)‡, leu-12, TCR†, TLR1, TLR2†‡, TLR3*‡, TLR4†‡, TLR6, TREM2‡, NKG2D‡, CCR, CCR1 (CD191)‡, CCR2 (CD192)*†‡, CCR4 (CD194)*†‡, CCR6 (CD196)‡, CCR7‡, low affinity IL-2 receptor†‡, IL-7 receptor‡, IL-12 receptor‡, IL-15 receptor‡, IL-18 receptor‡, and IL-21 receptor‡. In further embodiments, a tLNP comprises a binding moiety specific for an HSC surface molecule selected from CD117†, CD34*‡, CD44*‡, CD45†‡, CD90 (Thy1)‡, CD105‡, CD133‡, BMPR2‡, and Sca-1; or specific for an MSC surface molecules selected from CD70*‡, CD105‡, CD73‡, Stro-1‡, SSEA-3‡, SSEA-4‡, CD271‡, CD146‡, GD2*†‡, SUSD2, Stro-4, MSCA-1, CD56‡, CD200*†‡, PODXL‡, CD13‡, CD29*‡, CD44*‡, and CD10‡. In various embodiments, a binding moiety is an antibody or antigen-binding portion thereof. (* indicates that exemplary antibodies with the indicated specificity from which a binding moiety could be derived can be found in U.S. Pat. No. 11,326,182B2 Table 9 or 10. † indicates that exemplary antibodies with the indicated specificity from which a binding moiety could be derived can be found in Wilkinson & Hale, 2022. Both references cited and incorporated by reference above. $ indicates that exemplary antibodies with the indicated specificity from which a binding moiety could be derived can be found in the Therapeutic Antibody Database (TABS) at tabs.craic.com). Other suitable antibodies can be found in Appendix A.)

The following paragraphs provide non-exhaustive examples of known antibodies that bind to cell surface markers on immune cells (lymphocytes and monocytes) and stem cells (HSC and MSC). These antibodies or the antigen binding domains thereof can be used as binding moieties to target the disclosed LNP. Collectively these antibodies and polypeptides comprising the antigen binding domains thereof constitute means for binding cell surface markers or means for binding immune and stem cells.

In some embodiments, the tLNP is targeted to CD2+ cells and the binding moiety comprises the antigen binding domain of an anti-CD2 antibody. CD2 contains three well-characterized epitopes (T11.1, T11.2, and T11.3/CD2R). T11.3/CD2R are membrane proximal and exposure is increased upon T cell activation and CD2 clustering. Accordingly, in some such embodiments, the anti-CD2 antibody comprises, RPA-2.10; OKT11, UMCD2, 0.1, and 3T4-8B5 (T11.1 epitope); 9.6 and 1OLD2-4C1 (T11.2 epitope); 1Mono2A6 (T11.3 epitope), siplizumab (T11.2/T11.3 epitope), HuMCD2, TS2/18, TS1/8, AB75, LT-2, T6.3, MEM-65, OTI4E4, or an antigen-binding portion thereof. Additionally, the ligand of CD2, CD58 (LFA-3) can be used as a CD2 binding moiety as can alefacept, a CD58-Fc fusion. Each of these constitutes a means for binding CD2 (Li et al., 1996, *J Mol Biol.* 263:209-26; Binder et al., 2020, *Front Immunol.* 9:11:1090).

In some embodiments, the tLNP is targeted to CD3+ cells and the binding moiety comprises the antigen binding domain of an anti-CD3 antibody. Accordingly, in some such embodiments, the antibody comprises muromonab-CD3 (OKT3), teplizumab, otelixizumab, visilizumab, cevostamab, teclistamab, elranatamab pavurutamab, vibecotamab, odronextamab, or an antigen-binding portion thereof. Each of these constitutes a means for binding CD3.

In some embodiments, the tLNP is targeted to CD4+ cells and the binding moiety comprises the antigen binding domain of an anti-CD4 antibody. Accordingly, in some such embodiments, the antibody comprises ibalizumab, inezetamab, semzuvolimab, zanolimumab, tregalizumab, UB-421, priliximab, MTRX1011A, cedelizumab, clenoliximab, keliximab, M-T413, TRX1, hB-F5, MAX. 16H5, IT208, or an antigen-binding portion thereof. Each of these constitutes a means for binding CD4.

In some embodiments, the tLNP is targeted to CD5+ cells and the binding moiety comprises the antigen binding domain of an anti-CD5 antibody. Accordingly, in some such embodiments, the antibody comprises 5D7, UCHT2, L17F12, H65, HE3, OKT1, MAT304, as well as those disclosed in WO1989006968, WO2008121160, U.S. Pat. No. 8,679,500, WO2010022737, WO2019108863, WO2022040608, or WO2022127844, each of which is incorporated by reference for all that they teach about anti-CD5 antibodies and their properties, or an antigen-binding portion thereof. Each of these constitutes a means for binding CD5.

In some embodiments, the tLNP is targeted to CD7+ cells and the binding moiety comprises the antigen binding domain of an anti-CD7 antibody. Accordingly, in some such embodiments, the antibody comprises TH-69, 3A1E, 3A1F, Huly-m2, WT1, YTH3.2.6, T3-3A1, grisnilimab, as well as those disclosed in U.S. Pat. No. 10,106,609, WO2017213979, WO2018098306, U.S. Pat. No. 11,447,548, WO2022136888, WO2020212710, WO2021160267, WO2022095802, WO2022095803, WO2022151851, or WO2022257835 each of which is incorporated by reference for all that they teach about anti-CD7 antibodies and their properties, or an antigen-binding portion thereof. Each of these constitutes a means for binding CD7.

In some embodiments, the tLNP is targeted to CD8+ cells and the binding moiety comprises the antigen binding domain of an anti-CD8 antibody. Accordingly, in some such embodiments, the antibody comprises crefmirlimab (IAB22M), 3B5, SP-16, LT8, 17D8, MEM-31, MEM-87, RIV11, UCHT4, YTC182.20, RPA-T8, OKT8, SK1, 51.1, TRX2, MT807-R1, HIT8a, C8/144B, RAVB3, SIDI8BEE, BU88, EPR26538-16, 2ST8.5H7, as well as those disclosed in U.S. Pat. No. 10,414,820, WO2015184203, WO2017134306, WO2019032661, WO2020060924, U.S. Pat. No. 10,730,944, WO2019033043, WO2021046159, WO2021127088, WO2022081516, U.S. Pat. No. 11,535,869, or WO2023004304 each of which is incorporated by reference for all that they teach about anti-CD8 antibodies and their properties, or an antigen-binding portion thereof. Additionally, humanized anti-CD8 antibodies are described in U.S. application Ser. No. 18/983,294, filed on Dec. 16, 2024, which is incorporated by reference for all that it teaches about these humanized anti-CD8 antibodies and their properties, or an antigen-binding portion thereof. Each of the foregoing anti-CD8 antibodies constitutes a means for binding CD8.

In some embodiments, the tLNP is targeted to CD10+ cells and the binding moiety comprises the antigen binding domain of an anti-CD10 antibody. Accordingly, in some such embodiments, the antibody comprises the one produced by the hybridoma represented by Accession No. NITE BP-02489 (disclosed in WO2018235247 which is incorporated by reference for all that they teach about anti-CD10 antibodies and their properties), FR4D11, or REA877, or an antigen-binding portion thereof. Each of these constitutes a means for binding CD10.

In some embodiments, the tLNP is targeted to CD11b+ cells and the binding moiety comprises the antigen binding domain of an anti-CD11b antibody. Accordingly, in some such embodiments, the antibody comprises ASD141 or MAB107 as well as those disclosed in US20150337039, U.S. Pat. No. 10,738,121, WO2016197974, U.S. Pat. No. 10,919,967, or WO2022147338 each of which is incorporated by reference for all that they teach about anti-CD11b antibodies and their properties, or an antigen-binding portion thereof. Each of these constitutes a means for binding CD11b.

In some embodiments, the tLNP is targeted to CD13+ cells and the binding moiety comprises the antigen binding domain of an anti-CD13 antibody. CD13 is also known as aminopeptidase N (APN). Accordingly, in some such embodiments, the antibody comprises MT95-4 or Nbl57 (disclosed in WO2021072312 which is incorporated by reference for all that they teach about anti-CD13 antibodies and their properties), as well as those disclosed in WO2023037015 which is incorporated by reference for all that it teaches about anti-CD13 antibodies and their properties, or an antigen-binding portion thereof. Each of these constitutes a means for binding CD13.

In some embodiments, the tLNP is targeted to CD14+ cells and the binding moiety comprises the antigen binding domain of an anti-CD14 antibody. Accordingly, in some such embodiments, the antibody comprises atibuclimab or r18D11 as well as those disclosed in WO2018191786 or WO2015140591 each of which is incorporated by reference for all that they teach about anti-CD14 antibodies and their properties, or an antigen-binding portion thereof. Each of these constitutes a means for binding CD14.

In some embodiments, the tLNP is targeted to CD16a+ cells and the binding moiety comprises the antigen binding domain of an anti-CD16a antibody. Accordingly, in some such embodiments, the antibody comprises AFM13, sdA1, sdA2, or hu3G8-5.1-N297Q as well as those disclosed in U.S. Pat. No. 11,535,672, WO2018158349, WO2007009065, U.S. Pat. No. 10,385,137, WO2017064221, U.S. Pat. No. 10,758,625, WO2018039626, WO2018152516, WO2021076564, WO2022161314, or WO2023274183 each of which is incorporated by reference for all that they teach about anti- CD16A antibodies and their properties, or an antigen-binding portion thereof. Each of these constitutes a means for binding CD16a.

In some embodiments, the tLNP is targeted to CD25+ cells and the binding moiety comprises the antigen binding domain of an anti-CD25 antibody. Accordingly, in some such embodiments, the antibody comprises daclizumab, basiliximab, camidanlumab, tesirine, inolimomab, RO7296682, HuMax-TAC, CYT-91000, STI-003, RTX-003, or an antigen-binding portion thereof. Each of these constitutes a means for binding CD25.

In some embodiments, the tLNP is targeted to CD28+ cells and the binding moiety comprises the antigen binding domain of an anti-CD28 antibody. Accordingly, in some such embodiments, the antibody comprises GN1412, acazicolcept, lulizumab, prezalumab, theralizumab, FR104CD, and davoceticept, as well as those disclosed in U.S. Pat. Nos. 8,454,959, 8,785,604, 11,548,947, 11,530,268, 11,453,721, 11,591,401, WO2002030459, WO2002047721, US20170335016, US20200181260, U.S. Pat. No. 11,608,376, WO2020127618, WO2021155071, or WO2022056199 each of which is incorporated by reference for all that they teach about anti-CD28 antibodies and their properties, or an antigen-binding portion thereof. Each of these constitutes a means for binding CD28.

In some embodiments, the tLNP is targeted to CD29$^+$ cells and the binding moiety comprises the antigen binding domain of an anti-CD29 antibody. Accordingly, in some such embodiments, the antibody comprises OS2966, 6D276, 12G10, REA1060, or an antigen-binding portion thereof. Each of these constitutes a means for binding CD29.

In some embodiments, the tLNP is targeted to CD32A$^+$ cells and the binding moiety comprises the antigen binding domain of an anti-CD32A antibody. Accordingly, in some such embodiments, the antibody comprises VIB9600, humanized IV.3, humanized AT-10, or MDE-8 as well as those disclosed in U.S. Pat. Nos. 9,688,755, 9,284,375, 9,382,321, 11,306,145, or WO2022067394 each of which is incorporated by reference for all that they teach about anti-CD32A antibodies and their properties, or an antigen-binding portion thereof. Each of these constitutes a means for binding CD32A.

In some embodiments, the tLNP is targeted to CD34$^+$ cells and the binding moiety comprises the antigen binding domain of an anti-CD34 antibody. Accordingly, in some such embodiments, the antibody comprises h4C8, 9C5, 2E10, 5B12, REA1164, C5B12, C2e10, or an antigen-binding portion thereof. Each of these constitutes a means for binding CD34.

In some embodiments, the tLNP is targeted to CD40$^+$ cells and the binding moiety comprises the antigen binding domain of an anti-CD40 antibody. Accordingly, in some such embodiments, the antibody comprises cifurtilimab, sotigalimab, iscalimab, dacetuzumab, selicrelumab, bleselumab, lucatumumab, or mitazalimab as well as those disclosed in U.S. Pat. No. 10,633,444, each of which is incorporated by reference for all that they teach about anti-CD40 antibodies and their properties, or an antigen-binding portion thereof. Each of these constitutes a means for binding CD40.

In some embodiments, the tLNP is targeted to CD44$^+$ cells and the binding moiety comprises the antigen binding domain of an anti-CD44 antibody. Accordingly, in some such embodiments, the antibody comprises RO5429083, VB6-008, PF-03475952, or RG7356, as well as those disclosed in WO2008144890, U.S. Pat. No. 8,383,117, WO2008079246, US20100040540, WO2015076425, U.S. Pat. No. 9,220,772, US20140308301, WO2020159754, WO2021160269, WO2021178896, WO2022022749, WO2022022720, or WO2022243838, each of which is incorporated by reference for all that they teach about anti-CD44 antibodies and their properties, or an antigen-binding portion thereof. Each of these constitutes a means for binding CD44.

In some embodiments, the tLNP is targeted to CD45$^+$ cells and the binding moiety comprises the antigen binding domain of an anti-CD45 antibody. Accordingly, in some such embodiments, the antibody comprises apamistamab, BC8-B10, as well as those disclosed in WO2023183927, WO2023235772, U.S. Pat. No. 7,825,222, WO2017009473, WO2021186056, U.S. Pat. Nos. 9,701,756, 9,701,756, WO2020092654, WO2022040088, WO2022040577, WO2022064191, WO2022063853, or WO2024064771, each of which is incorporated by reference for all that they teach about anti-CD45 antibodies and their properties, or an antigen-binding portion thereof. Each of these constitutes a means for binding CD45.

In some embodiments, the tLNP is targeted to CD56+ cells and the binding moiety comprises the antigen binding domain of an anti-CD56 antibody. Accordingly, in some such embodiments, the antibody comprises lorvotuzumab, adcitmer, or promiximab, as well as those disclosed in WO2012138537, U.S. Pat. Nos. 10,548,987, 10,730,941, or US20230144142, each of which is incorporated by reference for all that they teach about anti-CD56 antibodies and their properties, or an antigen-binding portion thereof. Each of these constitutes a means for binding CD56.

In some embodiments, the tLNP is targeted to CD64$^+$ cells and the binding moiety comprises the antigen binding domain of an anti-CD64 antibody. Accordingly, in some such embodiments, the antibody comprises HuMAb 611 or H22 as well as those disclosed in U.S. Pat. No. 7,378,504, WO2014083379, US20170166638, or WO2022155608 each of which is incorporated by reference for all that they teach about anti-CD64 antibodies and their properties, or an antigen-binding portion thereof. Each of these constitutes a means for binding CD64.

In some embodiments, the tLNP is targeted to CD68$^+$ cells and the binding moiety comprises the antigen binding domain of an anti-CD68 antibody. Accordingly, in some such embodiments, the antibody comprises Ki-M7, PG-M1, 514H12, ABM53F5, 3F7C6, 3F7D3, Y1/82A, EPR20545, CDLA68-1, LAMP4-824, or an antigen-binding portion thereof. Each of these constitutes a means for binding CD68.

In some embodiments, the tLNP is targeted to CD70$^+$ cells and the binding moiety comprises the antigen binding domain of an anti-CD70 antibody. Accordingly, in some such embodiments, the antibody comprises cusatuzumab, vorsetuzumab, MDX-1203, MDX-1411, AMG-172, SGN-CD70A, ARX305, PRO1160, as well as those disclosed in US9,765,148, US8,124,738, IS10,266,604, WO2021138264, US9,701,752, US10,108,123, WO2014158821, US10,689,456, WO2017062271, US11,046,775, US11,377,500, WO2021055437, WO2021245603, WO2022002019, WO2022078344, WO2022105914, WO2022143951, WO2023278520, WO2022226317, WO2022262101, US11,613,584, or WO2023072307, each of which is incorporated by reference for all that they teach about anti-CD70 antibodies and their properties, or an antigen-binding portion thereof. Each of these constitutes a means for binding CD70.

In some embodiments, the tLNP is targeted to CD73$^+$ cells and the binding moiety comprises the antigen binding domain of an anti-CD73 antibody. Accordingly, in some such embodiments, the antibody comprises oleclumab, uliledlimab, mupadolimab, AK119, IBI325, BMS-986179, NZV930, JAB-BX102, Sym024, TB19, TB38, HBM1007, 3F7, mAb19, Hu001-MMAE, IPH5301, or INCA00186, as well as those disclosed in US9,938,356, US10,584,169, WO2022083723, WO2022037531, WO2021213466, WO2022083049, US10,822,426, WO2021259199, US10,100,129, US11,312,783, US11,174,319, US11,634,500, WO2021138467, WO2017118613, US9,388,249, WO2020216697, US11,180,554, US11,530,273, WO2019173692, WO2019170131, US11,312,785, WO2020098599, WO2020143836, WO2020143710, US11,034,771, US11,299,550, WO2020253568, WO2021017892, WO2021032173, WO2021032173, WO2021097223, WO2021205383, WO2021227307, WO2021241729, WO2022096020, WO2022105881, WO2022179039, WO2022214677, or WO2022242758, each of which is incorporated by reference for all that they teach about anti-CD73 antibodies and their properties, or an antigen-binding portion thereof. Each of these constitutes a means for binding CD73.

In some embodiments, the tLNP is targeted to CD90$^+$ cells and the binding moiety comprises the antigen binding domain of an anti-CD90 antibody. Accordingly, in some such embodiments, the antibody comprises REA897, OX7, 5E10, K117, L127, or an antigen-binding portion thereof. Each of these constitutes a means for binding CD90.

In some embodiments, the tLNP is targeted to CD105$^+$ cells and the binding moiety comprises the antigen binding domain of an anti-CD105 antibody. Accordingly, in some such embodiments, the antibody comprises carotuximab, TRC205, or huRH105, as well as those disclosed in U.S. Pat. Nos. 8,221,753, 9,926,375, WO2010039873, WO2010032059, WO2012149412, WO2015118031, WO2021118955, US20220233591, or US20230075244, each of which is incorporated by reference for all that they teach about anti-CD105 antibodies and their properties, or an antigen-binding portion thereof. Each of these constitutes a means for binding CD105.

In some embodiments, the tLNP is targeted to CD117$^+$ cells and the binding moiety comprises the antigen binding domain of an anti-CD117 antibody. Accordingly, in some such embodiments, the antibody comprises briquilimab, barzolvolimab, CDX-0158, LOP628, MGTA-117, NN2101, CK6, JSP191, Ab85, 104D2, or SR1, as well as those disclosed in U.S. Pat. No. 7,915,391, WO2022159737, U.S. Pat. No. 9,540,443, WO2015050959, U.S. Pat. Nos. 9,789,203, 8,552,157, 10,406,179, 9,932,410, WO2019084067, WO2020219770, U.S. Pat. No. 10,611,838, WO2020076105, WO2021107566, U.S. Pat. No. 11,208,482, WO2021044008, WO2021099418, WO2022187050, or WO2023026791, WO2021188590, each of which is incorporated by reference for all that they teach about anti-CD117 antibodies and their properties, or an antigen-binding portion thereof. Each of these constitutes a means for binding CD117.

In some embodiments, the tLNP is targeted to CD133$^+$ cells and the binding moiety comprises the antigen binding domain of an anti-CD133 antibody. Accordingly, in some such embodiments, the antibody comprises AC133, 293C3, CMab-43, or RW03, as well as those disclosed in WO2018045880, U.S. Pat. Nos. 8,722,858, 9,249,225, WO2014128185, U.S. Pat. Nos. 10,711,068, 10,106,623, WO2018072025, or WO2022022718, each of which is incorporated by reference for all that they teach about anti-CD133 antibodies and their properties, or an antigen-binding portion thereof. Each of these constitutes a means for binding CD133.

In some embodiments, the tLNP is targeted to CD137$^+$ cells and the binding moiety comprises the antigen binding domain of an anti-CD137 antibody. CD137 is also known as 4-1BB. Accordingly, in some such embodiments, the antibody comprises YH004, urelumab (BMS-663513), utomilumab (PF-05082566), ADG106, LVGN6051, PRS-343, as well as those disclosed in WO2005035584, WO2012032433, WO2017123650, US11,203,643, US11,242,395, US11,555,077, US20230067770, US11,535,678, US11,440,966, WO2019092451, US10,174,122, US11,242,385, US10,716,851, WO2020011966, WO2020011964, or US11,447,558, each of which is incorporated by reference for all that they teach about CD137 antibodies and their properties, or an antigen-binding portion thereof. Each of these constitutes a means for binding CD137.

In some embodiments, the tLNP is targeted to CD146$^+$ cells and the binding moiety comprises the antigen binding domain of an anti-CD146 antibody. Accordingly, in some such embodiments, the antibody comprises imaprelimab, ABX-MA1, huAA98, M2H, or IM1-24-3, as well as those disclosed in US10,407,506, US10,414,825, US6,924,360, US9,447,190, WO2014000338, US9,782,500, WO2018220467, US11,427,648, WO2019133639, WO2019137309, WO2020132190, or WO2022082073, each of which is incorporated by reference for all that they teach about CD146 antibodies and their properties, or an antigen-binding portion thereof. Each of these constitutes a means for binding CD146.

In some embodiments, the tLNP is targeted to CD166$^+$ cells and the binding moiety comprises the antigen binding domain of an anti-CD166 antibody. Accordingly, in some such embodiments, the antibody comprises praluzatamab, AZN-L50, REA442, or AT002, as well as those disclosed in US10,745,481, US11,220,544, or WO2008117049, each of which is incorporated by reference for all that they teach about CD166 antibodies and their properties, or an antigen-binding portion thereof. Each of these constitutes a means for binding CD166.

In some embodiments, the tLNP is targeted to CD200$^+$ cells and the binding moiety comprises the antigen binding domain of an anti-CD200 antibody. Accordingly, in some such embodiments, the antibody comprises samalizumab, OX-104, REA1067, B7V3V2, HPAB-0260-YJ, or TTI-CD200, as well as those disclosed in WO2007084321 or WO2019126536, each of which is incorporated by reference for all that they teach about CD200 antibodies and their properties, or an antigen-binding portion thereof. Each of these constitutes a means for binding CD200.

In some embodiments, the tLNP is targeted to CD205$^+$ cells and the binding moiety comprises the antigen binding domain of an anti-CD205 antibody. CD205 is also known as DEC205. Accordingly, in some such embodiments, the antibody comprises 3G9-2D2 (a component of CDX-1401) or LY75_A1 (a component of MEN1309) as well as those disclosed in US8,236,318, US10,081,682, or US11,365,258, each of which is incorporated by reference for all that they teach about anti-CD205 antibodies and their properties, or an antigen-binding portion thereof. Each of these constitutes a means for binding CD205.

In some embodiments, the tLNP is targeted to CD271$^+$ cells and the binding moiety comprises the antigen binding domain of an anti-CD271 antibody. Accordingly, in some such embodiments, the antibody comprises REA844 or REAL709 as well as those disclosed in WO2022166802 which is incorporated by reference for all that it teaches about anti-CD271 antibodies and their properties, or an antigen-binding portion thereof. Each of these constitutes a means for binding CD271.

In some embodiments, the tLNP is targeted to BMPR2+ cells and the binding moiety comprises the antigen binding domain of an anti-BMPR2 antibody. Accordingly, in some such embodiments, the antibody comprises TAB-071CL (Creative Biolabs catalog no.) as well as those disclosed in U.S. Pat. No. 11,292,846 or WO2021174198, each of which is incorporated by reference for all that they teach about anti-BMPR2 antibodies and their properties, or an antigen-binding portion thereof. Each of these constitutes a means for binding BMPR2.

In some embodiments, the tLNP is targeted to CTLA-4+ cells and the binding moiety comprises the antigen binding domain of an anti-CTLA-4 antibody. Accordingly, in some such embodiments, the antibody comprises botensilimab, ipilimumab, nurulimab, quavonlimab, tremelimumab, zalifrelimab, ADG116, ADG126, ADU-1604, AGEN1181, BCD-145, BMS-986218, BMS-986249, BT-007, CS1002, GIGA-564, HBM4003, IBI310 JK08, JMW-3B3, JS007, KD6001, KN044, ONC-392, REGN4659, TG6050, XTX101, YH001, or an antigen-binding portion thereof. Each of these constitutes a means for binding CTLA-4.

In some embodiments, the tLNP is targeted to GD2+ cells and the binding moiety comprises the antigen binding domain of an anti-GD2 antibody. Accordingly, in some such embodiments, the antibody comprises dinutuximab, ganglidiximab, naxitamab, nivatrotamab, EMD 273063, hu14.18k322A, MORAb-028, 3F8BiAb, BCD-245, KM666, ATL301, Ektomab, as well as those disclosed in U.S. Pat. Nos. 9,777,068, 9,315,585, WO2004055056, U.S. Pat. Nos. 9,617,349, 9,493,740, US20210002384, U.S. Pat. No. 8,507,657, WO2001023573, WO2012071216, WO2018010846, U.S. Pat. No. 8,951,524, WO2023280880, U.S. Pat. No. 9,856,324, WO2015132604, WO2017055385, WO2019059771, WO2020020194, or an antigen-binding portion thereof. Each of these constitutes a means for binding GD2.

In some embodiments, the tLNP is targeted to GITR+ cells and the binding moiety comprises the antigen binding domain of an anti-GITR antibody. Accordingly, in some such embodiments, the antibody comprises ragifilimab, TRX518, MK-4166, AMG 228, MEDI1873, BMS-986156, REGN6569, ASP1951, MK-1248, FRA154, GWN323, JNJ-64164711, ATOR-1144, or an antigen-binding portion thereof. Each of these constitutes a means for binding GITR.

In some embodiments, the tLNP is targeted to low affinity IL-2 receptor+ cells (CD122+ and/or CD132+ cells) and the binding moiety comprises the antigen binding domain of an anti-IL-2 receptor antibody. Accordingly, in some such embodiments, the antiCD122 antibody comprises ANV419, FB102, MiK-Beta-1 and the anti CD122 antibodies disclosed in WO2011127324, WO2017021540, WO2022212848, WO2022221409, WO2023078113, US20230272090, WO2024073723, or an antigen-binding portion thereof. Accordingly, in some such embodiments, the anti-CD132 antibody comprises REGN7257 and the anti-CD132 antibodies disclosed in WO2020160242, WO2017021540, WO2022212848, WO2023078113, US20230272089, or an antigen-binding portion thereof. Each of these constitutes a means for binding the low affinity IL-2 receptor (CD122 or CD132, as appropriate), In some embodiments, the tLNP is targeted to high affinity IL-2 receptor+ cells (CD25+ and the binding moiety comprises the antigen binding domain of an anti-IL-2 receptor antibody. Accordingly, in some such embodiments, the antibody comprises daclizumab, basiliximab, camidanlumab, vopitug, inolimomab, HuMAx-TAC, Xenopax, STI-003, RA8, RTX-003, and the anti-CD25 antibodies disclosed in WO2023031403, WO2006108670, WO2019175223, WO2019175215, WO2019175226, WO2004045512, WO2022104009, WO2020102591, or an antigen-binding portion thereof. Each of these constitutes a means for binding the high affinity IL-2 receptor (CD25).

In some embodiments, the tLNP is targeted to IL-7 receptor+ (CD127+) cells and the binding moiety comprises the antigen binding domain of an anti-IL-7 receptor antibody. Accordingly, in some such embodiments, the antibody comprisesPF-06342674, GSK2618960, OSE-127, lusvertikimab, bempikibart, and the anti-CD127 antibodies disclosed in WO2011104687, WO2011094259, WO2013056984, WO2015189302, WO2017062748, WO2020154293, WO2020254827, WO2021222227, WO2023201316, or an antigen-binding portion thereof. Each of these constitutes a means for binding the CD127.

In some embodiments, the tLNP is targeted to IL-12 receptor+ cells and the binding moiety comprises the antigen binding domain of an anti-IL-12 receptor antibody. Accordingly, in some such embodiments, the antibody comprises CBYY-10413, REA333, or an antigen-binding portion thereof. Each of these constitutes a means for binding the IL-12 receptor.

In some embodiments, the tLNP is targeted to IL-15 receptor α+ cells and the binding moiety comprises the antigen binding domain of an anti-IL-15 receptor α antibody. Accordingly, in some such embodiments, the antibody comprises MAB1472-100, MAB5511, JM7A4, 5E3E1, JM7A4, 2639B, or an antigen-binding portion thereof. Each of these constitutes a means for binding the IL-15 receptor α.

In some embodiments, the tLNP is targeted to IL-18 receptor α+ cells and the binding moiety comprises the antigen binding domain of an anti-IL-18 receptor a antibody. Accordingly, in some such embodiments, the antibody comprises H44, or an antigen-binding portion thereof. Each of these constitutes a means for binding the IL-18 receptor α.

In some embodiments, the tLNP is targeted to IL-21 receptor+ cells and the binding moiety comprises the antigen binding domain of an anti-IL-21 receptor antibody. Accordingly, in some such embodiments, the antibody comprises 1D1C2, 19F5, 18A5, REA233, or an antigen-binding portion thereof. Each of these constitutes a means for binding the IL-21 receptor α.

In some embodiments, the tLNP is targeted to LAG-3+ cells and the binding moiety comprises the antigen binding domain of an anti-LAG-3 antibody. Accordingly, in some such embodiments, the antibody comprises relatlimab, tebotelimab, favezelimab, fianlimab, miptenalimab, HLX26, ieramilimab, GSK2831781, INCAGN2385, RO7247669, encelimab, FS118, SHR-1802, Sym022, IBI110, IBI323, bavunalimab, EMB-02, ABL501, INCA32459, AK129, or an antigen-binding portion thereof. Each of these constitutes a means for binding LAG-3.

In some embodiments, the tLNP is targeted to MSCA-1+ cells and the binding moiety comprises the antigen binding domain of an anti-MSCA-1 antibody. Accordingly, in some such embodiments, the antibody comprises REAL219, W8B2, X9C3, or an antigen-binding portion thereof. Each of these constitutes a means for binding MSCA-1.

In some embodiments, the tLNP is targeted to OX40+ cells and the binding moiety comprises the antigen binding domain of an anti-OX40 antibody. Accordingly, in some such embodiments, the antibody comprises MEDI6469, ivuxolimab, rocatinlimab, GSK3174998, BMS-986178, vonlerizumab, INCAGN1949, tavolimab, BGB-A445, INBRX-106, BAT6026, telazorlimab, ATOR-1015, MEDI6383, cudarolimab, FS120, HFB301001, EMB-09, HLX51, Hu222, ABM193, or an antigen-binding portion thereof. Each of these constitutes a means for binding OX40.

In some embodiments, the tLNP is targeted to PD-1+ cells and the binding moiety comprises the antigen binding domain of an anti-PD-1 antibody. Accordingly, in some such embodiments, the antibody comprises nivolumab, pembrolizumab, camrelizumab, torpalimab, sintilimab, tislelizumab, cemiplimab, spartalizumab, serplulimab, cadonilimab, penpulimab, dostarlimab, zimberelimab, retifanlimab, pucotenlimab, pidilizumab, pidilizumab, balstilimab, ezabenlimab, AK112, geptanolimab, cetrelimab, prolgolimab, tebotelimab, sasanlimab, SG001, vudalimab, MEDI5752, rulonilimab, peresolimab, IBI318, budigalimab, MEDI0680, pimivalimab, QL1706, AMG 404, RO7121661, lorigerlimab, nofazinlimab, sindelizumab, or an antigen-binding portion thereof. Each of these constitutes a means for binding PD-1.

In some embodiments, the tLNP is targeted to PODXL+ cells and the binding moiety comprises the antigen binding domain of an anti-PODXL antibody. Accordingly, in some such embodiments, the antibody comprises MAI1738, HPAB-3334LY, HPAB-MO612-YC, REA246, REA157, or an antigen-binding portion thereof. Each of these constitutes a means for binding PODXL.

In some embodiments, the tLNP is targeted to Sca-1+ cells and the binding moiety comprises the antigen binding domain of an anti-Sca-1 antibody. Accordingly, in some such embodiments, the antibody comprises CPP32 Apr. 1, 2018, 2D4-C9-F1, AMM22070N, or an antigen-binding portion thereof. Each of these constitutes a means for binding SCA-1.

In some embodiments, the tLNP is targeted to SSEA-3+ cells and the binding moiety comprises the antigen binding domain of an anti-SSEA-3 antibody. Accordingly, in some such embodiments, the antibody comprises MC631, 2A9, 8A7, ND-742, 3H420, as well as those disclosed in U.S. Pat. No. 11,643,456 or WO2021138378, each of which is incorporated by reference for all that they teach about anti-SSEA-3 antibodies and their properties, or an antigen-binding portion thereof. Each of these constitutes a means for binding SSEA-3.

In some embodiments, the tLNP is targeted to SSEA-4+ cells and the binding moiety comprises the antigen binding domain of an anti-SSEA-4 antibody. Accordingly, in some such embodiments, the antibody comprises ch28/11, REA101, MC-813-70, ND-942-80, as well as those disclosed in US11,446,379, US10,273,295, US11,643,456, WO2019190952, or WO2021044039, each of which is incorporated by reference for all that they teach about anti-SSEA-4 antibodies and their properties, or an antigen-binding portion thereof. Each of these constitutes a means for binding SSEA-4.

In some embodiments, the tLNP is targeted to Stro-1+ cells and the binding moiety comprises the antigen binding domain of an anti-Stro-1 antibody. Accordingly, in some such embodiments, the antibody comprises STRO-1, TUSP-2, as well as those disclosed in US20130122022, which is incorporated by reference for all that it teaches about anti-Stro-1 antibodies and their properties, or an antigen-binding portion thereof. Each of these constitutes a means for binding Stro-1.

In some embodiments, the tLNP is targeted to Stro-4+ cells and the binding moiety comprises the antigen binding domain of an anti-Stro-4 antibody. Accordingly, in some such embodiments, the antibody comprises STRO-4, efungumab, 4C5, as well as those disclosed in U.S. Pat. No. 7,722,869, US20110280881, U.S. Pat. Nos. 9,115,192, 10,273,294, 10,457,726, WO2023091148, each of which is incorporated by reference for all that they teach about anti-Stro-4 antibodies and their properties, or an antigen-binding portion thereof. Each of these constitutes a means for binding Stro-4 (also known as heat shock protein-90).

In some embodiments, the tLNP is targeted to SUSD2+ cells and the binding moiety comprises the antigen binding domain of an anti-SUSD2 antibody. Accordingly, in some such embodiments, the antibody comprises REA795, CBXS-3571, CBXS-1650, CBXS-1989, CBXS-1671, CBXS1990, CBXS-3676, 1279B, EPR8913 (2), W5C5, or an antigen-binding portion thereof. Each of these constitutes a means for binding SUSD2.

In some embodiments, the tLNP is targeted to TIM-3+ cells and the binding moiety comprises the antigen binding domain of an anti-TIM-3 antibody. Accordingly, in some such embodiments, the antibody comprises TQB2618, sabatolimab, cobolimab, RO7121661, INCAGN02390, AZD7789, surzebiclimab, LY3321367, Sym023, BMS-986258, SHR-1702, LY3415244, LB1410, or an antigen-binding portion thereof. Each of these constitutes a means for binding TIM-3.

In some embodiments, the tLNP is targeted to TREM2+ cells and the binding moiety comprises the antigen binding domain of an anti-TREM2 antibody. Accordingly, in some such embodiments, the antibody comprises PI37012 as well as those disclosed in U.S. Pat. Nos. 10,508,148, 10,676,525, WO2017058866, US11,186,636, 11,124,567, WO2020055975, US11,492,402, WO2020121195, WO2023012802, WO2021101823, WO2023047100, WO2022032293, WO2022241082, WO2023039450, or WO2023039612, each of which is incorporated by reference for all that they teach about anti-TREM2 antibodies and their properties, or an antigen-binding portion thereof. Each of these constitutes a means for binding TREM2.

In still further embodiments, the tLNP is targeted to a tumor cell. In some embodiments, the tumor cell expresses one of the antigens described above and the tLNP is targeted to antigen expressing tumors using the same means as described above. In other embodiments the tLNP is targeted to some other tumor antigen, such as those enumerated in U.S. Provisional Application No. 63/371,742, filed on Aug. 17, 2022, entitled CONDITIONING FOR IN VIVO IMMUNE CELL ENGINEERING which is incorporated by reference for all that it teaches about the delivery of nucleic acids into tumor cells using tLNP that is not inconsistent with the present disclosure.

Methods of Making an LNP or tLNP

In some aspects, the present disclosure provides a method of making a LNP or tLNP comprising mixing of an aqueous solution of a nucleic acid (or other negatively charged payload) and an alcoholic solution of the lipids in proportions disclosed herein. In particular embodiments, the mixing is rapid. The aqueous solution can be buffered at pH of about 3 to about 5, for example, without limitation, with citrate or acetate. In various embodiments, an alcohol can be ethanol, isopropanol, t-butanol, or a combination thereof. In some embodiments, the rapid mixing can be accomplished by pumping the two solutions through a T-junction or with an impinging jet mixer. Microfluidic mixing through a staggered herringbone mixer (SHM) or a hydrodynamic mixer (microfluidic hydrodynamic focusing), microfluidic bifurcating mixers, and microfluidic baffle mixers can also be used. After the LNPs are formed they can be diluted with buffer, for example phosphate, HEPES, or Tris, in a pH range of about 6 to about 8.5 to reduce the alcohol (ethanol) concentration. The diluted LNPs can be purified either by dialysis or ultrafiltration or diafiltration using tangential flow filtration (TFF) against a buffer in a pH range of about 6 to about 8.5 (for example, phosphate, HEPES, or Tris) to remove the alcohol. Alternatively, one can use size exclusion chromatography. Once the alcohol is completely removed the buffer can be exchanged with like buffer containing a cryoprotectant (for example, glycerol or a sugar such as sucrose, trehalose, or mannose). The LNPs can be concentrated to a desired concentration, followed by 0.2 μm filtration through, for example, a polyethersulfone (PES) or modified PES filter and filled into glass vials, stoppered, capped, and stored frozen. In alternative embodiments, a lyoprotectant can be used and the LNP lyophilized for storage instead of as a frozen liquid. Further methodologies for making LNP can be found, for example, in US20200297634, US20130115274, and WO2017/048770, each of which is incorporated by references for all that they teach about the production of LNP.

Some aspects are a method of making a tLNP comprising rapid mixing of an aqueous solution of a nucleic acid (or other negatively charged payload) and an alcoholic solution of the lipids as disclosed for LNP. In some embodiments, the lipid mixture includes functionalized PEG-lipid, for later conjugation to a targeting moiety. As used herein, functionalized PEG-lipid refers to a PEG-lipid in which the PEG moiety has been derivatized with a chemically reactive group (such as, maleimide, NHO ester, Cys, azide, alkyne, and the like) that can be used for conjugating a targeting moiety to the PEG-lipid, and thus, to the LNP comprising the PEG-lipid. In other embodiments, the functionalized PEG-lipid is inserted into an LNP subsequent to initial formation of an LNP from the other components. In either type of embodiment, the targeting moiety is conjugated to functionalized PEG-lipid after the functionalized PEG-lipid containing LNP is formed. Protocols for conjugation can be found, for example, in Example 1 as well as in Parhiz et al. *J. Controlled Release* 291:106-115, 2018, and Tombacz et al., *Molecular Therapy* 29 (11): 3293-3304, 2021, each of which is incorporated by reference for all that it teaches about conjugation of PEG-lipids to binding moieties. Alternatively, the targeting moiety can be conjugated to the PEG-lipid prior to insertion into pre-formed LNP In certain embodiments of the preparation methods of tLNP, the method comprises:
i) forming an initial LNP by mixing all components of the tLNP, in proportions disclosed herein, except for the one or more functionalized PEG-lipids and the one or more targeting moieties;
ii) forming a pre-conjugation tLNP by mixing the initial LNP with the one or more functionalized PEG-lipids; and
iii) forming the tLNP by conjugating the pre-conjugation tLNP with the one or more targeting moieties.

In certain embodiments of the preparation methods of tLNP, the method comprises:
i) forming a pre-conjugation tLNP by mixing all components of the tLNP, in proportions disclosed herein, including the one or more functionalized PEG-lipids, except for the one or more targeting moieties; and
ii) forming the tLNP by conjugating the pre-conjugation tLNP with the one or more targeting moieties.

In certain embodiments of the preparation methods of tLNP, the method comprises:
i) forming one or more conjugated functionalized PEG-lipids by conjugating the one or more functionalized PEG-lipids with the one or more targeting moieties; and
ii) forming the tLNP by mixing all components of the tLNP, in proportions disclosed herein, including the one or more conjugated functionalized PEG-lipids.

In certain embodiments of the preparation methods of tLNP, the method comprises:
i) forming one or more conjugated functionalized PEG-lipids by conjugating the one or more functionalized PEG-lipids with the one or more targeting moieties;
ii) forming an LNP by mixing all components of the tLNP, in proportions disclosed herein, except the one or more conjugated functionalized PEG-lipids; and
iii) forming the tLNP by mixing the initial LNP with the one or more conjugated functionalized PEG-lipids.

After the conjugation the tLNPs are purified by dialysis, tangential flow filtration, or size exclusion chromatography, and stored, as disclosed above for LNPs.

The encapsulation efficiency of the nucleic acid by the LNP or tLNP is typically determined with a nucleic acid binding fluorescent dye added to intact and lysed aliquots of the final LNP or tLNP preparation to determine the amounts of unencapsulated and total nucleic acid, respectively. Encapsulation efficiency is typically expressed as a percentage and calculated as $100\times(T-U)/T$ where T is the total amount of nucleic acid and U is the amount of unencapsulated nucleic acid. In various embodiments, the encapsulation efficiency is ≥80%, ≥85%, ≥90%, or ≥95%.

Methods of Delivering a Payload into a Cell

In some aspects, disclosed herein are methods of delivering a nucleic acid (or other negatively charged payload) into a cell comprising contacting the cell with tLNP of any of the foregoing aspects. Accordingly, each of the herein disclosed genera, subgenera, and or species of LNP or tLNP disclosed herein including those based on the inclusion or exclusion of particular lipids, particular lipid compositions, particular payloads, and/or particular targeting moieties can be used in defining the scope of the methods of delivering a payload to a cell. In some embodiments the contacting takes place ex vivo. In some embodiments, the contacting takes place in vivo. In some instances, the in vivo contacting comprises intravenous, intramuscular, subcutaneous, intranodal or intralymphatic administration. In further instances, transfection of hepatocytes is reduced as compared to tLNPs comprising a conventional ionizable cationic lipid, such as ALC-0315.

The herein disclosed LNP and tLNP compositions and formulations have reduced toxicity as compared to widely used prior LNP compositions such as those containing ALC-0315. In various embodiments the toxicity can be described as an observable toxicity, a substantial toxicity, a severe toxicity, or an acceptable toxicity, or a dose-limiting toxicity (such as but not limited to a maximum tolerated dose (MTD)). By an observable toxicity it is meant that while a change is observed the effect is negligible or mild. By substantial toxicity it is meant that there is a negative impact on the patient's overall health or quality of life. In some instances, a substantial toxicity may be mitigated or resolved with other ongoing medical intervention. By a severe toxicity it is meant that the effect requires acute medical intervention and/or dose reduction or suspension of treatment. The acceptability of a toxicity will be influenced by the particular disease being treated and its severity and the availability of mitigating medical intervention. In some embodiments, toxicity is confined (or largely confined) to an observable toxicity. In some embodiments, toxicity is confined (or largely confined) to grades of 0 or 1 or two.

In some embodiments, the payload is a nucleic acid and the method of delivering is a method of transfecting. In some embodiments, the nucleic acid payload comprises an mRNA, circular RNA, self-amplifying RNA, or guide RNA. Nucleic acid structures and especially mRNA structures, as well as individual RNA molecules encoding particular polypeptides, that are well-adapted to delivery by LNP or tLNP are disclosed in U.S. application Ser. No 18/934,237, filed on Nov. 1, 2024, which is incorporated by reference for all that it teaches about nucleic acid payloads for in vivo transfection and their design.

In some embodiments, the payload comprises a nucleic acid encoding an immune receptor or immune cell engager and the method of delivering is also a method of reprogramming an immune cell. In some embodiments, the payload comprises a nucleic acid that encodes, or is, a BRM and the method of delivering is also a method of providing a conditioning agent. In various embodiments, the BRM or conditioning agent is a gamma chain receptor cytokine such as IL-2, IL-7, IL-15, IL-15/15Ralpha, IL-21; an immune modulating cytokine such as IL-12, IL-18; a chemokine such as RANTES, IP10, MIG; or another BRM such as Flt3, GM-CSF, and G-CSF.

In some embodiments, the payload comprises a nucleic acid encoding a gene/genome editing enzyme and/or a guide RNA or other component of a gene/genome editing system and the method of delivering is also a method of reprogramming a cell. In some instances, the cell is an immune cell. In some instances, the cell is an HSC. In some instances, the cell is an MSC.

In certain embodiments comprising delivering the payload into an immune cell, the binding moiety binds to a lymphocyte surface molecule or a monocyte surface molecule. Lymphocyte surface molecules include CD2, CD3, CD4, CD5, CD7, CD8, CD28, 4-1BB (CD137), CD166, CTLA-4, OX40, PD-1, GITR, LAG-3, TIM-3, CD25, low affinity IL-2 receptor, IL-7 receptor, IL-12 receptor, IL-15 receptor, IL-18 receptor, and IL-21 receptor. Monocyte surface molecules include CD5, CD14, CD16a, CD32, CD40, CD11b (Mac-1), CD64, DEC205, CD68, and TREM2. Exemplary antibodies that can provide antigen binding domains to bind these surface molecules are disclosed herein above. Such antibodies, individually and collectively, constitute means for binding to an immune cell (or leukocyte)- or to a lymphocyte or monocyte, as indicated.

In certain embodiments comprising delivering the payload into a stem cell, the binding moiety binds to a HSC surface molecule or a MSC surface molecule. HSC surface molecules include CD117, CD34, CD44, CD90 (Thy1), CD105, CD133, BMPR2, and Sca-1. MSC surface molecules include CD70, CD105, CD73, Stro-1, SSEA-4, CD271, CD146, GD2, SSEA-3, SUSD2, Stro-4, MSCA-1, CD56, CD200, PODXL, CD13, CD29, CD44, and CD10. Exemplary antibodies that can provide antigen binding domains to bind these surface molecules are disclosed herein above. Such antibodies, individually and collectively, constitute means for binding to a stem cell- or to an HSC or MSC, as indicated.

Methods of Treatment

In certain aspects, this disclosure provides methods of treating a disease or disorder comprising administering a tLNP of this disclosure to a subject in need thereof. Each of the herein disclosed genera, subgenera, and or species of LNP or tLNP disclosed herein including those based on the inclusion or exclusion of particular lipids, particular lipid compositions, particular payloads, and/or particular targeting moieties can be used in defining the scope of the methods of treatment.

In some embodiments, a subject is a human. In some embodiments, a tLNP is administered systemically. In some embodiments, a tLNP is administered by intravenous or subcutaneous infusion or injection. In some embodiments, a tLNP is administered locally. In some embodiments, a tLNP is administered by intraperitoneal or intralesional infusion injection.

In further embodiments, a tLNP may be administered in combination with the standard of care for a particular indication, such as corticosteroids (e.g., prednisone) for management of myositis or lupus nephritis. In certain cases, myositis is also treated with methotrexate, which may be combined with immunosuppressive agents (e.g., azathioprine, mycophenolate mofetil, tacrolimus), which are usually required in addition to corticosteroids. For membranous nephropathy, cyclical steroids and cyclophosphamide might be used in combination with tLNPs of this disclosure. In other cases, an anti-IL-6, such as tocilizumab, may also be used as a pretreatment or in combination with tLNPs of this disclosure. These combinations may be administered concurrently or sequentially.

In some embodiments, the disease or disorder is an autoimmune disease. Examples of autoimmune disease include, without limitation, myocarditis, acute idiopathic thrombocytopenic purpura, chronic idiopathic thrombocytopenia purpura, dermatomyositis, Sydenham's chorea, myasthenia gravis, systemic lupus erythematosus, fibrosing alveolitis, multiple sclerosis, rheumatic fever, polyglandular syndromes, agranulocytosis, autoimmune hemolytic anemias, bullous pemphigoid, Wegener's granulomatosis, membranous nephropathy, amyotrophic lateral sclerosis, tabes dorsalis, giant cell arteritis/polymyalgia, pernicious anemia, rapidly progressive glomerulonephritis, IgA nephropathy, polyarteritis nodosa, ankylosing spondylitis, allergic responses, insulin-resistant diabetes, psoriasis, diabetes mellitus, Addison's disease, Grave's disease, diabetes, endometriosis, celiac disease, Crohn's disease, Henoch-Schonlein purpura, ulcerative colitis, Goodpasture's syndrome, thromboangitisubiterans, Sjögren's syndrome, aplastic anemia, rheumatoid arthritis, sarcoidosis, scleritis, a T cell-mediated autoimmunity or a B cell-mediated autoimmunity, a B cell-mediated (antibody-mediated) autoimmune disease, necrotizing myopathy, chronic inflammatory demyelinating polyneuropathy (CIDP), neuromyelitis optica (NMO) myositis, neuromyelitis optica spectrum disorders, pemphigus vulgaris, systemic sclerosis, antisynthetase syndrome (idiopathic inflammatory myopathy), lupus nephritis, membranous nephropathy, Fanconi anemia, and vasculitis.

In some embodiments, the autoimmune disease is a T cell-mediated autoimmunity or a B cell-mediated autoimmunity. In some instances, the B cell-mediated autoimmune disease is myositis (such as anti-synthetase myositis), lupus nephritis, membranous nephropathy, systemic lupus erythematosus, anti-neutrophilic cytoplasmic antibody (ANCA) vasculitis, neuromyelitis optica spectrum disorder (NMOSD), myasthenia gravis, pemphigus vulgaris, rheumatoid arthritis, dermatomyositis, immune mediated necrotizing myopathy, anti-synthetase syndrome, polymyositis, systemic sclerosis, diffuse cutaneous systemic sclerosis, limited cutaneous systemic sclerosis, anti-synthetase syndrome (idiopathic inflammatory myopathy), multiple sclerosis, relapsing-remitting multiple sclerosis, secondary progressive multiple sclerosis, primary progressive multiple sclerosis, non-active secondary progressive multiple sclerosis, Sjörgen's syndrome, IgA nephropathy, or Fanconi anemia. In certain embodiments, the B cell-mediated autoimmune disease is myositis, lupus nephritis, membranous neuropathy, scleroderma, systemic lupus erythematosus, myasthenia gravis, ANCA vasculitis, multiple sclerosis, or pemphigus vulgaris. In certain embodiments, the B cell-mediated autoimmune disease is myositis, lupus nephritis, membranous neuropathy, or scleroderma. In certain embodiments, the B cell-mediated autoimmune disease is myositis. In some instances, the myositis is anti-synthetase myositis. In certain embodiments, the B cell-mediated autoimmune disease is systemic lupus erythematosus, myasthenia gravis, ANCA vasculitis, multiple sclerosis, or pemphigus vulgaris.

In some embodiments, the disease or disorder is rejection of an allogeneic organ or tissue graft. Pre-existing antibodies and/or B cells, in their role as antigen presenting cells, can facilitate rapid immune rejection through known mechanisms hence depleting a large number of B cells may help prevent allograft rejection.

In some embodiments, the disease or disorder is a cancer. Examples of cancers include, without limitation, carcinomas, sarcomas, and hematologic cancers. In some embodiments, the hematologic cancer is a lymphoma, leukemia, or myeloma. In some instances, the hematologic cancer is a B lineage or T lineage cancer. In some instances, the B lineage cancer is multiple myeloma, diffuse large B cell lymphoma, acute myeloid leukemia, Mantle Cell lymphoma, follicular lymphoma, B acute lymphoblastic leukemia, chronic lymphocytic leukemia, or myelodysplastic syndrome. In some embodiments, the cancer is a sarcoma. In some embodiments, the cancer is a carcinoma, such as breast cancer, colon cancer, ovarian cancer, lung cancer, testicular cancer, or pancreatic cancer. In some embodiments, the cancer is melanoma.

In some embodiments, the disease or disorder is a genetic disease or disorder such as a monogenic genetic disease. In some instances, the genetic disease or disorder is a hemoglobinopathy, for example, sickle cell disease or B-thalassemia.

In some embodiments, the disease or disorder is a fibrotic disease or disorder. In some instances, the fibrotic disease is cardiac fibrosis, arthritis, idiopathic pulmonary fibrosis, and nonalcoholic steatohepatitis (also known as metabolic dysfunction-associated steatohepatitis). In other instances, the disorder involves tumor-associated fibroblasts.

In some embodiments, a tLNP of this disclosure comprises a nucleic acid encoding a chimeric antigen receptor (CAR). The receptors are chimeric because they combine both antigen-binding and T cell activating functions into a single receptor. In some embodiments, a nucleic acid encoding a CAR refers to one or more nucleic acid species encoding one or more CARs; for example, a single or multiple species of nucleic acid encoding a single CAR species, or multiple species of nucleic acid encoding multiple CAR species. In some instances, these multiple CAR species have a same specificity while in other instances they have multiple specificities. In some embodiments, a CAR of this disclosure is multispecific, for example, bispecific, comprising multiple antigen binding moieties each specific for separate antigens. In some embodiments, a CAR may comprise an extracellular binding domain that specifically binds a target antigen, a transmembrane domain, and one or more intracellular signaling domains. In some embodiments, a CAR may further comprise one or more additional elements, including one or more signal peptides, one or more extracellular hinge domains, or one or more intracellular costimulatory domains. Domains may be directly adjacent to one another, or there may be one or more amino acids linking the domains. The signal peptide can be derived from an antibody, a TCR, CD8 or other type 1 membrane proteins, preferably a protein expressed in a T or other immune cell. The transmembrane domain can be one associated with any of the potential intracellular domains or from another type 1 membrane protein, such as TCR alpha, beta, or zeta chain, CD3 epsilon, CD4, CD8, or CD28, amongst other possibilities known in the art. The transmembrane domain can further comprise a hinge domain located between the extracellular binding domain and the hydrophobic membrane-spanning region of the transmembrane domain. In some but not all embodiments, the hinge domain and transmembrane domain are contiguous sequences in the same source protein. In some instances, the hinge and membrane-spanning domains are derived from CD28. In other instances, the hinge and membrane-spanning domains are derived from CD8a. The intracellular signaling domain can be derived from the CD3 zeta chain, DAP10, DAP12, FcγRIII, FcsRI, or an immunoreceptor tyrosine-based activation motif (ITAM) bearing cytoplasmic domain, amongst other possibilities known in the art. The intracellular costimulatory domain can be derived from CD27, CD28, 4-1BB, OX40, or ICOS, amongst other possibilities known in the art.

In certain embodiments, CARs are used to treat a disease or condition associated with a target cell that expresses the antigen targeted by the CAR. For example, in some embodiments, an anti-CD19 or anti-CD20 CAR can be used to target and treat B cell malignancies or B cell-mediated autoimmune conditions or diseases (e.g., having an immune cell targeting moiety, such as an anti-CD8 antibody). In other embodiments, an anti-FAP CAR can be used to target and treat solid tumors or fibrosis (e.g., cardiac fibrosis, cancer-associated fibroblasts), which can also have an immune cell targeting moiety, such as an anti-CD8 antibody. Examples of CARs that may be used in accordance with the embodiments described herein include to those disclosed in U.S. Pat. No. 7,446,190 (anti-CD19), US 10,287,35 (anti-CD19), US2021/0363245 (anti-CD19 and anti-CD20), U.S. Pat. No. 10,543,263 (anti-CD22), U.S. Pat. No. 10,426,797 (anti-CD33), U.S. Pat. No. 10,844,128 (anti-CD123), U.S. Pat. No. 10,428,141 (anti-ROR1), and US2021/0087295 (anti-FAP), each of which is incorporated by reference for all that it teaches about CAR structure and function generically and with respect to the CAR's antigenic specificity and target indications to the extent that it is not inconsistent with the present disclosure.

Exemplary target antigens against which a CAR, TCR, or ICE can have specificity include, but are not limited to, B cell maturation agent (BCMA)†‡, CA9†‡, CD†‡, CD19*†‡, CD20 (MS4A1)*†‡, CD22*†‡, CD23*†‡, CD30 (TNFRSF8)*†‡, CD33*†‡, CD38*†‡, CD44*‡, CD70*†‡, CD133‡, CD174, CD274 (PD-L1)*†‡, CD276 (B7-H3)†‡, CEACAM5*†‡, CLL1‡, CSPG4*‡, EGFR*†‡, EGFRvlll*, EPCAM*†‡, EPHA2*‡, ERBB2*‡, FAP*†‡, FOLH1, FOLR1*†‡, GD2*†‡, GPC3*†‡, GPNMB*‡, IL1RAP†‡, IL3RA*‡, IL13RA2*‡, Kappa*, KDR (VEGFR2)*‡, CD171 (L1CAM)*‡, Lambda*, MET*‡, MSLN (mesothelin)*†‡, MUC1*†‡, NCAM1 (CD56)*‡, PD-1 (CD279)†‡, PSCA‡, ROR1†‡, CD138 (SDC1)*‡, CD319 (SLAMF7)*†‡, CD248 (TEM1)‡, ULBP1, ULBP2, and G-protein coupled receptor family C group 5 member D (GPRC5D)†‡ (associated with leukemias); CD319 (SLAMF7)*†‡, CD38*†‡, CD138†‡, GPRC5D†‡, CD267 (TACI)‡, and BCMA†‡ (associated with myelomas); and GD2*†‡, HER2*†‡, EGFR*‡, EGFRvlll*, CD276 (B7H3)†‡, PSMA*†‡, PSCA‡, CAIX (CA9)†‡, CD171 (L1-CAM)*‡, CEA*‡, CSPG4*‡, EPHA2*‡, FAP*†‡, LRRC15†‡, FOLR1*†‡, IL-13Ra*†‡, Mesothelin*†‡, MUC1*†‡, MUC16*†‡, and ROR1†‡ (associated with solid tumors). (* indicates that exemplary antibodies with the indicated specificity from which a binding moiety could be derived can be found in U.S. Pat. No. 11,326,182B2 Table 9 or 10. † indicates that exemplary antibodies with the indicated specificity from which a binding moiety could be derived can be found in Wilkinson & Hale, 2022. Both references cited and incorporated by reference above. ‡ indicates that exemplary antibodies with the indicated specificity from which a binding moiety could be derived can be found in the Therapeutic Antibody Database (TABS) at tabs.craic.com). Other suitable antibodies can be found in Appendix A.) Many of these target antigens are themselves receptors that could bind to their ligand if expressed on an immune cell. Accordingly, in some embodiments, the extracellular binding domain of the CAR comprises a ligand of a receptor expressed on the target cell. In still further embodiments, the extracellular binding domain of the CAR comprises a ligand binding domain of a receptor for a ligand expressed on the target cell. The advantages of the aspects and embodiments disclosed herein are independent of the specificity of the binding moiety. As such, the disclosed aspects and embodiments are generally agnostic to binding specificity. In certain embodiments, a particular binding specificity can be required.

In some embodiments, the tLNP comprises a nucleic acid encoding an anti-CD19 chimeric antigen receptor (CAR). In some embodiments, the nucleic acid comprises mRNA. Examples of anti-CD19 CARs include those incorporating a CD19 binding moiety derived from the human antibody 47G4 or the mouse antibody FMC63. FMC63 and the derived scFv have been described in Nicholson et al., Mol. Immun. 34 (16-17): 1157-1165 (1997) and PCT Application Publication Nos. WO 2018/213337 and WO 2015/187528, the entire contents of each of which are incorporated by reference herein for all that they teach about anti-CD19 CARs and their use. CAR based on 47G4 are disclosed in U.S. Pat. No. 10,287,350 which is incorporated by reference herein for all that it teaches about anti-CD19 CARs and their use. In some instances, the anti-CD19 CAR is the CAR found in tisagenlecleucel, lisocabtagene maraleucel, axicabtagene ciloleucel, or brexucabtagene autoleucel. The entire contents of each of foregoing references in this paragraph are incorporated by reference for all that they teach about the design, structure, and activity of anti-CD19 CARs. In any of the aforementioned tLNP embodiments, certain embodiments include tLNPs encapsulating a CD19 CAR payload encoded by RNA and having a T cell targeting moiety, such as an anti-CD8 antibody.

In some embodiments, the tLNP comprises a nucleic acid encoding an anti-CD20 chimeric antigen receptor (CAR). CD20 is an antigen found on the surface of B cells as early as the pro-B phase and progressively at increasing levels until B cell maturity, as well as on the cells of most B-cell neoplasms. CD20 positive cells are also sometimes found in cases of Hodgkin's disease, myeloma, and thymoma. In some embodiments, the nucleic acid comprises mRNA. Examples of anti-CD20 CARs include those incorporating a CD20 binding moiety derived from an antibody specific to CD20, including, for example, Leu16, IF5, 1.5.3, rituximab, obinutuzumab, ibritumomab, ofatumumab, tositumomab, odronextamab, veltuzumab, ublituximab, and ocrelizumab. In some embodiments, the anti-CD20 CAR is derived from a CAR specific to CD20, including, for example, MB-106 (Fred Hutchinson Cancer Research Center, see Shadman et al., Blood 134 (Suppl. 1): 3235 (2019)) UCART20 (Cellectis, www.cellbiomedgroup.com), or C-CAR066 (Cellular Biomedicine Group, see Liang et al., J. Clin. Oncol. 39 (15) suppl: 2508 (2021)). In some embodiments, the extracellular binding domain of the anti-CD20 CAR comprises an scFv derived from the Leu16 monoclonal antibody, which comprises the heavy chain variable region ($V_H$) and the light chain variable region ($V_L$) of Leu16 connected by a linker. See Wu et al., Protein Engineering. 14 (12): 1025-1033 (2001). The entire contents of each of foregoing references in this paragraph are incorporated by reference for all that they teach about the design, structure, and activity of anti-CD20 CARs. In any of the aforementioned tLNP embodiments, certain embodiments include tLNPs encapsulating a CD20 CAR payload encoded by RNA and having a T cell targeting moiety, such as an anti-CD8 antibody.

In some embodiments, the tLNP comprises a nucleic acid encoding an anti-BCMA chimeric antigen receptor (CAR). BCMA is a tumor necrosis family receptor (TNFR) member expressed on cells of the B cell lineage, with the highest expression on terminally differentiated B cells or mature B lymphocytes. BCMA is involved in mediating the survival of plasma cells for maintaining long-term humoral immunity. The expression of BCMA has been recently linked to a number of cancers, such as multiple myeloma, Hodgkin's and non-Hodgkin's lymphoma, various leukemias, and glioblastoma. In some embodiments, the nucleic acid comprises mRNA. Examples of anti-BCMA CARs include those incorporating a BCMA binding moiety derived from C11D5.3, a Mouse monoclonal antibody as described in Carpenter et al., Clin. Cancer Res. 19 (8): 2048-2060 (2013). See also PCT Application Publication No. WO 2010/104949. In some embodiments, the extracellular binding domain of the BCMA CAR comprises an scFv derived from another Mouse monoclonal antibody, C12A3.2, as described in Carpenter et al., Clin. Cancer Res. 19 (8): 2048-2060 (2013) and PCT Application Publication No. WO2010104949. In some embodiments, the extracellular binding domain of the BCMA CAR comprises an scFv derived from a Mouse monoclonal antibody with high specificity to human BCMA, referred to as BB2121 in Friedman et al., Hum. Gene Ther. 29 (5): 585-601 (2018). See also, PCT Application Publication No. WO2012163805. In some embodiments, the extracellular binding domain of the BCMA CAR comprises single variable fragments of two heavy chains (VHH) that can bind to two epitopes of BCMA as described in Zhao et al., J. Hematol. Oncol. 11 (1): 141 (2018), also referred to as LCAR-B38M. See also, PCT Application Publication No. WO 2018/028647. In some embodiments, the extracellular binding domain of the BCMA CAR comprises a fully human heavy-chain variable domain (FHVH) as described in Lam et al., Nat. Commun. 11 (1): 283 (2020), also referred to as FHVH33. See also, PCT Application Publication No. WO 2019/006072. In some embodiments, the extracellular binding domain of the BCMA CAR comprises an scFv derived from CT103A (or CAR0085) as described in U.S. Pat. No. 11,026,975 B2. Further anti-BCMA CARs are disclosed in U.S. Application Publication Nos. 2020/0246381 and 2020/0339699. Further anti-BCMA CARs include Allo-605 (described in U.S. Patent Publication No. 20200261503), CT053 (described in U.S. Patent No. U.S. Pat. No. 11,525, 006), Descartes-08 (described in U.S. Pat. No. 10,934,337), LCAR-B38M (described in U.S. Pat. No. 10,934,363), PersonGen anti-BCMA CAR (described in CN114763383), Pregene Bio anti-BCMA CAR (described in U.S. Patent Publication No. US20220218746), the CAR in ciltacabtagene autoleucel (binding moiety described in US20170051068), and the CAR in idecabtagene vicleucel (described in U.S. Pat. No. 10,383,929). Further antibodies comprising an anti-BCMA antigen binding domains that can be used in construction a CAR include AMG224 (described with other anti-BCMA antibodies in U.S. Pat. No. 9,243,058), EMB-06 (described with other anti-BCMA antibodies in U.S. Patent Publication No. US20230002489), HPN217 (described in U.S. Pat. No. 11,136,403), MEDI2228 (described in U.S. Pat. No. 10,988,546), REGN5459 (described in U.S. Pat. No. 11,384,153), SAR445514 (described in U.S. Patent Publication No. 20240034816), SEA-BCMA (described in U.S. Pat. No. 11,078,291), TNB-383B (described in U.S. Pat. No. 11,505,606), TQB2934 (described in U.S. Patent Publication No. 20230193292), WV078 (described in U.S. Pat. No. 11,492,409), alnuctamab (described in U.S. Pat. No. 10,683,369), belantamab (described in U.S. Pat. No. 9,273,141), elranatamab (described in U.S. Pat. No. 11,814,435), ispectamab (described in U.S. Patent Publication No. 20210130483), linvoseltamab (described in U.S. Pat. No. 11,919,965), pavurutamab (described in U.S. Pat. No. 11,419,933), and teclistamab (described in U.S. Pat. No. 10,072,088). The entire contents of each of foregoing references in this paragraph are incorporated by reference for all that they teach about the design, structure, and activity of anti-BCMA CARs and anti-BCMA antibodies that can provide an antigen binding domain for a CAR or immune cell engager. In any of the aforementioned tLNP embodiments, certain embodiments include tLNPs encapsulating a BCMA CAR payload encoded by RNA and having a T cell targeting moiety, such as an anti-CD8 antibody.

Cellular therapy involving the administration of genetically engineered cells to a patient has generally required depleting or ablative conditioning to facilitate engraftment of the engineered cells (for example, T cells or HSC). In the context of in vivo engineering and reprogramming such conditioning would be counterproductive as the conditioning would eliminate the very cells that are to be engineered. Instead, one can utilize activating and/or adjuvant conditioning to increase the number of cells amenable to engineering, to mobilize them to the locus of pathology, to make the locus of pathology (for example, a tumor microenvironment) more susceptible to treatment, to augment the therapeutic effect, etc., as appropriate for the particular disease and primary treatment. Conditioning agents include biological response modifiers (BRMs) that can be delivered directly to a subject or encoded in nucleic acid molecules, including as mRNA, and delivered to a subject using the LNP and tLNP compositions and formulations disclosed herein.

Accordingly, certain aspects are methods of conditioning a subject who receives an engineering agent comprising providing a tLNP comprising a nucleic acid molecule encoding a conditioning agent to the subject prior to, concurrently with, or subsequent to administration of the engineering agent. In various embodiments, an encoded conditioning agent comprises a y-chain receptor agonist, an inflammatory chemokine, a pan-activating cytokine, an antigen presenting cell activity enhancer, an immune checkpoint inhibitor, or an anti-CCR4 antibody. In some embodiments, the y-chain receptor cytokine comprises IL-15, IL-2, IL-7, or IL-21. In some embodiments, the immune checkpoint inhibitor comprises an anti-CTLA-4, anti-PD-1, anti-PD-L1, anti-Tim-3, or anti-LAG-3 antibody. In some embodiments, the inflammatory chemokine comprises CCL2, CCL3, CCL4, CCL5, CCL11, CXCL1, CXCL2, CXCL-8, CXCL9, CXCL10, or CXCL11. In some embodiments, the antigen presenting cell activity enhancer comprises Flt-3 ligand, gm-CSF, or IL-18. In some embodiments, a pan-activating cytokine comprises IL-12 of IL 18. In certain embodiments, a conditioning agent comprises a transcription factor, for example, one selected from the group consisting of nuclear factor of activated T-cells (NFAT), NF-κB, T-bet, signal transducer and activator of transcription 4 (STAT4), Blimp-1, c-Jun, and Eomesodermin (Eomes) and the tLNP is targeted to a T cell. In some embodiments, a tLNP encapsulating the nucleic acid-encoded conditioning agent is administered systemically, for example, by intravenous or subcutaneous infusion or injection. In other embodiments, the tLNP is administered locally, for example, by intralesional or intraperitoneal injection or infusion. In some embodiments, nucleic acid molecules encoding the conditioning agent and the engineering agent are encapsulated in the same tLNP while in other embodiments they are encapsulated in separate tLNPs. These two modes of delivery of conditioning agents are described in greater detail in PCT application PCT/US 2023/072426 which is incorporated by reference for all that it teaches about conditioning agents and their delivery of LNPs or tLNPs that is not inconsistent with the present disclosure. In some embodiments, the nucleic acid comprises mRNA.

The term "treating" or "treatment" broadly includes any kind of treatment activity, including the mitigation, cure or prevention of disease, or aspect thereof, in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like, that are then acted upon by any other person including other healthcare professionals or the patient him/herself. In some embodiments, the orders, instructions, and advice aspect of treatment activity can also include encouraging, inducing, or mandating that a particular medicament, or combination thereof, be chosen for treatment of a condition—and the medicament is actually used-by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used —by a policy or practice standard as might be established by a hospital, clinic, health maintenance organization, medical practice or physicians group, and the like. All such orders, instructions, and advice are to be seen as conditioning receipt of the benefit of the treatment on compliance with the instruction. In some instances, a financial benefit is also received by the patient for compliance with such orders, instructions, and advice. In some instances, a financial benefit is also received by the healthcare professional for compliance with such orders, instructions, and advice.

Some embodiments of these methods of treatment comprise administration of an effective amount of a compound or a composition disclosed herein. Some instances relate to a therapeutically (or prophylactically) effective amount. A therapeutically effective amount is not necessarily a clinically effective amount, that is, while there can be therapeutic benefit as compared to no treatment, a method of treatment may not be equivalent or superior to a standard of care treatment existing at some point in time. Other instances relate to a pharmacologically effective amount, that is an amount or dose that produces an effect that correlates with or is reasonably predictive of therapeutic (or prophylactic) utility. As used herein, the term "therapeutically effective amount" is synonymous with "therapeutically effective dose" and means at least the minimum dose of a compound or composition disclosed herein necessary to achieve the desired therapeutic or prophylactic effect. Similarly, a pharmacologically effective dose means at least the minimum dose of a compound or composition disclosed herein necessary to achieve the desired pharmacologic effect. Some embodiments refer to an amount sufficient to prevent or disrupt a disease process, or to reduce the extent or duration of pathology. Some embodiments refer to a dose sufficient to reduce a symptom associated with the disease or condition being treated. An effective dosage or amount of a compound or a composition disclosed herein can readily be determined by the person of ordinary skill in the art considering all criteria (for example, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof) and utilizing his best judgment on the individual's behalf. Exemplary dosages are also disclosed in the Examples herein below.

Tolerability

Conventional LNPs deliver primarily to the liver. Liver toxicity has been the major dose limiting parameter observed with LNP-containing pharmaceuticals. For example, ONPATTRO®, comprising the ionizable lipid MC3, has a NOAEL (no observed adverse effect level) of only 0.3 mg/kg for multiple dosing in rats. A benchmark LNP comprising the ionizable cationic lipid ALC-0315, used in the SARS-COV-2 vaccine COMIRNATY®, causes elevated levels of liver enzymes and acute phase proteins at single doses of ≥1 mg/kg in the rat. Merely attaching an antibody to the benchmark LNP partially reverses that elevation and the reversal is greater if the antibody directs the LNP to some other tissue (that is, a tLNP). However, use of an ionizable cationic lipid disclosed herein reduced delivery to the liver and associated liver enzyme and acute phase protein levels to a greater extent for LNP, antibody-conjugated LNP, and tLNP. tLNP compositions comprising CICL1 were generally well tolerated in both rat and non-human primate (NHP) at single doses of up to at least 3 mg/kg.

Examples

The following examples are intended to illustrate various embodiments of the invention. As such, the specific embodiments discussed are not to be constructed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein, to the extent that they do not contradict or are not inconsistent with this disclosure. Some examples make use of donor material and donors are numbered separately in each Example so that Donor 1 in one Example is not necessarily the same as Donor 1 or different than Donor 2 of another Example, unless explicitly stated otherwise.

Example 1: Establishing Benchmarks

There is relatively little experience in the field with tLNP and much of that relying on compositions and formulations developed for untargeted LNP. A first step in obtaining superior performance is establishing a baseline from which improvement of one or another parameter might be judged. One of the major determinants of an LNP's encapsulation efficiency and transfection efficiency is the cationic lipid used. Accordingly, tLNP incorporating CICL1 in a basic lipid composition plus a functionalized PEG-lipid was compared to tLNPs comprising one of seven ionizable cationic lipids known in the art in the same lipid composition. The payload was a CleanCap® mCherry 5-methoxyuridine (5moU) mRNA encoding the fluorescent protein mCherry (Trilink).

The ionizable cationic lipids used for benchmarking included [(4-Hydroxybutyl) azanediyl]di(hexane-6,1-diyl) bis(2-hexyldecanoate) (ALC-0315), 8-[(2-hydroxyethyl) [6-oxo-6-(undecyloxy) hexyl]amino]-octanoic acid, 1-octylnonyl ester (SM-102), (6Z,9Z,28Z,31Z)-Heptatriaconta-6,9,28,31-tetraen-19-yl 4-(dimethylamino) butanoate (MC-3), each of which is a component of an FDA-approved product, and bis(2-butyloctyl) 10-(N-(3-(dimethylamino) propyl) nonanamido) nonadecanedioate (Lipid A9). The ionizable cationic lipids 10a, 10f, and 10p were also used. They are described in *J. Med. Chem.* 63:12992-13012, 2020 which is incorporated by reference for all that it teaches about the structure and properties of these lipids.

The common lipid composition in this experiment was ionizable cationic lipid: DSPC: cholesterol: DMG-PEG-2000: DSPE-PEG-2000-maleimide in a ratio of 50:10:38.5:1.4:0.1. The terminal group of the non-functionalized PEG was methoxy throughout the Examples unless stated otherwise. The N/P ratio (the ratio of positively-chargeable lipid amine (N=nitrogen) groups to negatively-charged nucleic acid phosphate (P) groups) was 6. After initial LNP formation a SATA-modified anti-CD5 antibody was reacted with the maleimide moiety to provide the final tLNP.

The mRNA was encapsulated in LNP incorporating the DSPE-PEG-2000-maleimide using a self-assembly process in which an aqueous solution of mRNA at pH=3.5 was rapidly mixed with a solution of the lipids dissolved in ethanol, then followed by stepwise phosphate and Tris buffer dilution and tangential flow filtration (TFF) purification. LNPs were stored at 4° C. until conjugation. Next, the anti-CD5 mAb was conjugated to the above LNP to generate tLNP. Purified rat anti-mouse CD5 antibody, clone 53-7.3 (BioLegend), was coupled to LNP via N-succinimidyl S-acetylthioacetate (SATA)-maleimide conjugation chemistry. The antibody was modified with SATA (Sigma-Aldrich) to introduce sulfhydryl groups at accessible lysine residues allowing conjugation to maleimide. SATA was deprotected using 0.5 M hydroxylamine followed by removal of the unreacted components by G-25 Sephadex Quick Spin Protein columns (Roche Applied Science, Indianapolis, IN). The reactive sulfhydryl group on the antibody was then conjugated to maleimide moieties on the LNPs using thio-ether conjugation chemistry. Purification was performed using Sepharose CL-4B gel filtration columns (Sigma-Aldrich). tLNPs (LNPs conjugated with a targeting antibody)

were frozen at −80° C. Others had conjugated antibody to free functionalized PEG-lipid and then incorporated the conjugated lipid into pre-formed LNP. However, the procedure disclosed herein was more controllable and produced more consistent results.

The particle size (hydrodynamic diameter) and polydispersity index of the targeted lipid nanoparticles were determined using dynamic light scattering (DLS) on a Malvern Zetasizer Nano ZS (Malvern Instruments, Worcestershire, UK). Size measurement was carried out in pH 7.4 Tris buffer at 25° C. in disposable capillary cells. A non-invasive back scatter system (NIBS) with a scattering angle of 173° was used for size measurements. mRNA content was determined using a Quant-iT™ RiboGreen RNA assay kit (Invitrogen™). Encapsulation efficiency was calculated by determining the unencapsulated mRNA content by measuring the fluorescence intensity (Fi) upon the addition of RiboGreen® reagent to the LNP and comparing this value to the total fluorescence intensity (Ft) of the RNA content that is obtained upon lysis of the LNPs by 1% Triton X-100, where % encapsulation=(Ft−Fi)/Ft×100).

TABLE 1A

Physicochemical properties of the tLNP

| Cationic lipid in composition | Particle Size (nm) | PDI* | Encapsulation Efficiency (%) |
|---|---|---|---|
| ALC-0315† | 82 | 0.14 | 94 |
| MC-3 | 108 | 0.14 | 87 |
| SM-102 | 85 | 0.20 | 94 |
| Lipid A9 | 101 | 0.08 | 96 |
| 10a | 86 | 0.14 | 86 |
| 10f | 91 | 0.19 | 93 |
| 10p | 77 | 0.18 | 96 |
| CICL1‡ | 93 | 0.11 | 96 |

*polydispersity index
†This composition is referred to as BF1 in subsequent Examples
‡This composition is referred to as F1 in subsequent Examples As seen in Table 1, all of these LNP compositions had hydrodynamic diameters and polydispersity indices within the acceptable ranges of 50-150 nm and ≤0.2 for PDI. Encapsulation efficiency is acceptable at ≥80% although ≥85% and ≥90% are preferred.

To assess the performance of tLNP they were used to transfect mouse T cells by injecting the tLNP into live mice and evaluated for their ability to generate murine T cells that expressed the mCherry reporter gene in vivo. All tLNP test articles were thawed at room temperature for 30 minutes and then diluted 1:2 with sterile water for injection to achieve a final dose concentration of 100 μg mRNA/mL. 100 μL (10 μg mRNA) of each test article was then injected via the tail vein into 8-week-old female C57Bl/6 mice. All treated mice were then sacrificed at 24 hours post-treatment and their spleens collected. Each spleen was then dissociated to single cell suspension and stained with antibodies to identify T cells, B cells, monocytes, and non-hematopoietic cells. Stained samples were then analyzed by flow cytometry for expression of mCherry in immune cell subsets, and non-hematopoietic cells. Data analysis was performed using FlowJo (Version 10.8.1) and GraphPad Prism (9.4.1.).

Figure 1C:
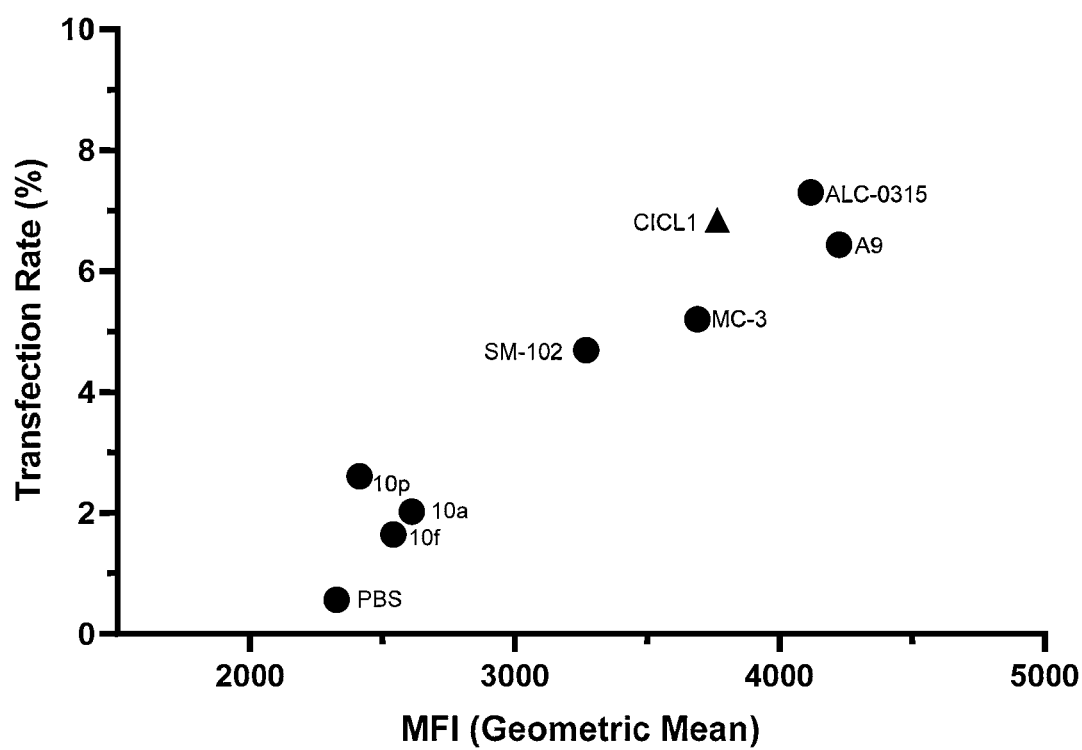
FIG. 1C depicts the transfection rate (percentage of T cells expressing the mRNA) versus expression level (as mean fluorescence intensity (MFI)) in spleen T cells from C57BL/6 mice administered targeted LNPs (tLNPs) comprising a lipid composition varying only in the structure of the ionizable cationic lipid. The binding moiety of the tLNPs was an anti-CD5 antibody and the payload was an mRNA encoding mCherry.

As seen in FIG. 1C, all of the tLNP compositions successfully transfected splenic T cells, although with different transfection rates (the proportion of cells expressing mCherry) and levels of expression (as judged by mean fluorescence intensity (MFI) of the mCherry signal). The tLNP composition incorporating CICL1 (F1) achieved comparable or superior performance to the tLNP compositions incorporating the benchmark ionizable cationic lipids with respect to both transfection rate and expression level. The tLNP composition comprising ALC-0315 was chosen for use as a benchmark composition in further experiments (BF1).

A number of lipid compositions based around CICL1 have been made (Table 1B below) and found to successfully form LNPs. The properties of many of these LNPs and tLNP made from them are demonstrated in the subsequent examples.

TABLE 1B

LNP Compositions

| Composition Code | Lipid Composition [Ratios] | N/P |
|---|---|---|
| BF1 | ALC-0315:DSPC:CHOL:DMG-PEG(2k):DSPE-PEG(2k)-MAL [50:10:38.5:1.4:0.1] | 6 |
| F1 | CICL1:DSPC:CHOL:DMG-PEG(2k):DSPE-PEG(2k)-MAL [50:10:38.5:1.4:0.1] | 6 |
| F2 | CICL1:DSPC:CHOL:DMG-PEG(2k):DSPE-PEG(2k)-MAL [50:10:38.5:1.3:0.2] | 3 |
| F3 | CICL1:DSPC:CHOL:DMG-PEG(2k):DSPE-PEG(2k)-MAL [50:10:38.5:1.425:0.075] | 9 |
| F4 | CICL1:DSPC:CHOL:DMG-PEG(2k):DSPE-PEG(2k)-MAL [42:10:46.5:1.4:0.1] | 6 |
| F5 | CICL1:DSPC:CHOL:DMG-PEG(2k):DSPE-PEG(2k)-MAL [58:10:30.5:1.4:0.1] | 6 |
| F6 | CICL1:DSPC:CHOL:DSG-PEG(2k):DSPE-PEG(2k)-MAL [35:10:53.5:1.4:0.1] | 6 |
| F7 | CICL1:DSPC:CHOL:DSG-PEG(2k):DSPE-PEG(2k)-MAL [42:10:46.5:1.4:0.1] | 6 |
| F8 | CICL1:DSPC:CHOL:DSG-PEG(2k):DSPE-PEG(2k)-MAL [50:10:38.5:1.4:0.1] | 6 |
| F9 | CICL1:DSPC:CHOL:DSG-PEG(2k):DSPE-PEG(2k)-MAL [58:10:30.5:1.4:0.1] | 6 |
| F10 | CICL1:DSPC:CHOL:DSG-PEG(2k):DSPE-PEG(2k)-MAL [62:10:26.5:1.4:0.1] | 6 |
| F11 | CICL1:DSPC:CHOL:DMG-PEG(2k):DSPE-PEG(2k)-MAL [58:7:33.5:1.4:0.1] | 6 |
| F12 | CICL1:DSPC:CHOL:DPG-PEG(2k):DSPE-PEG(2k)-MAL [58:7:33.5:1.4:0.1] | 6 |
| F13 | CICL1:DSPC:CHOL:DSG-PEG(2k):DSPE-PEG(2k)-MAL [58:7:33.5:1.4:0.1] | 6 |
| F14 | CICL1:DSPC: CHOL:DMG-PEG(2k):DSPE-PEG(2k)-MAL [58:7:34:0.9:0.1] | 6 |
| F15 | CICL1:DSPC:CHOL:DSG-PEG(2k):DSPE-PEG(2k)-MAL [58:10:30:1.9:0.1] | 6 |
| F16 | CICL1:DSPC:CHOL:DSG-PEG(2k):DSPE-PEG(2k)-MAL [50:10:39.5:0.4:0.1] | 6 |
| F17 | CICL1:DSPC:CHOL:DSG-PEG(2k):DSPE-PEG(2k)-MAL [50:10:39:0.9:0.1] | 6 |
| F18 | CICL1:DSPC:CHOL:DSG-PEG(2k):DSPE-PEG(2k)-MAL [50:10:38.5:1.4:0.1] | 6 |
| F19 | CICL1:DSPC:CHOL:DSG-PEG(2k):DSPE-PEG(2k)-MAL [50:10:38:1.9:0.1] | 6 |

TABLE 1B-continued

LNP Compositions

| Composition Code | Lipid Composition [Ratios] | N/P |
|---|---|---|
| F20 | CICL1:DSPC:CHOL:DSG-PEG(2k):DSPE-PEG(2k)-MAL [50:10:37.5:2.4:0.1] | 6 |
| F21 | CICL1:DSPC:CHOL:DSG-PEG(2k):DSPE-PEG(2k)-MAL [50:10:37:2.9:0.1] | 6 |
| F22 | CICL1:DSPC:CHOL:DSG-PEG(2k):DSPE-PEG(2k)-MAL [58:10:31:0.9:0.1] | 6 |
| F23 | CICL1:DSPC:CHOL:DSG-PEG(2k):DSPE-PEG(2k)-MAL [58:10:30: 1.9:0.1] | 6 |
| F24 | CICL1:DSPC:CHOL:DSG-PEG(2k):DSPE-PEG(2k)-MAL [58:10:29.5:2.4:0.1] | 6 |
| F25 | CICL1:DSPC:CHOL:DSPE-PEG(0.75k):DSPE-PEG(2k)-MAL [58:10:30.5:1.4:0.1] | 6 |
| F26 | CICL1:DSPC:CHOL:DSPE-PEG(1k):DSPE-PEG(2k)-MAL [58:10:30.5:1.4:0.1] | 6 |
| F27 | CICL1:DSPC:CHOL:DMPE-PEG(1k):DSPE-PEG(2k)-MAL [58:10:30.5:1.4:0.1] | 6 |
| F29 | CICL1:DSPC:CHOL:DSG-PEG(5k):DSPE-PEG(5k)-MAL [58:10:31.4:0.5:0.1] | 6 |
| F30 | CICL1:DSPC:CHOL:DMG-PEG(2k):DSG-PEG(2k)-MAL [58:10:30.5:1.4:0.1] | 6 |
| F31 | CICL1: DSPC:CHOL:DSG-PEG(2k):DSG-PEG(2k)-MAL [58:10:30.5:1.4:0.1] | 6 |
| F32 | CICL1:DSPC:CHOL:DSPE-PEG(2k):DSPE-PEG(2k)-MAL [58:10:30.5:1.4:0.1] | 6 |
| F33 | CICL1:DSPC:CHOL:DSG-PEG(2k):DSPE-PEG(5k)-MAL [58:10:30.5:1.4:0.1] | 6 |
| F34 | CICL1:DSPC:CHOL:DSG-PEG(2k):DSPE-PEG(2k)-MAL [58:13:27.5:1.4:0.1] | 6 |
| F35 | CICL1:DMPC:CHOL:DSG-PEG(2k):DSPE-PEG(2k)-MAL [58:10:30.5:1.4:0.1] | 6 |
| F36 | CICL1:DPPC:CHOL:DSG-PEG(2k):DSPE-PEG(2k)-MAL [58:10:30.5:1.4:0.1] | 6 |
| F37 | CICL1:DAPC:CHOL:DSG-PEG(2k):DSPE-PEG(2k)-MAL [58:10:30.5:1.4:0.1] | 6 |
| F38 | CICL1:18:1 PA:CHOL:DSG-PEG(2k):DSPE-PEG(2k)-MAL [58:10:30.5:1.4:0.1] | 6 |
| F40 | CICL1:DSPC:CHOL:20(S)-Hydroxycholesterol:DSG-PEG(2k):DSPE-PEG(2k)-MAL [58:10:22.9:7.6:1.4:0.1] | 6 |
| F41 | CICL1:DSPC:CHOL:β-Sitosterol:DSG-PEG(2k):DSPE-PEG(2k)-MAL [58:10:22.9:7.6:1.4:0.1] | 6 |
| F42 | CICL1:DSPC:CHOL:β-Sitosterol:DSG-PEG(2k):DSPE-PEG(2k)-MAL [58:10: 15.25:15.25:1.4:0.1] | 6 |

Example 2: Assessment of the Effect of Binder Presence and Density

To assess the effect of the presence of a binding moiety on the LNPs and the effect of the amount of conjugated binding moiety (binder density) various amounts of the anti-CD5 antibody were conjugated to LNP with the BF1 lipid and mRNA composition, including a composition with no antibody. Antibody was added to the conjugation reaction (essentially as described in Example 1) at antibody: mRNA ratios over the range of 0 to 2 (w/w). The maleimide in the zero antibody sample was unreacted. After conjugation final tLNP antibody to mRNA weight ratio (binder density) was determined with the BCA (bicinchoninic acid) total protein assay and Ribogreen® assay of mRNA content. The tLNPs were also characterized by DLS. As seen in Table 2 (below), the BF1-based LNP and tLNPs had similar physicochemical properties and encapsulation efficiency.

TABLE 2A

Physicochemical properties of the tLNP

| Input Binder Ratio | Measured Final Binder Ratio | Particle Size (nm) | PDI* | Encapsulation Efficiency (%) |
|---|---|---|---|---|
| 0 | Not Applicable | 76 | 0.10 | 94 |
| 0.20 | 0.27 | 76 | 0.14 | 95 |
| 0.30 | 0.32 | 77 | 0.20 | 93 |
| 0.50 | 0.49 | 80 | 0.16 | 93 |
| 1.00 | 0.71 | 81 | 0.13 | 95 |
| 1.50 | 1.35 | 82 | 0.15 | 97 |
| 2.00 | 1.84 | 80 | 0.17 | 96 |

*polydispersity index

Figure 2A:
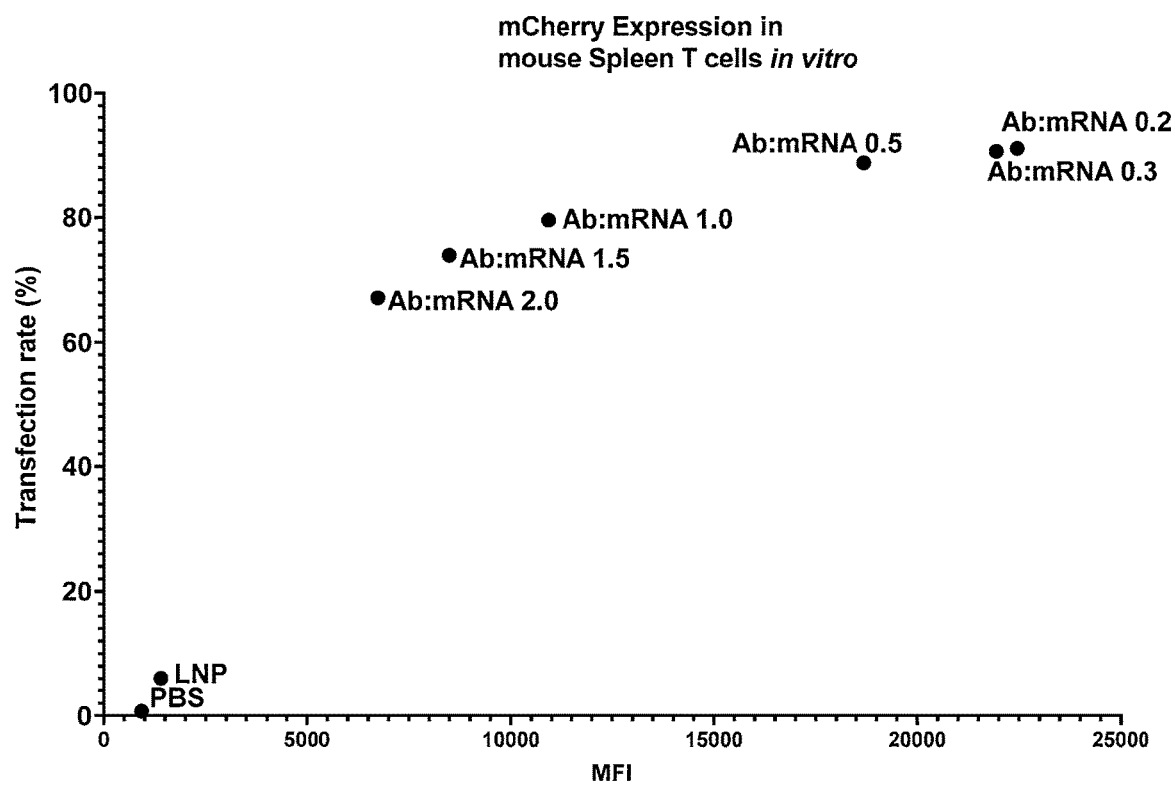
FIGS. 2A-F depict transfection rate or transfection rate and expression level (as MFI) for tLNP with different input antibody density expressed as ratios of conjugated antibody to mRNA (w/w).
Figure 2B:
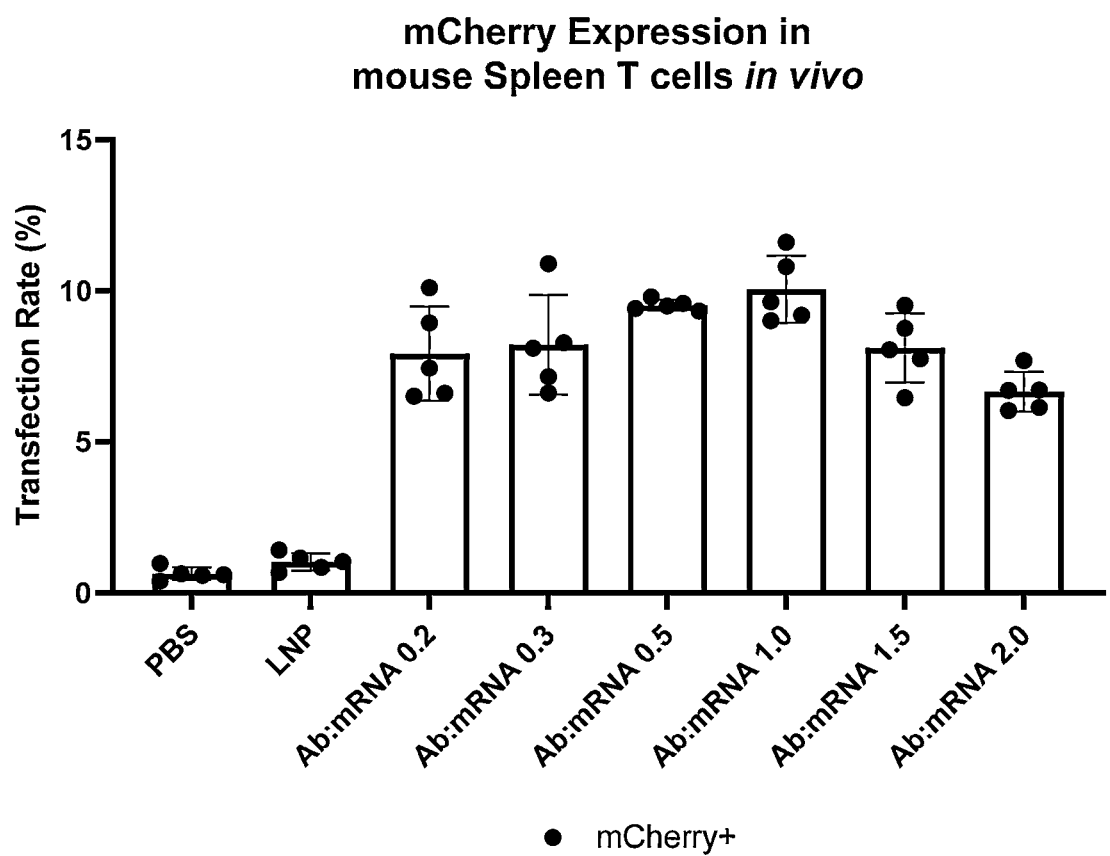

The BF1-based LNP and tLNPs were evaluated on mouse splenic T cells in vitro. Without antibody conjugation, BF1-based LNP showed no mCherry expression in mouse splenic T cells. Transfection rate was essentially the same for tLNP with antibody: mRNA ratios (w/w) of 0.2 to 0.5 but decreased as binder density increased above that range (FIGS. 2A-B). Expression level (as judged by mean fluorescence intensity (MFI)) decreased with the increasing antibody density. These data demonstrated a desired range of 0.2 to 0.5 for both input antibody ratio and measured tLNP binder ratio for the tested embodiments of tLNPs.

Figure 2C:
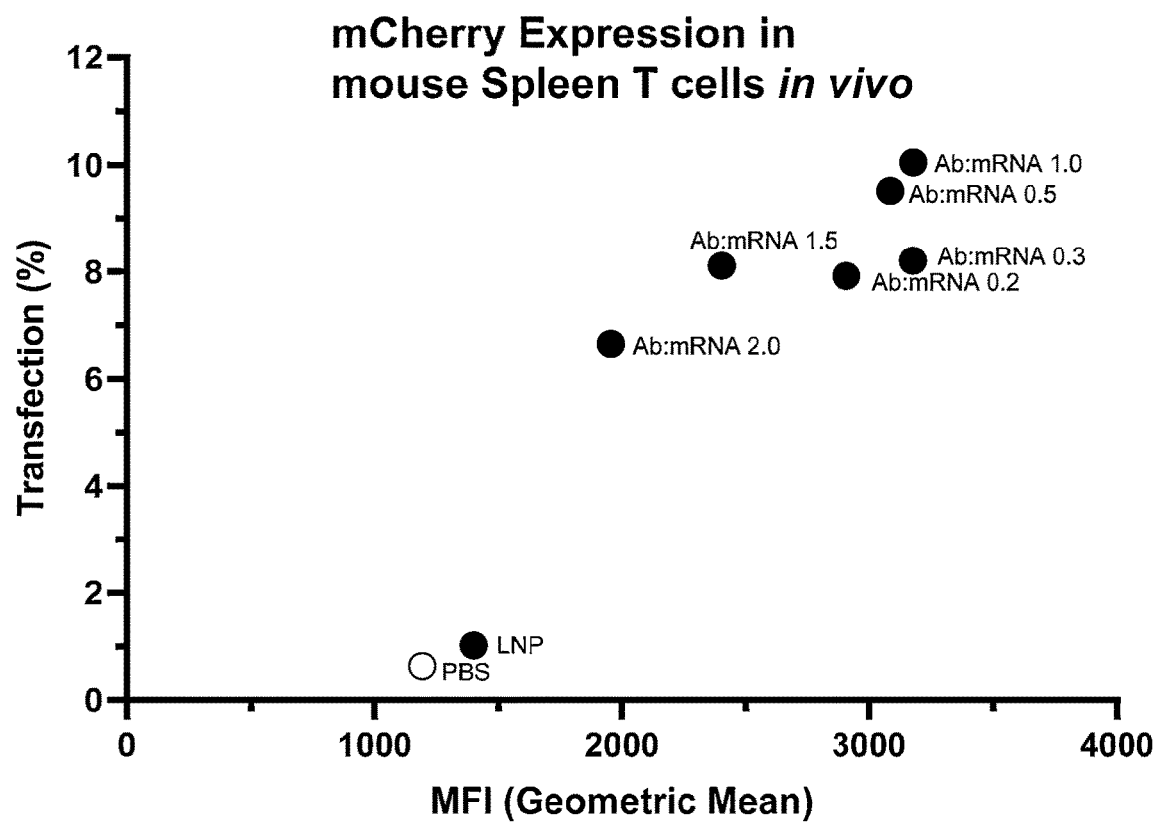
Figure 2D:
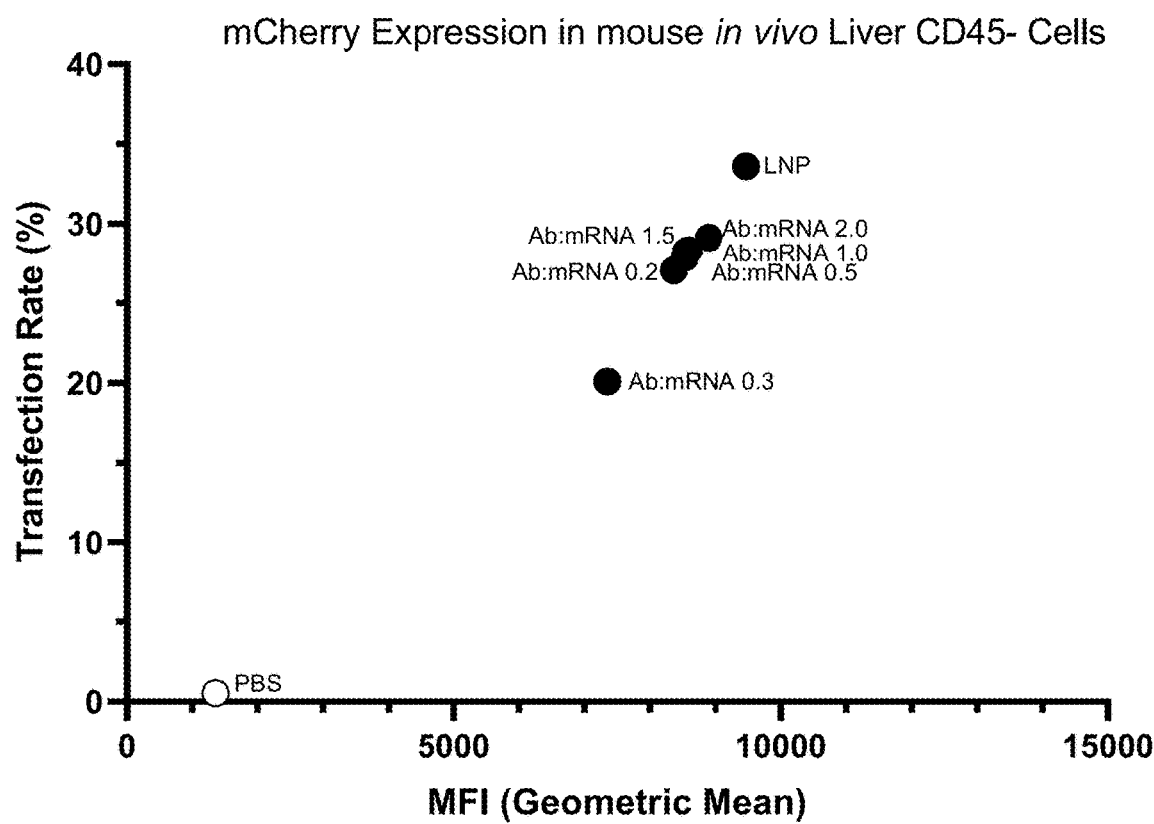
Figure 2E:
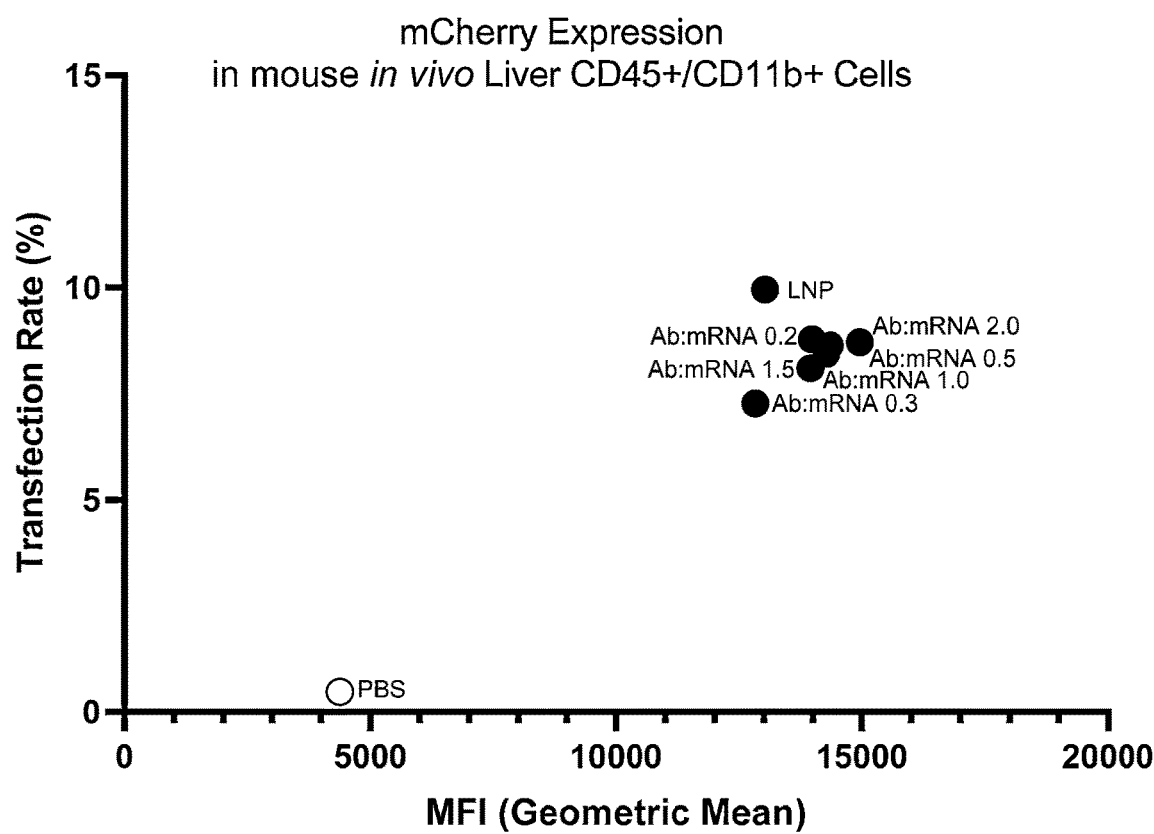

The same LNP and tLNP were also evaluated in vivo in wild type C57BL/6 mice. Without antibody conjugation, BF1-based LNP showed no mCherry expression in mouse spleen T cells in vivo (FIG. 2C), but higher transfection rates and at least similar expression levels in liver CD45-cells (hepatocyte staining) and liver CD45$^+$CD11b$^+$ cells (Kupffer cell staining) as compared to the CD5-targeted tLNP (FIGS. 2D-E). In contrast, the tLNP showed substantial transfection rates and levels of expression in the splenic T cells. In liver CD45-cells and liver CD45$^+$CD11b$^+$ cells, all BF1-based tLNPs had comparable mCherry expression, although both transfection rate and expression level were somewhat reduced in hepatocytes as was transfection rate in Kupffer cells (FIGS. 2D-E) compared to the LNP. Thus, conjugation of antibody to an LNP suppressed transfection rate in liver in addition to increasing transfection rate in cells expressing the target antigen (T cells, which express CD5, in this example). Transfection rate showed a bell curve with increasing antibody density in mouse spleen T cells, with the peak occurring in the range of 0.5 to 1 for input antibody ratio and about 0.5 to about 0.7 for the measured ratio in the tLNPs (FIG. 2B, Table 2A). However, values of 0.2 to 2.0 for input antibody to payload ratios provided useful tLNP (FIGS. 2B-C).

To confirm the applicability of the preferred binder density across species, additional tLNPs were prepared with input antibody: mRNA ratios (w/w) in the range of 0.1 to 1.0, but the antibody was chimeric 5D7 (ch5D7). 5D7 is a mouse antibody that recognizes human and non-human primate (NHP; at least rhesus and cynomolgus macaque) CD5. In the chimeric antibody the mouse constant domains were replaced with human sequences. The tLNPs were evaluated as before, including final measured binder ratio, and as shown in Table 2B (below).

TABLE 2B

Physicochemical properties of the tLNP

| Input Binder Ratio | Measured Final Binder Ratio | Particle Size (nm) | PDI | Encapsulation Efficiency (%) |
|---|---|---|---|---|
| 0.10 | 0.24 | 75 | 0.15 | 94 |
| 0.30 | 0.35 | 77 | 0.15 | 95 |
| 0.50 | 0.43 | 77 | 0.13 | 96 |
| 1.00 | 0.77 | 82 | 0.14 | 97 |

Figure 2F:
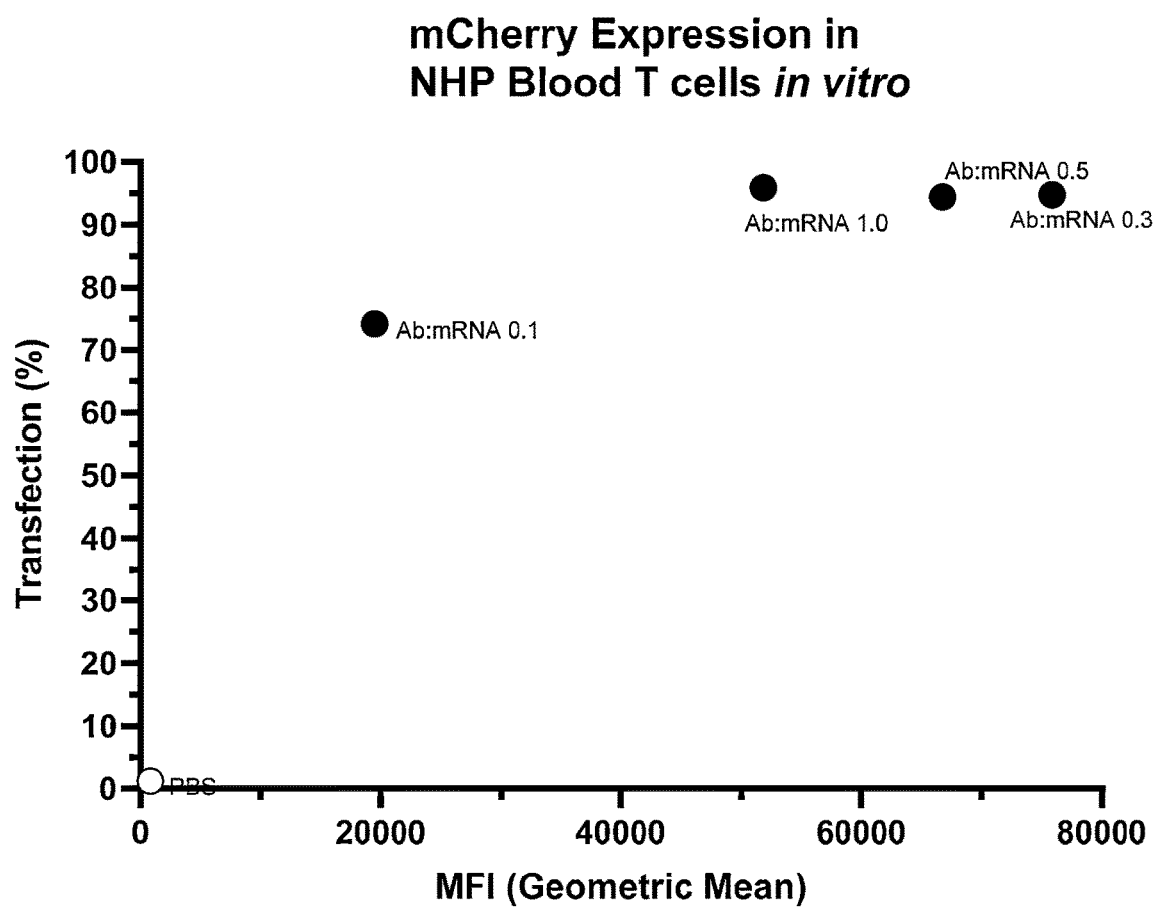

These tLNPs were then tested for their ability to transfect NHP blood T cells in vitro. Transfection rate was essentially the same for input binder ratios of 0.3 to 1.0 with expression level being the highest for tLNPS with input binder ratios of 0.3 and 0.5 (FIG. 2F). This demonstrated effectively the same preferred binder densities in the two species for input binder ratio for full length IgG antibody.

In light of all these data an input binder ratio to 0.5 to 0.7 was used for all tLNP for the subsequent Examples.

Example 3: Assessment the Effect of N/P Ratio

In general, one wants to maximize the amount of payload (mRNA) in a dose, but one also needs to have sufficient lipid, particularly the ionizable cationic lipid, for the tLNP to function optimally as a delivery vehicle releasing the payload into the cytoplasm. To establish the sensitivity of tLNP performance to variations in mRNA content the N/P ratio was varied while holding the other parameters constant.

To aid in comparability within and between experiments, a fixed dosage of mRNA was used. Thus, if the lipid ratios were held constant, a change in N/P ratio would lead to a greater or lesser amount of each lipid in a dose, including the functionalized PEG-lipid. This would lead to dosages having greater or lesser amounts of conjugated binding moiety without a compensatory adjustment. Consequently, while the total amount of PEG-lipid was held constant in this experiment, the amount of functionalized PEG-lipid, that was, DSPE-PEG-2000-maliemide, was adjusted to at least partially mitigate any such effect. Thus, for the general lipid composition of CICL1: DSPC: cholesterol: DMG-PEG-2000: DSPE-PEG-2000 the lipid ratio was 50:10:38.5: (1.5-X): X. When N/P was 3, X was 0.2; when N/P was 6, X was 0.1 and when N/P was 9, X was 0.075. Formation of the tLNP and conjugation of the anti-CD5 antibody was as described above.

between these compositions and the benchmark composition (BF1) was greater than those in the previous experiment.

Figure 3A:
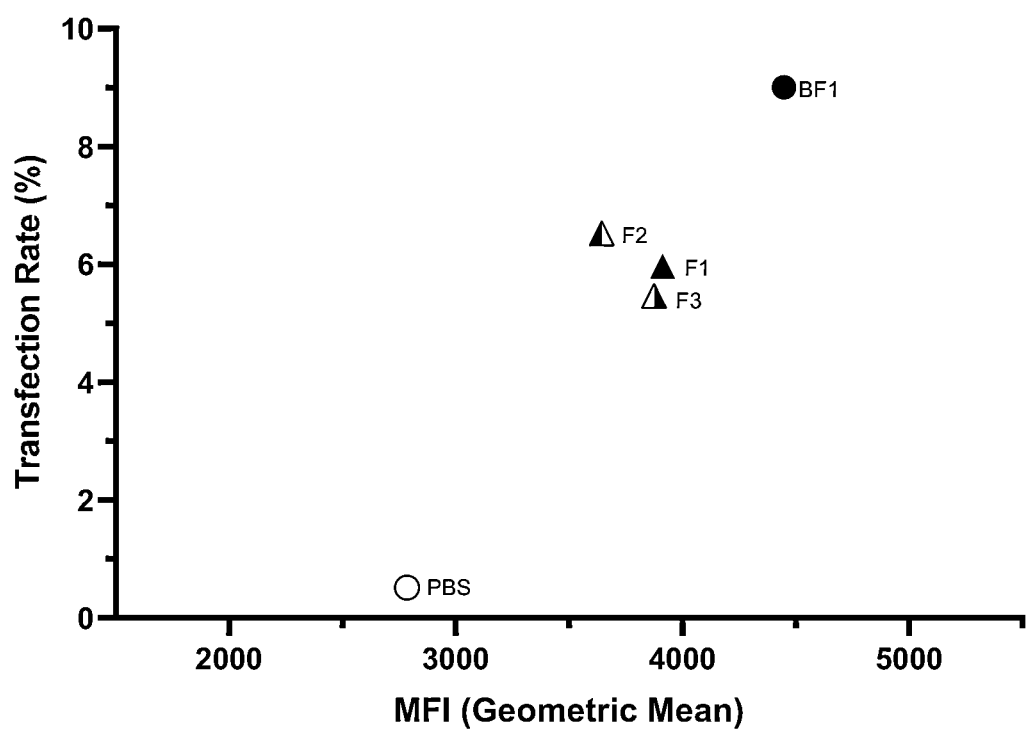
FIGS. 3A-C depict the transfection rate (percentage of T cells expressing the mRNA) and expression level (MFI) in cells from C57BL/6 mice administered tLNPs comprising tLNP compositions comprising the ionizable cationic lipid CICL1 and varying only in N/P ratio. They were further compared to a benchmark composition, BF1, in which the ionizable cationic lipid was ALC-0315. BF1 and F1 were identical to the compositions containing ALC-0315 and CICL1 in FIG. 1C. The binding moiety of the tLNPs was an anti-CD5 antibody and the payload was an mRNA encoding mCherry. Data is presented for splenic T cells (FIG. 3A), CD45$^-$ liver cells (FIG. 3B), and CD45$^+$ CD11$^b$+ liver cells (FIG. 3C).
Figure 3B:
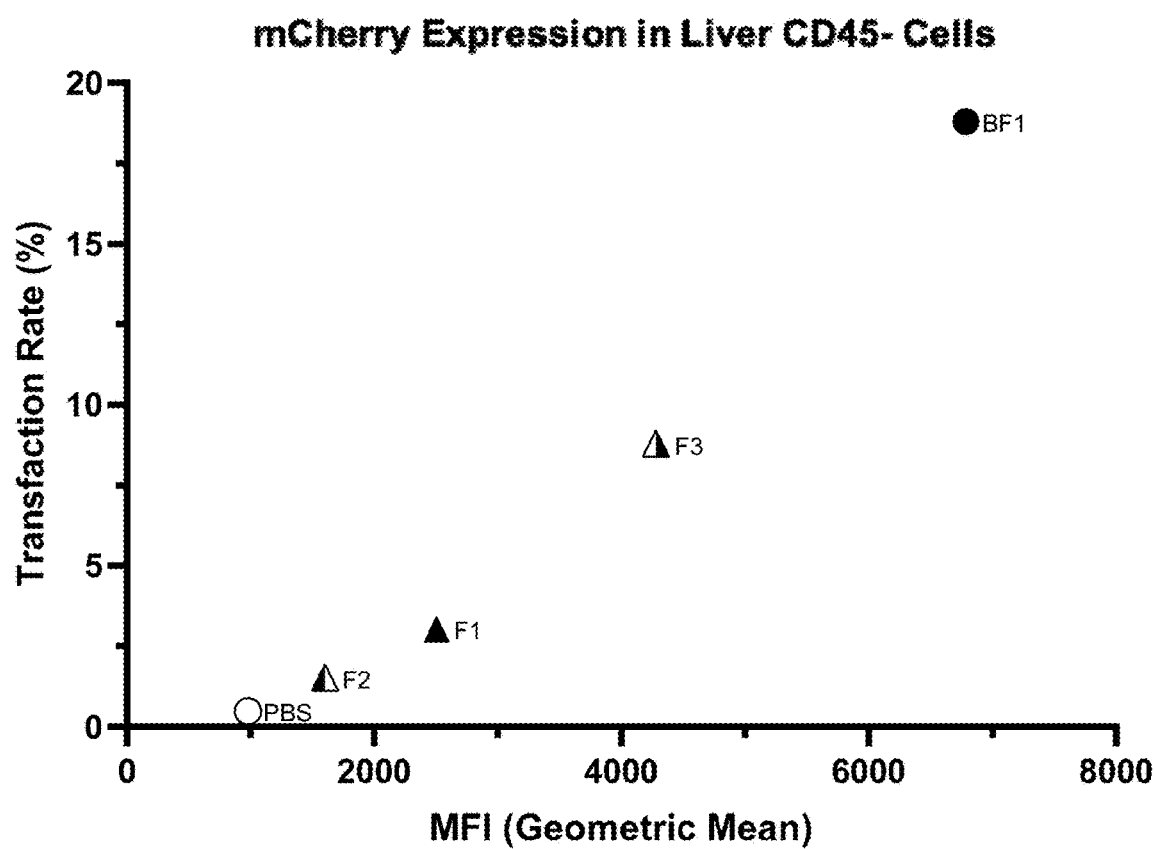
Figure 3C:
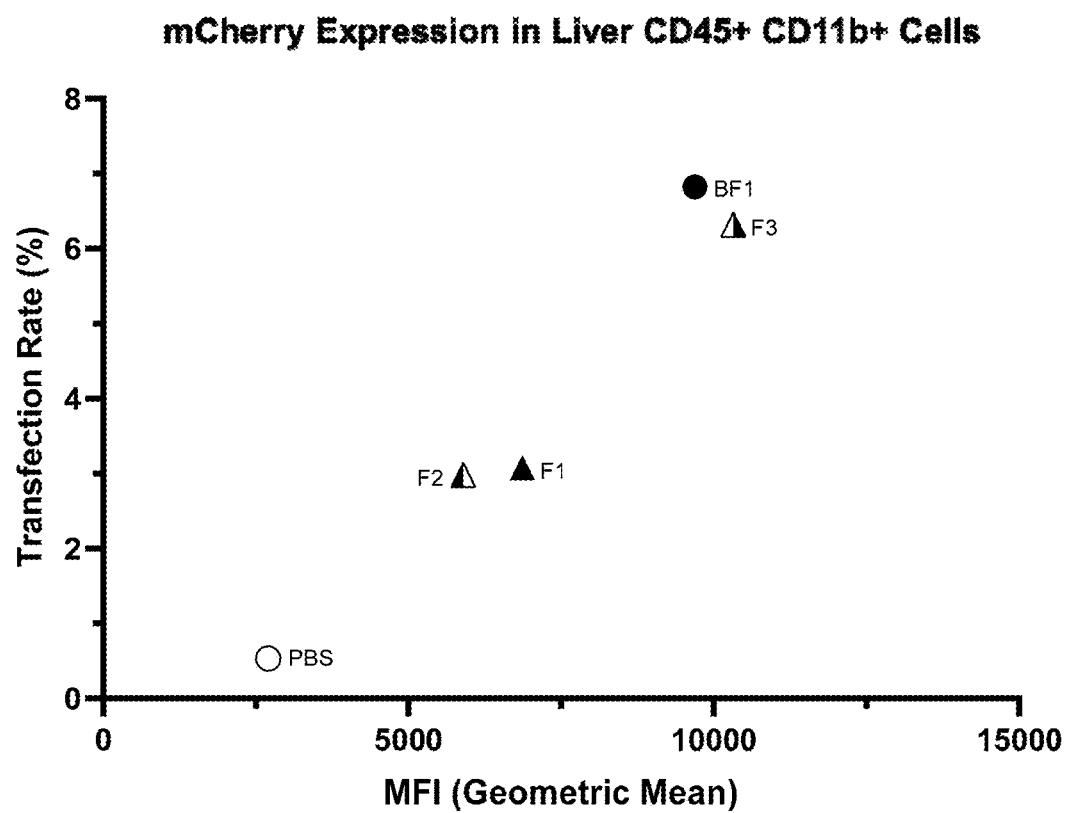

In addition to maximizing expression in T cells, it is often desirable to minimize expression in the liver. Therefore, mCherry expression in liver $CD45^-$ cells (hepatocytes) and liver $CD45^+CD11b^+$ cells (Kupffer cells) were assessed. Here, N/P ratio had a surprisingly pronounced effect with the tLNP with N/P ratios of 3 and 6 producing substantially lower levels of expression in both hepatocytes and Kupffer cells than the tLNP with an N/P ratio of 9 or the benchmark tLNP incorporating ALC-0315 (FIGS. 3B-C). Thus, considering expression in the liver as well as in T cells, N/P ratios of from 3 to 6 were seen as superior to an N/P ratio of 9. Compositions with N/P=6 produced somewhat better encapsulation efficiency and were chosen for evaluation of further parameters.

Example 4: Assessment of the Effect of Ionizable Cationic Lipid Content

As noted above, one of the major determinants of (t) LNP performance is the ionizable cationic lipid. Here we varied the proportion ionizable cationic lipid in the composition making tLNP comprising CICL1: DSPC: cholesterol: DMG-PEG-2000: DSPE-PEG-2000-maleimide in a ratio of Y: 10: (38.5-Y): 1.4:0.1, where Y was 42 (F4), 50 (F1), or 58 (F5), N/P was 6. Formation of the tLNP and conjugation of the anti-CD5 antibody was as described above.

The apparent (that is, measured) pKa of ionizable lipid in the lipid nanoparticle was determined using 6-(p-toluidino)-2-naphthalenesulfonic acid sodium salt (TNS salt, Toronto Research Chemicals, Toronto, ON, Canada). Lipid nanoparticles were diluted in 1×Dulbecco's PBS to a concentration of 1 mM total lipids. TNS salt was prepared as a 1 mg/mL stock solution in DMSO and then further diluted using distilled water to a working solution of 60 μg/mL (179 mM). Diluted lipid nanoparticle samples were further diluted to 90 μM total lipids in 165 μL of buffered solution containing 10 mM HEPES, 10 mM MES, 10 mM ammonium acetate, 130 mM NaCl, and final TNS concentration of 1.33 μg/mL (4 μM) with the pH ranging from 3.5 to 12.2. Following pipette mixing and incubation at room temperature in the dark for 15 min, fluorescence intensity was measured at room temperature in a BioTek Synergy H1 plate reader using excitation and emission wavelengths of 321 and 445 nm, respectively. The fluorescence signal was blank subtracted and plotted as a function of the pH, then analyzed using a nonlinear (Boltzmann) regression analysis with the apparent pKa determined as the pH giving rise to half maximal fluorescence intensity as calculated by the Henderson-Hasselbalch equation.

TABLE 3

Physicochemical properties of the tLNP

| Composition | N/P | Particle Size (nm) | PDI | Encapsulation Efficiency (%) |
|---|---|---|---|---|
| BF1 | 6 | 77.5 | 0.1 | 94 |
| F2 | 3 | 91.3 | 0.1 | 93 |
| F1 | 6 | 88.8 | 0.1 | 98 |
| F3 | 9 | 82.6 | 0.1 | 98 |

As shown in Table 3, all of the tLNPs had similar physicochemical properties and encapsulation efficiency. It was found that varying N/P ratio in this range had little effect on T-cell expression (FIG. 3A), although the difference

TABLE 4

Physicochemical properties of the tLNP

| Composition Description | Particle Size (nm) | PDI | Encapsulation Efficiency (%) | Measured lipid pKa in tLNP |
|---|---|---|---|---|
| BF1 | 77.5 | 0.1 | 94 | 6.49 |
| F4 | 86.1 | 0.1 | 98 | 6.73 |
| F1 | 88.8 | 0.1 | 97 | 6.65 |
| F5 | 101.8 | 0.1 | 92 | 6.55 |

The physicochemical properties of these tLNP were comparable, including measured pKa. The measured pKa of the ionizable cationic lipid in the tLNP in the range of 6 to 7, which allowed ionization as the endosome acidified and promoted endosomal release of the contents of the (t) LNP into the cytoplasm. The proportion of ionizable cationic lipid in the (t) LNP might affect the observed pKa, though as seen in Table 4, in this case the effect was minor. There was a trend of increasing particle size with increasing ionizable cationic lipid, but it remained within a preferred range.

Figure 4A:
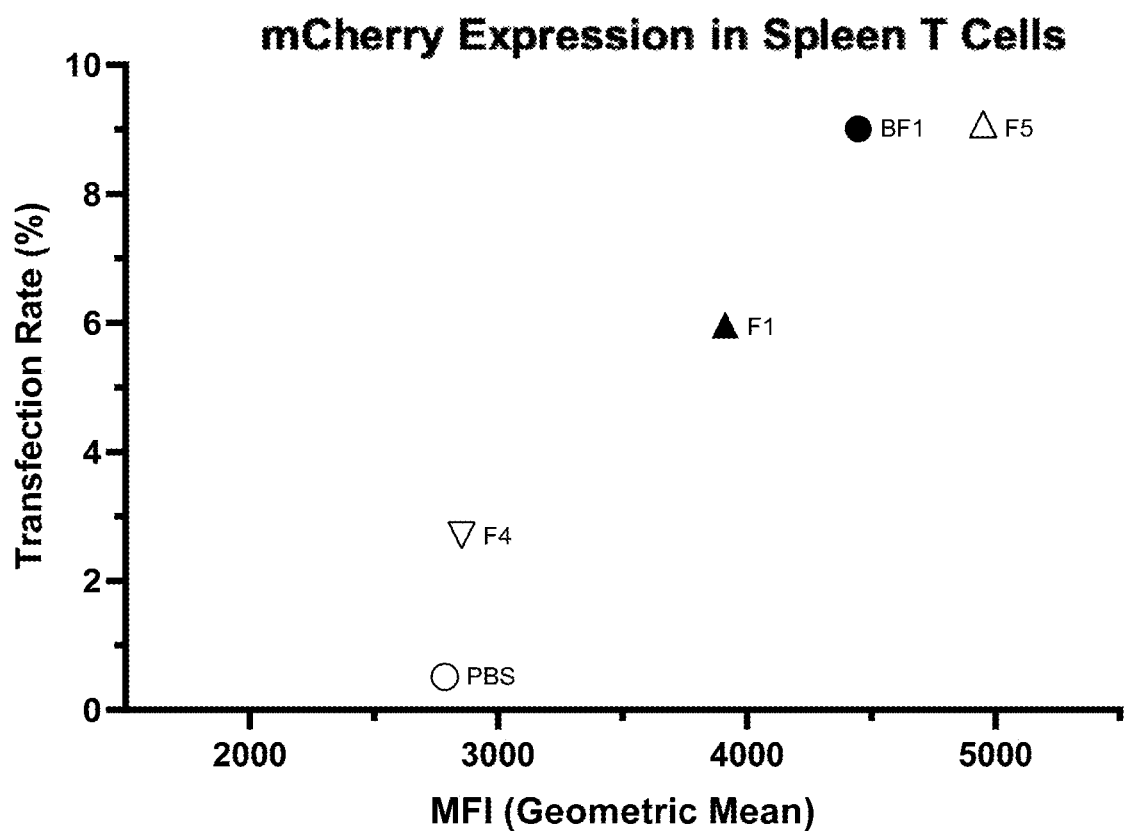
FIGS. 4A-C depicts the transfection rate (percentage of T cells expressing the mRNA) and expression level (as mean fluorescence intensity (MFI)) in cells from C57BL/6 mice administered tLNPs comprising tLNP compositions comprising the ionizable cationic lipid CICL1 but varying only the amounts of CICL1 and cholesterol. The mol % of CICL1 was 42 (F4), 50 (F1), and 58 (F5) with compensatory adjustments to the mol % of cholesterol. They were further compared to benchmark composition BF1. The binding moiety of the tLNPs was an anti-CD5 antibody and the payload was an mRNA encoding mCherry. Data is presented for splenic T cells (FIG. 4A), CD45$^-$ liver cells (FIG. 4B), and CD45$^+$ CD11$^b$+ liver cells (FIG. 4C).
Figure 4B:
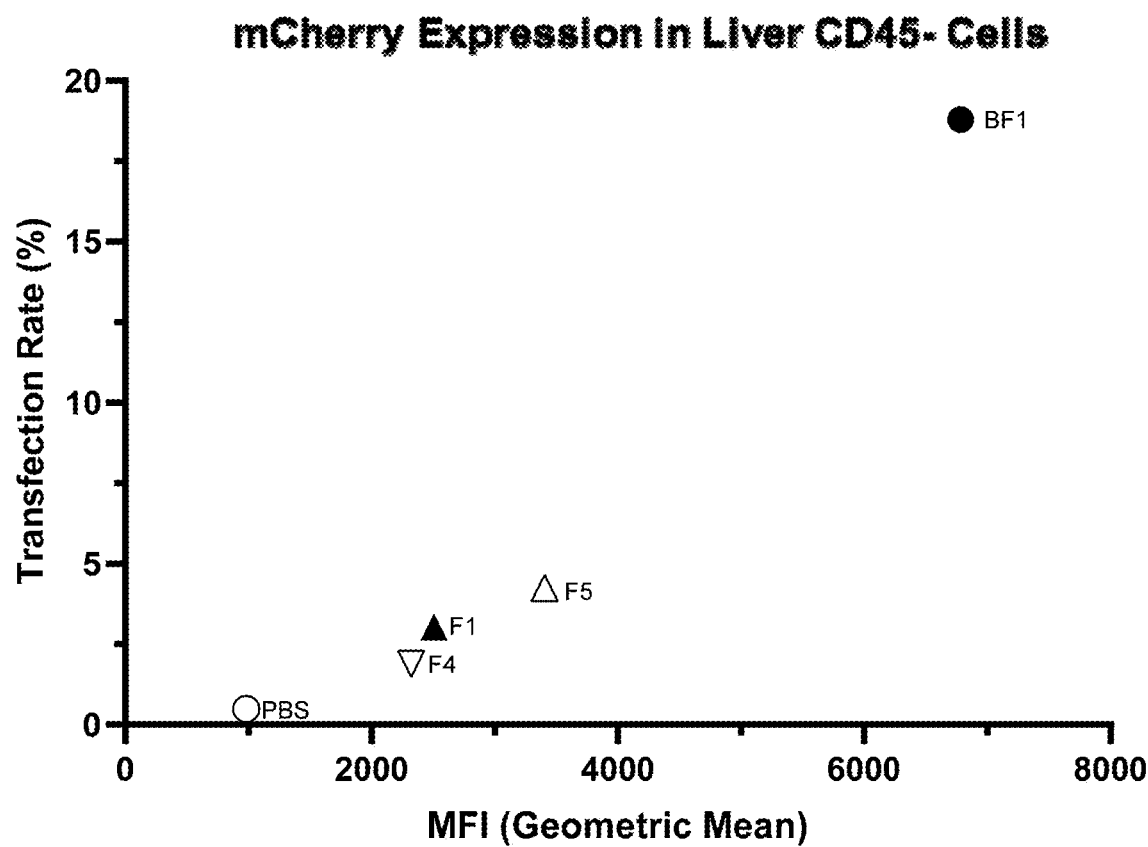
Figure 4C:
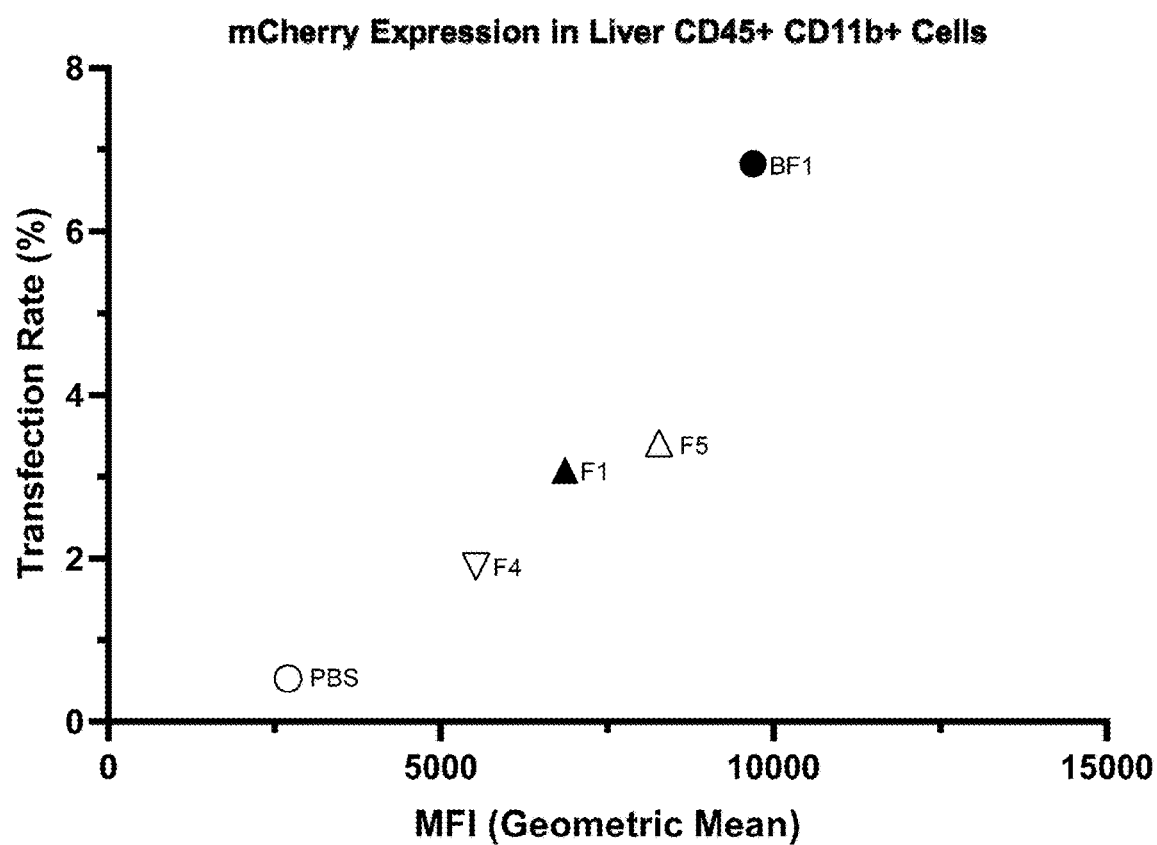

The tLNP were administered to C57BL/6 mice by tail vein injection, spleen and liver harvested and disaggregated, and expression of mCherry in splenic T cells, hepatocytes, and Kupffer cells assessed by flow cytometry. There was a clear trend of increasing transfection rate and level of expression with increasing CICL1 content, with the 58% CICL1 composition (F5) exhibiting performance superior to the previous 50% CICL1 composition (F1) and the benchmark composition (FIG. 4A). The same trend was observed in hepatocytes and Kupffer cells but the difference between the compositions was much reduced and both transfection rate and expression level were much less than with the benchmark BF1 (FIGS. 4B-C). This demonstrates that ionizable cationic lipid content is an important factor in T cell-targeted delivery by tLNP with higher content within the tested range being favorable. Accordingly, 58% CICL1 (F5) was used as a baseline in the evaluation of further parameters.

Example 5: Assessment of PEG-Lipid Anchor Length

To assess the effect of PEG-lipids with varying anchor carbon chain lengths tLNP with the general composition CICL1: DSPC: CHOL: PEG-LIPID: DSPE-PEG-2000-MAL [58:7:33.5:1.4:0.1] were made essentially as described above, in which unfunctionalized PEG-LIPID was DMG-PEG-2000 (F11), DPG-PEG-2000 (F12) or DSG-PEG-2000 (F13). As before, N/P was 6, the mRNA was CleanCap® mCherry 5-methoxyuridine (5moU) mRNA encoding the fluorescent protein mCherry (Trilink), and whole IgG recognizing mouse CD5 was conjugated to the DSPE-PEG (2k)-MAL. Physicochemical characterization is reported in Table 5A.

TABLE 5A

Physicochemical properties of the tLNP

| Composition Description | Unfunctionalized PEG-Lipid anchor | Particle Size (nm) | PDI* | Encapsulation Efficiency (%) |
|---|---|---|---|---|
| F11 | 14 | 112 | 0.05 | 81 |
| F12 | 16 | 110 | 0.06 | 91 |
| F13 | 18 | 109 | 0.11 | 93 |

Figure 5A:
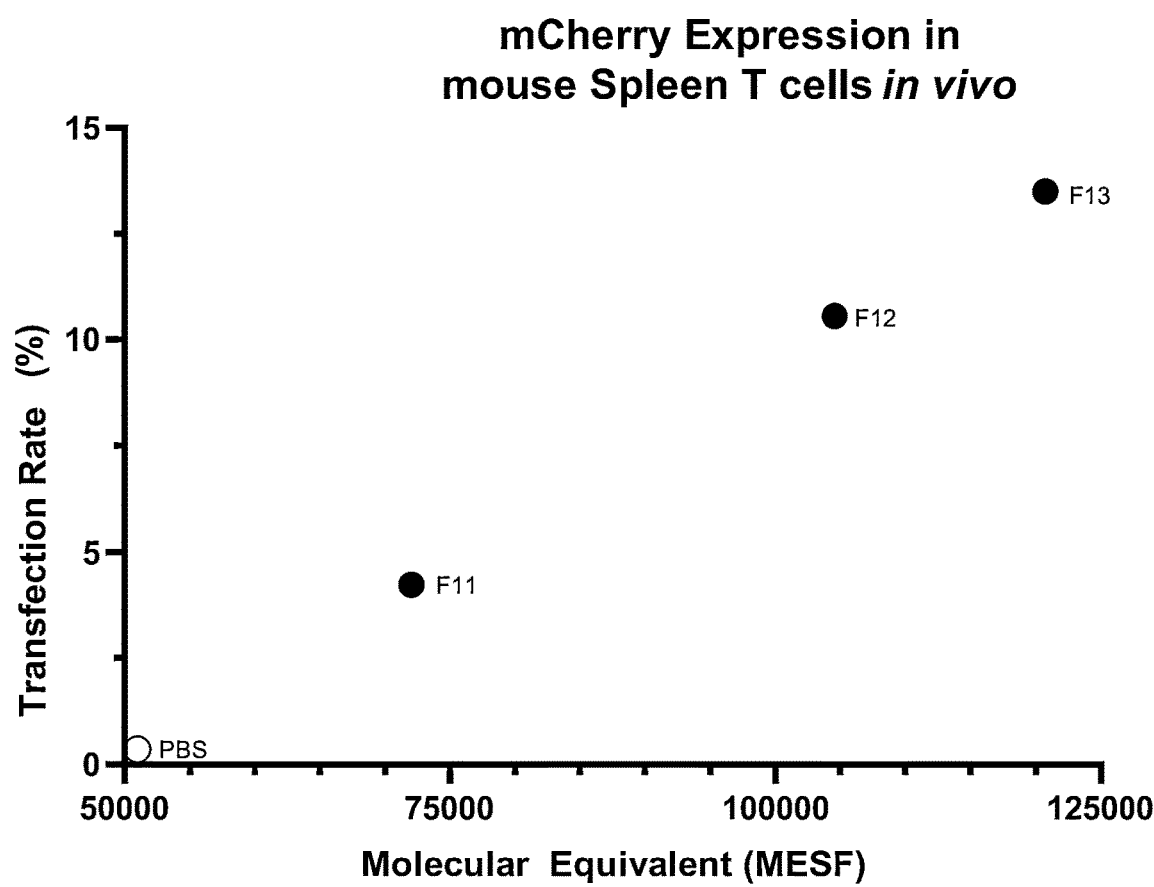
FIGS. 5A-F depict the transfection rate (percentage of T cells expressing the mRNA) and expression level (as MFI) in cells from C57BL/6 mice administered tLNPs comprising varying non-functionalized PEG-lipids with different lipid anchor lengths for splenic T cells (FIGS. 5A and 5D), CD45$^-$ liver cells (FIGS. 5B and 5E), and CD45$^+$ CD11$^b$+ liver cells (FIGS. 5C and 5F).
Figure 5B:
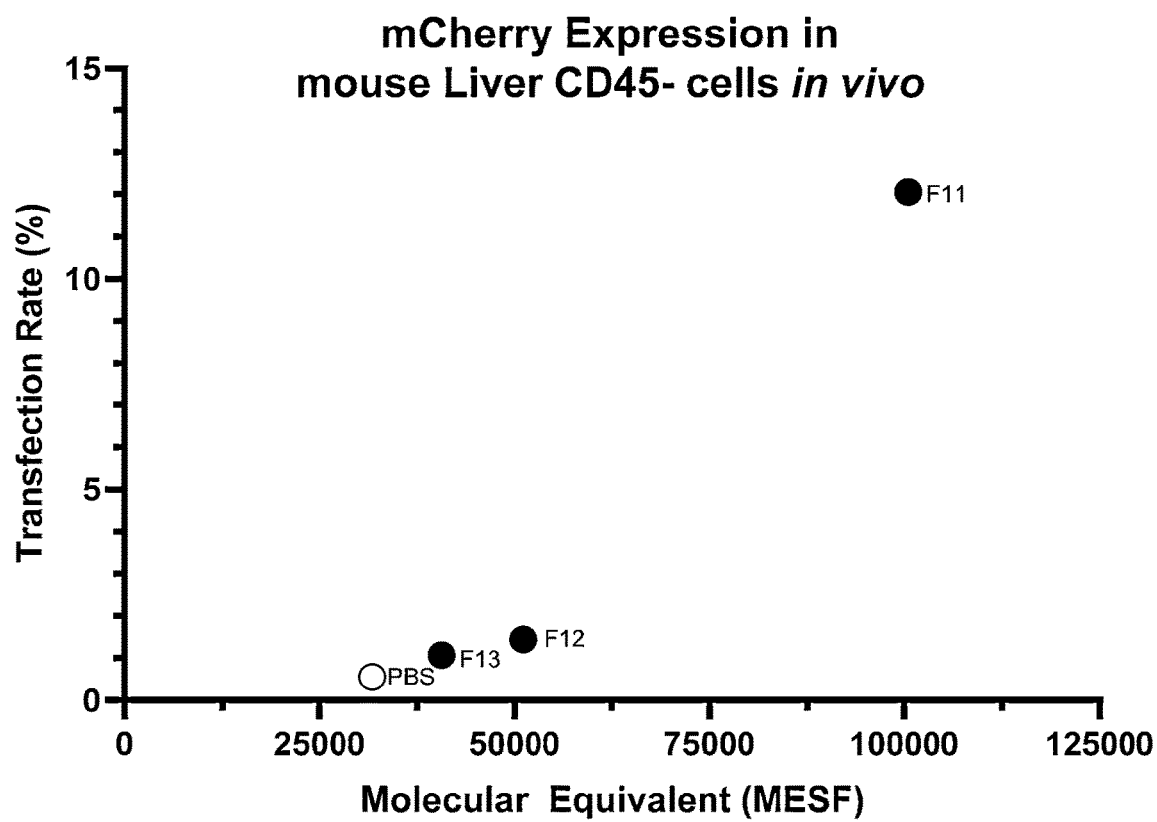
Figure 5C:
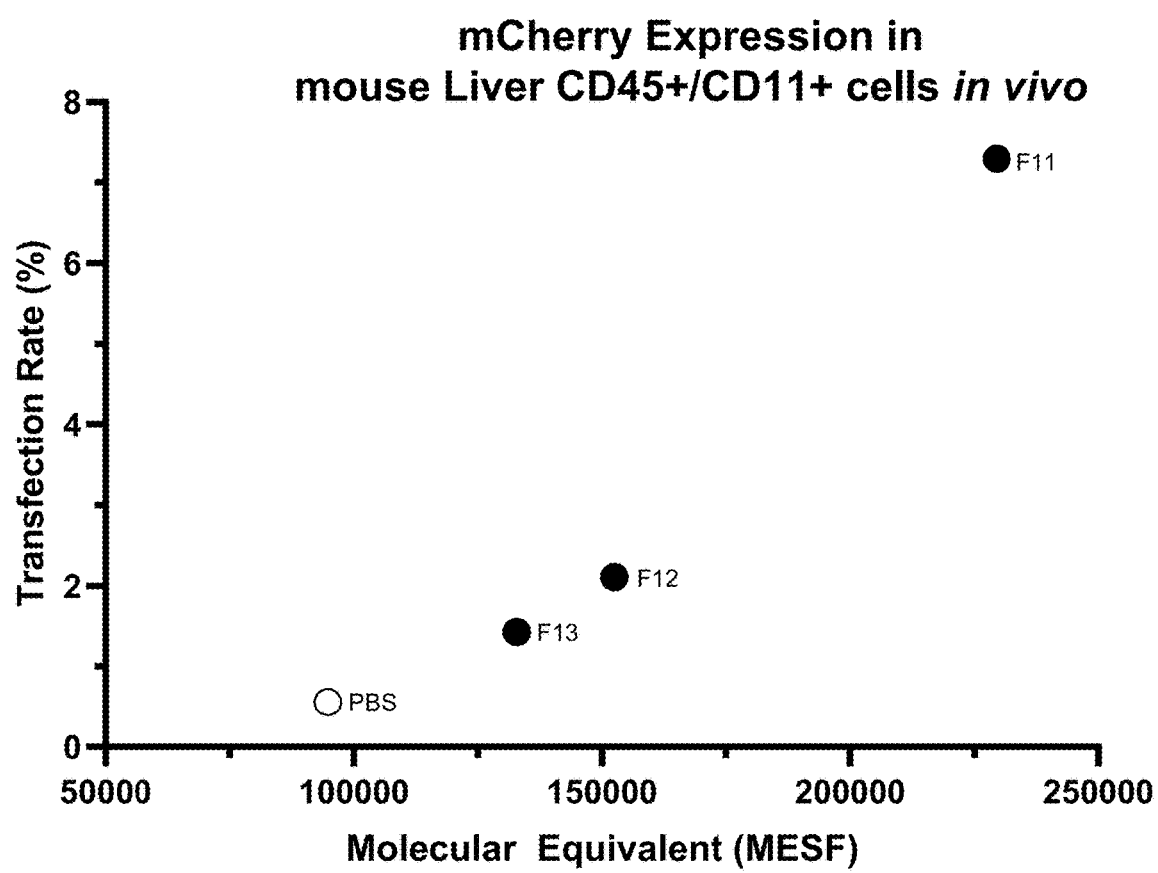

The ability of these tLNP to transfect cells in vivo was tested by injection into C57BL/6 mice. For splenic T cells, both transfection rate and expression level (Molecules of Equivalent Soluble Fluorochrome (MESF)) markedly improved with increasing anchor chain length with the tLNP comprising DSG-PEG-2000 (F13) achieving almost three times the transfection rate and expression level as the tLNP comprising DMG-PEG-2000 (F11) (FIG. 5A). At the same time there was minimal expression (transfection rate <2%) with compositions F12 and F13 in hepatocytes (CD45⁻ liver cells) (FIG. 5B). Transfection of Kupffer cells (CD45⁺/CD11⁺liver cells) was similarly reduced with F12 and F13 and was only about half that of hepatocytes with F11, though expression levels in transfected Kupffer cells appeared to be substantially greater than in hepatocytes (FIGS. 5B-C). The improved transfection rate and expression level achieved in T cells (increased) and liver cells (decreased) with increasing anchor chain length for the unfunctionalized PEG-lipid may reflect increased circulation time of the tLNP due to reduced shedding of the PEG-lipid and resulting inhibition of apoE-mediated delivery to the liver.

Whereas the tLNP in previous Examples had comprised 10% DSPC, the composition of F11-F13 comprised 7% DSPC with compensatory reduction of cholesterol content. The effect of PEG-lipid anchor carbon chain length was evaluated in tLNP in the context of a 10% DSPC content using the F5 lipid combination in comparison to one in which the DMG-PEG-2000 of F5 was replaced with DSG-PEG-2000. That is, the lipid composition of the tLNP was CICL1: DSPC: CHOL: PEG-LIPID: DSPE-PEG-2000-MAL [58:10:30.5:1.4:0.1] where PEG-LIPID was DMG-PEG-2000 (F5) or DSG-PEG-2000 (F9). These tLNP differed from those described above in that they encapsulated a N1-methylpseudouridine (m1ψ) substituted mRNA encoding the fluorescent protein mCherry. mRNA substituted with m1ψ were generally expressed at higher levels than those substituted with 5moU, but there was no apparent reason this change should have a substantial impact on transfection rate. As before, N/P was 6 and whole IgG recognizing mouse CD5 was conjugated to the DSPE-PEG-2000-MAL. Physicochemical characterization is reported in Table 5B.

TABLE 5B

Physicochemical properties of the tLNP

| Composition Description | Unfunctionalized PEG-Lipid anchor | Particle Size (nm) | PDI | Encapsulation Efficiency (%) |
|---|---|---|---|---|
| F5 | 14 | 90 | 0.09 | 96 |
| F9 | 18 | 88 | 0.03 | 97 |

Figure 5D:
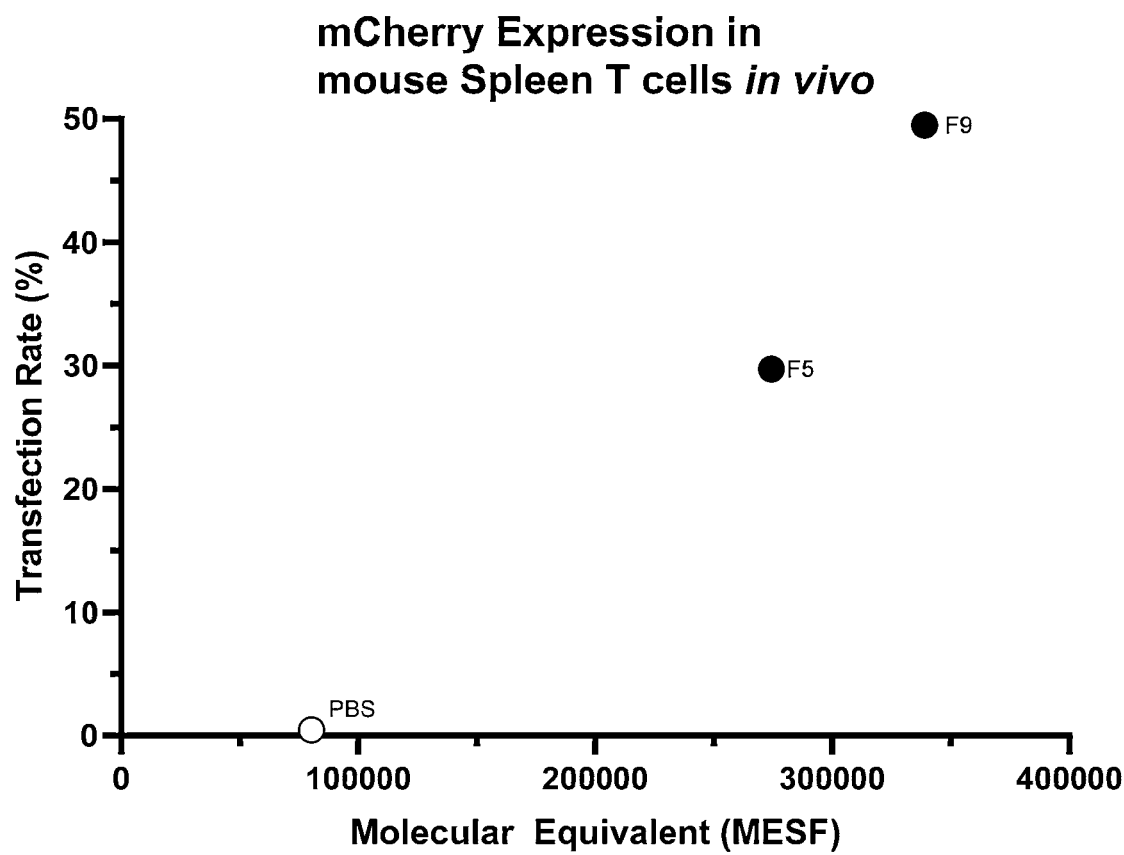
Figure 5E:
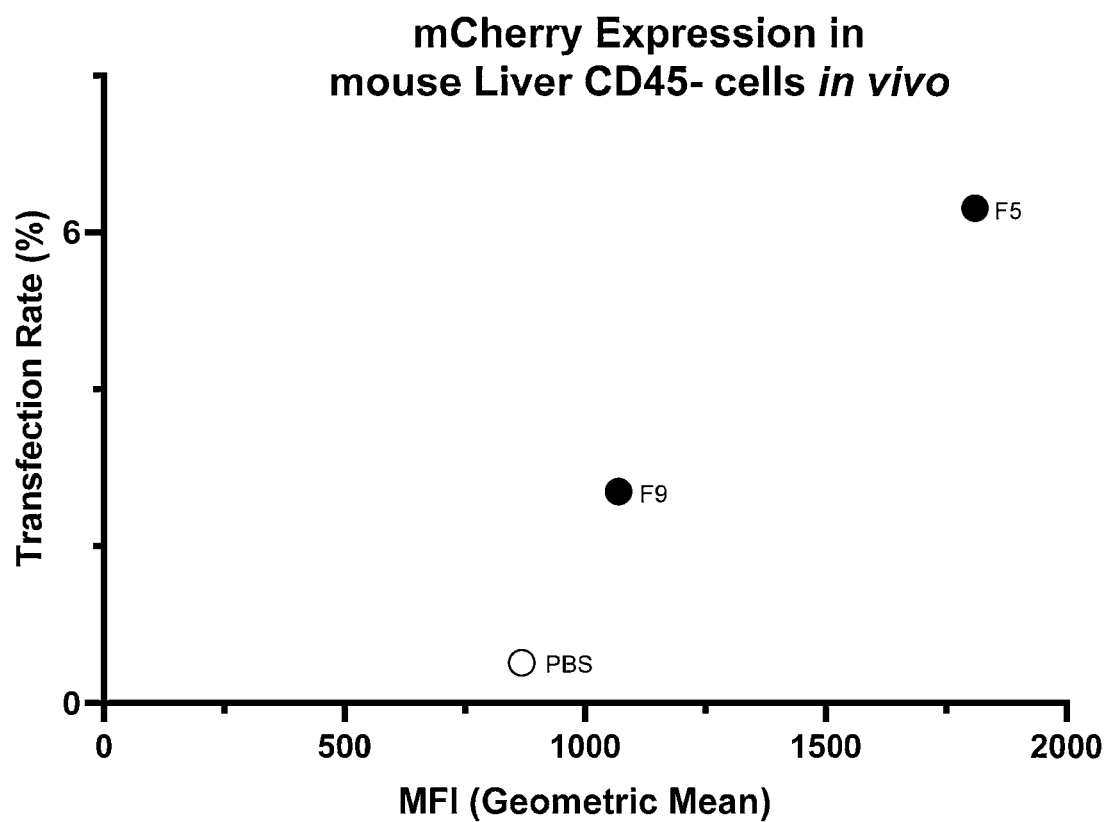
Figure 5F:
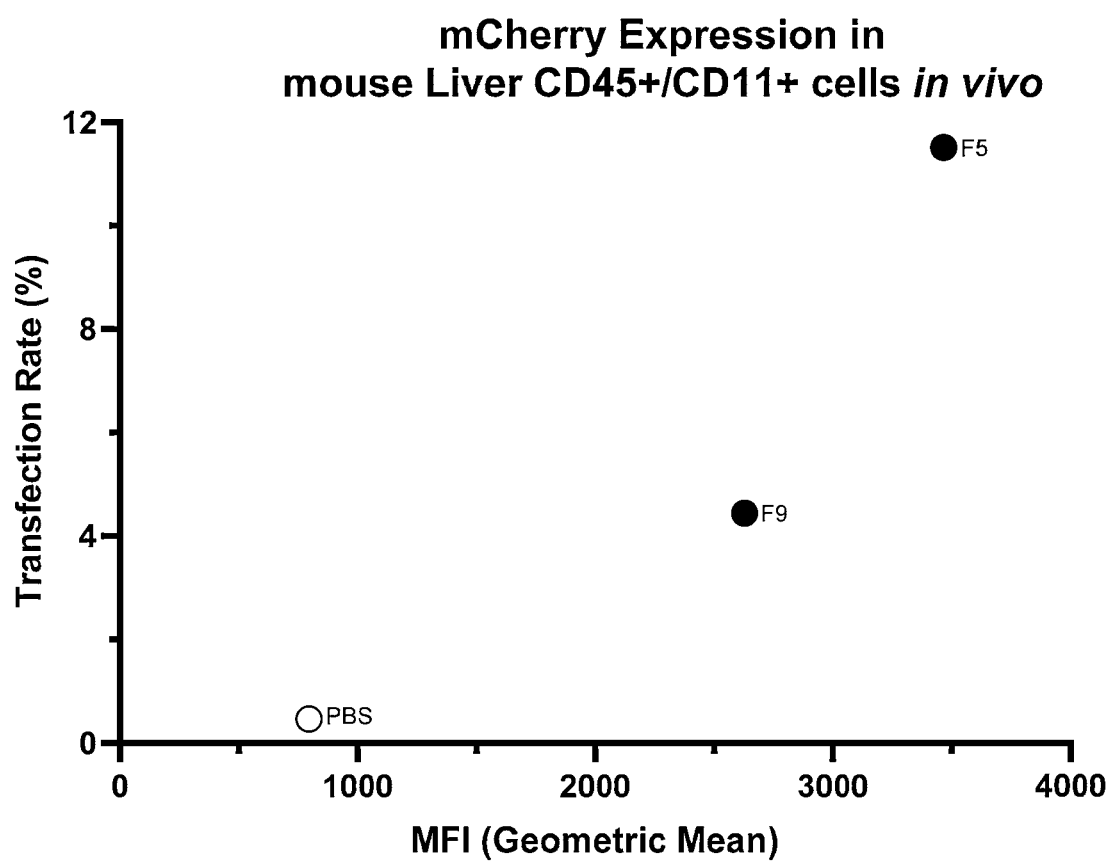

Upon injection into C57BL/6 mice the improved performance of the tLNP with the longer chain PEG-lipid was again observed in both spleen and liver cells (FIG. 5D-F).

Example 6: Assessment of PEG-Lipid Content

The effect of increasing the content of unfunctionalized and total PEG-lipid content was assessed by comparing tLNP with lipid composition F11 with one in which the unfunctionalized lipid content was reduced from 1.4% to 0.9% with a compensatory reduction in cholesterol and consequent reduction in total PEG-lipid. Specifically, the lipid content was CICL1: DSPC: CHOL: PEG-DMG2000: DSPE-PEG-2000-MAL [58:7:33.5:1.4:0.1](F11) and [58:7:34:0.9:0.1](F14). As before, N/P was 6, the mRNA was CleanCap® mCherry 5-methoxyuridine (5moU) mRNA encoding the fluorescent protein mCherry (Trilink), and whole IgG recognizing mouse CD5 was conjugated to the DSPE-PEG-2000-MAL. Physicochemical characterization is reported in Table 6.

TABLE 6

Physicochemical properties of the tLNP

| Composition Description | Particle Size (nm) | PDI | Encapsulation Efficiency (%) |
|---|---|---|---|
| F11 | 112 | 0.05 | 81 |
| F14 | 115 | 0.04 | 94 |

Figure 6A:
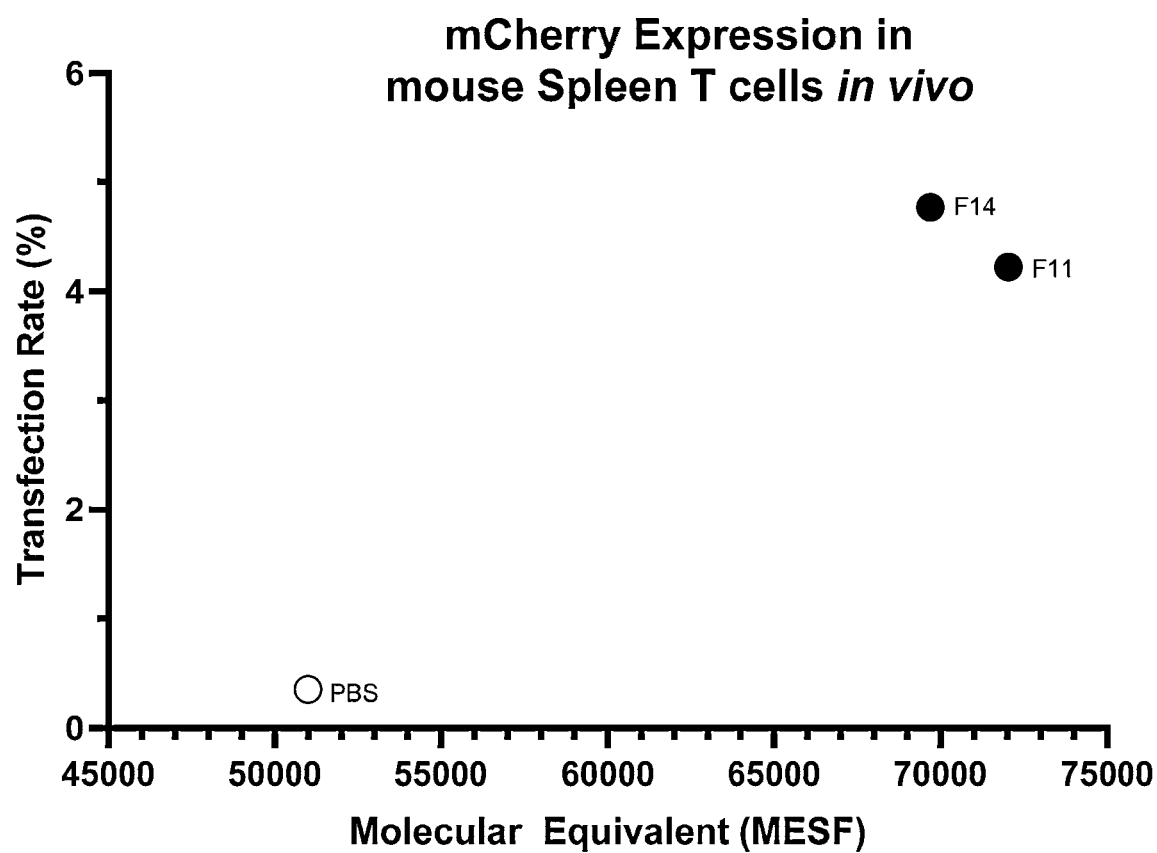
FIGS. 6A-C depict the transfection rate (percentage of T cells expressing the mRNA) and expression level (as Molecules of Equivalent Soluble Fluorochrome (MESF)) in cells from C57BL/6 mice administered tLNPs comprising different amounts of non-functionalized PEG-lipid but the same amount of total PEG-lipid for splenic T cells (FIG. 6A), CD45⁻ liver cells (FIG. 6B), and CD45⁺ CD11$^b$+ liver cells (FIG. 6C).
Figure 6B:
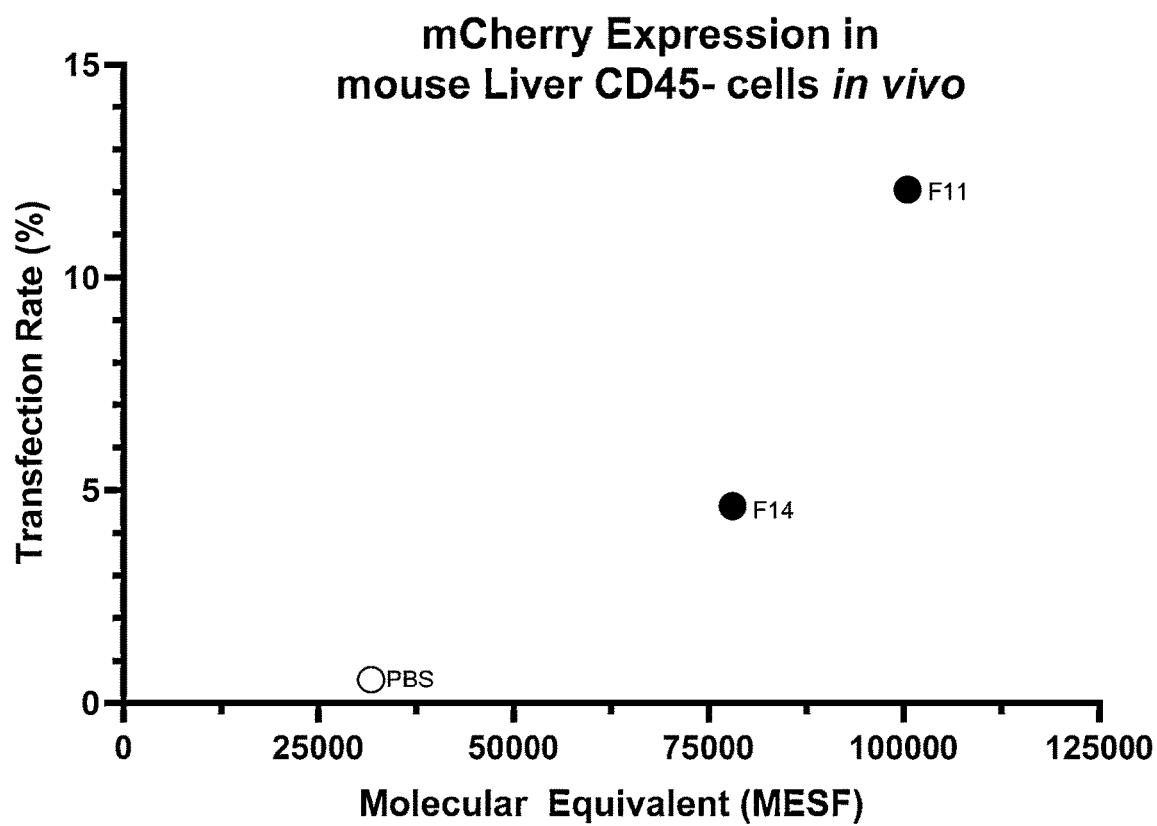
Figure 6C:
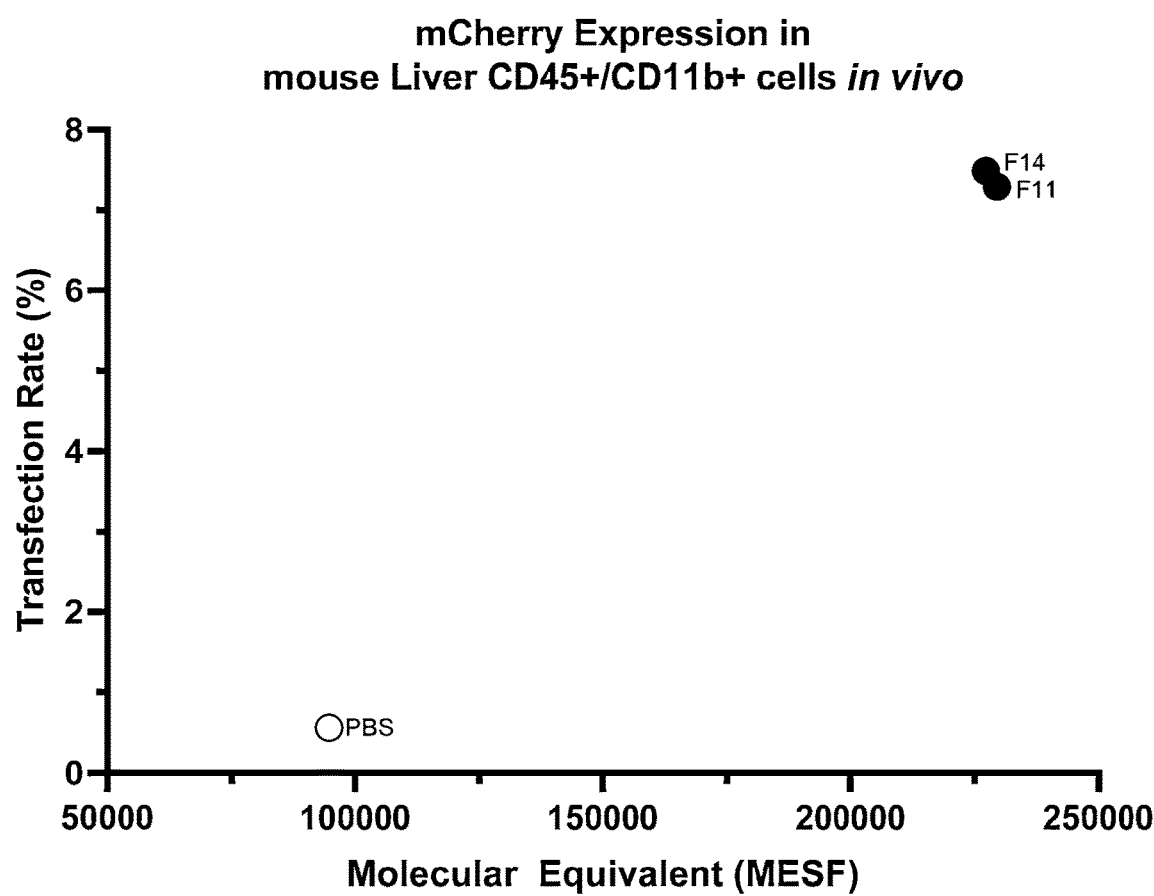

Upon injection into C57BL/6 mice the two compositions had similar transfection rates and expression levels in mouse spleen T cells and liver Kupffer cells but F14 tLNP provided a lower transfection rate and expression level (FIGS. 6A-C). However, in consideration of other factors including favorable physicochemical properties, potential toxicities, and stability, and our other strategies to avoid liver hepatocytes uptake, we continued to use 1.5% as our total PEG-lipid ratio.

Example 7. Assessment of Various Functionalized/Non-Functionalized PEG-Lipid Combinations There were several potential choices for the functionalized and non-functionalized PEG-lipid to use in a tLNP. The PEG-lipid could have a longer or shorter and the lipid could be a diacyl glycerol or a diacyl phospholipid. To gain some insight into the effect of these variables various combinations were selected for testing. With respect to the functionalized PEG-lipid which anchored the binding moiety (after conjugation) it was important that the lipid not be shed from the tLNP. Thus, only longer carbon chain lipids were selected, specifically DSPE (a diacyl phospholipid) and DSG (a diacyl glycerol) based PEG-lipids. For the non-functionalized lipid DMG-PEG-2000 (a shorter carbon chain lipid) was used in addition to DSG-PEG-200 and DSPE-PEG2000.

tLNP were made encapsulating the m1ψ-substituted mCherry mRNA with an N/P ratio of 6 and the general lipid composition CICL1: DSPC: CHOL: PEG-LIPID: PEG-MAL LIPID [58:7:33.5:1.4:0.1]. Whole IgG recognizing mouse CD5 was conjugated to the PEG-MAL LIPID essentially as described above. The particular PEG-LIPID and PEG-MAL LIPID combinations and the physicochemical characterization of the tLNPs are reported in Table 7.

TABLE 7

Physicochemical properties of the tLNP

| Composition Code | PEG-LIPID | PEG-MAL LIPID | Particle size (nm) | PDI | Encapsulation Efficiency (%) |
|---|---|---|---|---|---|
| F5 | DMG-PEG2000 | DSPE-PEG2000-MAL | 90 | 0.1 | 96 |
| F30 | DMG-PEG2000 | DSG-PEG2000-MAL | 94 | 0.1 | 94 |
| F9 | DSG-PEG2000 | DSPE-PEG2000-MAL | 88 | 0.03 | 97 |
| F31 | DSG-PEG2000 | DSG-PEG2000-MAL | 87 | 0.04 | 96 |
| F32 | DSPE-PEG2000 | DSPE-PEG2000-MAL | 90 | 0.1 | 93 |

As seen in the table, all of these particles had similar physicochemical properties. However, aggregation was seen during purification of the F32 tLNP indicating the lipid combination may not be optimal to form stable nanoparticles.

Figure 7A:
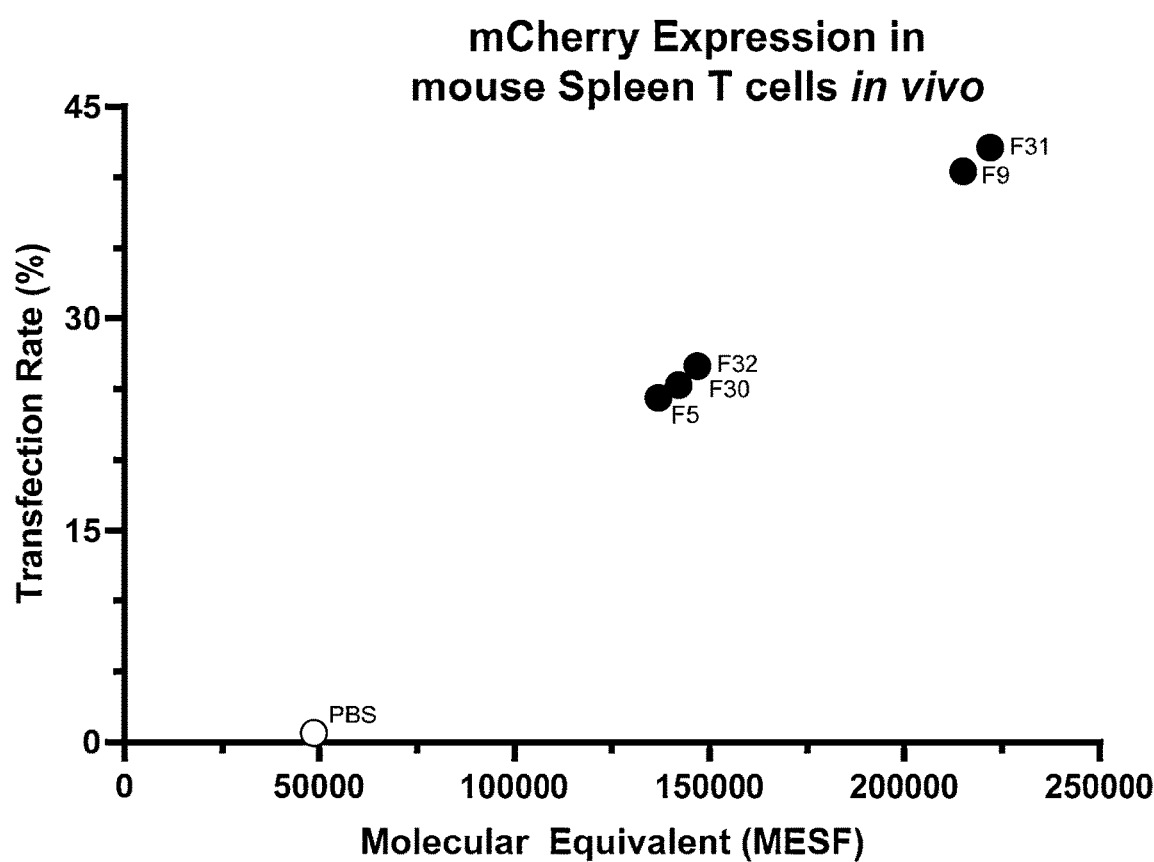
FIGS. 7A-C depict the transfection rate (percentage of T cells expressing the mRNA) and expression level (as MESF) in cells from C57BL/6 mice administered tLNPs comprising various combinations of functionalized and non-functionalized PEG-lipid for splenic T cells (FIG. 7A), CD45⁻ liver cells (FIG. 7B), and CD45⁺ CD11$^b$+ liver cells (FIG. 7C).

Upon injection into C57BL/6 mice the tLNPs with the F9 and F31 compositions performed markedly better than the other three compositions for transfection rate and expression level in splenic T cells (FIG. 7A). Both F9 and F31 contained the longer carbon chain diacyl glycerol, DSG-PEG2000, as its non-functionalized PEG-lipid indicating that not only the lipid tail length but also the glycerol-based as opposed to phosphatidyl scaffold was important for the performance. Comparison of the F5 and F9 tLNP with the F30 and F31 tLNP, respectively, shows that there was no major effect from using the DSPE-versus the DSG-based functionalized PEG-lipid on performance in T cells in the tested embodiments.

Figure 7B:
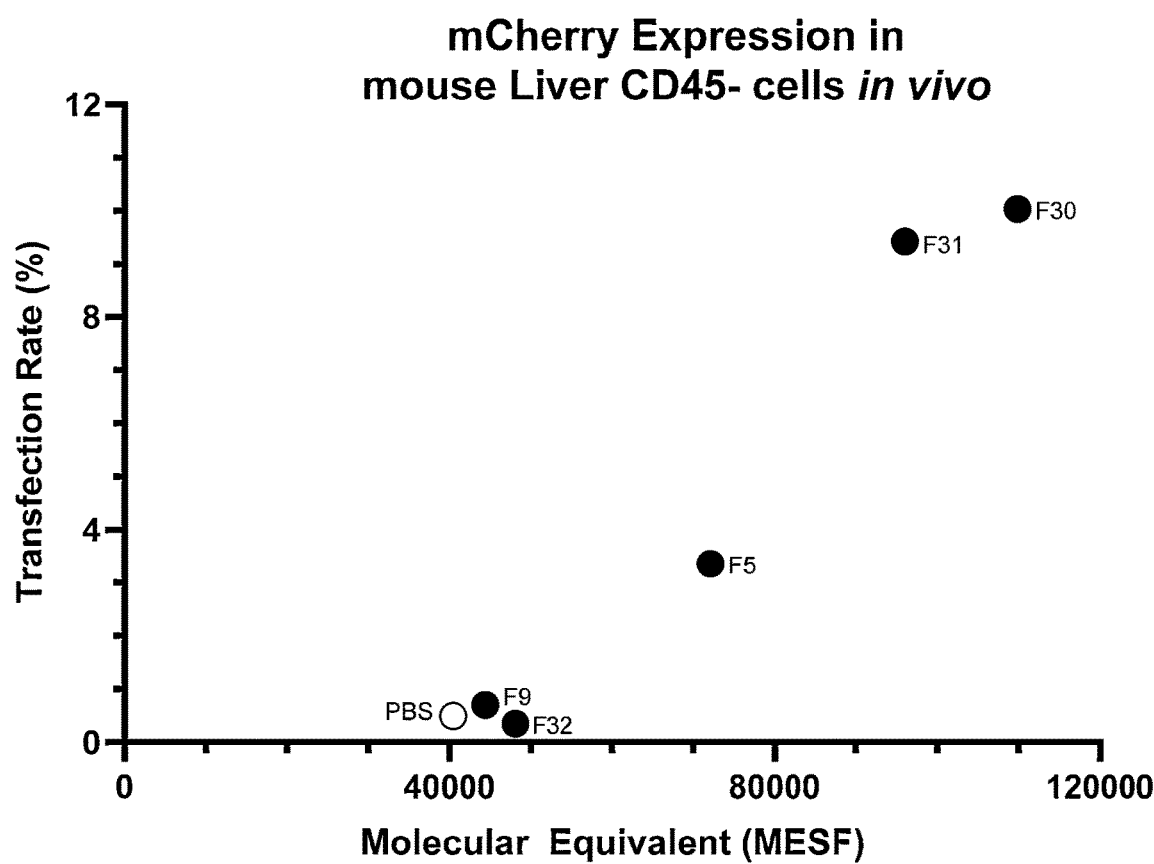

However, in hepatocytes, tLNPs with the F31 composition, along with tLNPs with the F30 provided substantial transfection rates and expression levels, that is, the two containing a functionalized diacyl glycerol, whereas tLNPs with the F9 or F32, both of which contain the diacyl phospholipid DSPE, provided very low levels of transfection and expression. Thus, use of the phospholipid in the functionalized PEG-lipid appeared to be critical in avoiding hepatic transfection. tLNPs with the composition F5, which also contained a DSPE-based functionalized lipid but also the shorter carbon chain DMG-based non-functionalized lipid, provided intermediate performance (FIG. 7B) reflecting the importance of lipid carbon chain length seen in Example 5, but further indicating that the lipid's scaffold (glycerol or phosphatide) had little importance, for avoiding uptake by hepatocytes.

Figure 7C:
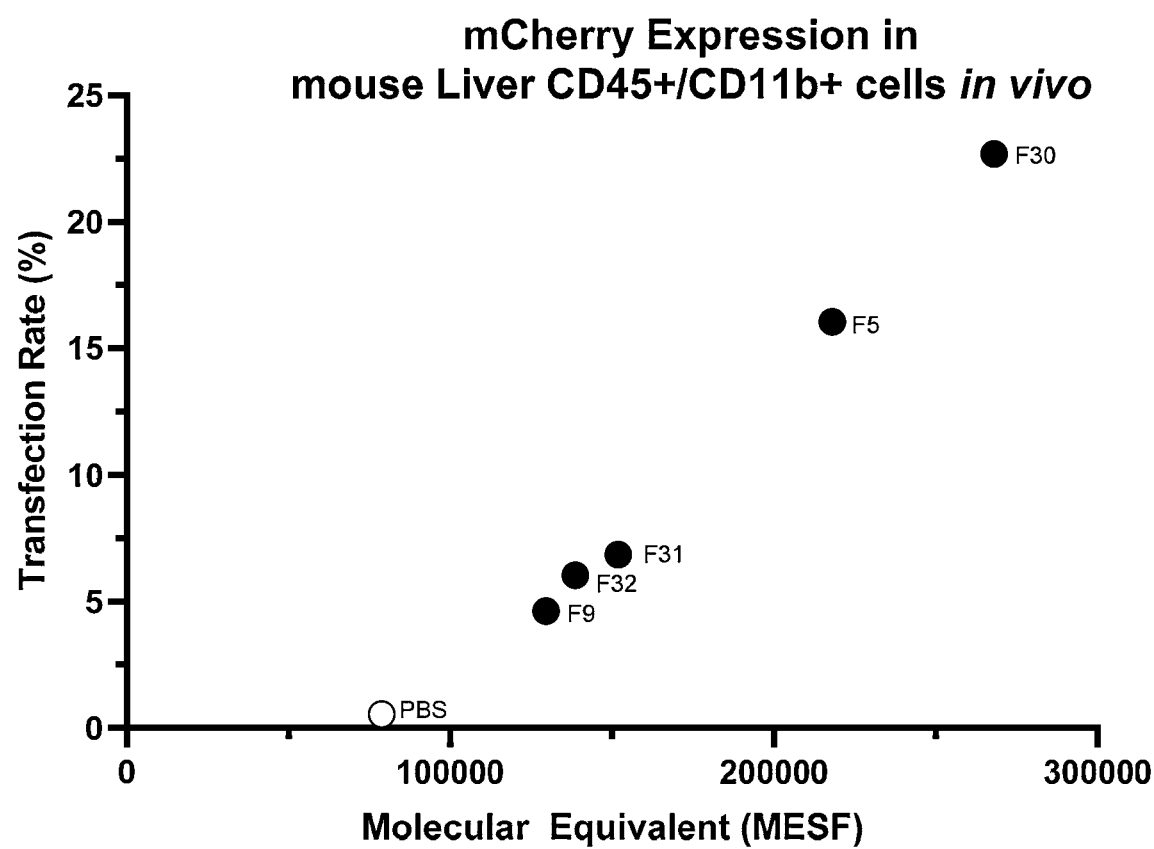

In Kupffer cells tLNPs with the F9, F31 and F32 compositions provided low levels of transfection and expression, again reflecting the importance of longer carbon chain length in the non-functionalized PEG-lipid for avoiding liver uptake of the tLNPs. The somewhat lower expression provided the F9 tLNPs than the F32 tLNPs supported the preference noted above for a glycerol-based lipid scaffold in the non-functionalized PEG-lipid to avoid liver uptake. tLNPs with the F5 composition showed intermediate levels and tLNP with the F30 composition, quite substantial levels (FIG. 7C) of transfection of and expression in Kupffer cells. Comparison of the performance of the F5 and F30 tLNPs, which incorporated different non-functionalized PEG-lipid, showed the importance of their common component DSPE-PEG-MAL, the phosphatidyl functionalized PEG-lipid, in avoiding liver uptake of the tLNPs.

Overall, the F9 tLNPs, comprising DSG-PEG2000 and DSPE-PEG2000-MAL, showed the best performance in transfecting T cells but avoiding uptake in the liver.

Example 8. Assessment of the Effect of Phospholipid Content

Phospholipid content can influence the formation, structure, and stability of LNPs, among other characteristics. Here the proportion of DSPC was varied and compensatory adjustments to the cholesterol content were made in the context of either DMG-PEG2000 or DSG-PEG2000 as the non-functionalized PEG-lipid. Specifically, the tLNP comprised CICL1: DSPC: CHOL: DMG-PEG2000: DSPE-PEG2000-MAL in the ratio of [58: M: (40.5-M): 1.4:0.1] where M was 10 (F5) or 7 (F11) or CICL1: DSPC: CHOL: DSG-PEG2000: DSPE-PEG2000-MAL in the ratio of [58: N: (40.5-N): 1.4:0. 1] where N was 10 (F9) or 7 (F13). tLNP were made encapsulating the m1ψ-substituted mCherry mRNA with an N/P ratio of 6. Formation of the tLNP and conjugation of the anti-CD5 antibody was as described above. The particular PEG-lipid and DSPC combinations and the physicochemical characterization of the tLNPs are reported in Table 8.

TABLE 8

Physicochemical properties of the tLNP

| Composition Code | PEG-LIPID | DSPC Content (%) | Particle size (nm) | PDI | Encapsulation Efficiency (%) |
|---|---|---|---|---|---|
| F11 | DMG-PEG2000 | 7 | 99 | 0.09 | 86 |
| F5 | DMG-PEG2000 | 10 | 95 | 0.05 | 95 |
| F13 | DSG-PEG2000 | 7 | 100 | 0.05 | 92 |
| F9 | DSG-PEG2000 | 10 | 90 | 0.07 | 97 |

As seen in Table 8, the tLNPs with only 7% DSPC (F11 and F13) had lower mRNA encapsulation efficiency, and slightly larger particle sizes, suggesting 7% DSPC may not be sufficient to provide a stable structure for the LNPs.

Figure 8A:
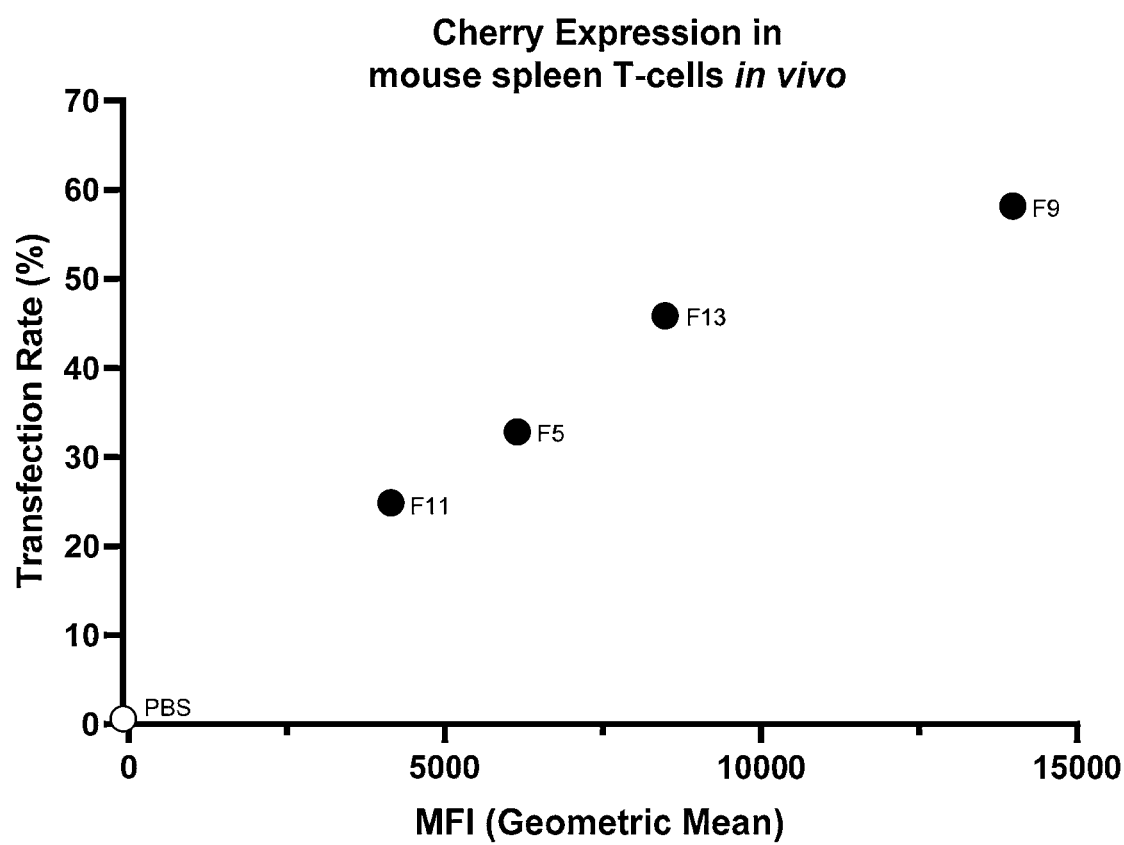
FIGS. 8A-C depict the transfection rate (percentage of T cells expressing the mRNA) and expression level (as MFI) in cells from C57BL/6 mice administered tLNPs comprising two different amounts of phospholipid and two different non-functionalized PEG-lipid for splenic T cells (FIG. 8A), CD45⁻ liver cells (FIG. 8B), and CD45⁺ CD11$^b$+ liver cells (FIG. 8C).
Figure 8B:
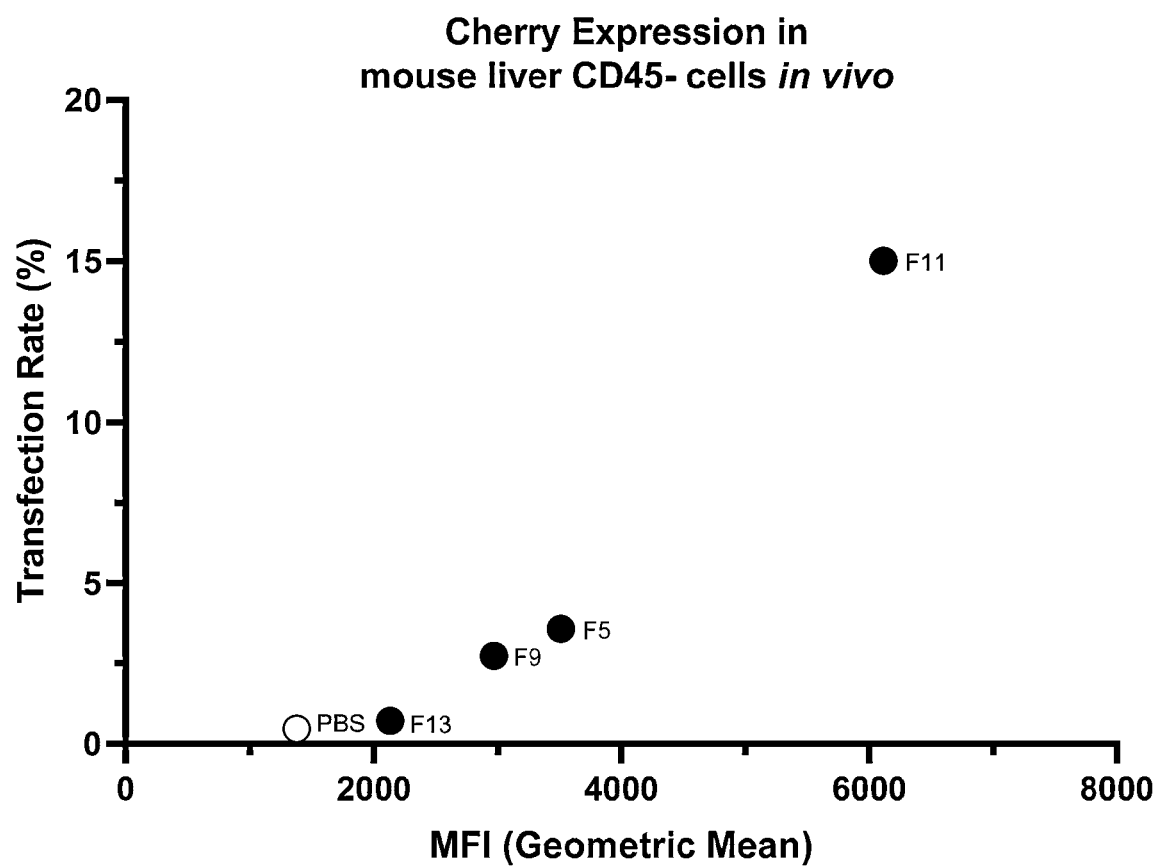
Figure 8C:
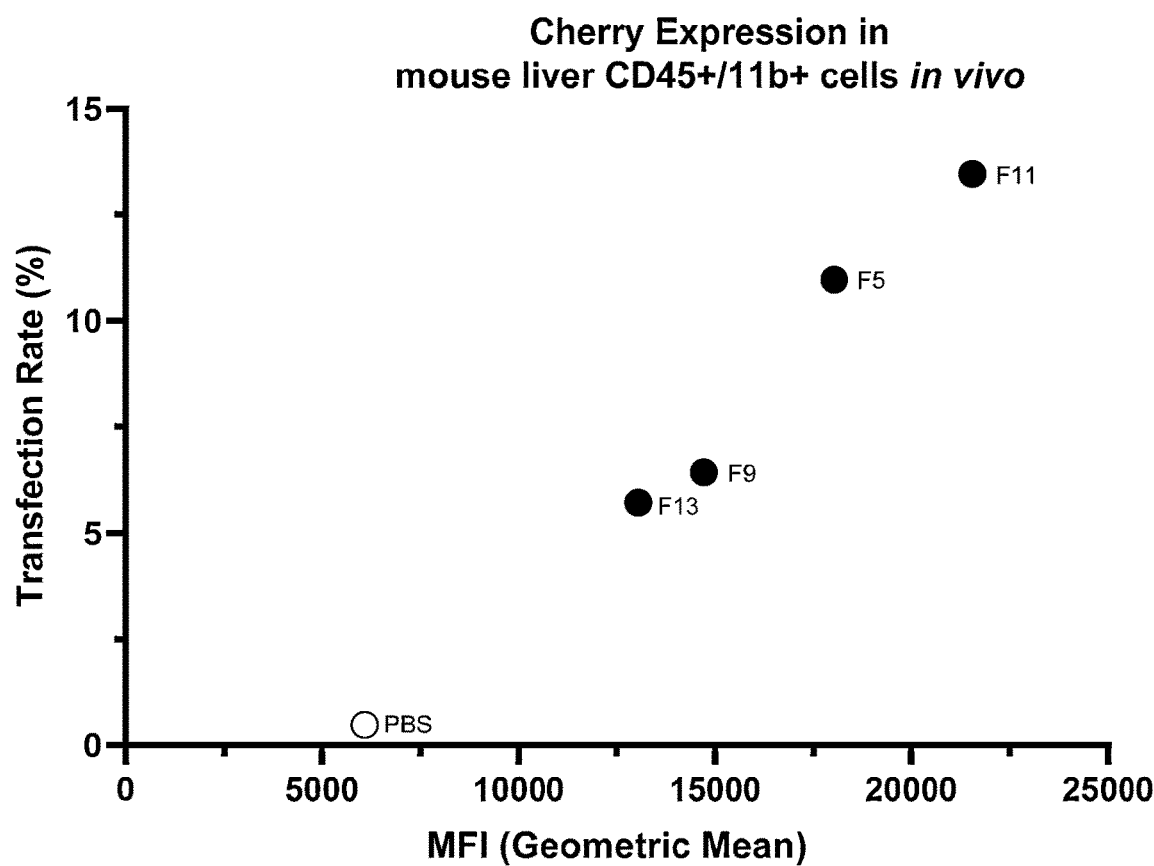

Upon injection into C57BL/6 mice, tLNPs comprising 10% DSPC (F5 and F9) and either DMG- or DSG-based non-functionalized PEG-lipid provided much higher mCherry expression in mouse splenic T cells compared to the corresponding 7% DSPC version (F11 and F13, respectively; FIG. 8A). This better performance may be due, at least in part, to the greater stability of the tLNPs comprising 10% DSPC as compared to those with 7% DSPC. Comparing the two pairs of DMG- and DSG-based tLNP with the same DSPC content again demonstrates the superiority of the longer carbon chain anchor on the PEG-lipid. The F11 tLNPs had much higher mCherry transfection and expression levels in both hepatocytes and Kupffer cells than F5 tLNPs indicating 10% DSPC was more favorable for avoiding liver uptake (FIGS. 8B-C). The F13 tLNPs had comparable or slightly diminished performance than the F9 tLNPs in the liver cells. However, due to the already low level of transfection and expression resulting from the uses of DSG-PEG2000, and considering the superior performance in T cells of the F9 composition over the F13 composition, the F9 tLNPs remained the overall better choice for delivery to T cells.

Example 9. Effects of Antibody Conjugation on Delivery Locus

Figure 9A:
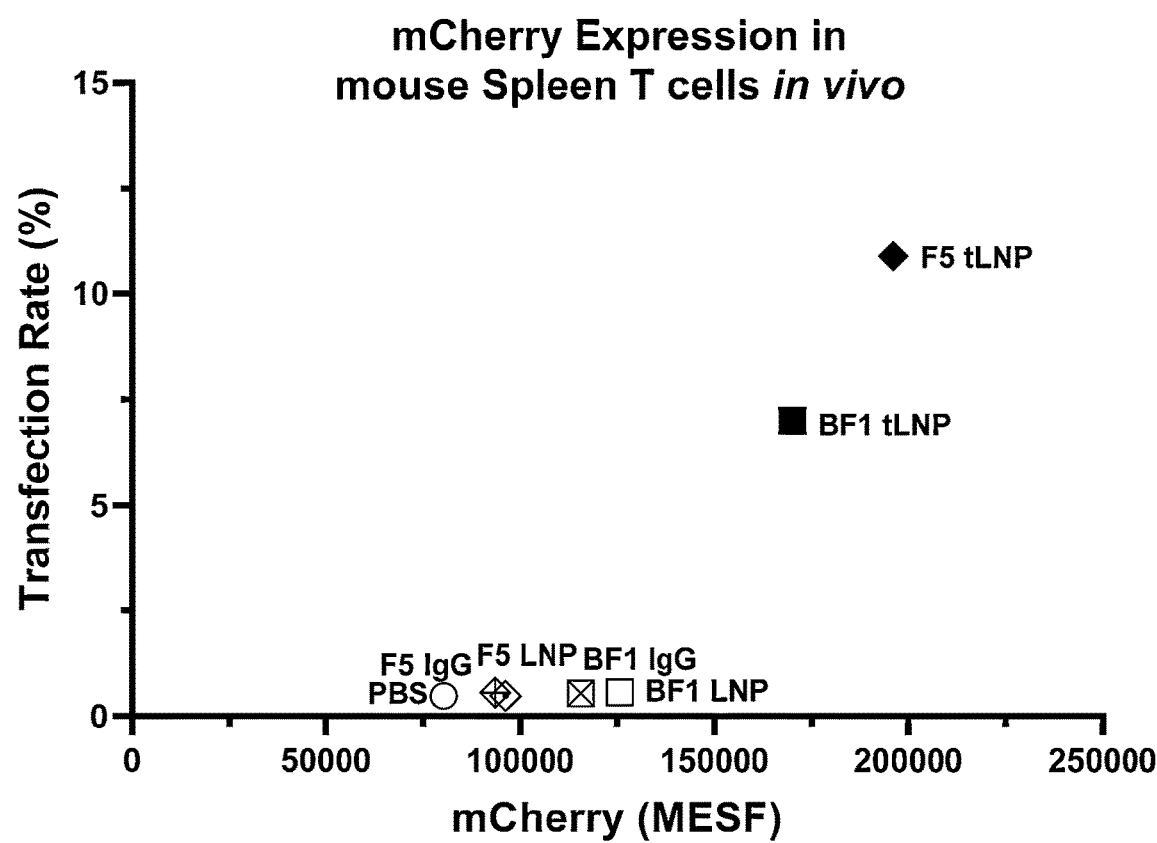
FIGS. 9A-B depict the transfection rate (percentage of T cells expressing the mRNA) and expression level (as MESF or MFI in 9A and 9B respectively) in cells from C57BL/6 mice administered tLNP (decorated with a targeting antibody), LNP decorated with an irrelevant antibody, and LNP with no antibody for splenic T cells (FIG. 9A), CD45⁻ liver cells (FIG. 9B).
Figure 9B:
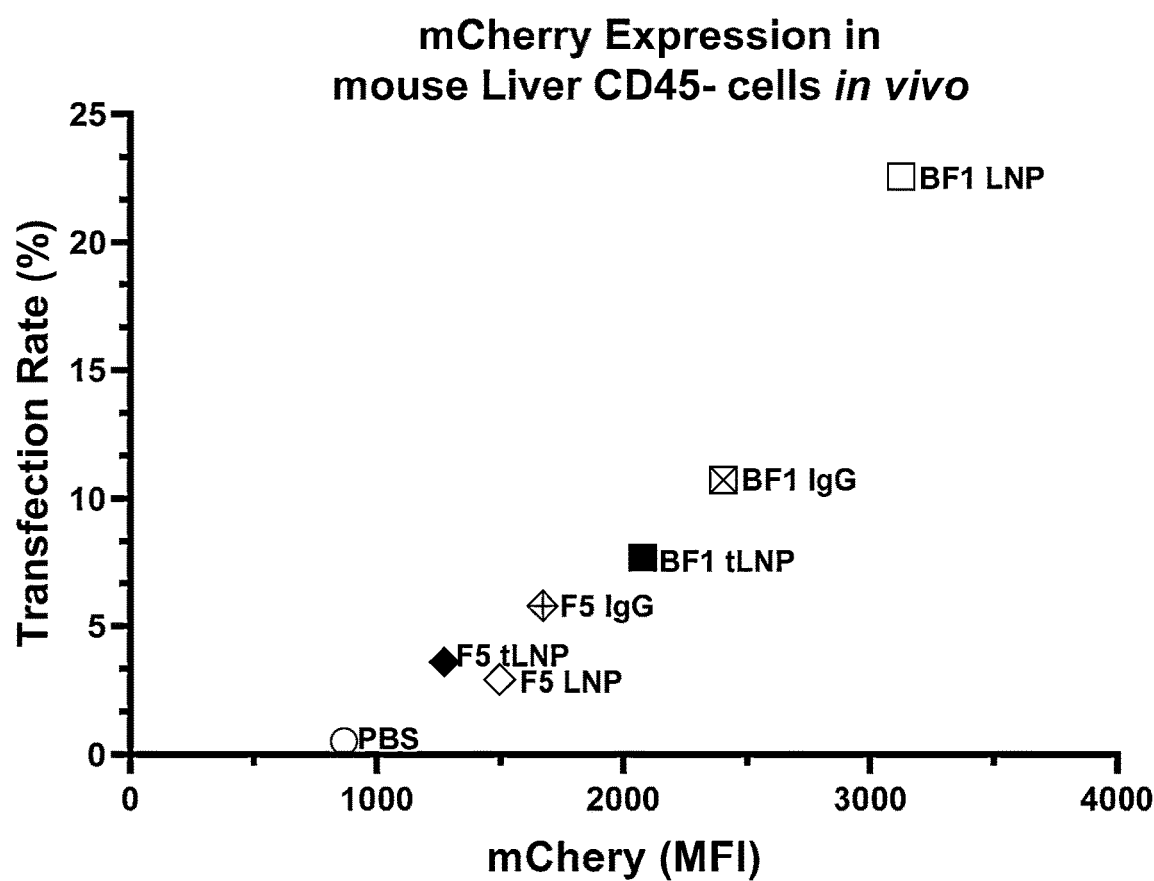

Conventional LNPs deliver their payload primarily to the liver following intravenous administration. Here we explored the effect of decorating LNP with antibody on payload delivery. Using the BF1 and F5 compositions, undecorated LNP, LNP decorated with irrelevant IgG, and tLNP decorated with the anti-mouse CD5 antibody were prepared and administered to C57BL/6 mice by tail vein injection. Only the tLNP with the anti-CD5 antibody provided substantial transfection rates in splenic T cells (FIG. 9A). With respect to CD45⁻ liver cells (hepatocytes) the BF1 LNP had a transfection rate of nearly 25%. Decorating the BF1 LNP with an irrelevant IgG reduced the transfection rate of hepatocytes by about half and decorating the BF1 LNP with the anti-CD5 antibody (a true tLNP) reduced the hepatocyte transfection rate to less than 10% (FIG. 9B). The F5 LNP already had a low transfection rate on hepatocytes, less than 5% and addition of antibody did not further reduce it in this experiment. Thus, adding antibody or changing the ionizable lipid both reduced delivery to the liver.

Figure 9C:
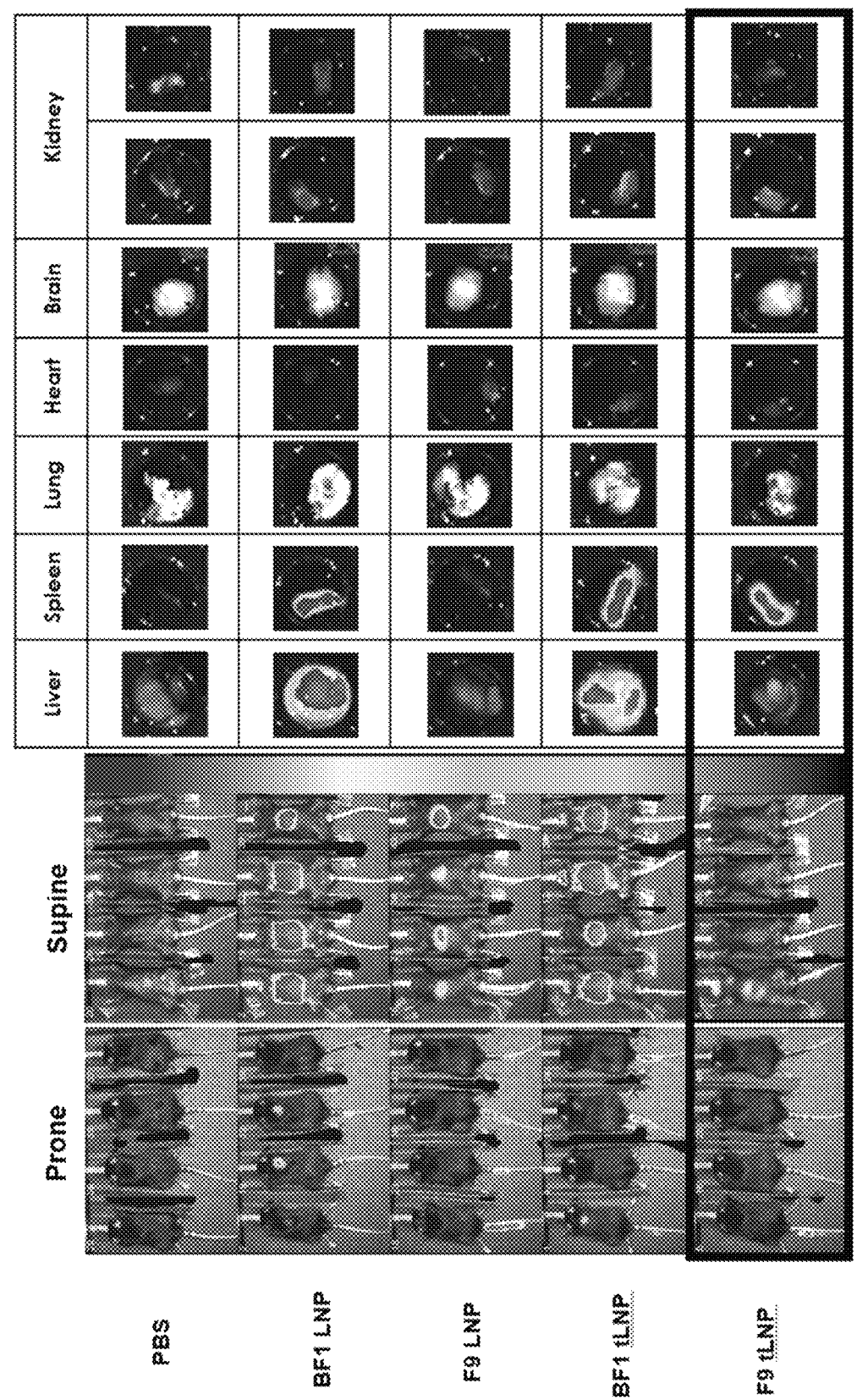
FIGS. 9C-D present whole-animal and individual organ bioluminescence images (FIG. 9C) and individual organ bioluminescence quantitation (FIG. 9D) for C57BL/6 mice administered BF1 LNPs, CD5-targeted BF1 tLNPs, F9 LNPs, or CD5-targeted F9 tLNPs.
Figure 9D:
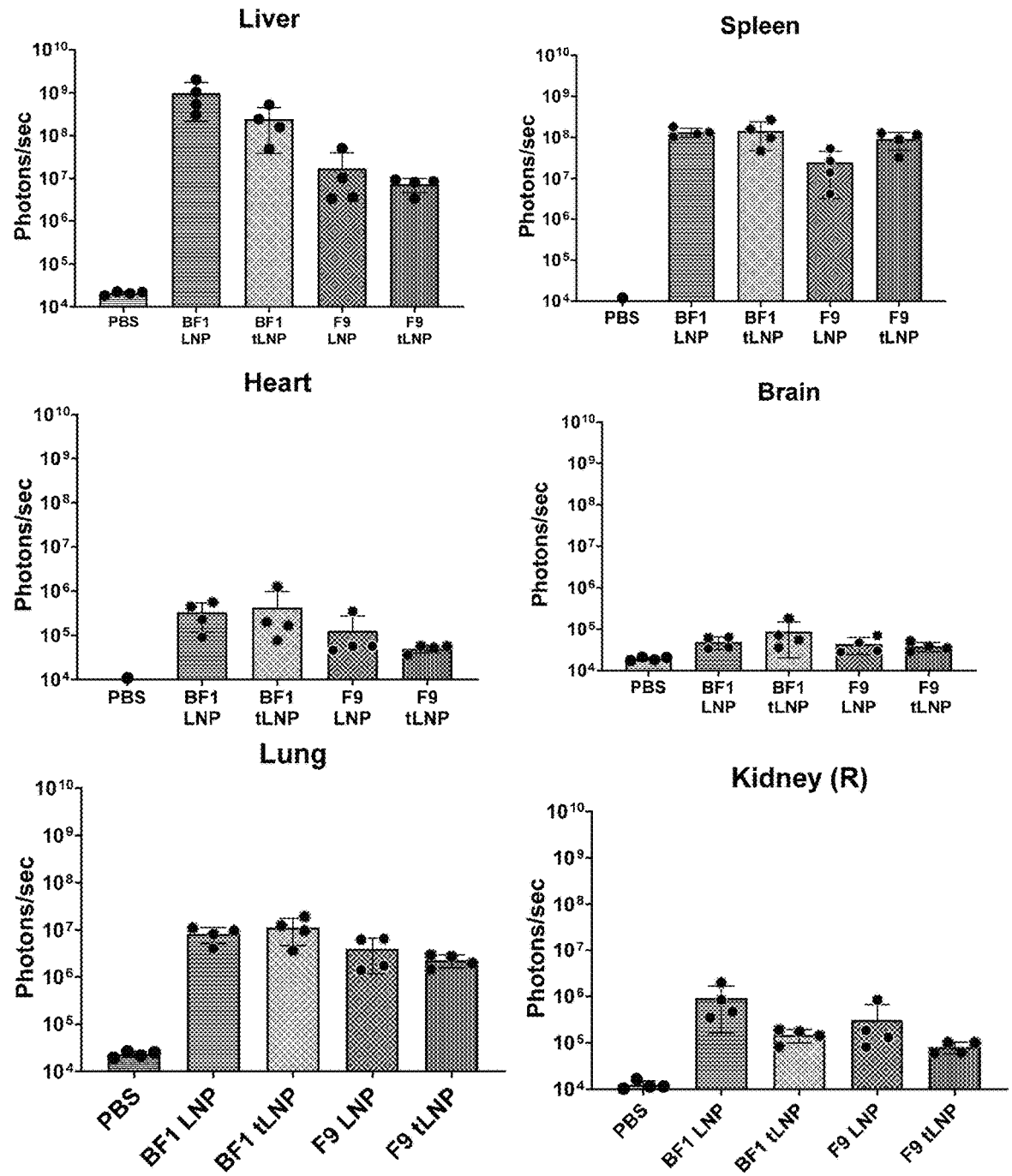

In a further study, nine-week-old female C57Bl/6 mice were intravenously injected with BF1 or F9 LNPs or CD5-targeted tLNPs encapsulating mRNA encoding luciferase at a dose of 2 µg mRNA/animal via the tail vein. At 6 hours post-injection, prone and supine bioluminescence images were collected from all mice (FIG. 9C). Following whole-animal imaging, the mice were sacrificed, perfused and the following tissues collected: liver, spleen, lung, kidneys (both), heart and brain. Tissues were placed into luciferin pre-filled black polystyrene well plates with spacing between tissues and bioluminescent images were collected (FIG. 9C). Quantitative results (FIG. 9D; data from right kidney (not shown) is similar to the left kidney data) show that use of CICL1 reduced bioluminescence in the liver about 2 logs compared to the BF1 compositions yet for the tLNP incorporating CICL1 bioluminescence in the spleen was similar to the BF1 compositions and about 1 log greater than its administration led to in the liver.

These compositions displayed the general pattern that bioluminescence in spleen>lung>kidney>heart>brain, with the CICL1 containing tLNP composition generally producing the least bioluminescence in each of the non-target organs.

Example 10. Comparison of tLNP Targeting CD5 and CD8 in a Mouse Tumor Model

LNP with the F9 composition were prepared and conjugated with either a humanized 5D7 (anti-CD5) antibody or a chimeric RPA-T8 (anti-CD8) antibody to generate tLNP. The tLNP encapsulated $N^1$-methylpseudouridine-substituted mRNA encoding an anti-CD19 CAR (CD5- and CD8-targeted tLNP) or 5-methoxyuridine-substituted mRNA encoding mCherry (CD5-targeted tLNP only).

NSG mice (approximately 10 weeks old) were purchased from The Jackson Laboratory and acclimated for at least 5 days. Ten million human T cells were injected intravenously via the tail vein. After 10 days of the T cell engraftment, 5×10⁵ Nalm6 cells constitutively expressing Firefly Luciferase (Nalm6-Luc) were injected intravenously. Five days following tumor cell engraftment mice were evaluated for T cell engraftment (frequency of human CD45+ cells in circulation) and tumor burden (assessed by luciferase signal) and staged in groups with similar averages of both readouts. From the 18th day following T cell engraftment, groups of mice were injected intravenously with one of the tLNPs comprising 20 µg mRNA twice weekly for a total of 5 doses. Tumor cell burden was evaluated by bioluminescence imaging (BLI) of the luciferase signal twice weekly. Additionally, at 24 hrs after the third dose, peripheral blood samples were analyzed by flow cytometry for mCherry expression and CAR expression (using a PE-conjugated antibody against the scFv linker) on T cells.

Figure 10A:
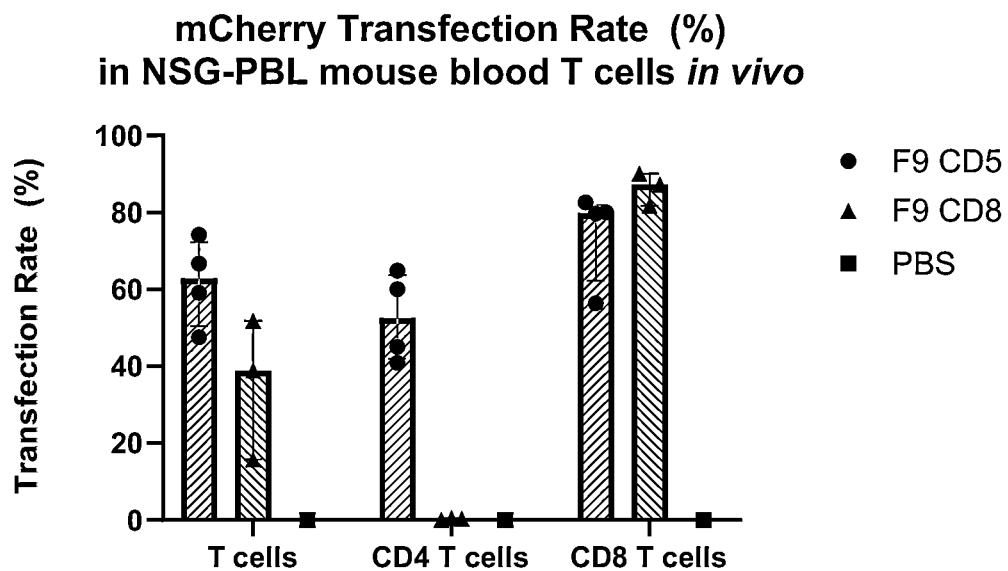
FIGS. 10A-F portray the results of studies in NSG mice engrafted with human peripheral blood lymphocytes and administered twice weekly up to five doses of tLNP composition F9 targeted to either CD5 or CD8 and encapsulating an mRNA encoding either mCherry or an anti-CD19 CAR.
Figure 10B:
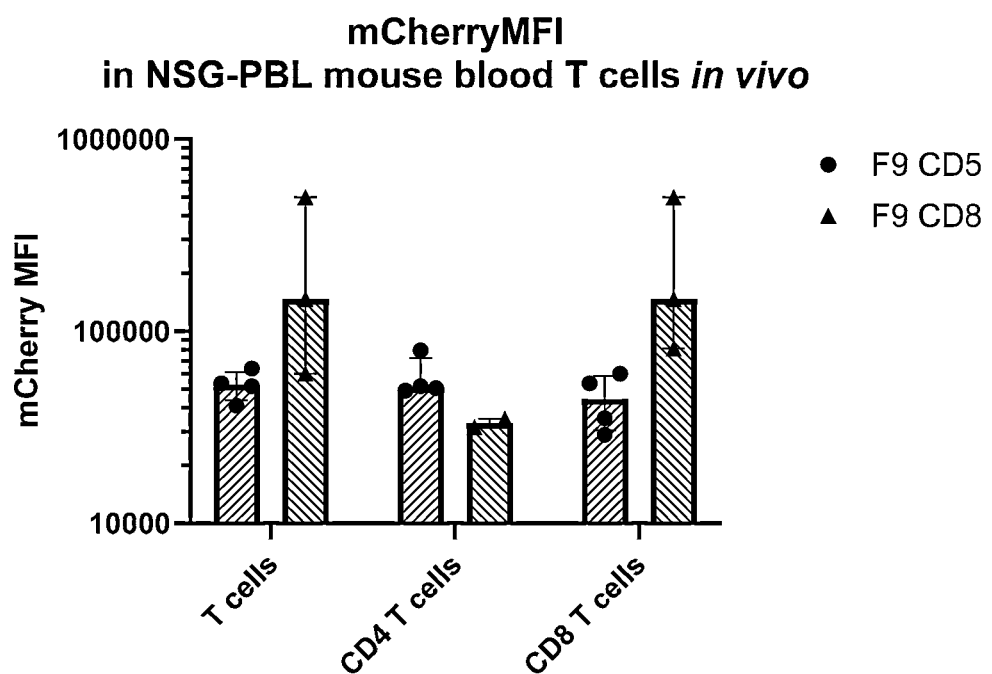
Figure 10C:
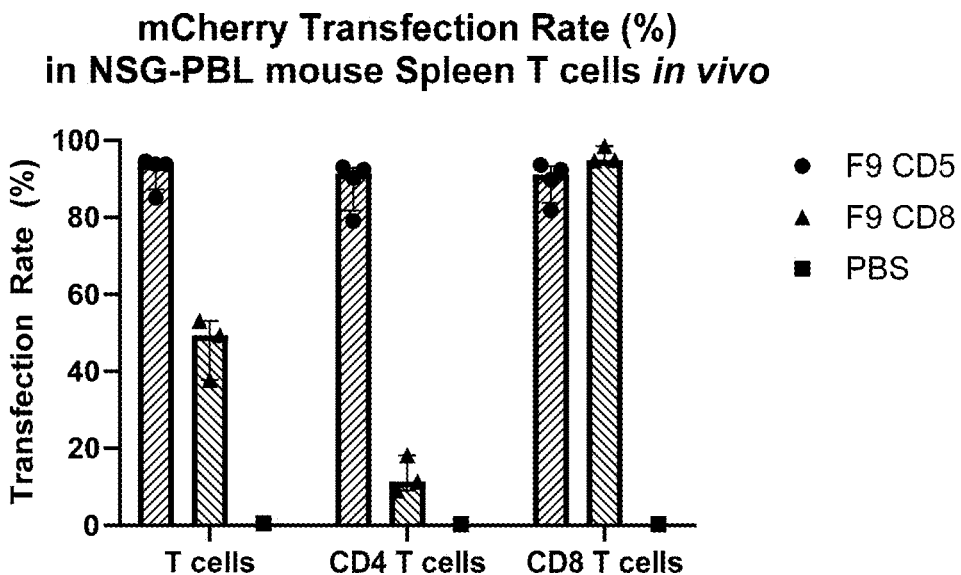
Figure 10D:
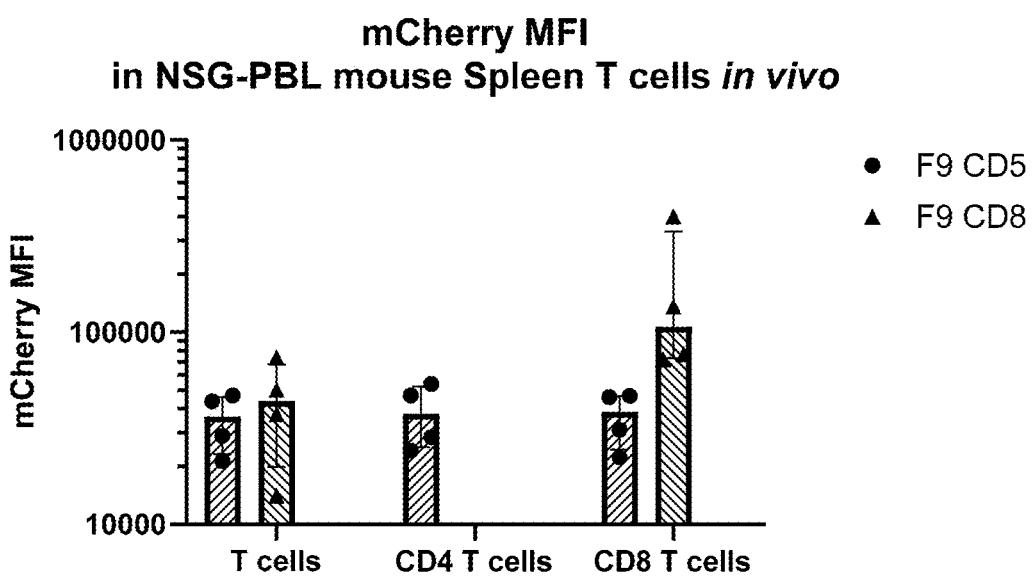
Figure 10:
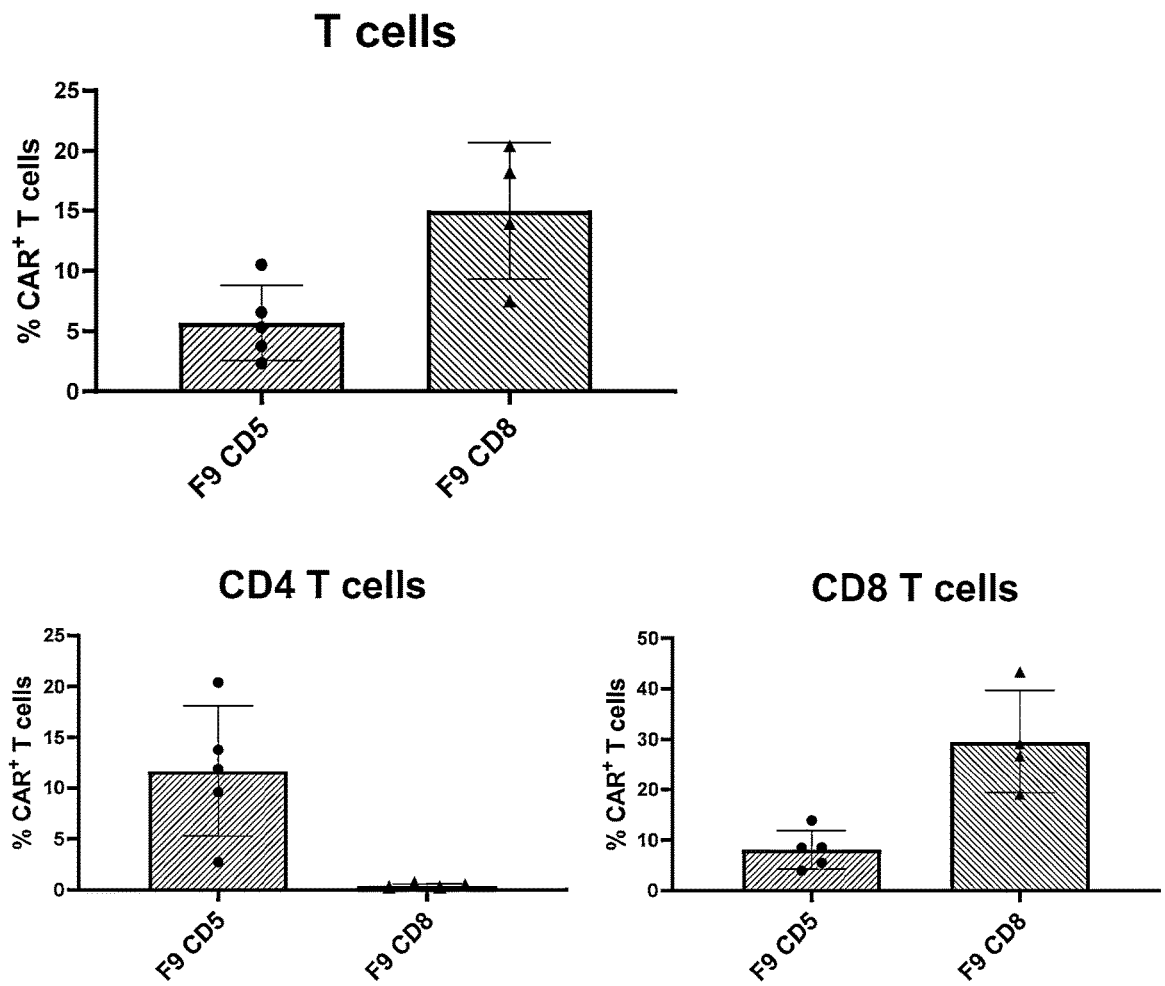

The tLNP decorated with the anti-CD5 and anti-CD8 antibodies achieved similar transfection rates in CD8⁺ blood T cells. As compared to the CD5-targeted tLNP (F9 CD5, solid circle), the transfection rate on T cells over all was reduced for the CD8-targeted tLNP (F9 CD8, solid triangle) due to their inability to transfect CD4⁺ T cells (FIG. 10A). PBS (solid square) was administered as a negative control. The CD8-targeted tLNP (F9 CD8, solid triangle) provided higher expression levels in CD8$^+$ and total T cells than did the CD5-targeted tLNP (F9 CD5, solid circle) likely reflecting the greater density of CD8 than CD5 on the cell surface (FIG. 10B). Similar patterns were observed in splenic T cells (FIGS. 10C-D). The anomalous expression in CD4$^+$ T cells treated with the CD8-targeted tLNP seen in blood (FIG. 10B) was an artifact of the small number of events in the flow cytometry and was not seen in the results for the splenic T cells where a much greater number of events were collected (FIG. 10D). These data support the relevance of data obtained with CD5-targeted tLNP to tLNP targeted to other cell surface antigens.

For the CAR, the transfection efficiency was higher with the CD8-targeted tLNP (F9 CD8) in both total T cells and CD8$^+$ T cells than with the CD5-targeted tLNP (F9 CD5) (FIG. 10E), although the rates of transfection were substantially less than seen with the mCherry mRNA. This likely reflects that the CAR mRNA had not be optimized for in vivo transfection using tLNP.

Figure 10F:
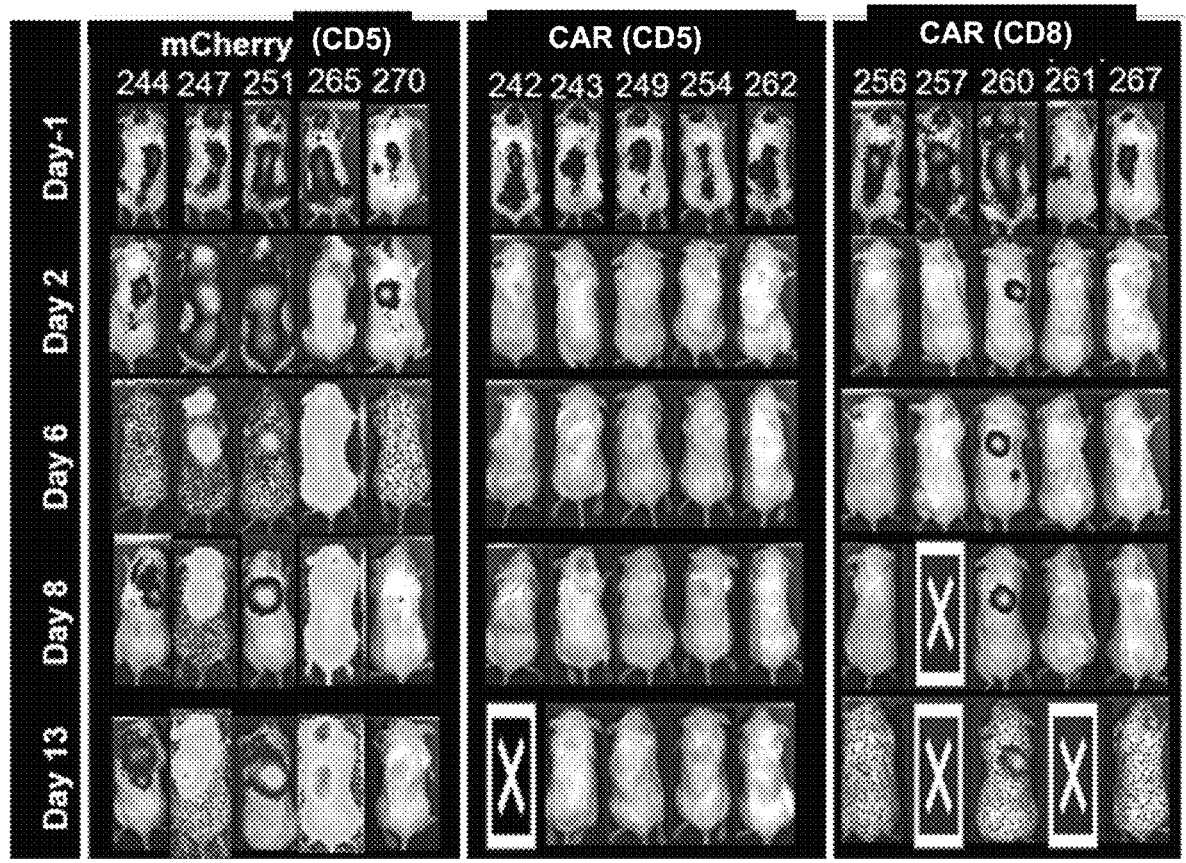

Evaluation of tumor burden via luciferase signal demonstrated that, in general, tumors grew in the mCherry treated groups while there was a significant reduction of tumor burden in the groups receiving the encoded anti-CD19 CAR, irrespective of whether they were treated with CD5 (CD5) or CD8 (CD8) targeting tLNPs of composition F9 (FIG. 10F). Indeed, in most of the treated mice apparently complete clearance was achieved by the 2$^{nd}$ day following the first administration of the tLNPs.

Example 11. Tolerability of BF1 LNP, BF1 tLNP, and F5 LNP and tLNP

Figure 11A:
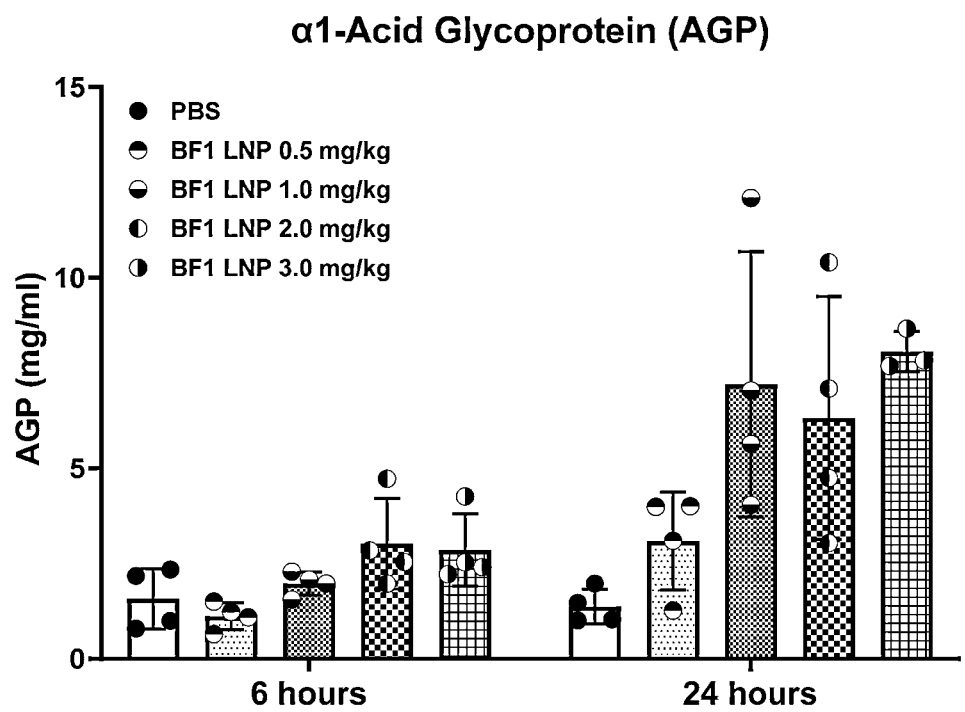
FIGS. 11A-L depict the levels of various liver enzymes and acute phase proteins in rats administered the benchmarks BF1 LNP or BF1 tLNP and tLNP with the F5 composition.
Figure 11B:
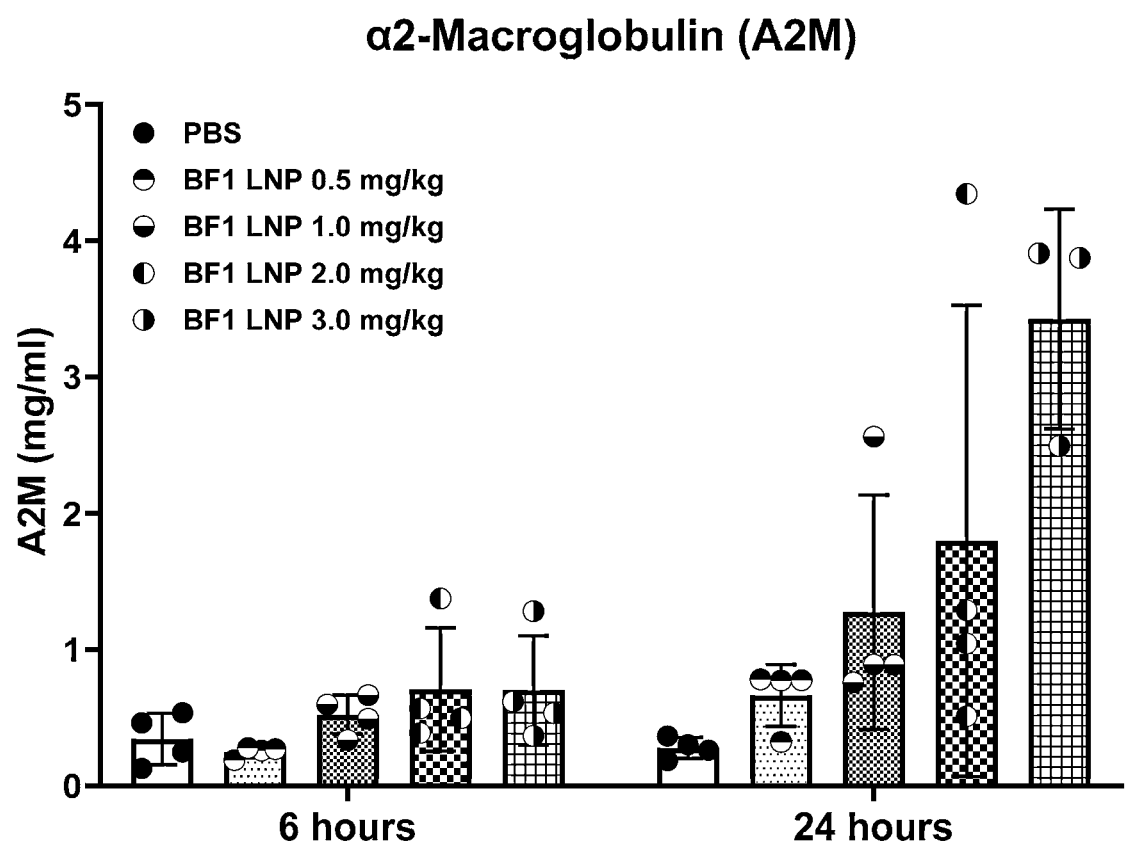
Figure 11C:
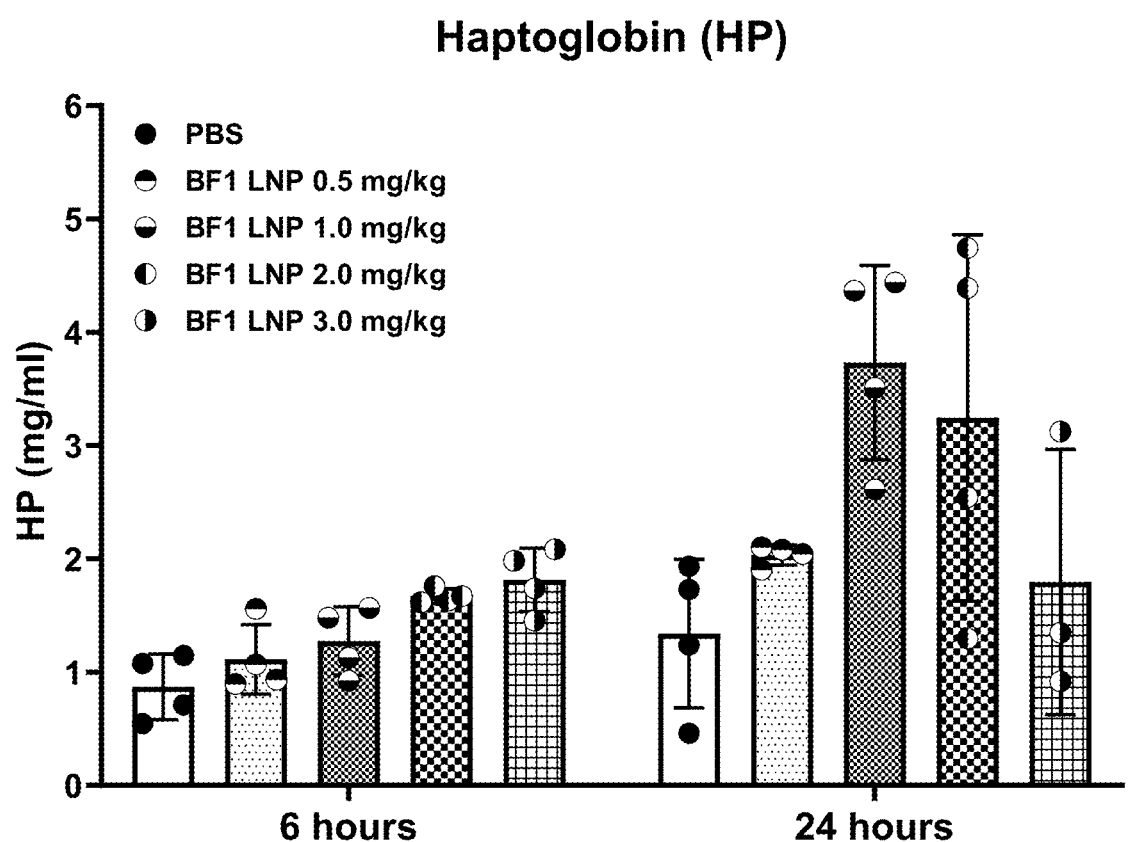
Figure 11D:
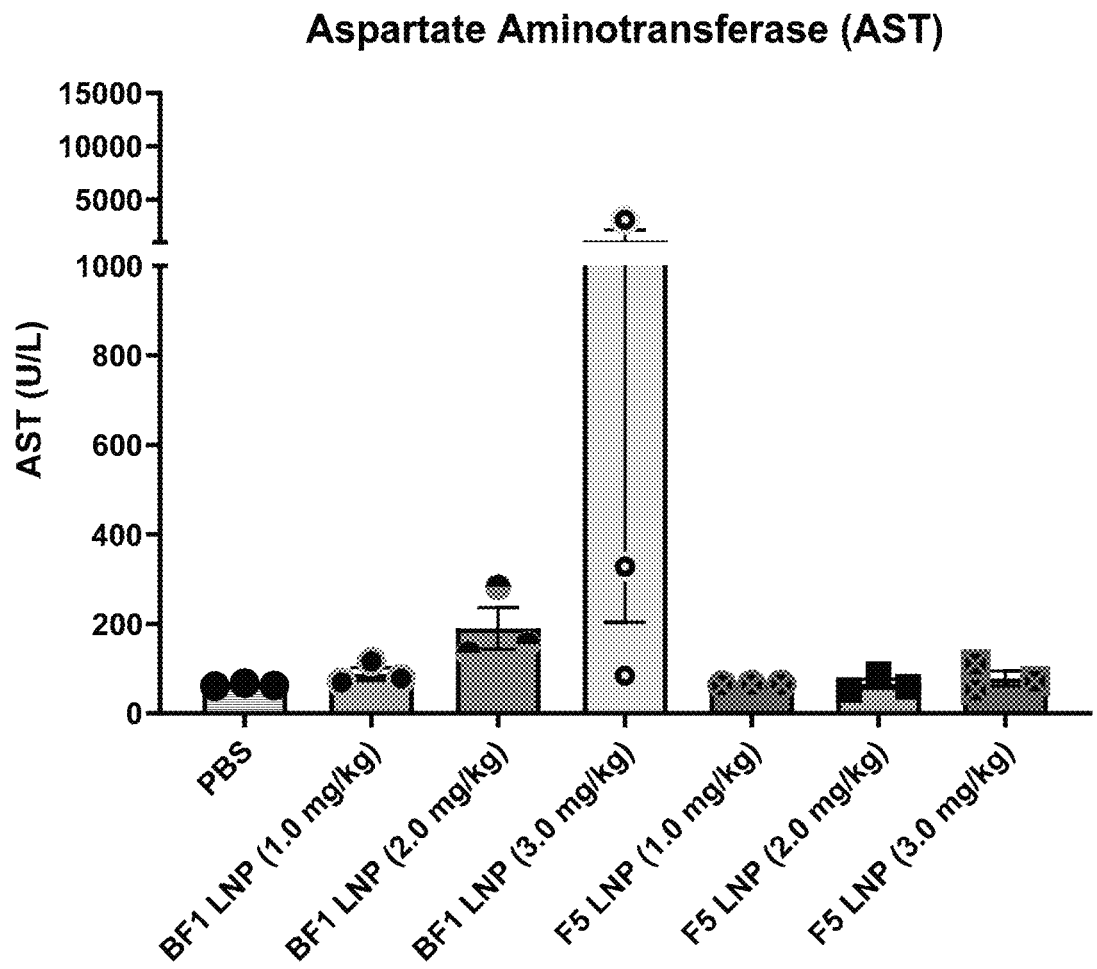
Figure 11E:
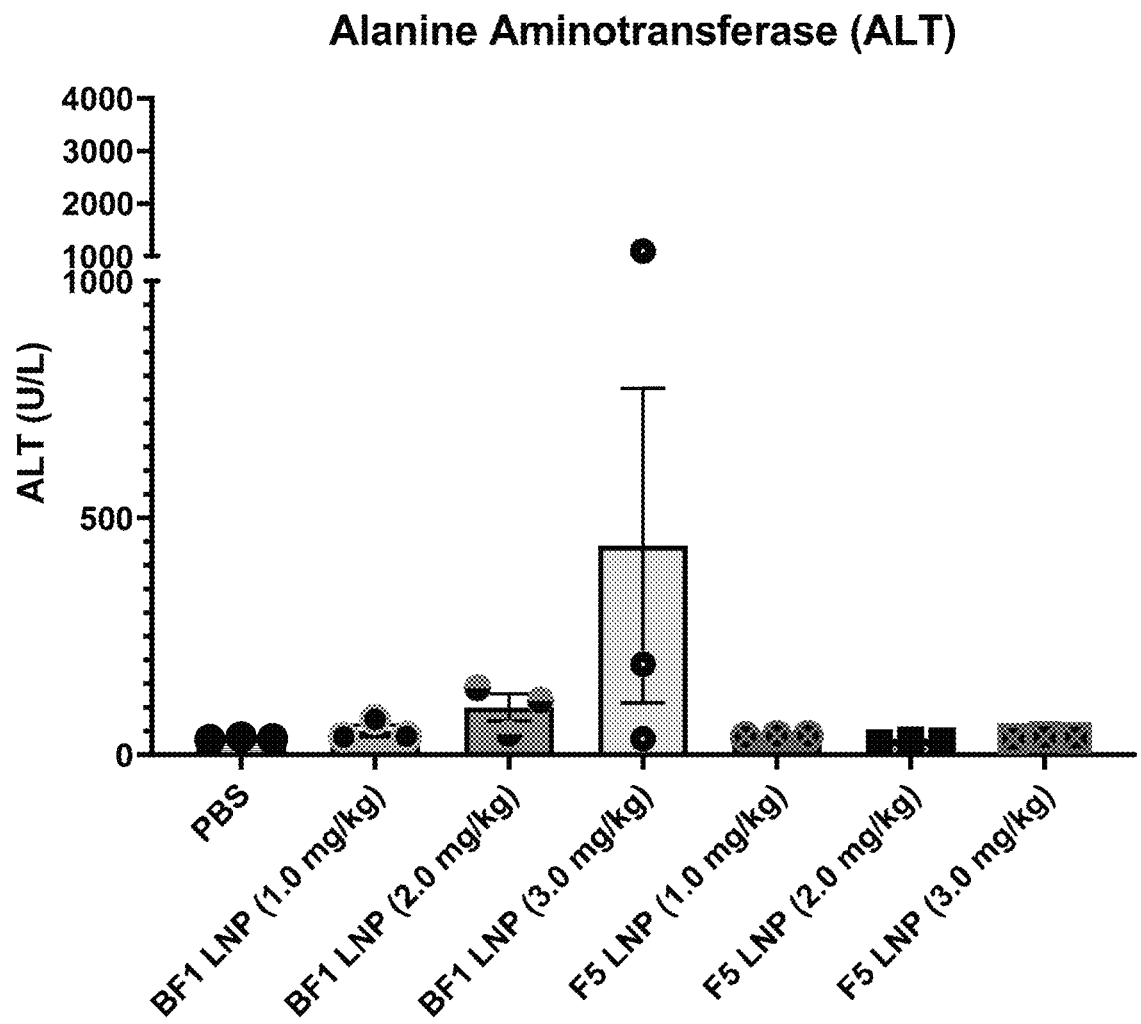
Figure 11F:
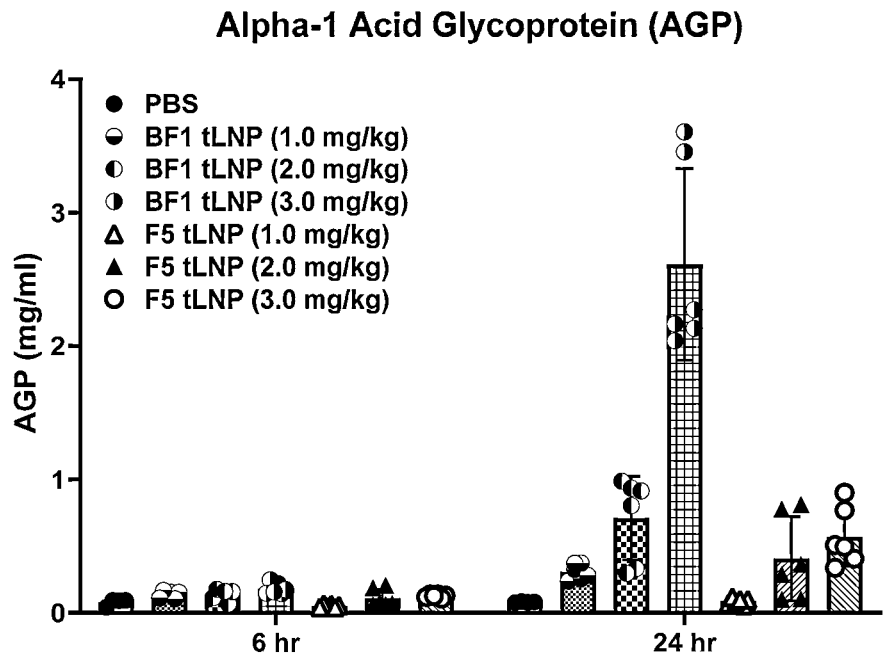
Figure 11G:
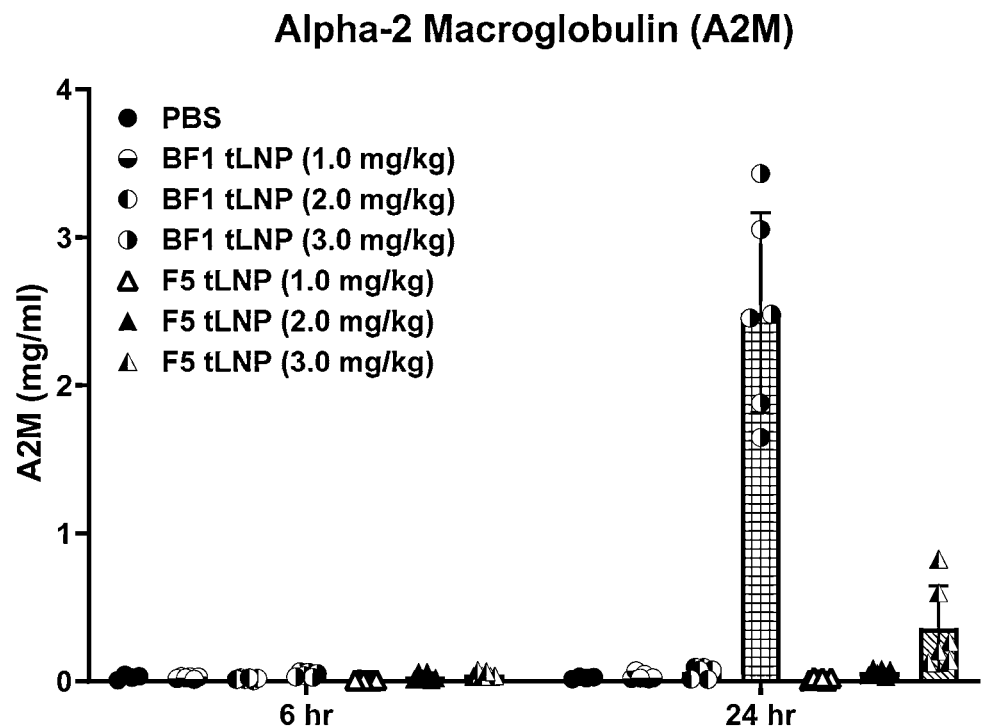
Figure 11H:
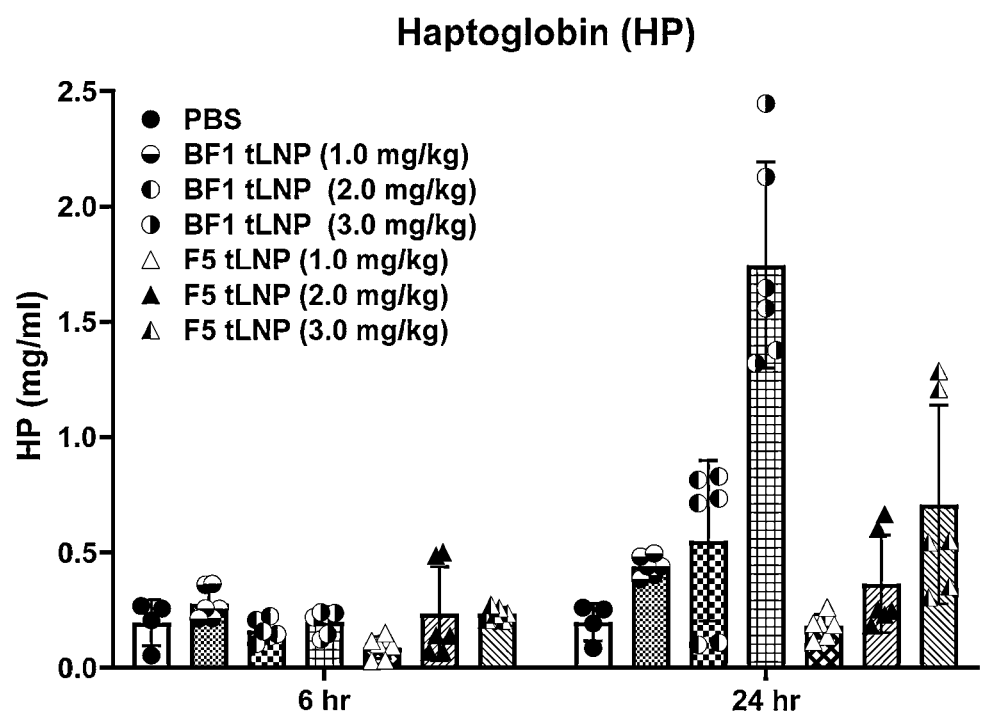
Figure 11I:
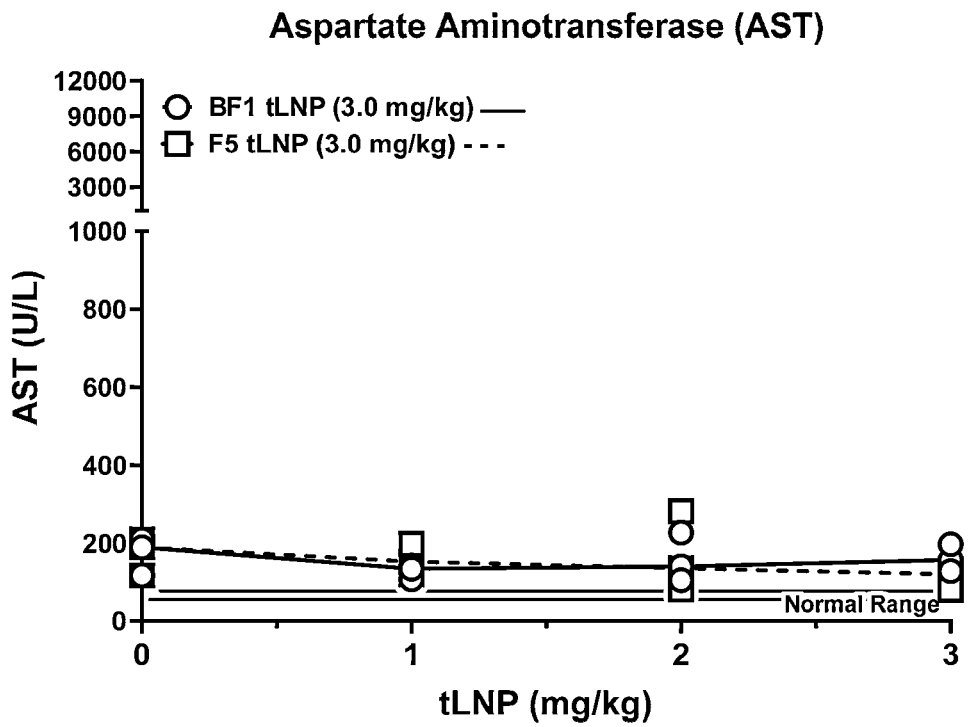
Figure 11J:
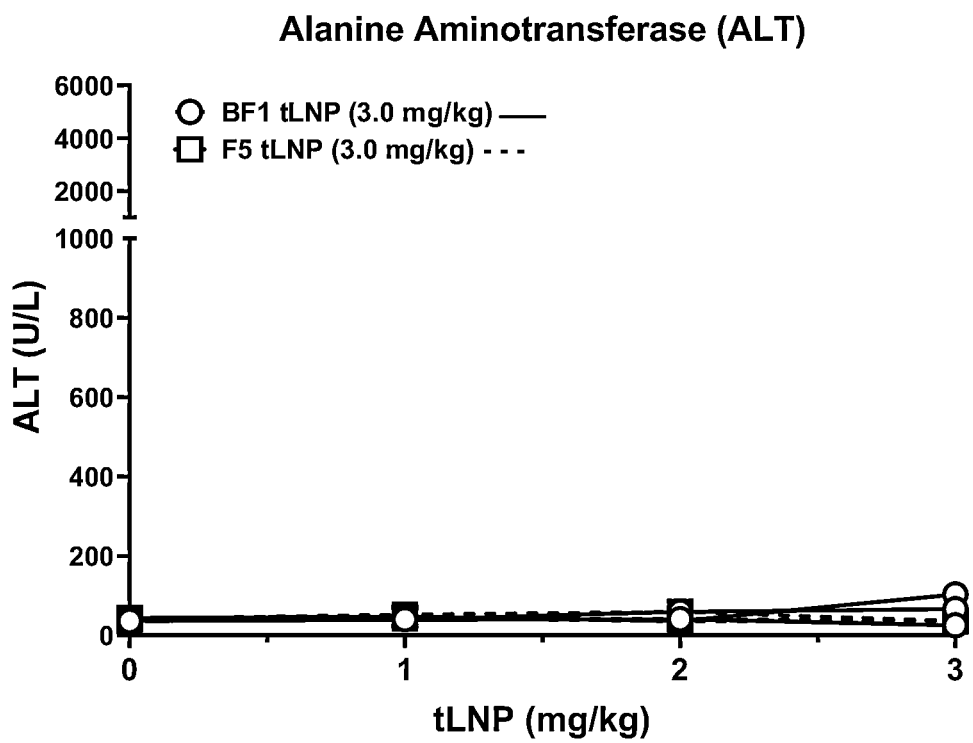

Upon administration to rats, the undecorated BF1 LNP showed a significant dose-effect increase (>1000 IU/L at 3 mg/kg) in liver enzymes (data not shown) and acute phase proteins with substantial elevations for doses ≥1 mg/kg (FIGS. 11A-C). A second study in rats comparing compositions BF1 and F5 head-to-head confirmed the elevation of liver enzymes seen with BF1, however a similar elevation of liver enzymes was not observed for F5 LNP (FIGS. 11D-E). For BF1 tLNP the elevations were largely reduced, though there was still some elevation of acute phase proteins, especially at 3 mg/kg. In contrast, the F5 tLNP showed no significant increase in liver enzymes or acute phase proteins up to 3 mg/kg, the highest dosage tested (FIG. 11F-J). The binding moiety in this experiment was the anti-CD5 antibody mentioned in Example 2 which did not recognize rat CD5 so that there was no targeting effect here and the simple presence of conjugated antibody accounted for a large part of the greater tolerability of the tLNPs, consistent with the effect seen with IgG in Example 9. However, the antibody was a neutral factor with respect to the difference in tolerability between the BF1 tLNP and the F5 tLNP. Thus, the different ionizable cationic lipid was likely to account for the superior tolerability of the F5 tLNP over the BF1 tLNP.

Figure 11K:
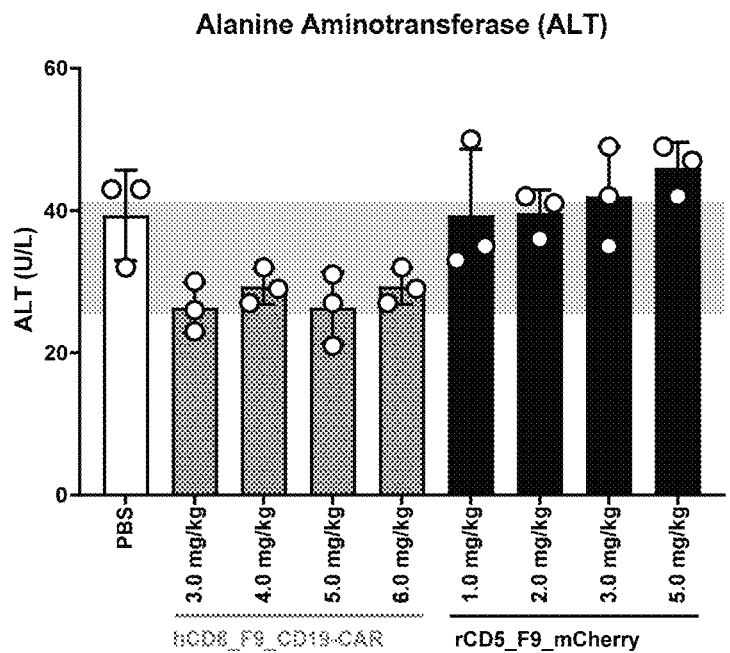
Figure 11L:
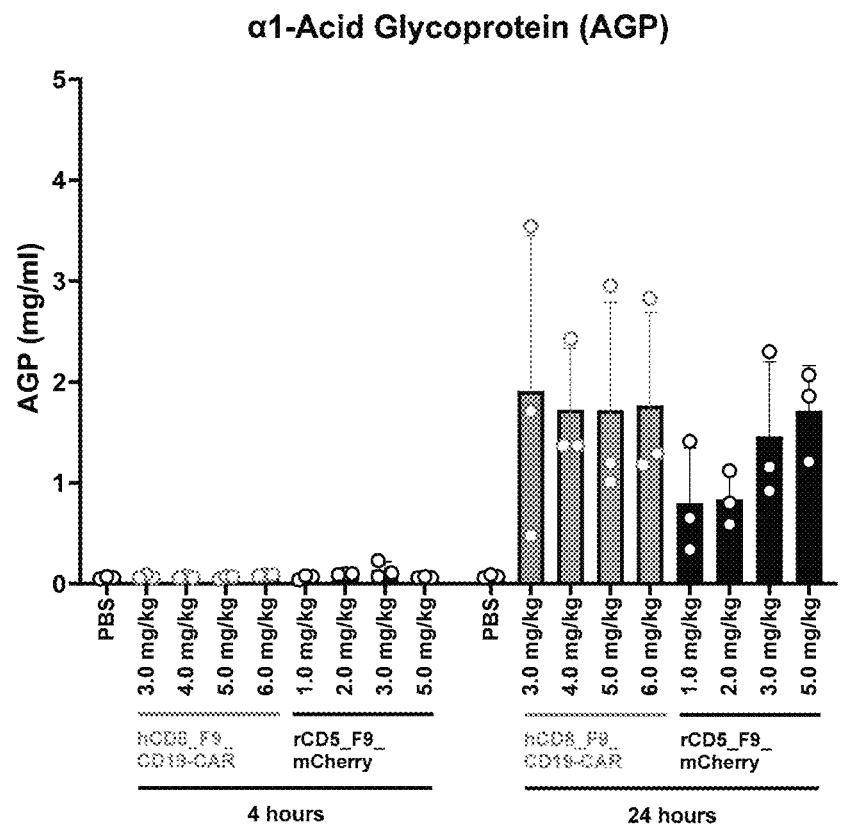

A further study in which various dosages of a rat CD5-targeted F9 tLNP encapsulating mCherry mRNA (up to 5 mg/kg) and a human CD8-targeted F9 tLNP encapsulating an anti-CD19 CAR mRNA (up to 6 mg/kg) were administered to rats. Again, liver enzymes and acute phase protein levels were assessed. The CD8 binding moiety was not cross reactive with rat CD8. Results for ALT (FIG. 11K) and AGP (FIG. 11L) demonstrate that even at these greater doses tLNPs incorporating CICL1 were well tolerated.

Example 12. Transfection of T Cells and Tolerability of tLNP Administered to Non-Human Primates In Vivo A first study was conducted to evaluate the tolerability and engineering efficiency of a single administration of CD5-targeted tLNP with an RNA payload encoding mCherry. CD5-targeted, composition BF1 and F5 tLNPs were administered as a single dose ranging from 0.5 mg mRNA/kg to 3.0 mg mRNA/kg. Clinical observations, clinical pathology, and toxicology biomarkers were evaluated to assess safety and tolerability. Pharmacological assessment was carried out by flow cytometry detection of mCherry in immune cell subsets in peripheral blood and tissues (spleen, bone marrow, lymph node, and liver).

For each CD5-targeted tLNP of composition BF1 or F5, pairs of cynomolgus macaques were administered doses containing 0.5, 1.0, 2.0, or 3.0 mg mRNA/kg as a 1-hour intravenous infusion at 6.25 mL/kg/hr and an additional control animal received PBS. Whole blood, serum, and plasma were collected at baseline and following test article administration at 4-, 8-, and 24-hours post-dose. Under sedation, biopsy samples were collected at 24-hour post-dose administration of lymph node, liver, and bone marrow tissues. The animals were euthanized at 24 hours post-dose to perform a complete necropsy. As the anti-CD5 antibody mentioned in Example 2 decorating the tLNP recognized cynomolgus macaque CD5, the tLNP provided true targeting in this model.

Figure 12A:
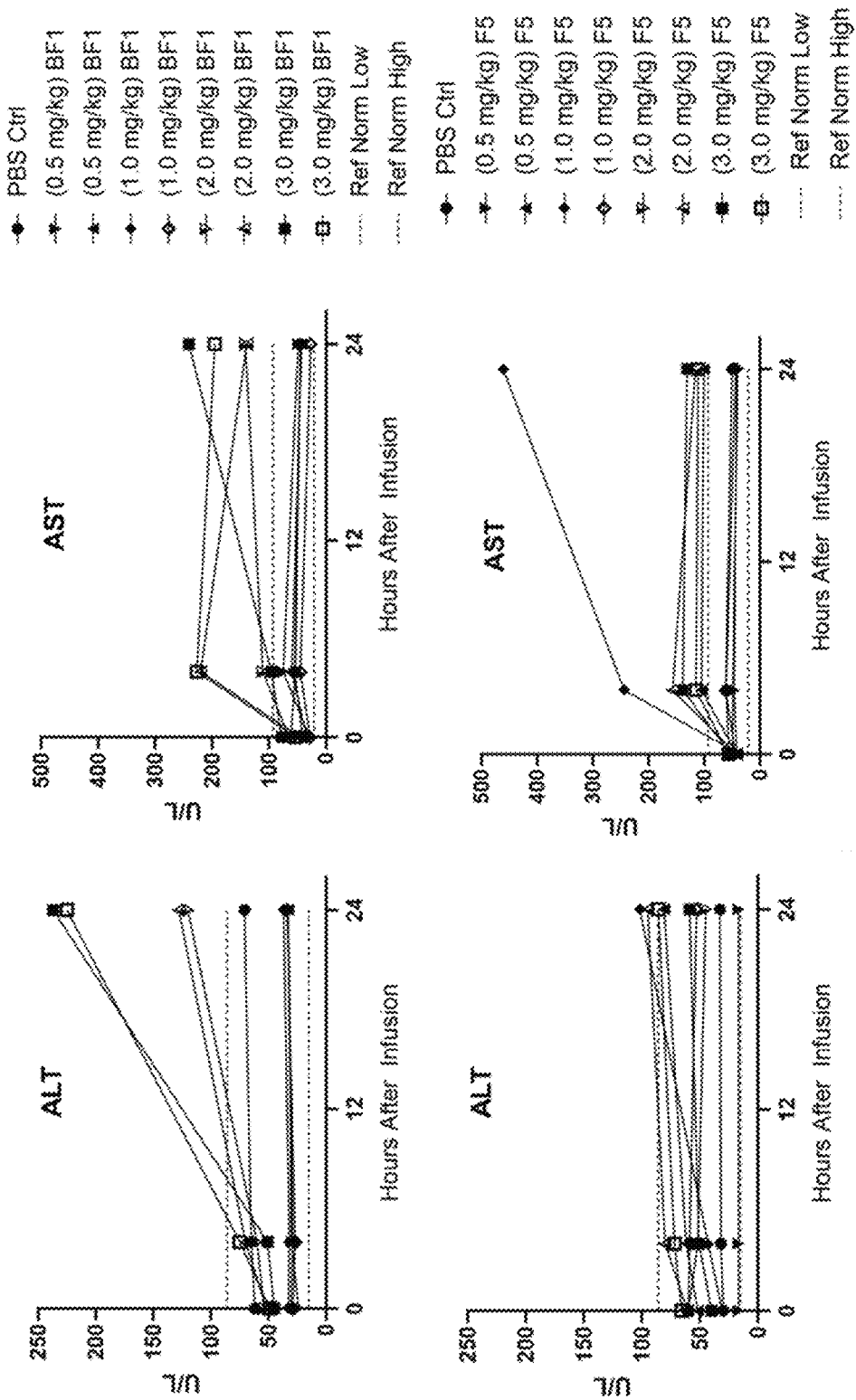
FIGS. 12A-L depict various data from two experiments in non-human primates (cynomolgus macaques).

Liver function tests showed elevations of ALT at 24 hours and of AST at 4 and 24 hours post-infusion for the 2.0 and 3.0 mg/kg doses of the BF1 composition which contained the ionizable cationic lipid ALC-0315 (FIG. 12A, upper panels). In contrast, for the F5 composition, containing the ionizable cationic lipid CICL1, was well-tolerated even at 3 mg/kg, the highest dosage tested, with no or only minor elevations observed (FIG. 12A, lower panels). (An anomalous elevation of AST in one animal receiving a 1 mg/kg dose was likely procedure-rather than test article-related).

Figure 12B:
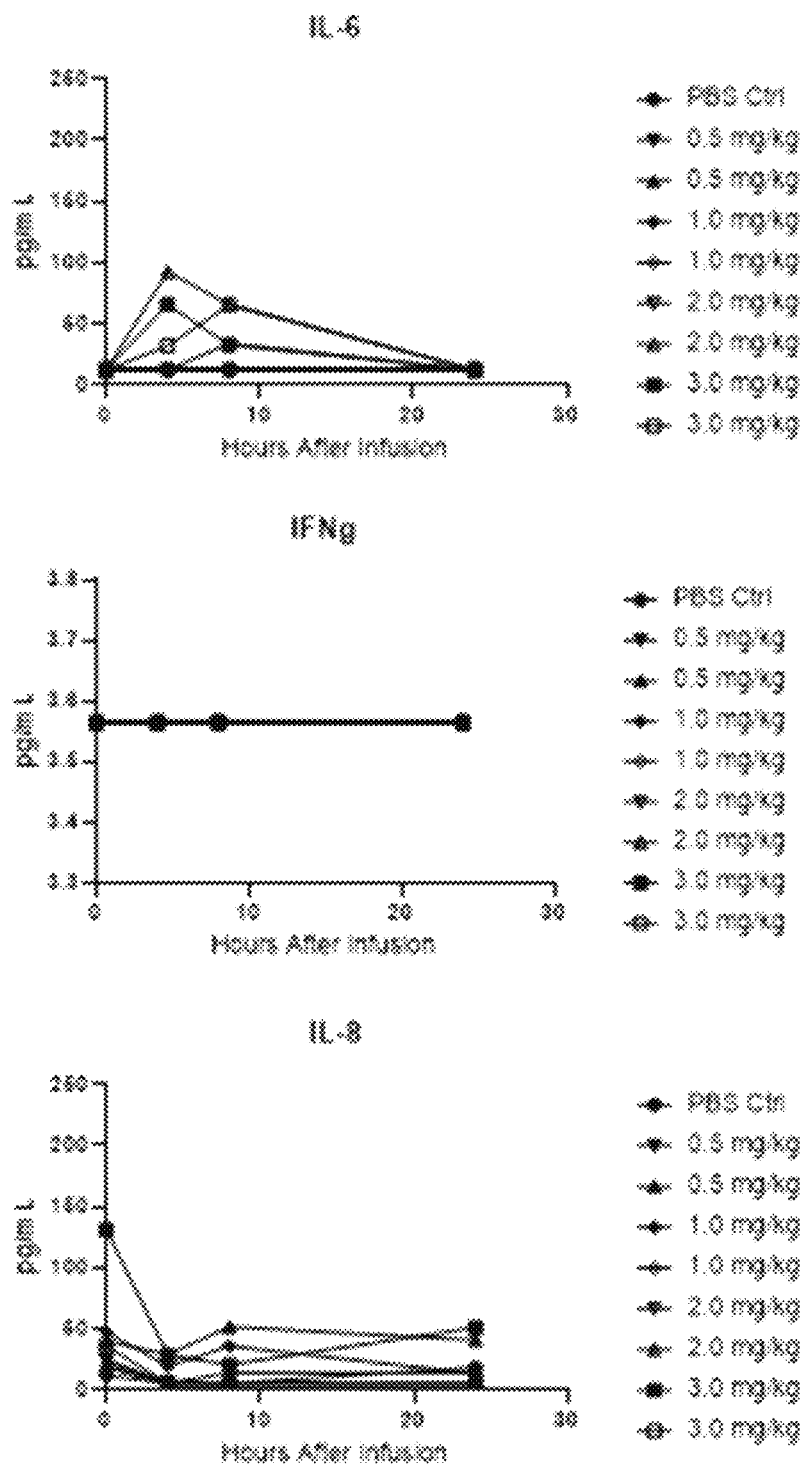
Figure 12B:
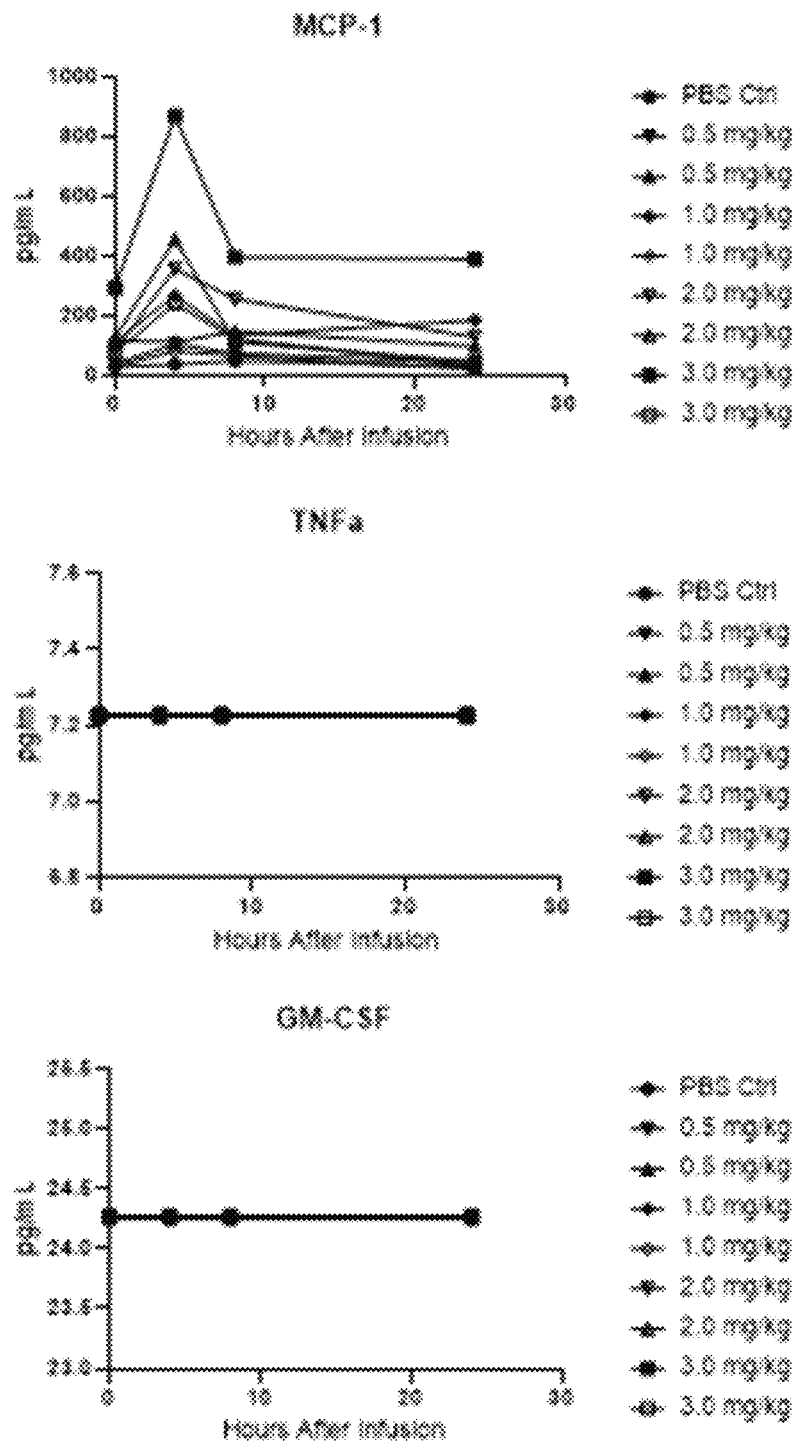
Figure 12B:
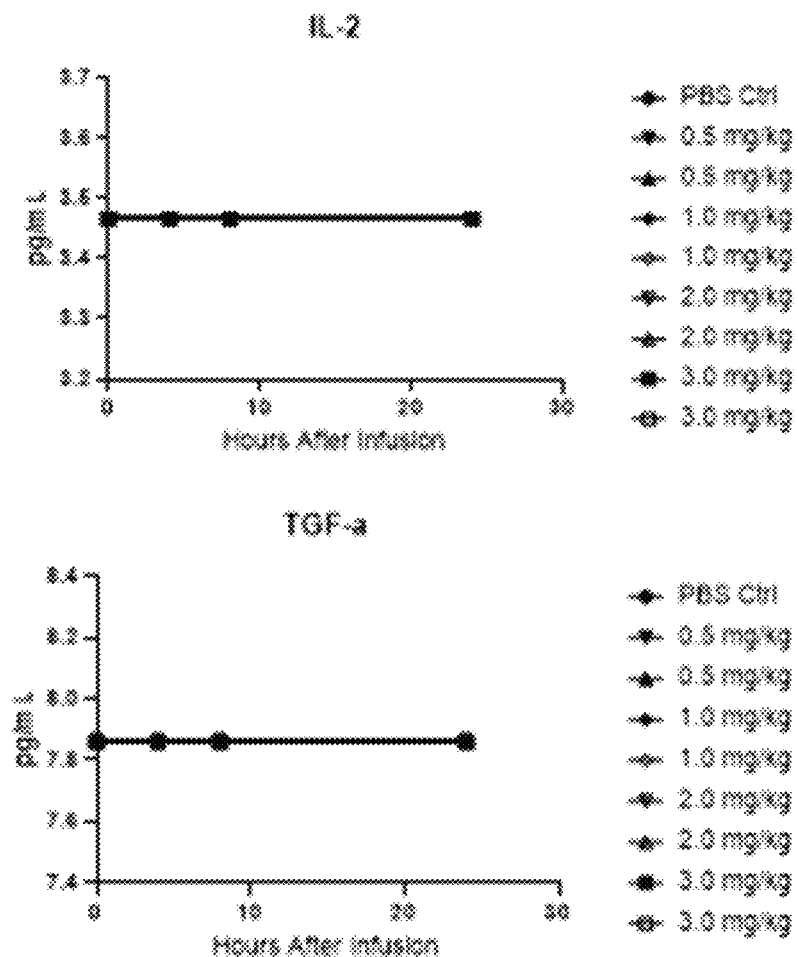
Figure 12B:
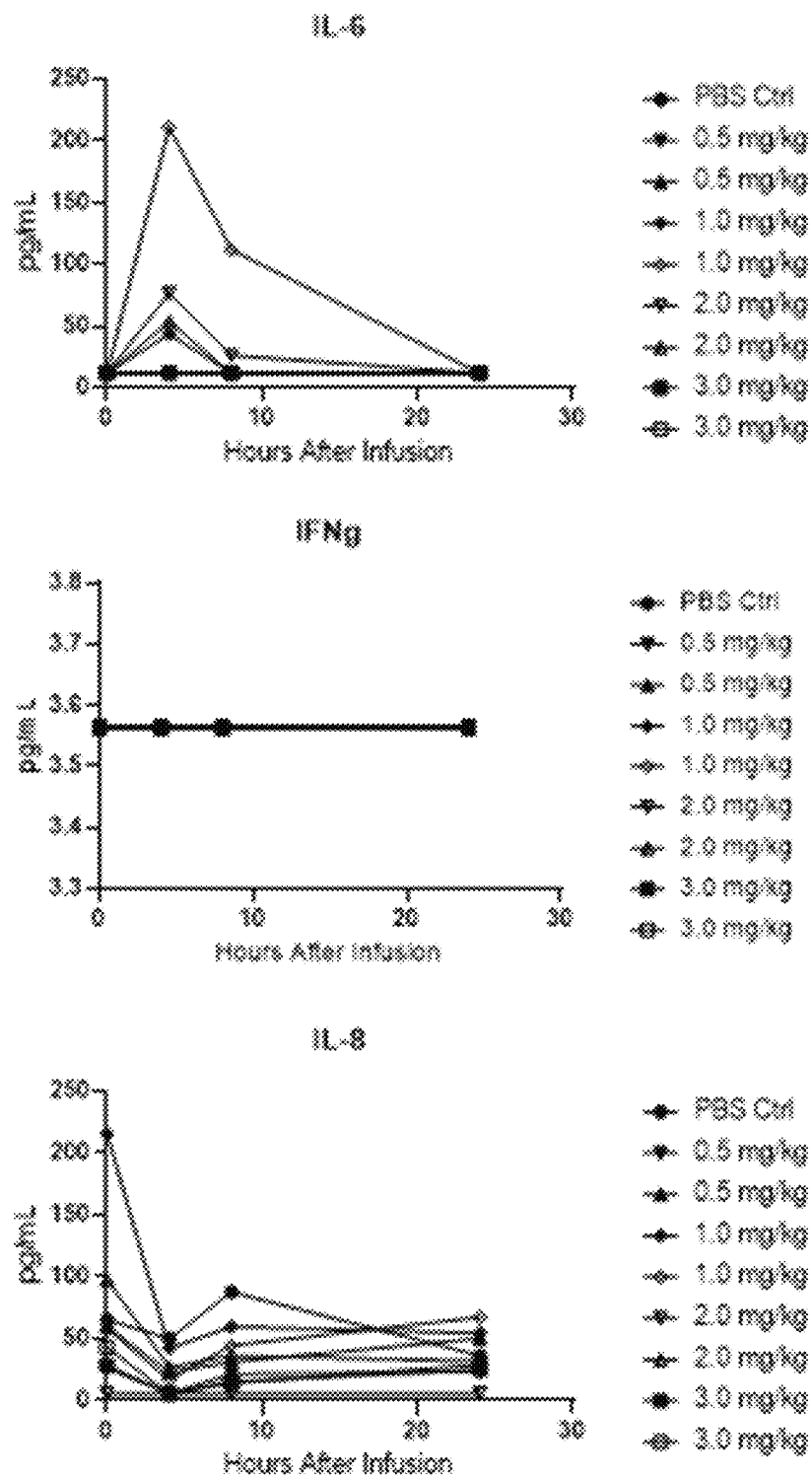
Figure 12B:
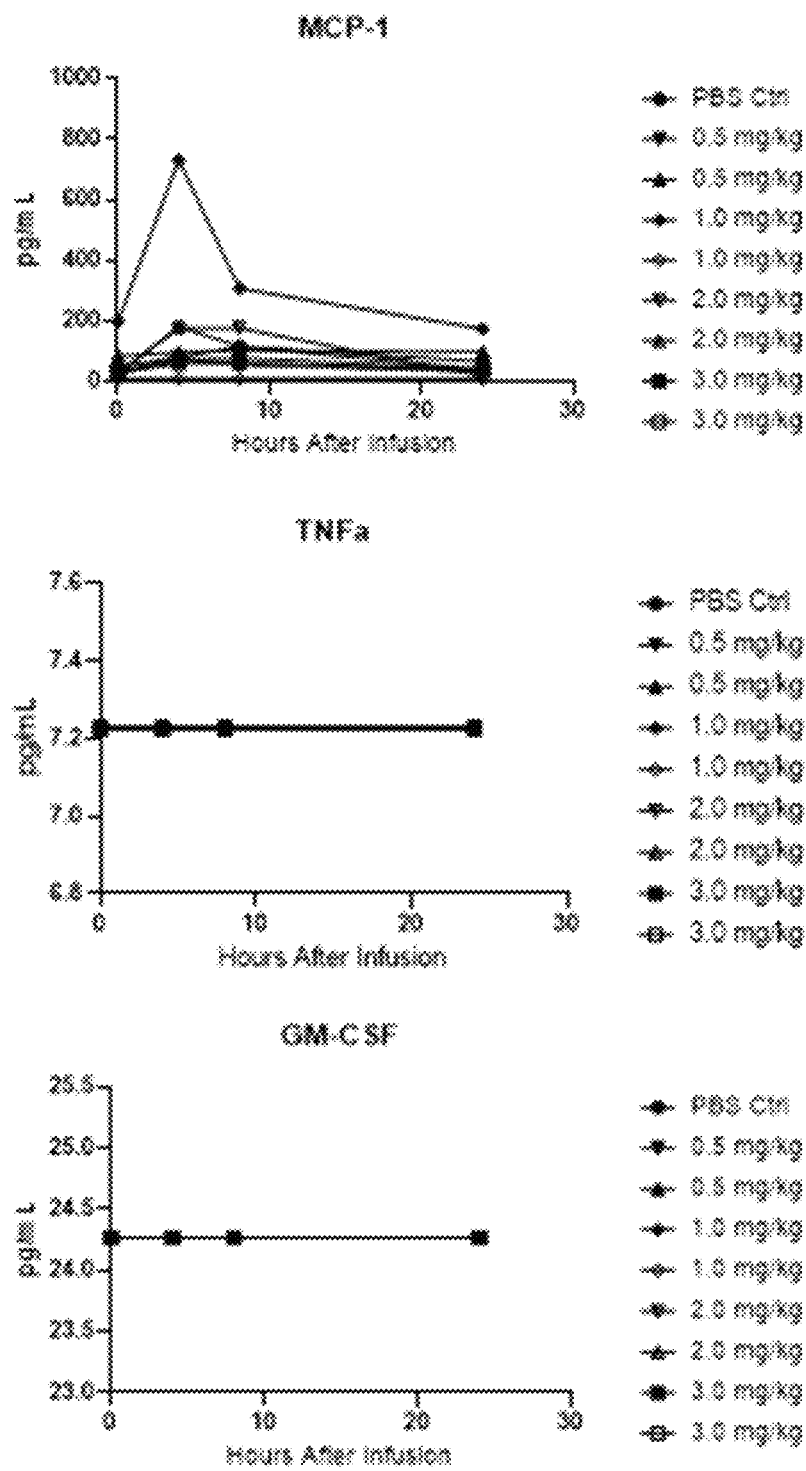
Figure 12B:
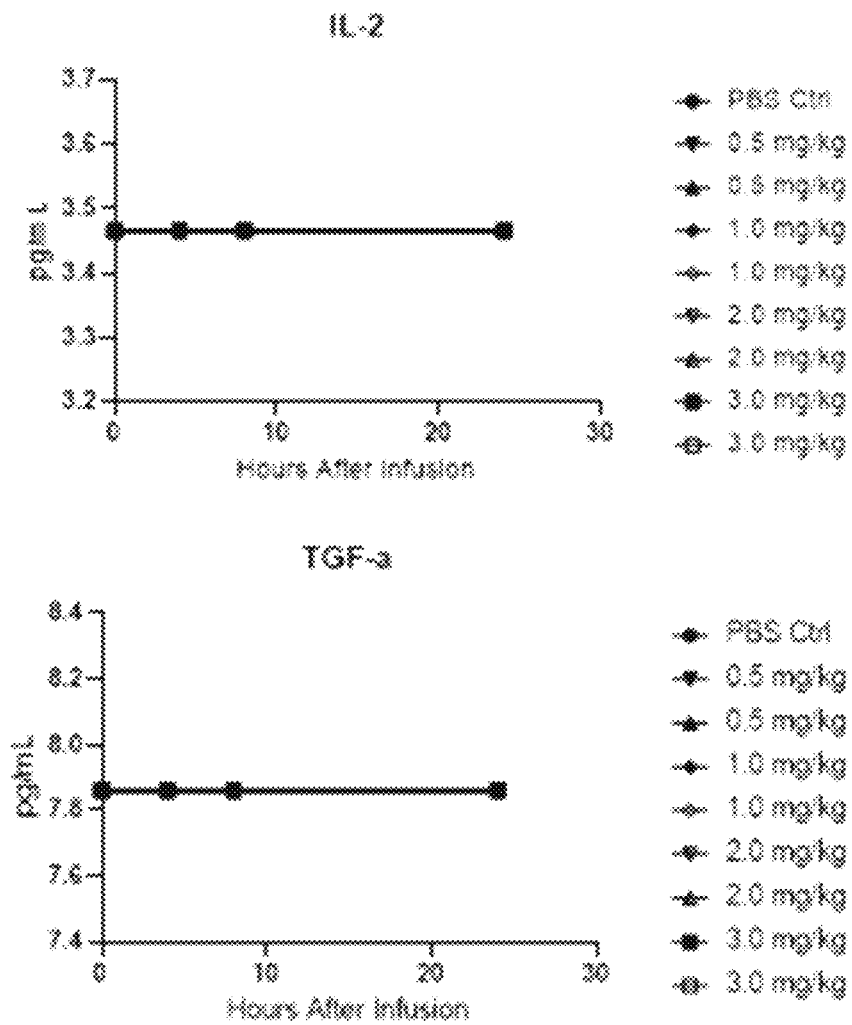

Cytokine secretion following administration of the tLNPs was also assessed for IL-6, MCP-1, IL-2, IFNγ, TNFα, TGFα, IL-8, and gm-CSF. There were minimal to mild transient elevations of IL-6 and MCP-1 following administration of the tLNPs but to still low levels (FIG. 12B).

Figure 12C:
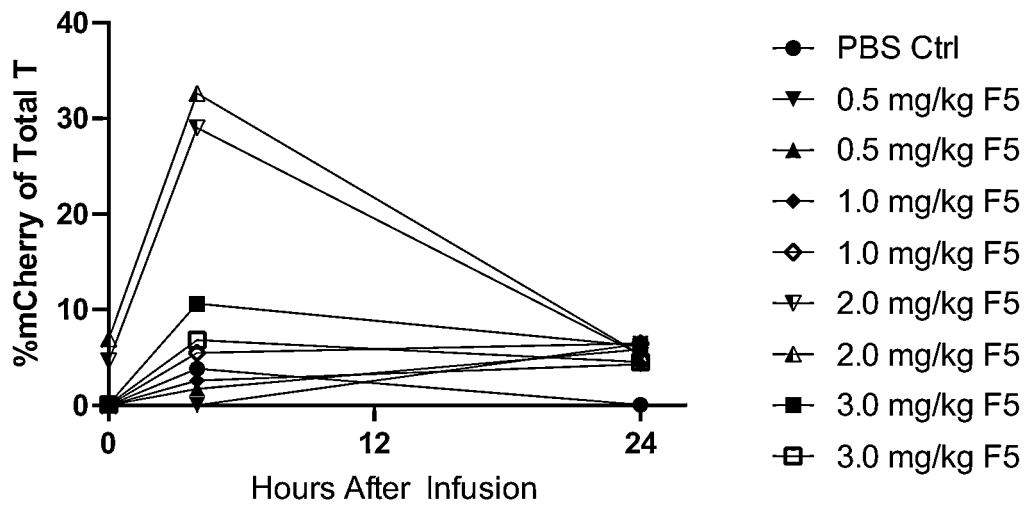
Figure 12D:
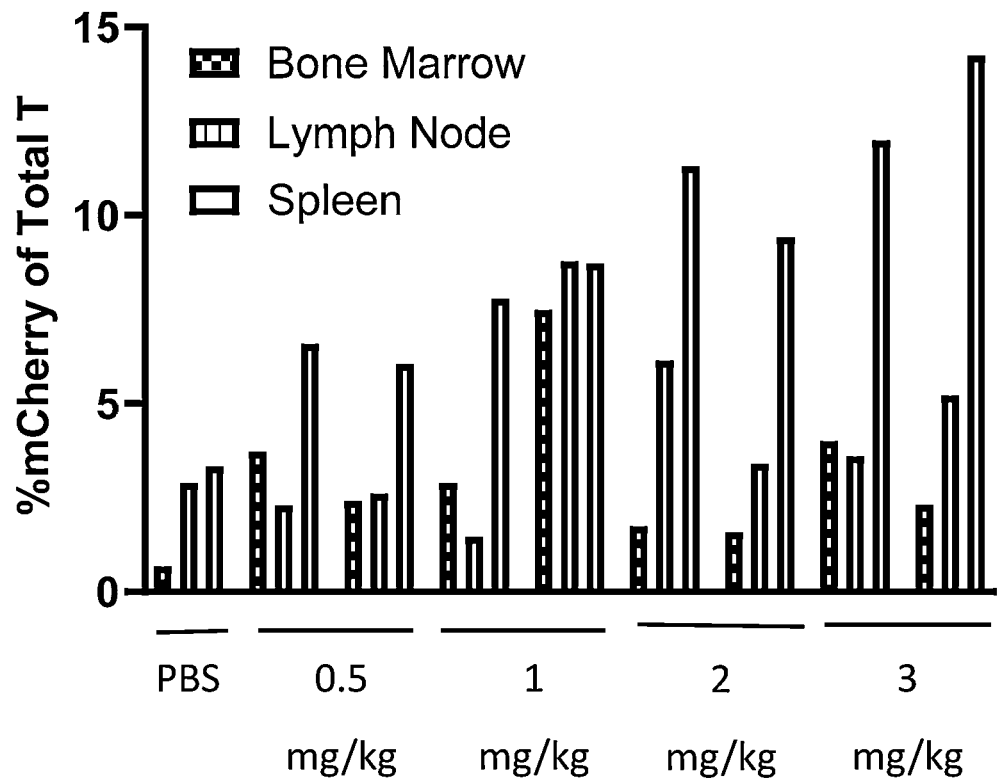

Transfection efficiency was assessed by flow cytometry as the percentage of mCherry$^+$ T cells in blood at 4 and 24 hours after infusion for animals receiving the CD5-targeted tLNP of F5 composition. As many as around 30% of total T cells were mCherry$^+$ at 4 hours. All tLNP-treated animals had about 4-6% mCherry$^+$ T cells at 24 hours demonstrating successful transfection with some degree of durability of expression (FIG. 12C). Transfection efficiency was also assessed in spleen, lymph node, and bone marrow T cells in tissue collected during necropsy, 24 hours after infusion. There was a clear trend to higher frequency of expression with increasing dose, with between 9 and 15% mCherry$^+$ T cells in spleen at the two highest dosages (FIG. 12D) demonstrating dose-proportional transfection. Either the tLNP successfully reaches and transfects T cells in these tissues or transfected T cells migrate into the tissues following transfection.

A second study was conducted with F9 tLNP to evaluate the tolerability and engineering efficiency of (1) a single administration of a CD5-targeted tLNP (humanized 5D7 targeting antibody) with an mRNA payload encoding an anti-CD19 CAR, (2) a single administration of a CD8-targeted tLNP (chimeric RPA-T8 targeting antibody) with an mRNA payload also encoding the anti-CD19 CAR, and (3) repeat administration (3 doses) of the CD5-targeted tLNP. The CD5-targeted tLNP was administered as a single dose at 3.0 mg/kg (Group 2, n=2) or as a repeat dose of 1.0 mg/kg at 72-hour intervals (Q72h) for three doses (Group 5, n=2). The CD8-targeted tLNP was administered as a single dose at 3.0 mg/kg with terminal take down at 24 hours post dose (Group 4, n=2) or 96 hours post dose (Group 3, n=2). As a control, PBS was administered (Group 1, n=1). All tLNP tested in the second study utilized composition F9. The tLNP formulations (tLNP compositions plus buffers and excipients) were administered by IV infusion at 6.25 mL/kg/hr and total duration of administration was 1 hour. Clinical observations, clinical pathology, and toxicology biomarkers were evaluated to assess safety and tolerability. Pharmacological assessment was carried out by flow cytometry detection of anti-CD19 CAR in immune cell subsets in peripheral blood and tissues (spleen, bone marrow, lymph node, and liver). It should be noted that the anti-human CD19 CAR has no significant pharmacological activity in NHP so the tolerability indicated by the studies in this Example relate only to the biochemical composition of the tLNPs (including encapsulated mRNA) and do not reflect any impact of immunological activity of the CAR.

Figure 12E:
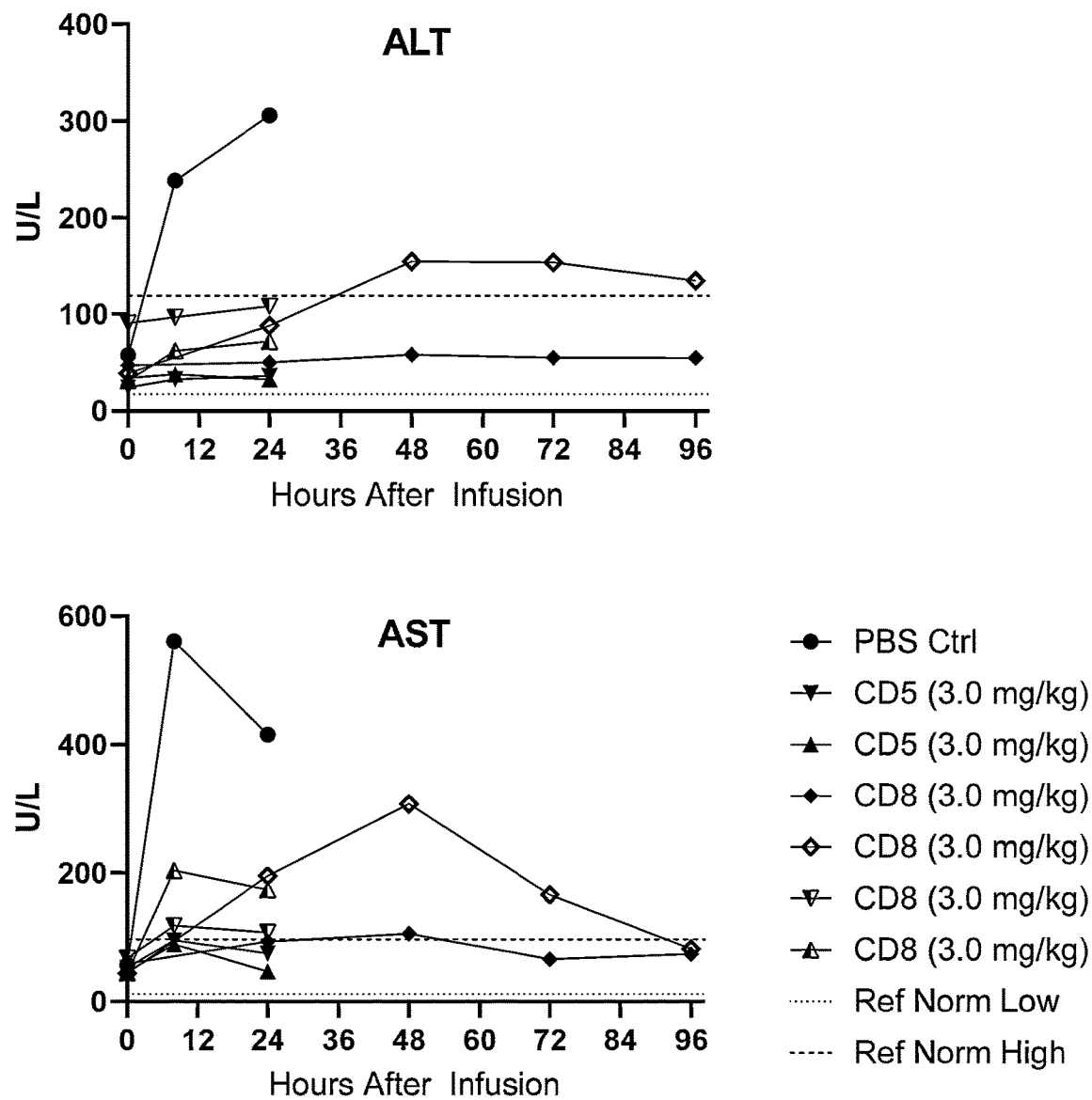
Figure 12F:
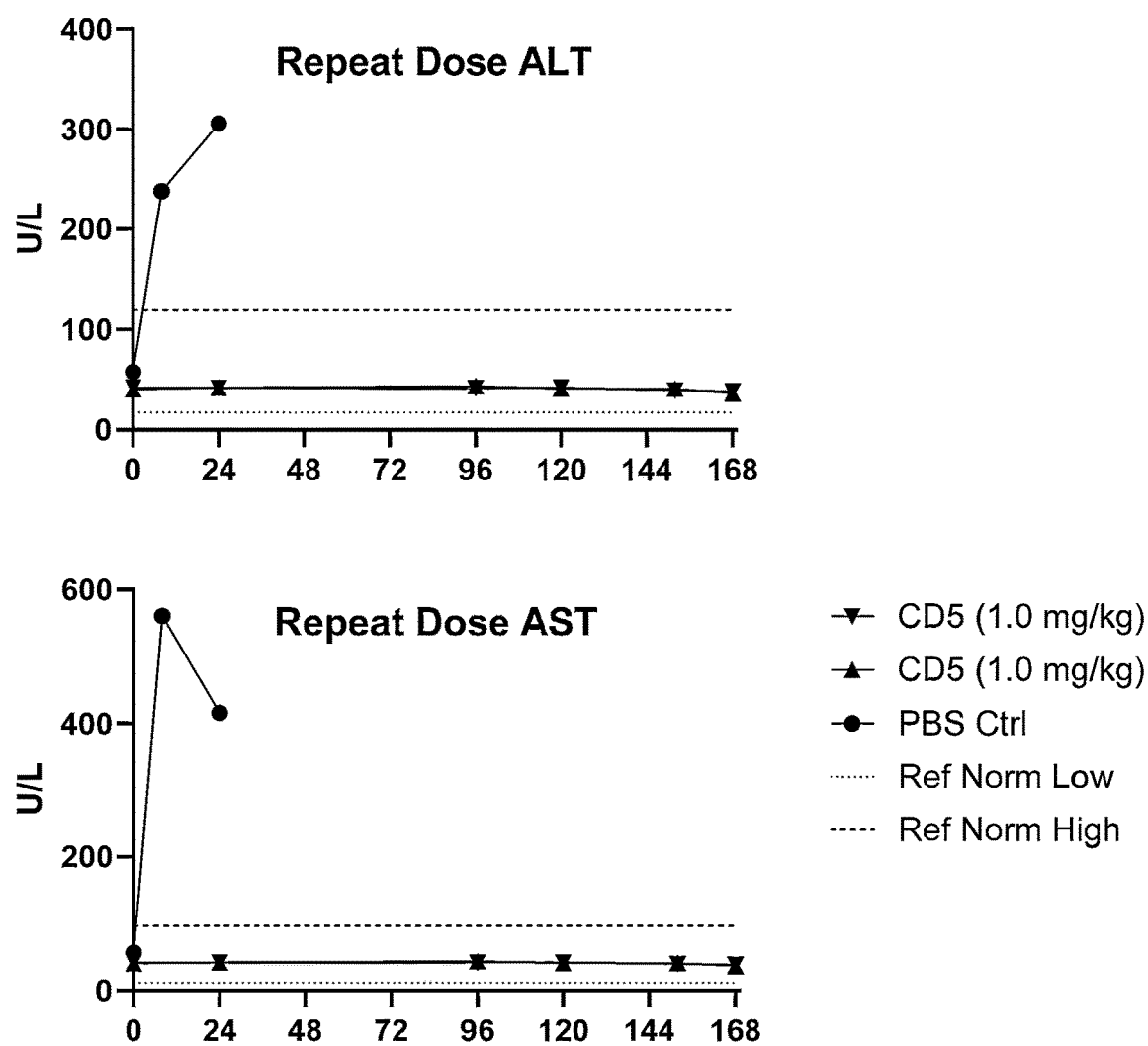

Liver function tests showed transient elevations of AST and/or ALT in a minority of animals receiving a single administration of tLNP at a dosage of 3 mg mRNA/kg, but the highest elevations were in the PBS control animals, suggesting that the elevations were procedure-related rather than test article-related (FIG. 12E). No elevation of ALT or AST was observed in the animals receiving 3 doses of the CD5-targeted tLNP at a dosage of 1 mg mRNA/kg (FIG. 12F). These data again indicate that the tLNP, and particularly the ionizable cationic lipid CICL1, was well tolerated.

Figure 12G:
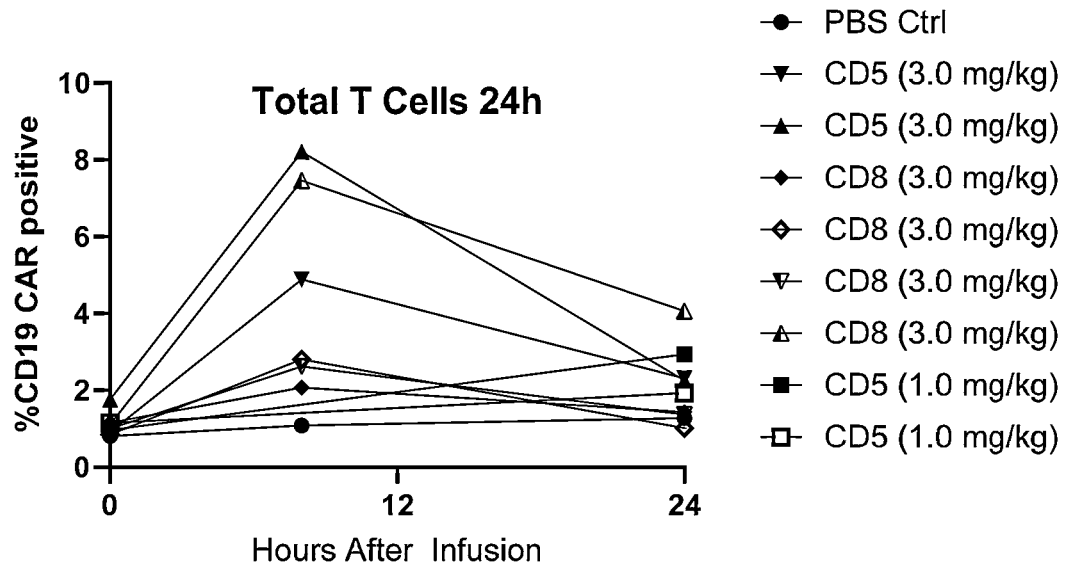
Figure 12H:
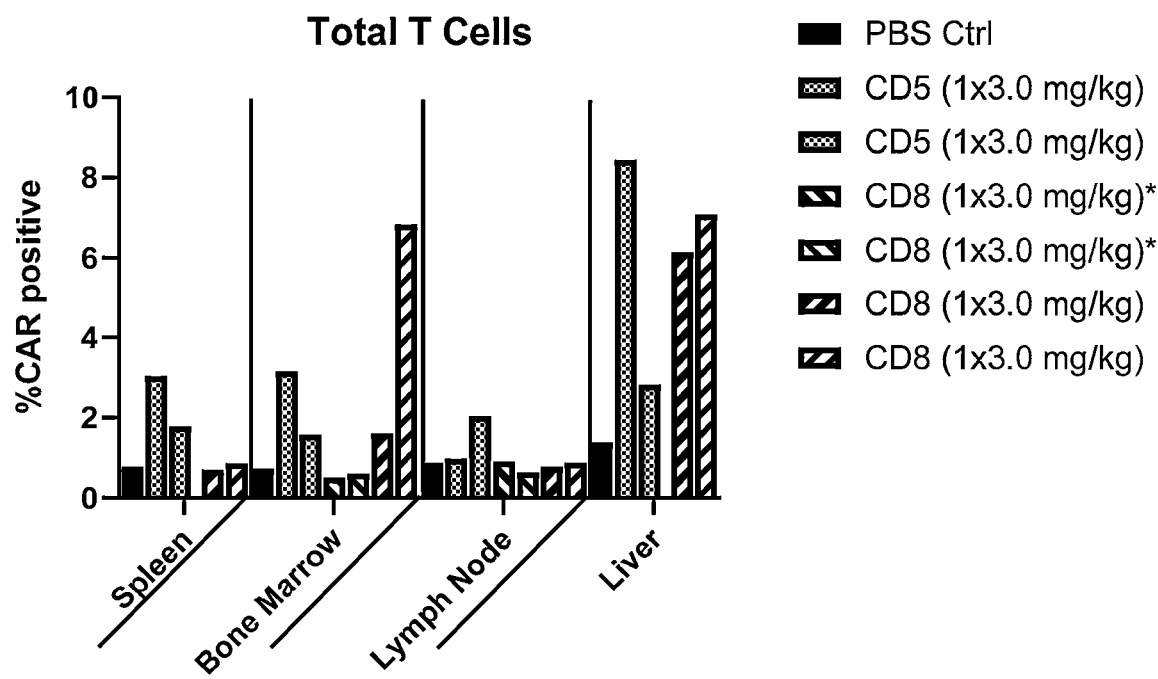
Figure 12I:
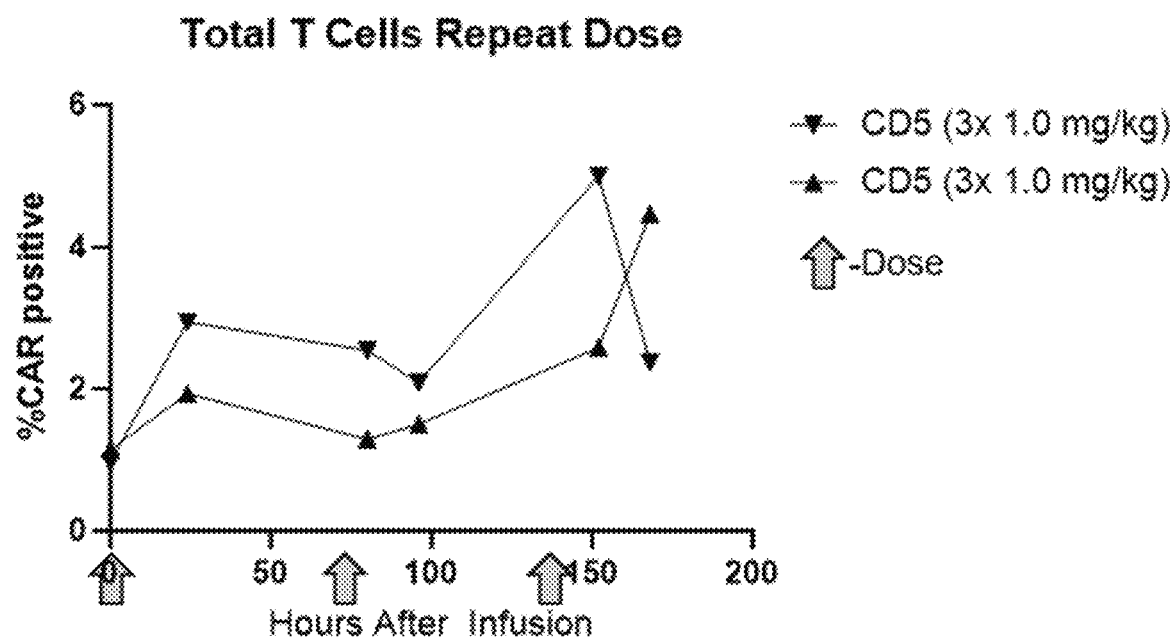
Figure 12J:
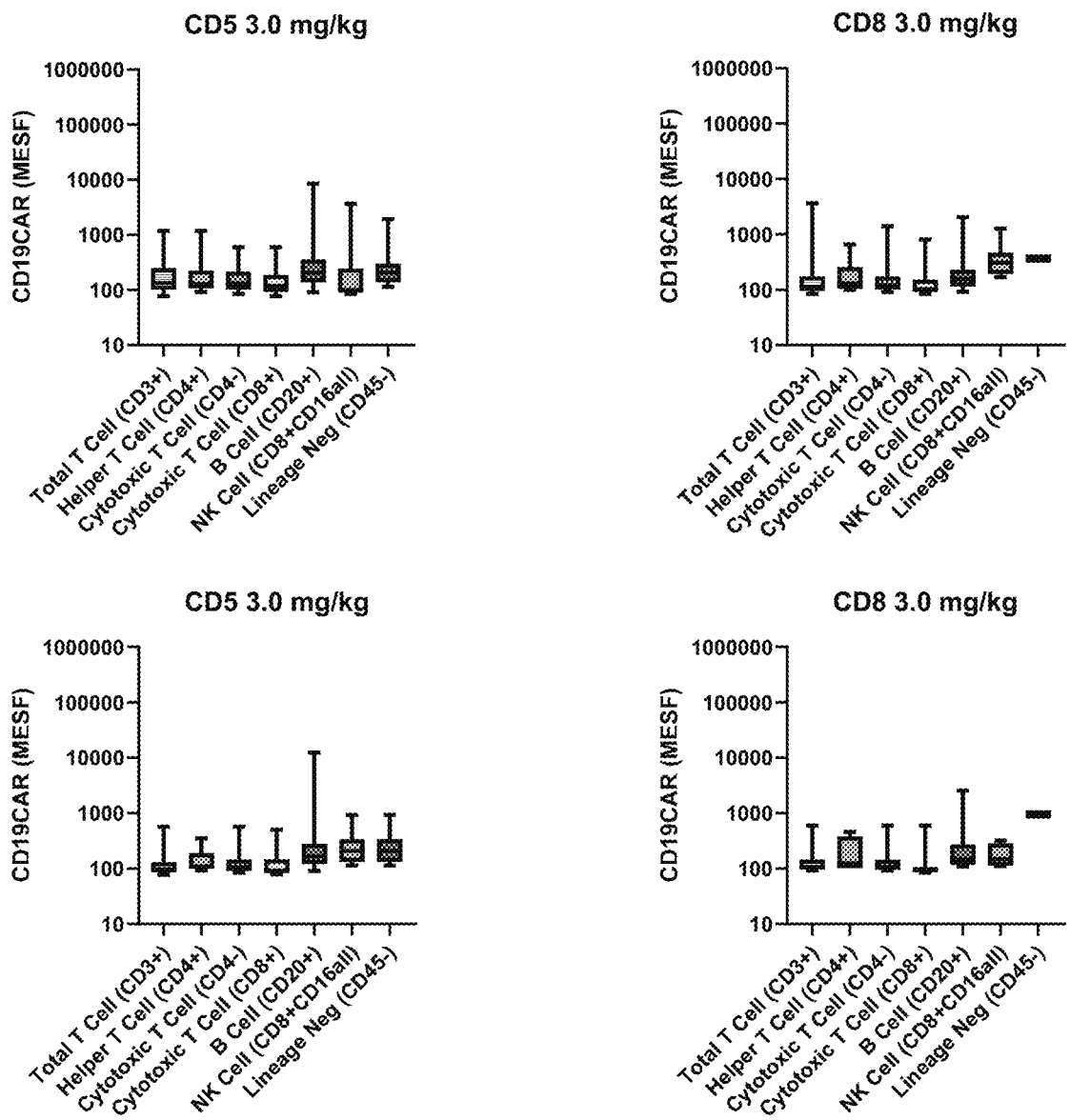

Transfection efficiency was assessed by flow cytometry as the percentage of anti-CD19 CAR+ T cells in blood at 8 and 24 hours after infusion for the animals receiving a single administration and at 24 hours. The general pattern seen with expression of the mCherry mRNA payload was repeated here with higher percentages of CAR+ T cells seen at the earlier time point, but still a substantial number of CAR+ T cells observed 24 hours after infusion (FIG. 12G). CAR+ T cells were also observed in spleen, bone marrow, and lymph nodes, as well as in liver, suggesting that the liver detargeting effect of the herein disclosed tLNP compositions may have been limited and did not extend to liver resident T cells (FIG. 12H). Repeat administration was able to maintain or increase the proportion of CAR+ T cells over the course of the experiment, 24 hours after the third infusion (FIG. 12I). At the 3 mg/kg dosage, transfection with both CD5-targeted and CD8-targeted tLNP led to expression of a similar number of CAR molecules across a variety of immune cell subtypes in spleen including helper T cells, cytotoxic T cells, B cells, NK cells, and lineage negative cells (FIG. 12J). With the anti-CD19 CAR encoding mRNA used in this experiment the number of CAR molecules per cell was about 100-1000 as molecules of equivalent soluble fluorochrome (MESF). However, it should be noted that the anti-CD19 CAR encoding mRNA had not been optimized for use in tLNP-mediated in vivo transfection and several fold higher levels of expression can be achieved with optimized mRNA.

Figure 12K:
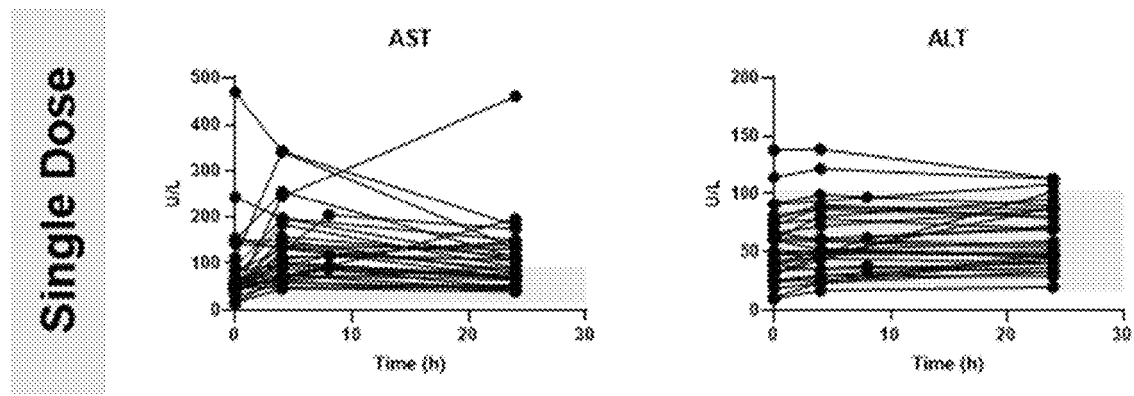

A third study in NHP with F9 tLNP targeted to CD8 and encapsulating an mRNA encoding an anti-CD19 CAR was also conducted and the single dose liver enzyme results of all three studies (doses ranging from 3.5 to 3.0 mg mRNA/kg) compiled into single plots of AST and ALT levels for a more global assessment (FIG. 12K). For AST many of the monkeys exhibited mild elevations (anything under 1000 U/L) above the nominal normal range (the grey shaded area) and indeed several of the monkeys had elevated AST levels prior to administration of tLNP which generally decreased after dosing. ALT levels in most of the monkeys were within the normal range or were slightly elevated prior to administration of tLNP (FIG. 12K). None of these results indicate a substantial toxicity related to administration of F5 or F9 tLNP compositions.

Figure 12L:
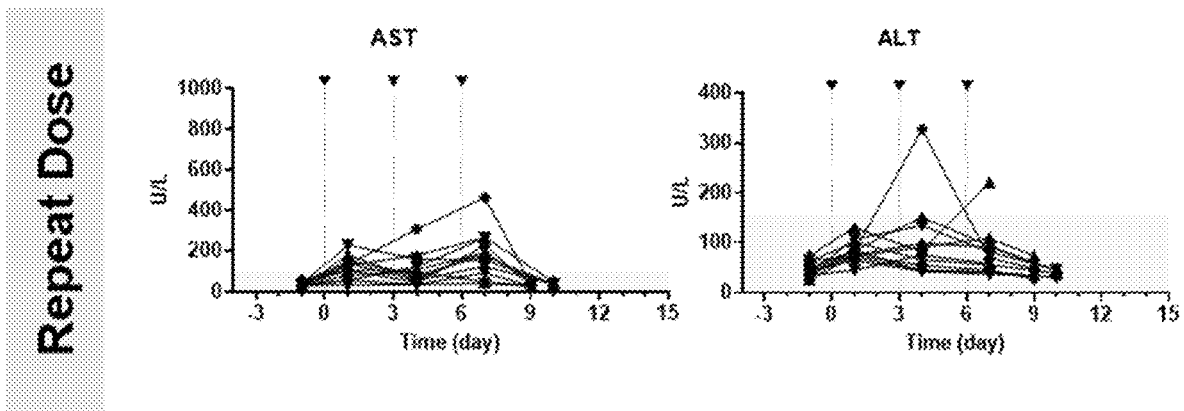

Two additional studies to further assess repeat dosing utilized three administrations at 72-hour intervals of CD8-targeted tLNP with composition F9 and encapsulating mRNA encoding an anti-CD19 CAR. Dosages ranged from 0.1-2.0 mg mRNA/kg. Mild or moderate transient AST or ALT elevations were observed in some monkeys (FIG. 12L). These elevations do not detract from the generally good biochemical tolerability of the tLNP and their components.

Example 13. Biodegradability of CICL1 in Non-Human Primate and Mouse

A determinant of tolerability of tLNPs is the ionizable cationic lipid. Whereas the other lipid components in the tLNP were either already present in the body or diet, or very similar to ones that are, the ionizable cationic lipids were not. This study was conducted to assess and compare the clearance of ionizable cationic lipids in blood, liver, and spleen after administration of tLNPs comprising them.

Figure 13A:
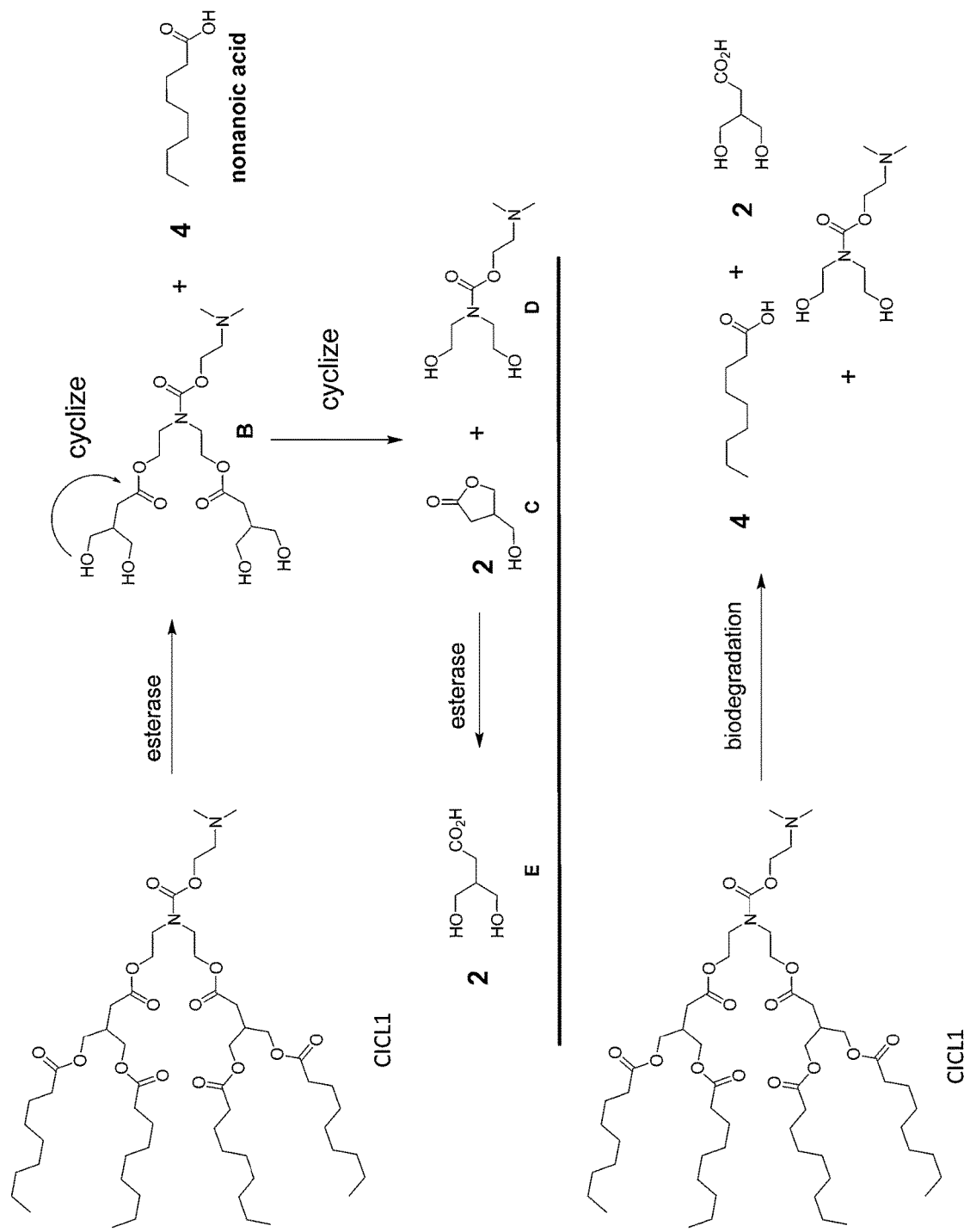
FIGS. 13A-H relate to the biodegradability of ionizable cationic lipids.

The CICL structure was designed to promote biodegradation without necessarily involving oxidative degradation in the liver as illustrated in the conceptual biodegradation scheme of FIG. 13A. Although this study does not demonstrate that it is correct, the data below are consistent with the conceptual biodegradation scheme.

Samples were taken from cynomolgus macaques that had been intravenously administered either BF1 or F5 tLNPs (two each) at a dosage of 3 mg mRNA/kg in the preceding example. The tLNPs were conjugated to anti-CD5 mentioned in Example 2 as the targeting moiety. 24 hours after administration the animals were sacrificed and plasma, liver, and spleen tissue collected from two animals in each group and assessed by mass spectrometry for presence of these ionizable cationic lipids in order to assess biodegradability and biodistribution of these ionizable cationic lipids.

Briefly, plasma was stabilized for mass spectrometry by addition of 10 μL of formic acid per mL of $K_2$EDTA plasma. Spleen and liver tissue were homogenized in 19 parts of homogenization buffer (50:40:10 0.1% formic acid in 1:1 methanol: acetone/10 mM ammonium formate with 0.2% formic acid/dimethylformamide (DMF)) to 1 part tissue (v/w) using a Geno/Grinder® (SPEX® SamplePrep) set to two minutes at 1500 rpms.

Calibration curves and quality control samples were prepared by spiking control matrix (plasma or homogenate) with CICL1 or ALC-0315 in DMF. The extraction was performed on wet ice by adding 300 μL of crashing solvent (0.1% formic acid in 1:1 methanol: acetonitrile) to 25 μL of sample to which 50 μL of internal standard was added (1:1 isopropyl alcohol: water). The extracts were mixed for four minutes at 1500 rpms and then centrifuged at 3000×g for ten minutes. 200 μL of supernatant was transferred to a clean 96 well plate for LC/MS/MS analysis.

Chromatography was performed on a Waters XBridge BEH C8 column (130 Å, 2.5 μm, 2.1×30 mm) using the following gradient. Mobile phase A (10 mM ammonium format in water with 0.2% formic acid) was held at 20% for 0.3 minutes before being reduced to 5% over 1.2 minutes. This condition was held for one minute before being returned to 80% B (0.1% formic acid in 1:1 methanol: acetonitrile) in 0.1 minutes. The column was then held at 80% B for 1.4 minutes. LC flow rate was held at 0.5 mL/min and the autosampler held at 2-8° C. The mass spectrum was obtained with a triple quadrupole apparatus using atmospheric pressure ionization (Sciex).

Quantitation was performed using a 1/X2 quadratic regression using the peak area for transition 1013.6→968.4 (CICL1) or 766.6→748.4 (ALC-0315) over peak area of transition 1040.6→995.4 of the internal standard.

Figure 13B:
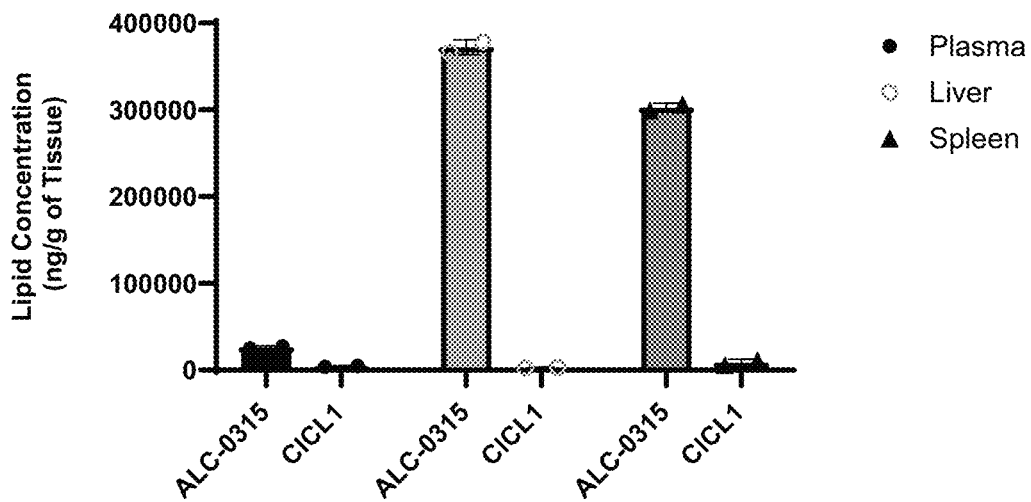

By 24 hours after administration, CICL1 was present in blood, liver, and spleen in only very small amounts. A substantially larger concentration, about 6-fold greater, of ALC-0315 (the ionizable cationic lipid used in Comirnaty®) remained in blood at this time. The concentrations of ALC-0315 in liver and spleen were approximately 14- and 11-fold greater, respectively. In contrast, the concentrations of CICL1 in blood, liver, and spleen were within 2-fold of each other and the liver and spleen concentrations were approximately 127- and 35-fold less than for ALC-0315, respectively (FIG. 13B).

These clearance data indicate that CICL1 was much more biodegradable than ALC-0315, at least at the initial step. Moreover, these data are consistent with the greater tolerability of CICL1 over ALC-0315 seen in Examples 11 and 12.

To obtain more detailed data a similar experiment was conducted in mice where it was possible to obtain a time course of disappearance of the ionizable cationic lipid and the encapsulated mRNA as well. Mice were intravenously administered 2 mg/kg tLNP of composition BF1 (comprising ALC-0315) or F9 (comprising CICL1) targeted to mouse CD8 and encapsulating an anti-human CD19 CAR, and monitored through 7 days. At each timepoint, 3 mice were sacrificed, and liver, spleen, and plasma were processed for LC-MS-based detection of lipid concentration and digital PCR detection of the mRNA. In plasma, mRNA level was normalized to a known amount of mRNA spiked in a control. In spleen and liver mRNA level was normalized to mRNA for the housekeeping gene GAPDH.

Figure 13C:
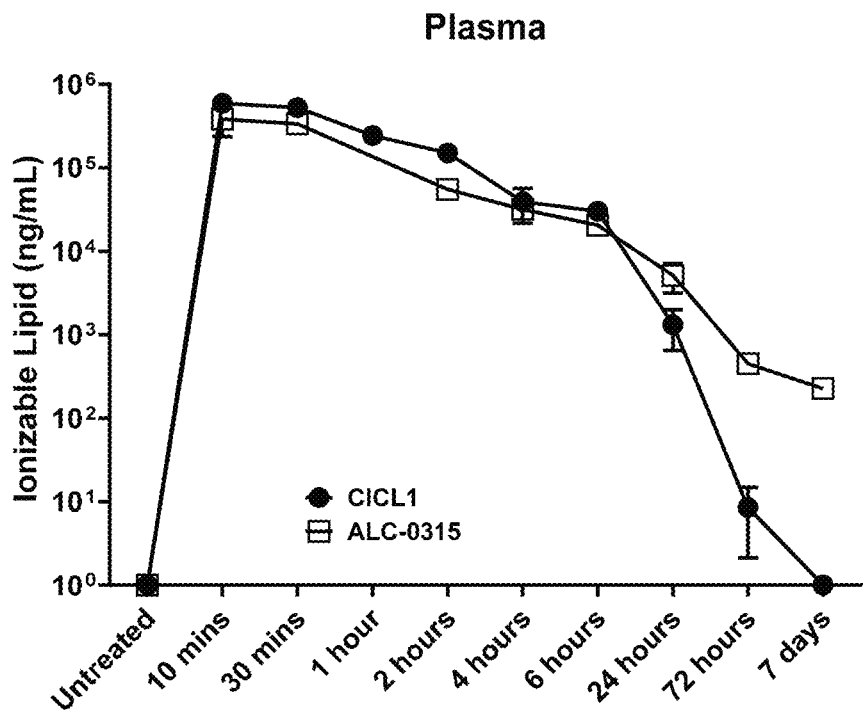
Figure 13D:
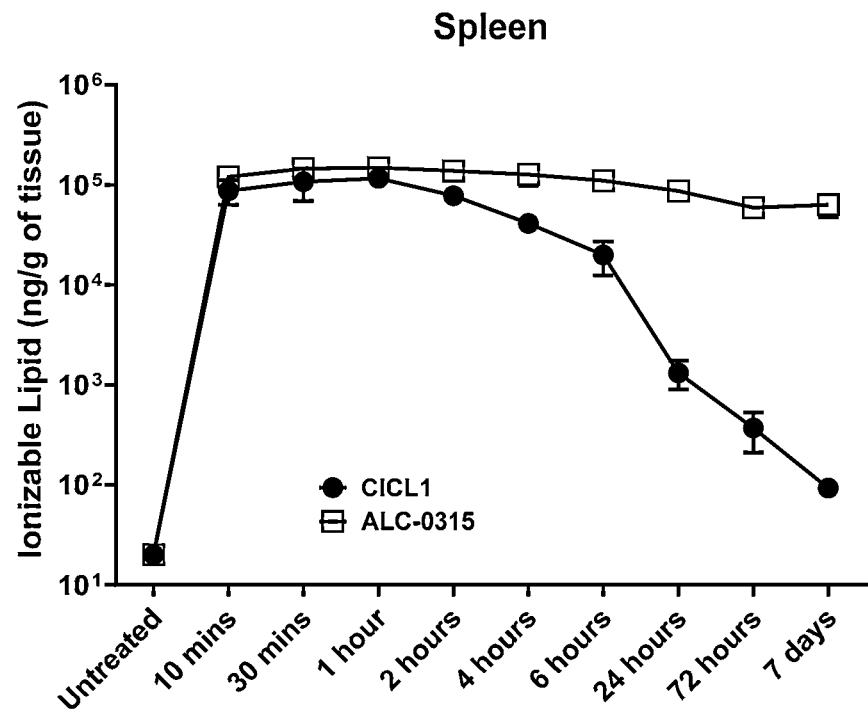
Figure 13E:
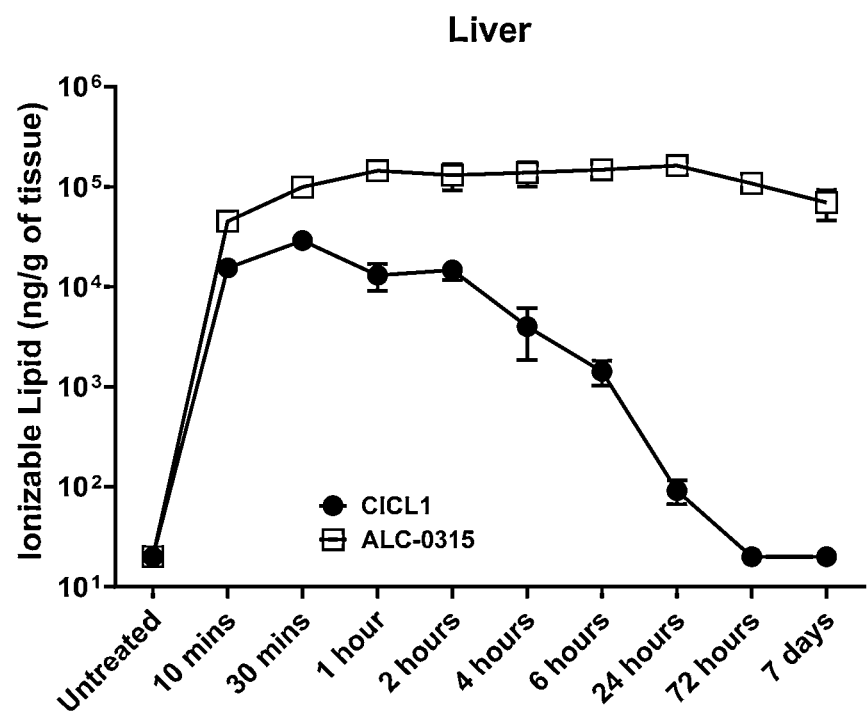
Figure 13F:
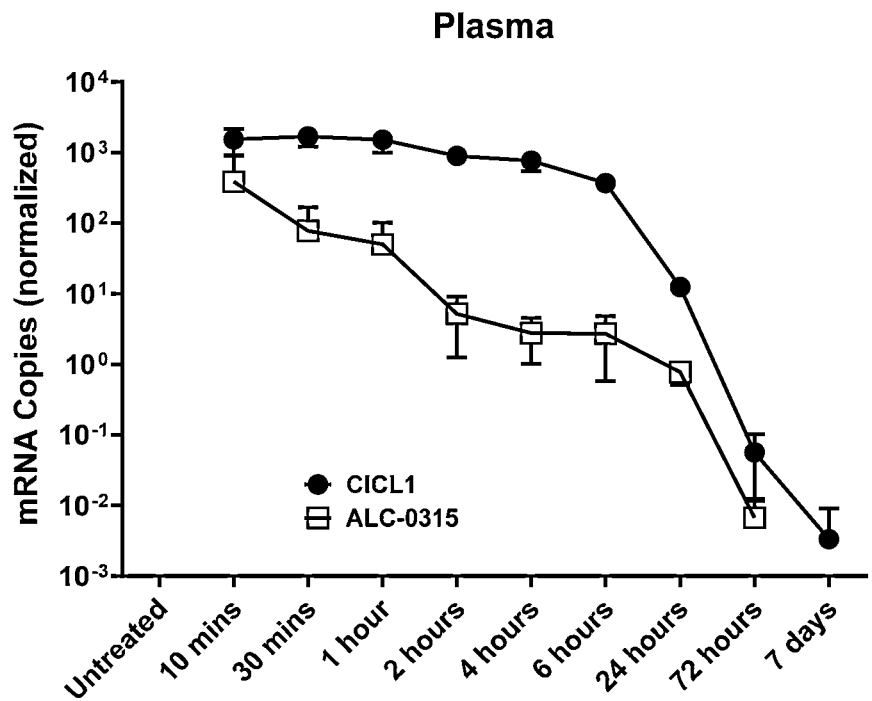
Figure 13G:
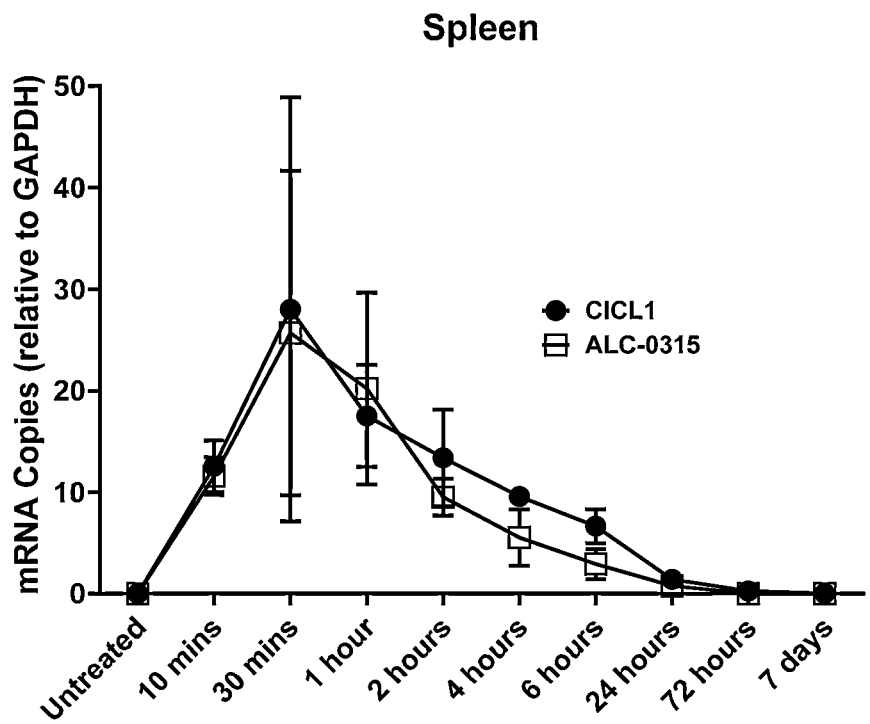
Figure 13H:
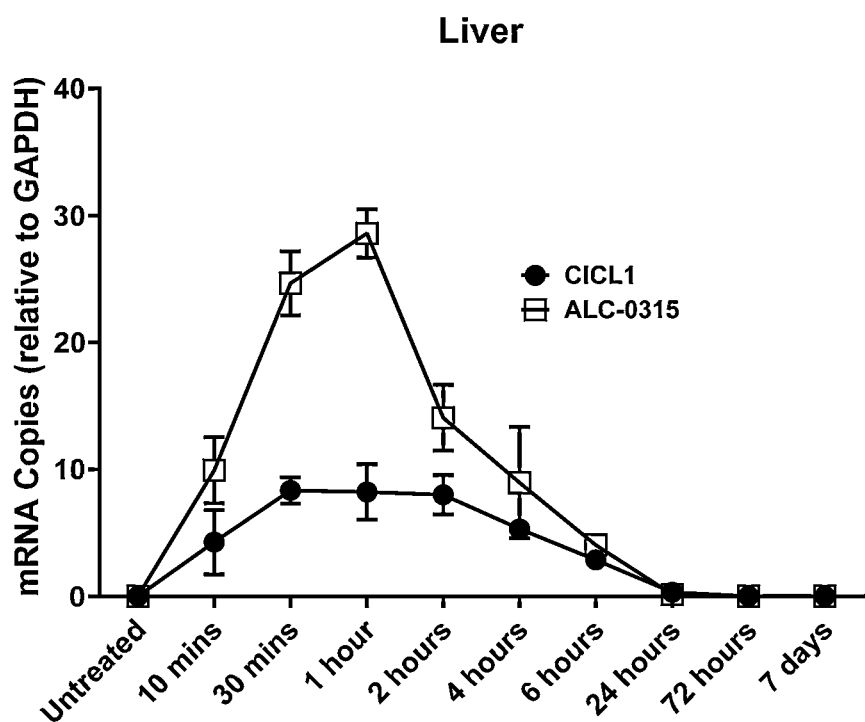

In plasma, both lipids initially disappeared at a similar rate, but by 24 hours the curves had begun to separate and CICL1 was clearly disappearing faster. At the conclusion of the study at 7 days, plasma levels of CICL1 had returned to baseline while a substantial about on ALC-0315 was still detected (FIG. 13C). In spleen and liver ALC-0315 levels remained almost unchanged throughout the 7 days while CICL1 levels were falling by 1 and 2 hours after administration in the spleen and liver, respectively (FIGS. 13D-E). The levels of mRNA in these three tissues did not correlate with ionizable cationic lipid. In plasma, mRNA level for the F9 tLNP (comprising CICL1) persisted with relatively little change for about 6 hours and then rapidly decayed while mRNA level for the BF1 LNP (comprising ALC-0315) was substantially lower and decayed more rapidly from initiation (FIG. 13F). mRNA levels in spleen were largely similar between the two lipid compositions (FIG. 13G). Substantially more mRNA was delivered to the liver by the BF1 tLNP than the F9 tLNP despite both tLNPs being targeted to CD8. The reduced liver delivery characteristics of CICL1 combined with its biodegradability properties and the targeting of the tLNP to CD8⁺T cells provided an expectation of minimized toxicity associated with ionizable lipid accumulation in the liver.

Example 14. Delivery of mRNA to T Cells can be Mediated by tLNP Targeted to a Variety of T Cell Surface Antigens To assess whether herein disclosed LNP compositions perform similarly well with different T cell targeting moieties, F5 tLNPs, encapsulating mCherry mRNA, conjugated individually to anti-CD2, anti-CD5, anti-CD4, and anti-CD8 antibodies were prepared. The tLNPs were used to transfect human T cells from two donors (Donor 1 and Donor 2, not necessarily related to similarly identified donors in other examples) using tLNP providing 0.6 µg mRNA per well containing $2 \times 10^5$ cells. 24 hours after transfection the cells were stained with anti-CD3/anti-CD4 antibodies or anti-CD3/anti-CD8 antibodies and analyzed by flow cytometry for mCherry expression.

Figure 14:
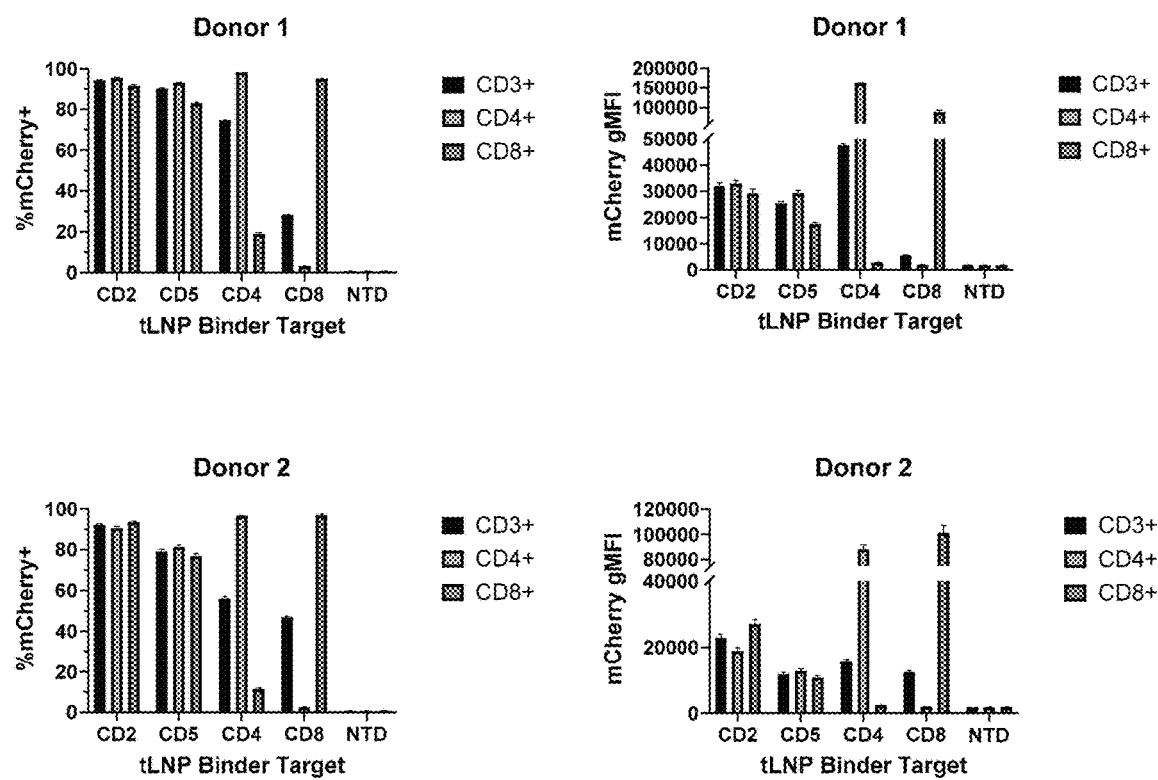
FIG. 14 depicts transfection efficiency as % mCherry positive cells (left panels) and expression level as geometric mean fluorescence intensity (gMFI; right panels) for human T cells from two donors (the upper (donor 1) and lower (donor 2) panels). The tLNPs comprised the F5 lipid composition and encapsulated mCherry mRNA and targeted CD2, CD5, CD4 or CD8. Data is plotted for $CD3^+$, $CD4^+$, and $CD8^+$ cells.

All four tLNPs targeted to the four different T cell markers, CD2, CD5, CD4, and CD8, performed similarly well on $CD3^+$, $CD4^+$, and $CD8^+$T cells for both transfection efficiency (% mCherry+ cells) and mCherry expression level (gMFI). As expected the CD4- and CD8-targeted tLNP provided only minimal transfection of $CD8^+$ and $CD4^+$ cells, respectively (FIG. 14). While this does not mean that all antibodies targeting CD2, CD5, CD4, CD8, or other T cell markers will transfect T cells similarly well, as antibody affinity and epitope recognized can impact transfection efficiency (data not shown), it does indicate that tLNP composition is permissive with respect to the target of the targeting moiety.

Example 15. Delivery of CRISPR Gene-Editing Components In Vitro

To deliver gene editing components into a cell generally will require delivery of at least two species of nucleic acid, for example an mRNA encoding an enzyme and a guide RNA. The sizes of these two components are disparate, for example, Cas 9 from *Staphylococcus pyogenes* Cas 9 (SpCas9) requires an mRNA approaching 5 kb (kilobases) while a guide RNA may be on the order of 100 bases. Both are different in size from the mCherry and CAR mRNA used in the Examples above. Moreover, the enzymes used in base-editing, prime editing, and similar techniques are generally fusions of two or more enzymes. We therefore tested the ability of a disclosed tLNP composition to encapsulate and deliver two RNA species of disparate sizes larger and smaller than the mRNA already utilized. Specifically, the F5 lipid composition was used to encapsulate SpCas9 mRNA and a single guide RNA (sgRNA) specific for the T Cell Receptor Alpha Constant (TRAC) locus. Transfection and knock-out efficiency were assessed.

T cells were isolated from fresh leukopaks with Easy-Sep™ Human T Cell Isolation Kit (#100-0695, STEMCELL Technologies) following manufacturer's manual. Briefly, a Leukopak was treated with ammonium chloride solution (#07800, STEMCELL Technologies) to lyse residual red blood cells and platelets and washed with EasySep™ Buffer (#20144, STEMCELL Technologies) with gentle centrifugations. The EasySep™ procedure involved magnetic beads and antibody complexes that recognized non-T cell antigens so that T cells were isolated after removing non-T cells in a magnet (Easy 250 EasySep™ magnet; #100-0821, STEMCELL Technologies. Isolated T cells were frozen in CryoStor® CS10 (#210502, STEMCELL Technologies) and stored in LN2 for future usage. T cell purity and phenotype were analyzed and confirmed by flow cytometry (Table 9).

TABLE 9

Phenotyping Antibody Panel

| Antigen | Clone | Fluoro | Antibody dilution | Company | Cat # |
|---|---|---|---|---|---|
| | | AmCyan* | n/a | Invitrogen | L34957 |
| CD4 | OKT4 | BV650 | 1:100 | Biolegend | 317436 |
| CD45 | HI30 | Qdot 800 (BV786) | 1:400 | Biolegend | 304048 |
| CD8 | HIT8a | FITC | 1:100 | Biolegend | 300906 |
| CD2 | RPA-2.10 | PE | 1:100 | Biolegend | 300208 |
| CD5 | 5D7 | APC | 1:100 | Thermo | MHCD0505 |
| CD3 | SP34-2 | APC-Cy7 | 1:100 | BD | BDB557757 |

*to discriminate live versus dead cells using Live/DeadTM Fixable Aqua Dead Cell Stain Kit Lipid composition F5 was used to encapsulate mRNA encoding SpCas9 and a single guide RNA (sgRNA) with an N/P ratio of 6. The sgRNA had a target sequence of GUCUCUCAGCUGGUACA (SEQ ID NO.: 2), modifications of 2'-O-Methyl at the three first and last bases, and 3' phosphorothioate bonds between first three and last two bases (ordered from Synthego, CRISPRevolution sgRNA EZ kit-modified), essentially as described above. The SpCas9 mRNA was approximately 4.7 kb in length and the sgRNA 100 nucleotides in length, substantially longer and shorter, respectively, than the CAR mRNA (approximately 1.9 kb) and mCherry mRNAs (approximately 1 and 1.1 kb) used in Examples 1-11 above. An anti-CD5 antibody (chimeric 5D7) was conjugated to the LNP to provide the tLNP (ch5D7-tLNP) which was frozen until use essentially as described above. The N/P ratio was 6 and the ratio of mRNA: sgRNA was 3:1 (w/w) or given the difference in size, approximately 3:47 (mol/mol). Previous work had shown that mRNA: sgRNA ratio of 9:1 and 1:1 (w/w) resulted in transfection rates of approximately a third less than 3:1 (w/w) (data not shown).

Three days prior to transfection with the tLNP, isolated T cells from two donors were thawed and placed into culture in complete T cell media containing OpTmizer™ T-cell Expansion basal Medium (A10485, Gibco), OpTimizer™ T-cell Expansion Supplement (A10484, Gibco), human serum heat-inactivated (HP1022HI, Valley Biomed), GlutaMax™ Supplement (35050061, Gibco), Pen/Strep (1514032, Gibco), and human IL-2 (202-IL, R&D). Immediately after thawing, T cells were activated with Dyna-Beads™ Human T-activator CD3/CD28 for T cell Expansion and Activation (#11161D, ThermoFisher) at 1:1 (bead:cell) ratio for 3 days. On the day of tLNP transfection, activated T cells were first de-beaded using Easy 250 EasySep™ magnet (#100-0821, STEMCELL Technologies) and resuspended in complete T cell media at $1\times10^6$ cells/mL. Cells were further seeded in to 96-well plates at 200 µL/well ($2\times10^5$ cells/well) prior to tLNP transfection. To maintain cell culture, T cells were passaged at 2 $\times10^5$ to $1\times10^6$/mL with complete T cell media every 2-3 days.

On the day of experiment, tLNPs were thawed and equilibrated to room temperature on the benchtop. Once completely thawed, tLNPs were diluted in sterile water for injection. Amounts of tLNPs that provided 0 (that is, no tLNP), 0.1, 0.3, 0.9, 2.7, or 8.1 µg payload were introduced to cells seeded in 96-well plate at $1\times10^6$ cells/mL. After 1 hr, 2 hr, 4 hr, or 24 hr incubation, cells were washed with PBS three times to remove free tLNPs (there was no 8.1 µg dose for the 4- and 24-hour timepoints). Transfected T cells were passaged and maintained in complete T cell media at $2\times10^5$ to $1\times10^6$/mL for 4 days before collection for knock-out analysis.

Four days after tLNP transfection, T cells were collected and stained with Aqua Live/Dead (#L34965, Invitrogen), anti-CD3-APC/Cy7 (BDB55775, BD), anti-CD4-BV650 (317436, BioLegend), and anti-CD8-FITC (300906, BioLegend) (see Table 9), and analyzed by multicolor flow cytometry. In the absence of TCR a chain CD3 was not expressed at the cell surface. Thus knock-out of TRAC can be assessed by staining for CD3.

Figure 15:
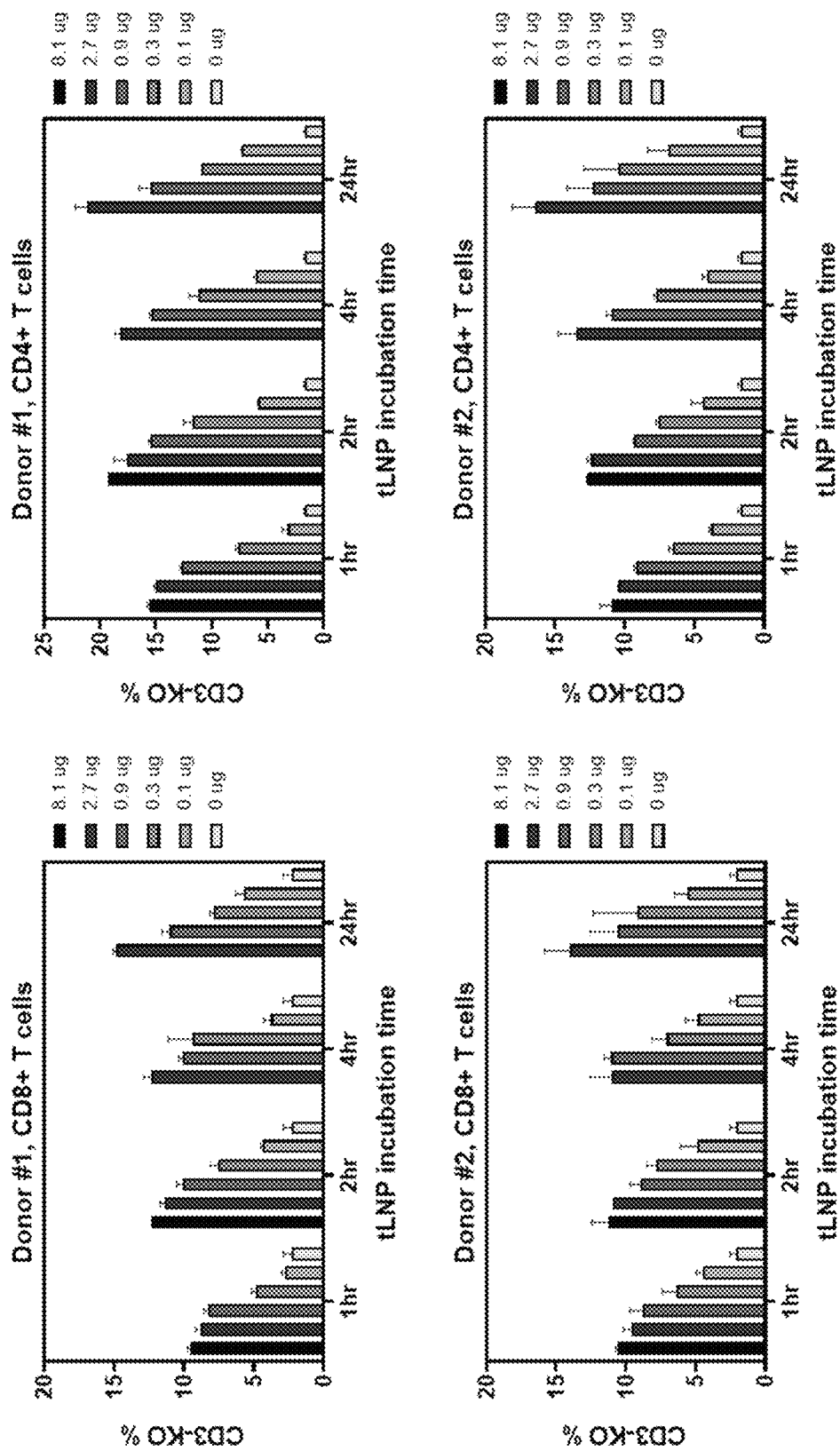
FIG. 15 depicts percent CD3 knock-out after disruption of the TRAC gene in primary human T cells at various time points after transfection of SpCas9 mRNA and a single guide RNA (sgRNA) targeting the TRAC locus using a tLNP decorated with an anti-CD5 monoclonal antibody (chimeric 5D7, also referred to as ch5D7) for various dosages of payload (μg of SpCas9 mRNA+sgRNA). The experiment was done with T cells obtained from two donors (the upper (donor #1) and lower (donor #2) panels). Results for $CD8^+$ T cells and $CD4^+$ T cells are presented separately in the left and right panels, respectively.

As seen in FIG. 15, at 1 hour the 0.9 µg dose achieved approximately 9% knock-out in $CD8^+T$ cells. Larger dosages did increase knock-out but not in proportion to the increased dose, possibly reflecting saturation of CD5 binding at the higher dosages. Prolonged exposure increased knock-out to approximately 15% in $CD8^+$ T cells and the dose response was more pronounced.

Example 16. Redosing of CRISPR Gene-Editing Components In Vitro

Whether a $2^{nd}$ exposure to tLNPs as described in the preceding Example would increase knock-out frequency was assessed. The tLNPs were thawed and equilibrated to room temperature on the benchtop. Once completely thawed, the tLNPs were diluted in sterile water for injection. Amounts of the tLNPs that provided 0 (that is, no tLNP), 0.1, 0.3, 0.9, 2.7, or 8.1 µg payload were introduced to cells seeded in 96-well plate at $1\times10^6$ cells/mL. After 1 hr, incubation cells were washed with PBS three times to remove free tLNPs. For those wells being redosed, 24 hr after the first transfection, cells were transfected with a $2^{nd}$ dose of tLNPs providing 0.3 or 2.7 µg of payload, again incubated for 1 hr, and then washed with PBS as before. Transfected T cells were passaged and maintained in complete T cell media at $2\times10^5$ to $1\times10^6$/mL for 4 days after the redosing before collection for knock-out analysis by flow cytometry essentially as described above.

Figure 16:
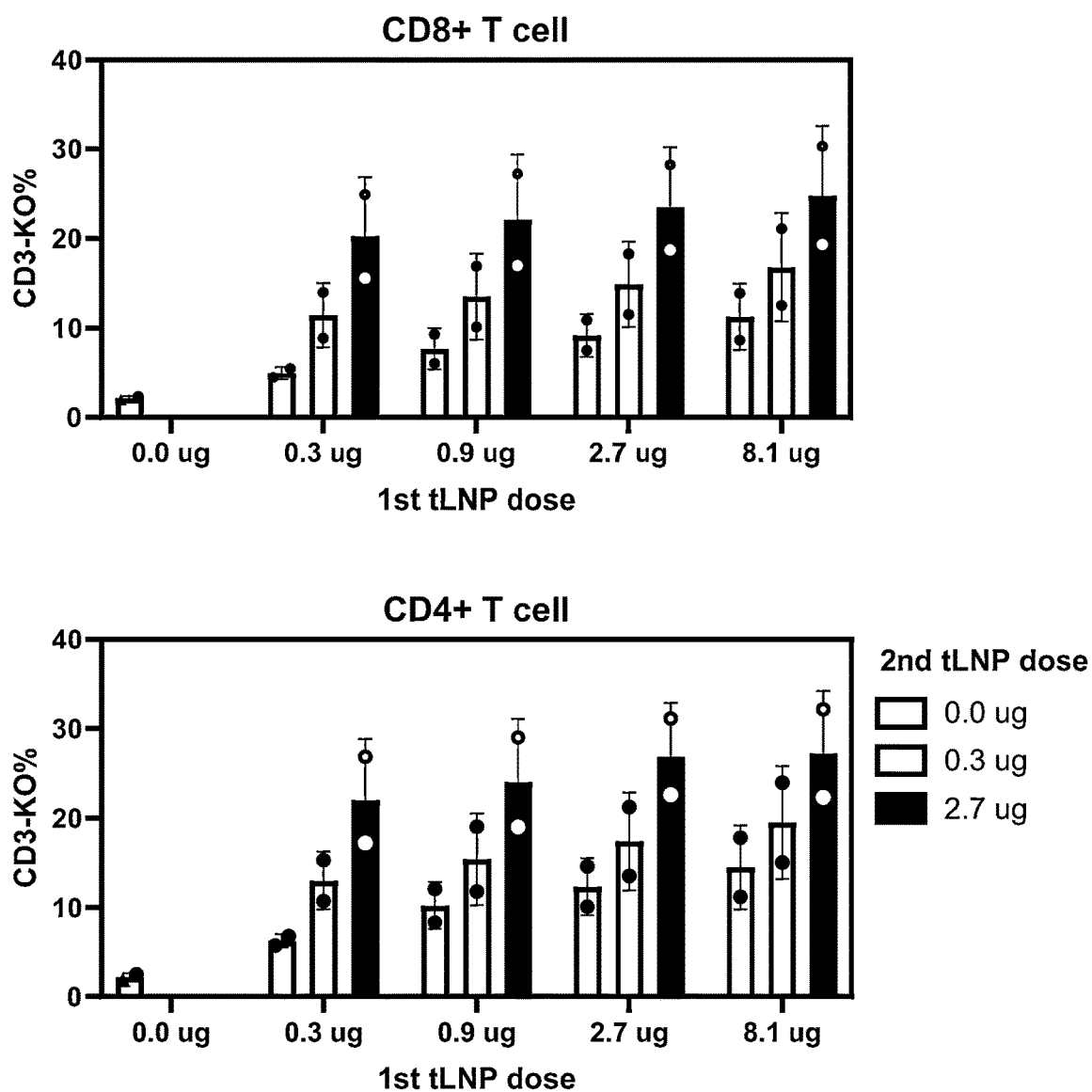
FIG. 16 depicts percent CD3 knock-out after disruption of the TRAC gene in primary human T cells after transfection of SpCas9 mRNA and a sgRNA targeting the TRAC locus using a tLNP decorated with an anti-CD5 monoclonal antibody for various dosages of payload (μg of SpCas9 mRNA+sgRNA) for both a first and second dose. Results for $CD8^+$ T cells and $CD4^+$ T cells are presented separately in the left and right panels, respectively. The bars represent the means from the results of two donors (the circles and the triangles).

As seen in FIG. 16, at each dosage tested, a second dose increased the % knock-out with the larger second dose having a greater effect. These results suggest that any limitation on transfection due to saturation of the target cell surface antigen, and thereby on % knock-out, may be overcome by repeated dosing.

Example 17. Redosing and Dual Targeting of CRISPR Gene-Editing Components In Vitro This experiment evaluated knock-out efficiency using CD8-targeted tLNP and using a combination of CD8- and CD5-targeted tLNP as well as redosing. Human T cell isolation and culture were as described above, as were the tLNP with the exception that some LNP encapsulating the SpCas9 mRNA and sgRNA payload were conjugated to an anti-CD8 antibody (chimeric RPA-T8, also referred to as chRPA-T8) instead of an anti-CD5 antibody (e.g., ch5D7).

On the first day of transfection, tLNPs were thawed and equilibrated to room temperature on the benchtop. Once completely thawed, the tLNPs were diluted in sterile water for injection. Anti-CD8-tLNPs (chRPA-T8-tLNP, FIG. 17) that provided 0 (that is, no tLNP), 0.03, 0.3, or 3 µg of payload were introduced to cells seeded in 96-well plate at $1\times10^6$/mL. For anti-CD5-tLNP and anti-CD8-tLNP co-delivery, tLNPs were pre-mixed at 3:1 wt/wt payload ratio and dosed at 0, 0.3, 0.9, or 3 µg total payload. After 1 hr tLNP incubation, cells were washed with PBS three times to remove free tLNPs. 24 hrs after the first transfection, cells were transfected with a 2nd dose of tLNPs comprising 3 µg of payload. This second tLNP administration was also incubated with the cells for 1 hr followed by PBS washes. Transfected T cells were passaged and maintained in complete T cell media at $2\times10^5$ to $1\times10^6$/mL for 5 days following the $2^{nd}$ transfection before collection for knock-out analysis.

Six days after the first tLNP transfection, T cells were collected and stained with Aqua Live/Dead (#L34965, ThermoFisher), anti-CD3-APC/Cy7 (BDB55775, BD), anti-CD4-BV650 (317436, BioLegend), and anti-CD8-FITC (300906, BioLegend), and analyzed by multicolor flow cytometry.

Figure 17:
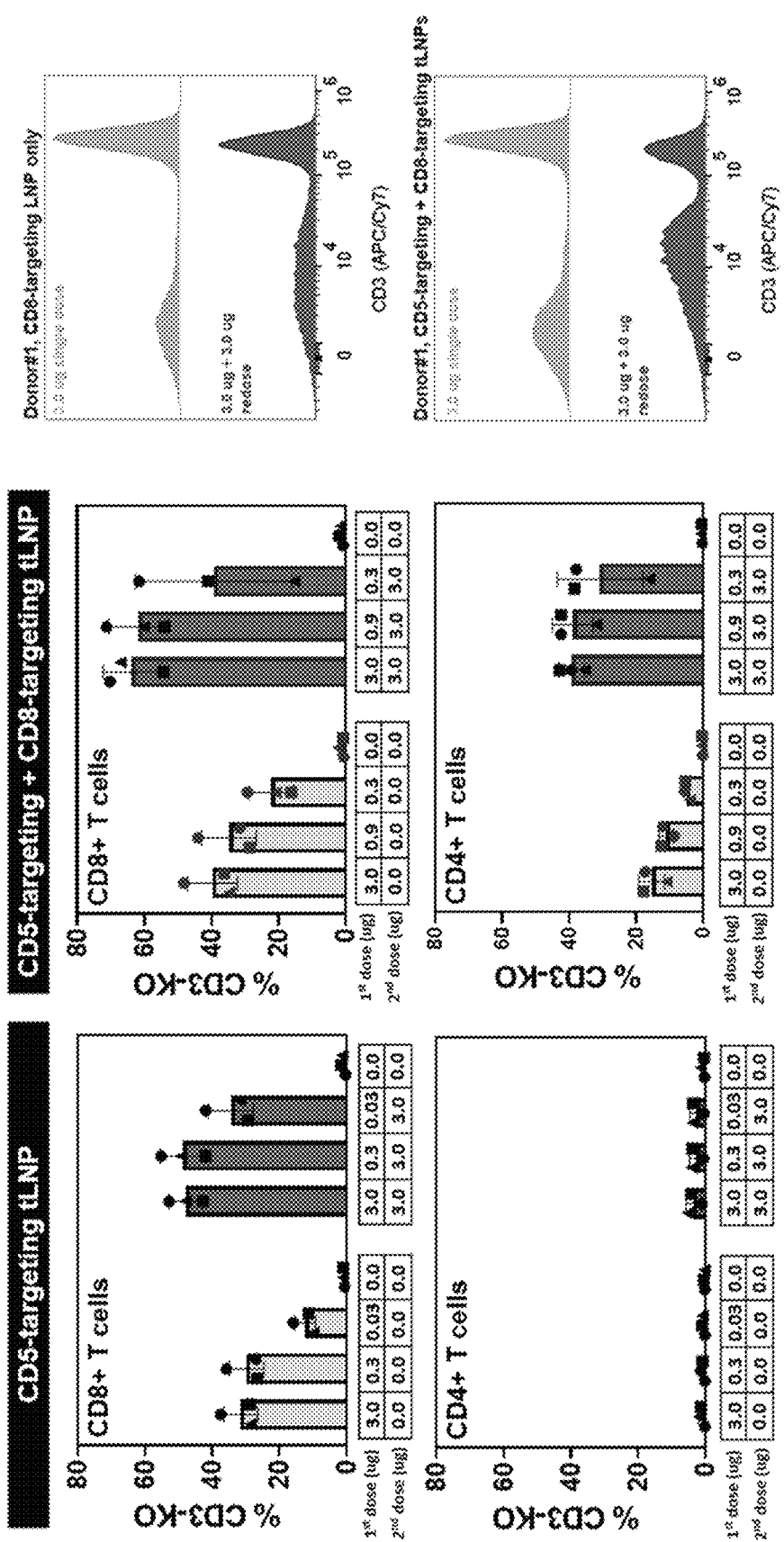
FIG. 17 depicts percent CD3 knock-out after disruption of the TRAC gene in primary human T cells after transfection of SpCas9 mRNA and a sgRNA targeting the TRAC locus using tLNPs decorated with an anti-CD8 monoclonal antibody (chRPA-T8-tLNP), or a combination of tLNPs decorated with anti-CD8 (chRPA-T8-tLNP) and an tLNPs decorated with an anti-CD5 monoclonal antibody (ch5D7-tLNP), monoclonal antibody for various dosages of payload (μg of SpCas9 mRNA+sgRNA) for both a first and second dose. In each of the four bar chart panels the results of a single dose are grouped to the left with the results with redosing are grouped to the right. The zero first and second dose data is plotted in both the single dose and redosed groupings. Results for $CD8^+$ T cells and $CD4^+$ T cells are presented separately in the upper and lower bar chart panels, respectively. The bars represent the means from the results of three donors (the circles, squares, and the triangles). Representative flow cytometry histograms of fluorescence versus number of events (cells) for each of the 3 μg dosage conditions from the $CD8^+T$ cells for Donor 1 (circles) are shown at the far right.

As seen in FIG. 16B (upper left panel), a single 0.3 μg dose of payload in the CD8-targeted tLNP (chRPA-T8-tLNP) was able to achieve between 30 and 40% CD3 knock-out in $CD8^+$ cells but increasing the single dosage to 3.0 μg did not further increase the % CD3 knock-out. A second dose of 3.0 μg however increased % CD3 knock-out to about 50% in $CD8^+$ cells for both the 0.3 and 3.0 μg initial dosage (FIG. 16A, upper left panel). Co-delivery of both CD8- and CD5-targeted tLNP (ch5D7-tLNP+chRPA-T8-tLNP) achieved approximately 35 to 50% CD3 knock-out in $CD8^+$ cells, depending on donor for both the 0.3 and 3.0 μg dosages (FIG. 17, upper middle panel). Redosing with 3.0 μg of the combination of tLNPs improved CD3 knock-out to approximately 50-70%, depending on donor, for both the 0.3 and 3.0 μg initial dosages (FIG. 16B, upper middle panel). In the right panel of FIG. 17 are representative flow cytometry histograms from each of the four conditions. As compared to the single dose histograms, the histograms for the redosed cells have a broader peak reaching to higher brightness reflecting the slow turnover of CD3 and one fewer days having elapsed since the last exposure to the tLNPs at the time of assessment. As expected, there was no significant CD3 knock-out in CD4 cells transfected with the CD8-targeted tLNPs alone (FIG. 17, lower left panel).

Example 18. Delivery of CRISPR Gene-Editing Components In Vivo

To assess the ability of the disclosed tLNP to deliver gene-editing components to human T cells in vivo, NSG mice with engrafted human T cells were administered CD5- and CD8-targeted tLNPs, alone or in combination, in one or two doses. As in the other gene-editing Examples, the tLNP used the F5 lipid composition with and overall N/p ration of 6 and a 3:1 (w/w) SpCas9: sgRNA payload, as above.

NSG mice were engrafted with $1\times10^6$ human T cells at day-20 (the mice were also infused with 0.5 million Nalm6, which was not relevant to this experiment). Groups of five mice were each transfected with CD5- or CD8-targeted tLNPs or a 3:1 mixture of CD5-: CD8-targeted tLNPs (w/w of payload) and there was a group of three untreated mice. At day 0, tLNPs containing 30 μg of payload in storage buffer were diluted to 100 μl with sterile water for injection and then infused into the tail vein of the mice. For the repeat dosing, tLNPs containing 20 μg of payload were infused 24 hrs after the first infusion in three of the five mice per group. Five days after the first infusion, blood samples were collected and stained with anti-human CD45, CD3, CD4, CD8 antibodies. Total human T cells were gated as $hCD45^+$ cells. Gating on $CD4^+$ and $CD8^+$ T cells were used to investigate CD4 and CD8 T cell subsets. TRAC knock-out T cells were gated as CD3-from the whole human T cell population, $CD4^+/CD3^-$, or $CD8^+/CD3^-$ T cells. The percentage of TRAC (CD3) knock-out cells was calculated from CD3-/CD45+, $CD3-CD4^+/CD45^+$, $CD3^-CD8^+/CD45^+$ cells for total, $CD4^+$, and $CD8^+$T cells, respectively.

Figure 18:
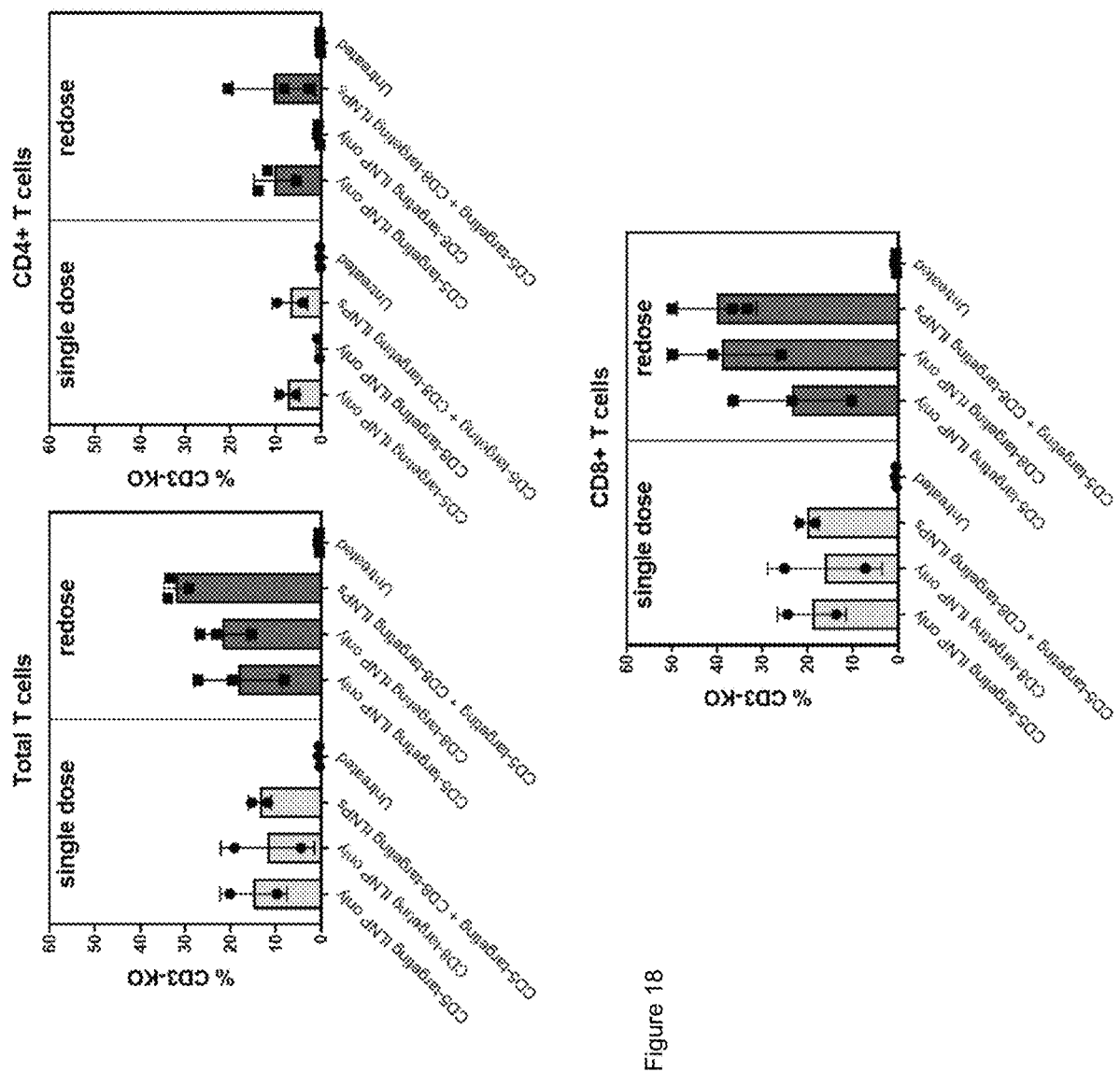
FIG. 18 depicts percent CD3 knock-out after disruption of the TRAC gene in human T cells engrafted in NSG mice after administration/transfection of ch5D7-tLNP only, chRPA-T8-tLNP only, or ch5D7-tLNP+chRPA-T8-tLNP each encapsulating payload (SpCas9 mRNA+sgRNA), given in a single dose or two doses of the tLNPs. Five mice were given an initial dose, among which 3 were redosed (squares) while 2 only received the single dose (circles). Three mice received no dose but are replotted in each grouping for comparison. The bars represent the mean of the two or three mice. Results are shown for total T cells, $CD4^+$ T cells, and $CD8^+$ T cells in the left, middle, and right panels, respectively. The single dose data is grouped to the left and the redosed data to the right in each panel.

The results are presented in FIG. 18 and demonstrate effective delivery of SpCas9 and the sgRNA into T cells in vivo. In this experiment the editing of $CD4^+$ T cells was less than 10% and redosing had minimal effect. Editing of total T or $CD8^+$ cells was approximately 15% or 20%, respectively, with a single dose of either CD5-(ch5D7-tLNP) or CD8-targeted (chRPA-T8-tLNP) tLNPs or a mixture of the two tLNPs. Redosing increased the percentage of CD3 knock-out in all cases but was most pronounced in the $CD8^+$ population for treatments including CD8-targeted tLNP for which editing was approximately 40% (FIG. 18).

Example 19. Transfection of CD117+Cells In Vitro

To assess the ability of the disclosed tLNP compositions to deliver mRNA to human HSC tLNP encapsulating mCherry mRNA and having various anti-CD117 antibodies as the binding moiety were used to transfect $CD34^+$ cells in vitro. tLNP of composition F5 were prepared essentially as described above with four different anti-CD117 antibodies, 104D2 (#1), JSP191 (#2), CK6 (#3), and Ab85 (#4). 104D2 does not block the action of SCF-1 (the ligand of CD117) while the other three anti-CD117 antibodies are blocking antibodies. tLNPs of composition F5 conjugated to teropavimab (an anti-HIV-1 gp120 antibody) were prepared as a negative control.

Plerixafor-mobilized human peripheral blood CD34+ hematopoietic stem cells were obtained from STEMCELL Technologies (#70075.1). One day before tLNP transfection, cells were thawed in X-VIVO 10 media (#BP04-743Q, Lonza) containing 3% human AB serum (#HP1022, Valley Biomed). Cells were then gently spun down and resuspended in CD34 pre-stimulation media, which consists of X-VIVO 10 media (#BP04-743Q, Lonza), 3% human AB serum (#HP1022, Valley Biomed), 100 ng/ml Flt3-L (#308-FK/CF, R&D Systems), 10 ng/ml TPO (#130-096-479, Miltenyi), 60 ng/ML IL-3 (#130-095-069, Miltenyi), 1 uM UM729 (#72332, STEMCELL Tech) and 1 uM StemRegenin1 (#72344, STEMCELL Tech).

On the day of tLNP transfection, cells were re-seeded in fresh CD34 pre-stimulation media at $2\times10^5$ cells/mL. tLNP were thawed and equilibrated to room temperature on the benchtop. Once completely thawed, tLNP were diluted in sterile water for injection. Amounts of tLNPs that provides 0 (that is, no tLNP), 2.5 μg, 5 μg, or 9 μg payload were introduced to cells in 48-well plate at $1\times10^5$ cells/well. After 1 hr of tLNP incubation, cells were washed with PBS three times to remove free tLNPs. Transfected cells were passaged into a new 48-well tissue culture plate and maintained in CD34 expansion media that is, StemSpan SFEM II (#09655, STEMCELL Tech) with 1X StemSpan $CD34^+$Expansion Supplement (#02691, STEMCELL Tech).

The 48-well plate then was placed in a live cell imager (IncuCyte Live-Cell Analysis System, Sartorius) for image acquisition with 10× magnification on phase and red channels for 72 hours. Image analysis was performed on IncuCyte software, calculating % $mCherry^+$ as ((total Red Area (per well)/Total Phase Area (per well)) (%)), and MFI as (Integrated Intensity of Red (per well)/total Red Area (per well)).

Figure 19B:
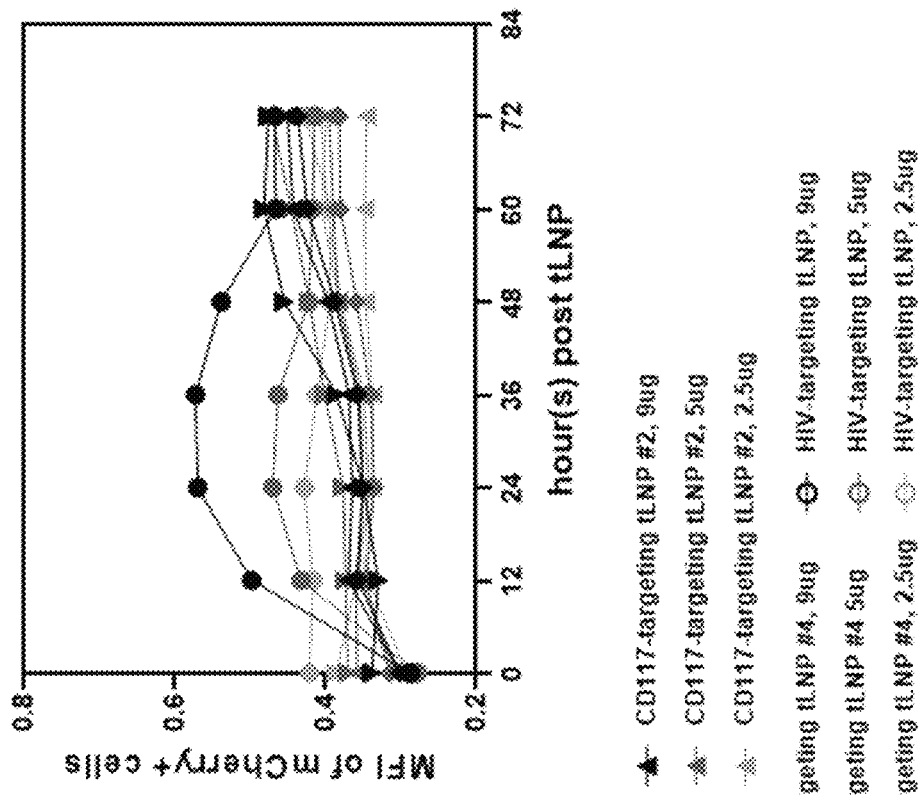
FIGS. 19A-B depict transfection rate (19A) and expression level (19B) over time for $CD34^+$ cells from human peripheral blood (that is, hematopoietic stem cells) contacted with CD117-targeted LNP in vitro at three doses of payload as indicated in the legend. The tLNP were targeted with one of four anti-CD117 antibodies: 104D2 (#1), JSP191 (#2), CK6 (#3), and Ab85 (#4). #1 is non-antagonistic while the other three are antagonistic. tLNP bearing the anti-HIV gp120 antibody teropavimab were used as a negative control.
Figure 19A:
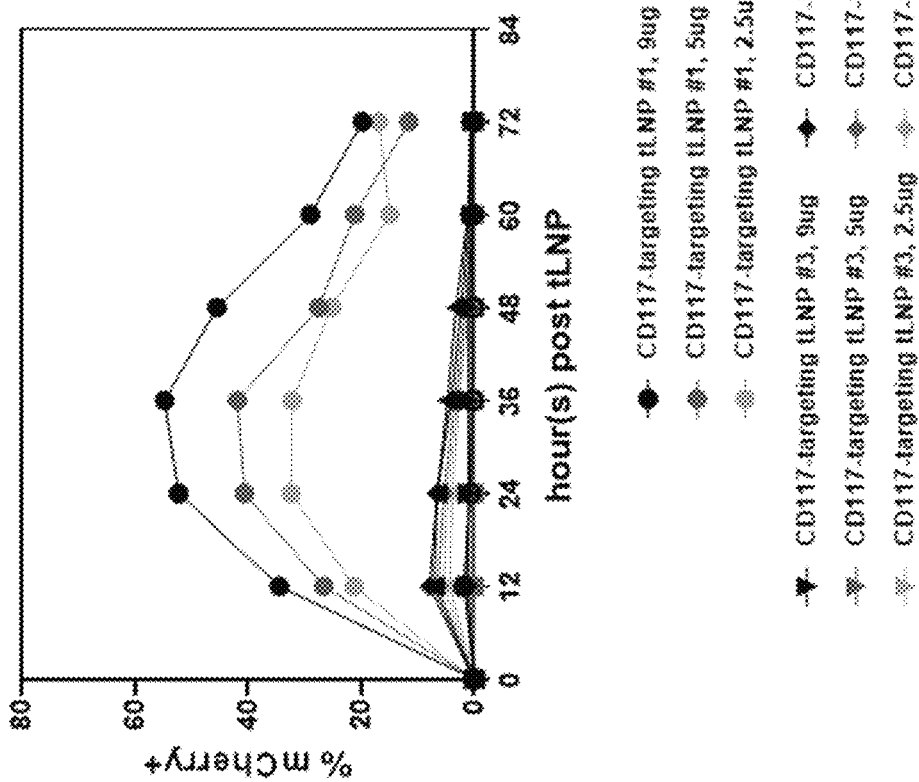

The tLNP targeted to $CD117^+$ cells with 104D2 showed productive transfection of the HSCs with clear dose effect with the % $mCherry^+$ cells peaking 24 to 36 hours after introduction of the tLNPs at around 30 to 55% for the three increasing doses (FIG. 19A). Expression level also peaked in the same time frame (FIG. 19B). The three anti-CD117 blocking antibodies had transfection rates less than approximately 4%. Thus, the disclosed tLNP compositions can be used to transfect HSC in addition to T cells.

Example 20. Comparison of Binding Moiety Conjugation Chemistries

Multiple chemistries are available for conjugating a binding moiety to an LNP. Here three chemistries for conjugating an antibody to an LNP comprising a maleimide-functionalized PEG-lipid were compared. One of the chemistries, AJICAP was site selective while the other two, SATA and TCEP, were not.

For antibody activation by SATA chemistry and tLNP conjugation, anti-CD5 (ch5D7) antibody was coupled to LNP encapsulating mCherry mRNA via N-succinimidyl S-acetylthioacetate (SATA)-maleimide conjugation chemistry. The anti-CD5 antibody in phosphate buffered saline (PBS) was modified with SATA (Sigma-Aldrich) (SATA: Ab molar ratio 5) to introduce sulfhydryl groups at accessible lysine residues allowing conjugation to maleimide. SATA was deprotected using sufficient 0.5 M hydroxylamine followed by removal of the unreacted components by Zeba Spin Desalting Columns (Thermo Scientific, Rockford, IL). The reactive sulfhydryl group on the antibody was then conjugated to maleimide moieties on the LNPs using thioether conjugation chemistry. Conjugated tLNP (LNP conjugated with a targeting antibody) purification was performed using Sepharose CL-4B gel filtration columns (Sigma-Aldrich). tLNPs were frozen at −80° C. until use.

For antibody activation by TCEP chemistry and tLNP conjugation, anti-CD5 antibody in PBS was conjugated by first partially reducing cystine bonds in an antibody with tris(2-carboxy)phosphine (TCEP, TCEP: Ab molar ratio 0.25) to generate thiol groups followed by removal of the unreacted components by Zeba Spin Desalting Columns (Thermo Scientific, Rockford, IL). The reactive sulfhydryl group on the antibody was then conjugated to maleimide moieties on the LNPs using thioether conjugation chemistry. Conjugated tLNP (LNP conjugated with a targeting antibody) purification was performed using TFF (tangential flow filtration). tLNPs were frozen at −80° C. until use.

For AJICAP tLNP conjugation, thiolated antibody was prepared by Ajinomoto Bio-Pharma Services generally as described in WO2019/240,287. Anti-CD5 AjiCap mono or bis thiolated antibodies were in 20 mM Acetate pH5.5, and ready for conjugation. The antibodies were thiolated at Lys248 of the heavy chain (EU numbering, or see Fujii T et al., *Bioconjugate Chem.* 2023, 34, 4, 728-738). To obtain antibody in which only one of the heavy chains has been thiolated (monothiol) the desired species was purified from an incomplete reaction. Both antibodies were conjugated through the maleimide moieties of the LNP using thioether conjugation chemistry. Purification of the conjugated tLNP (LNP conjugated with a targeting antibody) was performed using Sepharose CL-4B gel filtration columns (Sigma-Aldrich). tLNPs were frozen at −80° C. until use.

Physicochemical properties of the tLNP were within acceptable limits and are presented in Table 10.

TABLE 10

Physicochemical Properties of the tLNP

| Composition Description | Z-ave (nm) | PDI | Encapsulation Efficiency (%) | RNA Purity (%) by Fragment Analyzer | Ab:mRNA Ratio (wt:wt) by BCA |
|---|---|---|---|---|---|
| F5; SATA:Ab 5; Ab:mRNA 0.5 | 88 | 0.03 | 96 | 95 | 0.52 |
| F5; monothiol Ab:mRNA 0.3 | 87 | 0.05 | 96 | 95 | 0.36 |
| F5; bisthiol Ab:mRNA 0.3 | 88 | 0.03 | 96 | 89 | 0.42 |
| F5; TCEP:Ab 0.25 Ab:mRNA 3.2 | 86 | 0.07 | 97 | 94 | 0.47 |

The ability of these tLNP to deliver the mCherry mRNA into human T cells was tested in vitro and in an in vivo model.

Figure 20A:
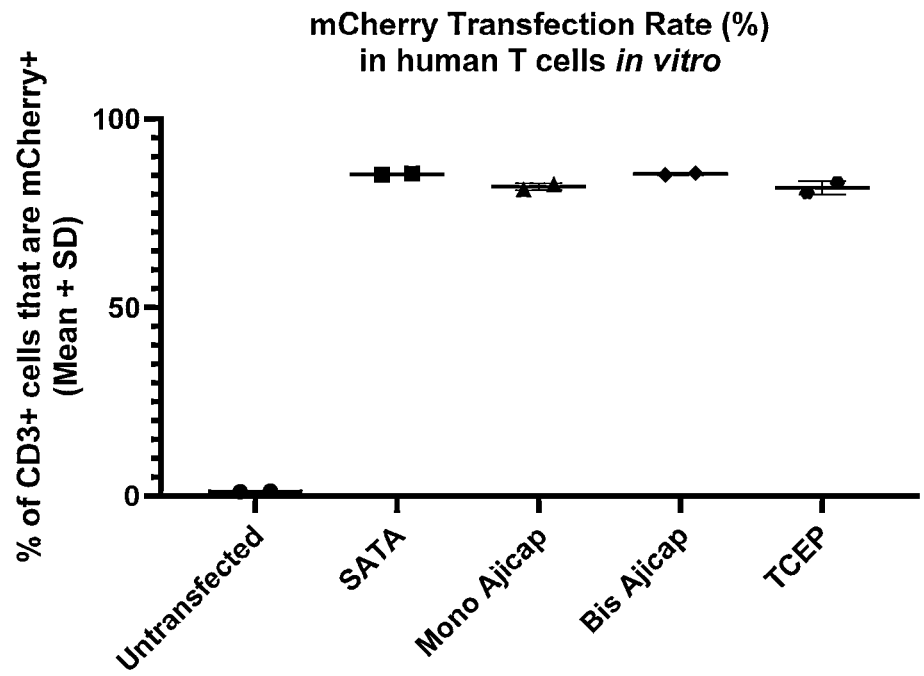
FIGS. 20A-D.
Figure 20B:
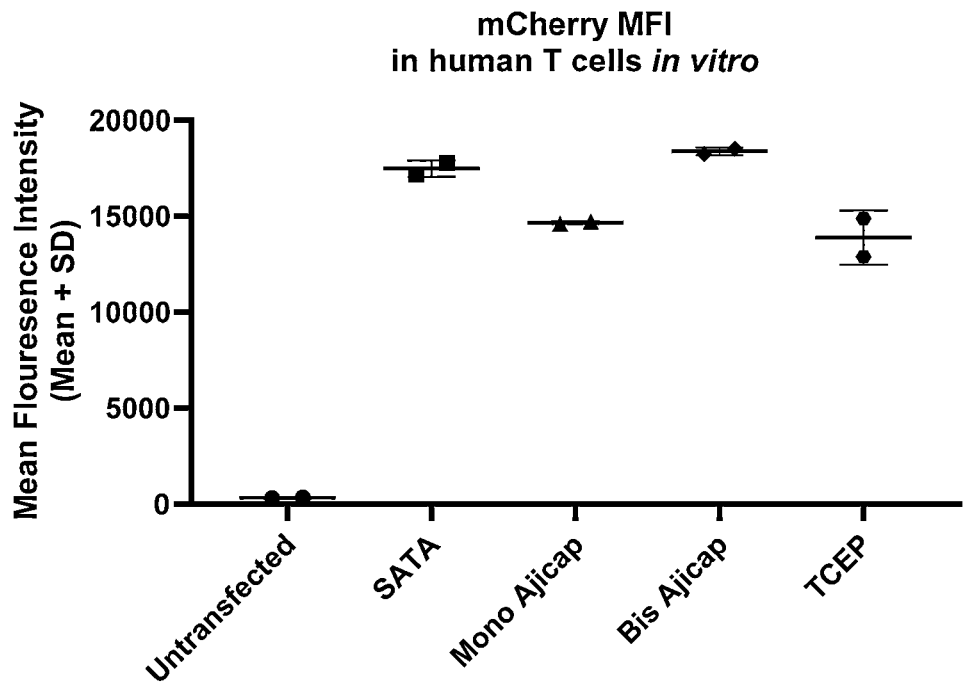

To assess transfection in vitro, human T cells from one healthy donor were activated by anti-CD3/CD28 antibodies (Dynabeads® Human T-Activator CD3/CD28) and transfected with CD5-targeting tLNP loaded with mCherry mRNA payload to provide 0.6 µg mRNA per 0.2 million cells in vitro. The tLNPs were incubated with the T cells for 1 hour inside a 37° C. $CO_2$ incubator and then was washed-off by using media (RPMI1640 +10% FBS supplemented with 100 IU/mL hIL-2). The T cells were then incubated with media inside a 37° C. $CO_2$ incubator for 24 hours and then mCherry expression in $CD3^+$ T cells was assessed by flow cytometry. Comparable transfection efficiency (% mCherry+$CD3^+$ T cells) and expression level (mean fluorescence intensity) was seen with all four tLNP preparations (FIGS. 20A-B).

To assess transfection in vivo, NSG mice (approximately 10 weeks old) were purchased from The Jackson Laboratory and acclimated for at least 5 days. Ten million human PBMCs were injected intravenously via the tail vein. Nineteen days after PBMC transfer, the frequency of human $CD45^+$ cells in circulation was evaluated by flow cytometry and animals were staged in groups with similar averages of human $CD45^+$ cells in the blood.

Figure 20C:
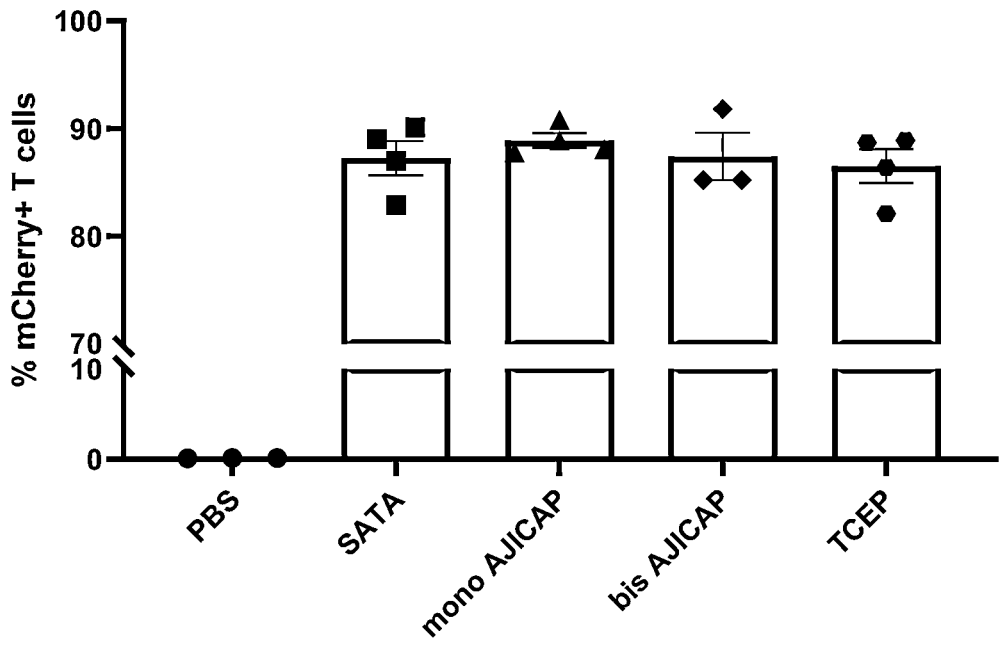
Figure 20D:
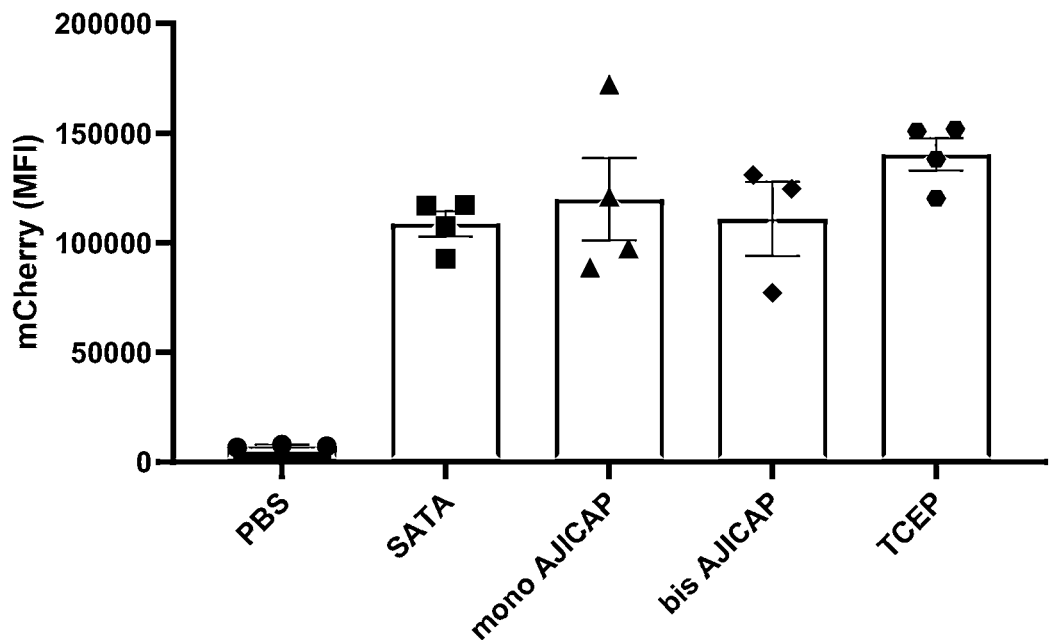

On day 20, the mice were injected intravenously with tLNPs comprising 10 µg mRNA (0.5 mg/Kg). 24 hours post injection, spleen samples were obtained, processed, and analyzed by flow cytometry for the presence of mCherry expression on human T cells. Comparable transfection efficiency (% $mCherry^+$ $CD3^+$ T cells) and expression level (mean fluorescence intensity) was seen with all four tLNP preparations (FIGS. 20C-D).

Example 21. Dual Conjugation of Antibody and Peptide to an LNP

LNP decorated with two distinct peptide moieties were formed by conjugation to two distinct functionalized PEG-lipid LNP components using complementary chemistries to demonstrate this capability. Specifically, an anti-mouse CD5 binding moiety and a peptide fragment of mouse CD47 were conjugated to an LNP comprising CICL1: DSPC: CHOL: DMG-PEG (2k): DSPE-PEG (2k)-Mal: DSPE-PEG (2k)-DBCO at a ratio of 58:10:30.5:1.3:0.1:0.1. However, this strategy can also be used to conjugate an LNP to two antibodies each having a distinct specificity.

The anti-CD5 antibody can serve as the targeting moiety for the tLNP. Using an antibody to target T cells is also expected to reduce uptake by liver hepatocytes consistent with results above.

CD47, a protein that promotes a "don't eat me" signal, binds to signal regulatory protein a (SIRPα) on macrophage to avoid phagocytosis [Tsai et al., 2008, *J Cell Biol.* 180 (5): 989-1003. doi: 10.1083/jcb.200708043. PMID: 18332220; PMCID: PMC2265407]. The interaction of CD47-SIRPα is highly conserved among various mammalian species, enabling the leverage of CD47 modification on drug delivery carriers to improve delivery efficacy. A short peptide sequence in CD47 has been reported to have 10-fold stronger binding affinity to SIRPα than full-length CD47 protein [Rodriguez et al., 2013, *Science* 339 (6122): 971-5. doi: 10.1126/science. 1229568. PMID: 23430657; PMCID: PMC3966479]. Thus, conjugating this CD47 peptide, NYTCEVTELSREGKTVIELK (SEQ ID NO: 3), to the tLNP could extend the in vivo circulation by inhibiting macrophage uptake.

The CD47 peptide was synthesized with an azide moiety, a functional group that is conjugatable with a dibenzocyclooctyne (DBCO) moiety by copper-free strain promoted azide alkyne (SPAAC) click reaction. The azide was attached to the N-terminus of the peptide separated by a polyethylene glycol (PEG4) linker so that the structure is $N_3$-PEG4-NYTCEVTELSREGKTVIELK-$NH_2$ (SEQ ID NO: 4). The azide moiety on the CD47 peptide therefore allowed covalent conjugation to LNP containing a DBCO functionalized lipid. The advantages of utilizing these functional groups (e.g., azide and DBCO) for a click chemistry reaction in tLNP formulation include: 1) fast reaction kinetics without additional catalysts to initiate the reaction, 2) a biocompatible reaction tolerant to a wide pH range, and 3) providing an additional or alternative conjugation strategy to the thiol-maleimide chemistry applied above for antibody conjugation to LNPs.

LNP intermediate was formed essentially as described in Example 1. The LNP comprised 0.1 mol % DSPE-PEG (2000)-DBCO and 0.1 mol % DSPE-PEG (2000)-maleimide and had good physicochemical properties (Table 11).

TABLE 11

Physicochemical Properties of the LNP intermediate

| Lipid formulation | Molar ratio | Size (nm) | PDI | Encapsulation Efficiency (%) |
|---|---|---|---|---|
| CICL1:DSPC:CHOL:DMG-PEG(2k):DSPE-PEG(2k)-Mal:DSPE-PEG(2k)-DBCO | 58:10:30.5:1.3:0.1:0.1 | 90 | 0.07 | 95 |

The antibody was modified with SATA essentially as described above and conjugated to the LNP. The system was designed for the SATA-modified antibody to react with the maleimide-functionalized PEG-lipid. The antibody was successfully added without significant change in the physicochemical properties of the LNP (Table 12). Protein (antibody): mRNA ratio was determined by BCA assay.

TABLE 12

Physicochemical Properties of the LNP after a Single Conjugation

| Batch # | Azide-CD47:DBCO molar ratio | Target Ab:mRNA wt/wt ratio | Size (nm) | PDI | Encapsulation Efficiency (%) | Ab:mRNA ratio (wt/wt) |
|---|---|---|---|---|---|---|
| 1 | 0 | 0.6 | 93 | 0.04 | 95 | 0.60 |
| 2 | 0 | 0.6 | 95 | 0.06 | 95 | 0.60 |
| 3 | 0 | 0.6 | 94 | 0.06 | 95 | 0.57 |
| 4 | 0 | 0.6 | 95 | 0.05 | 96 | 0.58 |

A second conjugation step was used to attach the CD47 peptide. The system was designed for the azide-modified peptide to react with the DBCO-functionalized PEG-lipid in a click chemistry reaction. The conjugation was carried out with peptide to DBCO molar ratios of 1:5, 1:10, and 1:20. Successful conjugation is reflected by the increase in particle size and protein: mRNA ratio (Table 13), the protein part of the ratio indicating the sum of antibody and CD47 peptide.

TABLE 13

Physicochemical Properties of the LNP after Dual Conjugation

| Batch ID | Azide-CD47:DBCO molar ratio | Ab:mRNA wt/wt ratio | Size | PDI | Encapsulation Efficiency (%) | Protein:mRNA ratio (wt/wt) |
|---|---|---|---|---|---|---|
| 2 | 5 | 0 | 97 | 0.01 | 95 | 0.66 |
| 3 | 10 | 0 | 100 | 0.08 | 94 | 0.66 |
| 4 | 20 | 0 | 113 | 0.08 | 93 | 0.80 |

Successful dual conjugation was observed only when mCD5 was conjugated first followed by conjugation of the CD47 peptide (contrary data not shown).

Embodiments

Embodiment 1: A lipid nanoparticle (LNP) comprising a lipid composition comprising:

about 35 to about 65 mol % an ionizable cationic lipid of structure

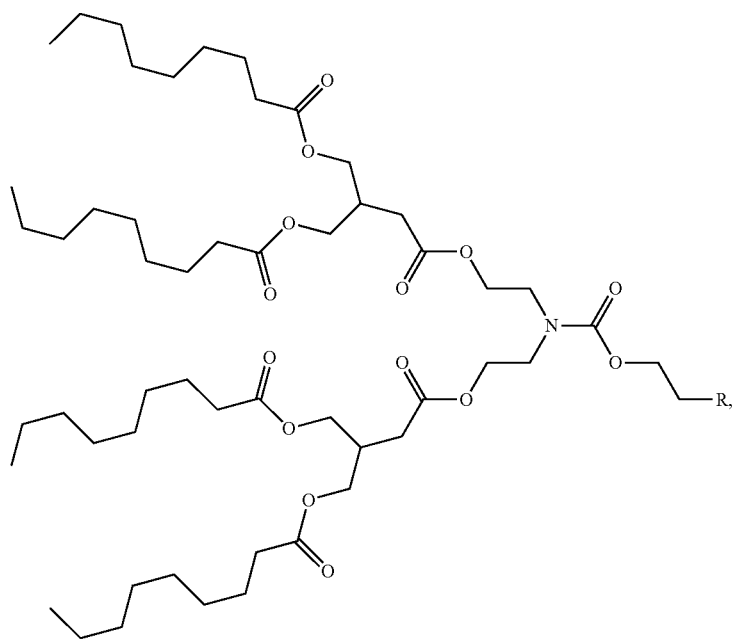

(C1CL)

wherein R is

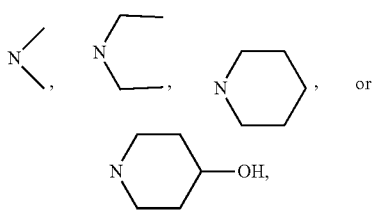

about 0.5 to about 3 mol % PEG-lipid comprising functionalized PEG-lipid and non-functionalized PEG-lipid,
about 7 to about 13 mol % a phospholipid, and
about 27 to about 50 mol % a sterol.

Embodiment 2: The LNP of embodiment 1, further comprising a payload with a net negative charge selected from a peptide, a polypeptide, a protein, a small molecule, a nucleic acid, and combinations thereof.

Embodiment 3: The LNP of embodiment 2, wherein the payload comprises a nucleic acid molecule.

Embodiment 4: The LNP of embodiment 3, wherein the N/P ratio is from about 3 to about 9, about 3 to about 7, about 3 to about 6, about 4 to about 7, or about 6.

Embodiment 5: The LNP of embodiment 3 or 4, wherein the nucleic acid comprises an mRNA.

Embodiment 6: The LNP of embodiment 3 or 5, wherein the nucleic acid molecule comprises a circular RNA, a self-replicating RNA, a microRNA (miRNA), an siRNA, an antisense RNA, a tracr (trRNA), a single guide RNA (sgRNA), a DNA, or a genetic engineering system.

Embodiment 7: The LNP of embodiment 5 or 6, wherein the mRNA encodes a T cell receptor (TCR), a chimeric antigen receptor (CAR), or an immune cell engager.

Embodiment 8: The LNP of embodiment 5 or 6, wherein the mRNA encodes a polypeptide comprising a gene editing nuclease.

Embodiment 9: The LNP of any one of embodiments 1 to 8, wherein the PEG-lipid comprises about 0.1 to about 0.3 mol % functionalized PEG-lipid.

Embodiment 10: The LNP of embodiment 9, wherein the non-functionalized PEG-lipid and the functionalized PEG-PEG-lipid are not the same PEG-lipid.

Embodiment 11: The LNP of embodiment 10, wherein the functionalized PEG-lipid comprises a diacyl phosphatidyl ethanolamine and the non-functionalized PEG-lipid comprises a diacyl glycerol.

Embodiment 12: The LNP of embodiment 11, wherein the functionalized PEG-lipid comprises distearoyl phosphatidyl ethanolamine (DSPE).

Embodiment 13: The LNP of embodiment 11 or 12, wherein the non-functionalized PEG-lipid comprises distearoyl glycerol (DSG).

Embodiment 14: The LNP of any one of embodiments 1-13, wherein the PEG moiety of the PEG-lipids has a molecular weight of about 1000 to about 5000.

Embodiment 15: The LNP of embodiment 14, wherein the PEG moiety is PEG2000 for both the functionalized and non-functionalized PEG-lipid.

Embodiment 16: The LNP of embodiment 15, wherein the PEG moiety of the functionalized PEG-lipid is larger than the PEG moiety of the non-functionalized PEG-lipid.

Embodiment 17: The LNP of any one of embodiments 9 to 16, wherein PEG moiety of the functionalized PEG-lipid comprises a terminal maleimide moiety.

Embodiment 18: The LNP of any one of embodiments 9 to 17, further comprising a binding moiety conjugated to the functionalized PEG-lipid.

Embodiment 19: The LNP of embodiment 18, wherein the functionalized PEG-lipid is conjugated to the binding moiety through the succinimide moiety, a hydrolyzed succinimide moiety, or a thiomaleimide moiety.

Embodiment 20: The LNP of embodiment 18 or 19, wherein the binding moiety comprises antibody or antigen binding domain thereof.

Embodiment 21: The LNP of embodiment 20, wherein the binding moiety is a whole antibody, a minibody, an F (ab) 2, an F (ab), a diabody, a single chain Fv (scFv), or a nanobody.

Embodiment 22: The LNP of any one of embodiments 18-21, wherein the binding moiety specifically binds to:
- a) an immune cell surface protein selected from the group consisting of CD2, CD3, CD4, CD5, CD7, CD8, CD28, 4-1BB, CD166, CTLA-4, GITR, LAG-3, OX40, PD-1, TIM-3, CD25, low affinity IL-2 receptor, IL-7 receptor, IL-12 receptor, IL-15 receptor, IL-18 receptor, IL-21 receptor, CD14, CD16a, CD32, CD40, CD11b (Mac-1), CD64, DEC205, and TREM2;
- b) a hematopoietic stem cell (HSC) surface protein selected from the group consisting of CD117, CD34, CD44, CD45, CD90, CD105, CD133, BMPR2, and Sca-1 or wherein the binding moiety specifically binds to a mesenchymal stem cell (MSC) surface protein selected from the group consisting of CD70, CD105, CD73, Stro-1, SSEA-4, CD271, CD146, GD2, SSEA-3, SUSD2, Stro-4, MSCA-1, CD56, CD200, PODXL, CD13, CD29, CD44, and CD10; or
- c) a mesenchymal stem cell (MSC) surface protein selected from the group consisting of CD70, CD105, CD73, Stro-1, SSEA-4, CD271, CD146, GD2, SSEA-3, SUSD2, Stro-4, MSCA-1, CD56, CD200, PODXL, CD13, CD29, CD44, and CD10.

Embodiment 23: The LNP of any one of embodiments 18-21, wherein the binding moiety specifically binds to a hematopoietic stem cell (HSC) surface protein selected from the group consisting of CD117, CD34, CD44, CD45, CD90, CD105, CD133, BMPR2, and Sca-1.

Embodiment 24: The LNP of any one of embodiments 18-21, wherein the binding moiety specifically binds to a mesenchymal stem cell (MSC) surface protein selected from the group consisting of CD70, CD105, CD73, Stro-1, SSEA-4, CD271, CD146, GD2, SSEA-3, SUSD2, Stro-4, MSCA-1, CD56, CD200, PODXL, CD13, CD29, CD44, and CD10.

Embodiment 25: The LNP of any one of embodiments 1-24, wherein the lipid composition has about 1 to about 2 mol % total PEG-lipid.

Embodiment 26: The LNP of any one of embodiments 1-25, wherein the lipid composition has about 0.1 mol % functionalized PEG-lipid.

Embodiment 27: The LNP of any one of embodiments 1-26, wherein the lipid composition has about 40 to about 60 mol % ionizable cationic lipid.

Embodiment 28: The LNP of embodiment 27, wherein the lipid composition has about 58 mol % ionizable cationic lipid.

Embodiment 29: The LNP of any one of embodiments 1-28, wherein the lipid composition has about 10 mol % phospholipid.

Embodiment 30: The LNP of embodiment 29, wherein the phospholipid is distearoyl phosphatidylcholine.

Embodiment 31: The LNP of embodiment 29, wherein the phospholipid is diarachidoyl phosphatidylcholine.

Embodiment 32: The LNP of any one of embodiments 1-31, wherein the lipid composition comprises about 33 to about 38 mol % sterol.

Embodiment 33: The LNP of any one of embodiments 1-32, wherein the sterol comprises cholesterol.

Embodiment 34: The LNP of any one of claims 1-33, wherein the sterol comprises a phytosterol.

Embodiment 35: The LNP of embodiment 34 wherein the phytosterol comprises campesterol, sitosterol, or stigmasterol, or combinations thereof.

Embodiment 36: The LNP of embodiment 33, wherein the sterol is cholesterol.

Embodiment 37: The LNP of f embodiment 4, comprising CICL1: DSPC: cholesterol: DSG-PEG2000: DSPE-PEG2000-maleimide in a ratio of 58:7:33.5:1.4:0.1 or 58:10:30.5:1.4:0.1.

Embodiment 38: The LNP of embodiment 4, comprising CICL1: DSPC: cholesterol: DPG-PEG2000: DSPE-PEG2000-maleimide in a ratio of 58:7:33.5:1.4:0.1 or 58:10:30.5:1.4:0.1.

Embodiment 39: The LNP of any one of embodiments 1-38, comprising: (a) a payload comprising an mRNA encoding a chimeric antigen receptor specific for human CD19, human CD20, human CD19 and human CD20; human BCMA; human FAP; or a payload comprising an mRNA encoding an RNA-guided nuclease and/or a guide RNA; and (b) a binding moiety comprising an antibody or an antigen-binding fragment thereof specific for human CD5, human CD8, or human CD2, wherein the antibody or antigen-binding fragment thereof is covalently attached to the functionalized PEG-lipid via a lysine or cysteine residue of the antibody or binding fragment thereof.

Embodiment 40: The LNP of any one of embodiments 1-38, comprising: (a) a payload comprising an mRNA encoding an RNA-guided nuclease and a guide RNA; and (b) a binding moiety comprising an antibody or an antigen-binding fragment thereof specific for human CD5, human CD8, or human CD2, wherein the antibody or antigen-binding fragment thereof is covalently attached to the functionalized PEG-lipid via a lysine or cysteine residue of the antibody or binding fragment thereof.

Embodiment 41: A composition comprising the LNP of any one of embodiments 1-40, further comprising one or more pharmaceutically acceptable carriers or excipients.

Embodiment 42: A method of delivering a payload into an immune cell or stem cell comprising contacting the LNP of any one of embodiments 1-40 with the immune cell or stem cell of a subject.

Embodiment 43: The method of embodiment 42, wherein delivering the payload comprises transfecting the immune cell or stem cell.

Embodiment 44: The method of embodiment 42 or 43, wherein the contacting takes place in vivo, extracorporeally, or ex vivo.

Embodiment 45: A method of reprogramming an immune cell or stem comprising administration of the LNP of any one of embodiments 1-40 or the composition of embodiment 41 to a subject.

Embodiment 46: The method of any one of embodiments 42-45, wherein the stem cell is a hematopoietic stem cell (HSC) or MSC.

Embodiment 47: The method of any one of embodiments 42-45, wherein the immune cell is a T cell.

Embodiment 48: A method of treating a disease comprising administration of the LNP of any one of embodiments 1-40 or the composition of embodiment 41 to a subject in need thereof.

Embodiment 49: A method of conditioning a subject who receives an engineering agent comprising providing the LNP of any one of embodiments 1-38 comprising a nucleic acid encoding a conditioning agent to the subject prior to, concurrently with, or subsequent to administration of the engineering agent.

Embodiment 50: The method of embodiment any one of embodiments 42-49, comprising intravenous administration to the subject.

Embodiment 51: A method of reprogramming an immune cell or an hematopoietic stem cell (HSC) comprising contacting the LNP of any one of embodiments 1-40 with the immune cell or HSC, wherein the reprogrammed immune cell or HSC does not comprise DNA encoding the reprogramming agent.

Embodiment 52: The method of embodiment 51, wherein the reprogrammed immune cell is a CAR-T cell.

Embodiment 53: A reprogrammed immune cell made by the method of embodiment 51 or 52.

Embodiment 54: A method of reprogramming an HSC comprising contacting the LNP of any one of embodiments 1-40 with the HSC, wherein the reprogrammed HSC does not comprise DNA encoding a component of a gene editing system.

All publications, patents, and patent applications mentioned in this specification are herein incorporated by reference to the same extent as if each individual publication, patent, and patent application was specifically and individually indicated to be incorporated by reference.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings the disclosure, and the appended claims. The mere fact that certain measures or features are recited in mutually different dependent claims does not indicate that the combination of these measures or features cannot be used. Any reference signs in the claims should not be construed as limiting the scope.

The invention claimed is:
1. A lipid nanoparticle (LNP) comprising a lipid composition comprising:
about 35 to about 65 mol % an ionizable cationic lipid of structure

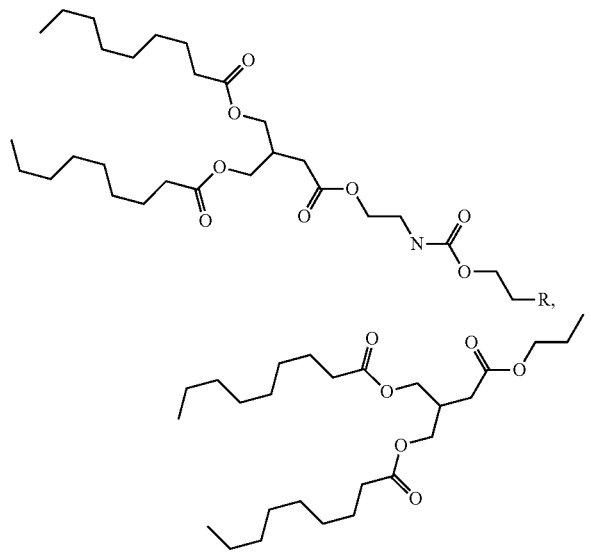

(CICL)

wherein R is

<br/> about 0.5 to about 3 mol % PEG-lipid comprising functionalized PEG-lipid and non-functionalized PEG-lipid,
about 7 to about 13 mol % a phospholipid, and
about 27 to about 50 mol % a sterol.

2. The LNP of claim 1, further comprising a payload with a net negative charge selected from a polypeptide, a small molecule, a nucleic acid, and combinations thereof.

3. The LNP of claim 2, wherein the payload comprises a nucleic acid molecule.

4. The LNP of claim 3, wherein lipid and nucleic acid components of the LNP have a N/P ratio that is from about 3 to about 9.

5. The LNP of claim 3, wherein the nucleic acid comprises an mRNA, a circular RNA, a self-replicating RNA, a microRNA (miRNA), an siRNA, or an antisense RNA.

6. The LNP of claim 3, wherein the nucleic acid molecule comprises an mRNA.

7. The LNP of claim 6, wherein the mRNA encodes a T cell receptor (TCR), a chimeric antigen receptor (CAR), an immune cell engager, or a gene editing nuclease.

8. The LNP of claim 1, wherein the PEG-lipid comprises about 0.1 to about 0.3 mol % functionalized PEG-lipid.

9. The LNP of claim 1, wherein the functionalized PEG-lipid comprises distearoyl phosphatidyl ethanolamine (DSPE).

10. The LNP of claim 9, wherein the non-functionalized PEG-lipid comprises distearoyl glycerol (DSG).

11. The LNP of claim 8, wherein the PEG moiety is PEG2000 for both the functionalized and non-functionalized PEG-lipid.

12. The LNP of claim 8, wherein the PEG moiety of the functionalized PEG-lipid comprises a terminal maleimide moiety.

13. The LNP of claim 8, further comprising a binding moiety conjugated to the functionalized PEG-lipid, wherein the binding moiety comprises a polypeptide, a carbohydrate, or a nucleic acid.

14. The LNP of claim 13, wherein the polypeptide is an antibody or antigen binding domain thereof.

15. The LNP of claim 13, wherein the binding moiety specifically binds to
an immune cell surface protein selected from the group consisting of CD2, CD3, CD4, CD5, CD7, CD8, CD28, 4-1BB, CD166, CTLA-4, GITR, LAG-3, OX40, PD-1, TIM-3, CD25, low affinity IL-2 receptor, IL-7 receptor, IL-12 receptor, IL-15 receptor, IL-18 receptor, IL-21 receptor, CD14, CD16a, CD32, CD40, CD11b (Mac-1), CD64, DEC205, and TREM2.

16. The LNP of claim 1, wherein the lipid composition comprises about 10 mol % phospholipid.

17. The LNP of claim 16, wherein the phospholipid is distearoyl phosphatidylcholine.

18. The LNP of claim 1, wherein the lipid composition comprises about 33 to about 38 mol % sterol.

19. The LNP of claim 1, wherein the sterol is cholesterol.

20. The LNP of claim 4, comprising CICL1: DSPC: cholesterol: DSG-PEG2000: DSPE-PEG2000-maleimide in a ratio of 58:10:30.5:1.4:0.1, wherein CICL1 is the CICL ionizable cationic lipid wherein R is <br/>

21. The LNP of claim 20, comprising:
a. a payload comprising an mRNA encoding a chimeric antigen receptor; and
b. a binding moiety comprising an antibody or an antigen-binding fragment thereof specific for human CD5, human CD8, or human CD2, wherein the antibody or antigen-binding fragment thereof is covalently attached to the functionalized PEG-lipid via a lysine or cysteine residue of the antibody or binding fragment thereof.

22. A composition comprising the LNP of claim 21, further comprising one or more pharmaceutically acceptable carriers or excipients.

23. A method of delivering a payload into an immune cell comprising contacting the LNP of claim 1 with the immune cell or stem cell of a subject.

24. A method of reprogramming an immune cell comprising administration of the composition of claim 22 to a subject.

25. The method of claim 23, wherein the immune cell is a T cell.

26. A method of treating a disease comprising administration of a composition comprising the LNP of claim 5 and one or more pharmaceutically acceptable carriers or excipients to a subject in need thereof, wherein the disease is an autoimmune disease, cancer, genetic disease, or fibrotic disease.

27. The method of claim 26, comprising intravenous administration to the subject.

28. A method of reprogramming an immune cell comprising contacting the LNP of claim 1 with the immune cell, wherein the reprogrammed immune cell does not comprise DNA encoding the reprogramming agent.

29. The method of claim 28, wherein the reprogrammed immune cell is a CAR-T cell.

30. The LNP of claim 11, wherein the functionalized PEG-lipid comprises 1,2-distearoyl-glycero-3-methoxy-polyethylene glycol (DSG).

* * * * *

UNITED STATES PATENT AND TRADEMARK OFFICE
CERTIFICATE OF CORRECTION

PATENT NO. : 12,311,033 B2
APPLICATION NO. : 18/731223
DATED : May 27, 2025
INVENTOR(S) : Priya Prakash Karmali et al.

It is certified that error appears in the above-identified patent and that said Letters Patent is hereby corrected as shown below:

In the Specification

In Column 27, Line 28, please delete "WO2019/240,247" and replace with "WO2019/240,287"

In the Claims

In Claim 1, Column 87, Lines 8-30, should read:

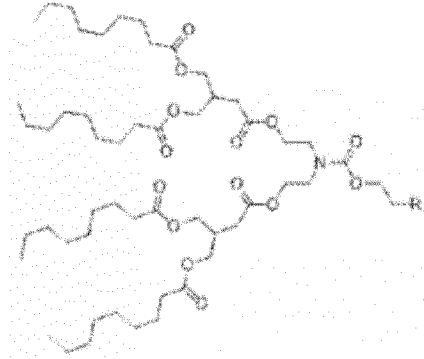

In Claim 7, Column 87, Lines 64 and 65, please delete ",or a gene editing nuclease" and please add "or" after "a chimeric antigen receptor (CAR),"

In Claim 23, Column 88, Line 59 please delete "or stem cell"

Signed and Sealed this
Twelfth Day of August, 2025

Coke Morgan Stewart
*Acting Director of the United States Patent and Trademark Office*